US012673937B2

(12) United States Patent
Pak et al.

(10) Patent No.: US 12,673,937 B2
(45) Date of Patent: Jul. 7, 2026

(54) LIGHT-EMITTING DEVICE INCLUDING HETEROCYCLIC COMPOUND AND ELECTRONIC APPARATUS INCLUDING LIGHT-EMITTING DEVICE

(71) Applicant: Samsung Display Co., Ltd., Yongin-si (KR)

(72) Inventors: Hankyu Pak, Yongin-si (KR); Dongjun Kim, Yongin-si (KR); Minji Kim, Yongin-si (KR); Eunjae Jeong, Yongin-si (KR); Sanghyun Han, Yongin-si (KR); Byeongwook Yoo, Yongin-si (KR); Sohee Jo, Yongin-si (KR); Hyunbin Park, Yongin-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 1011 days.

(21) Appl. No.: 17/816,671

(22) Filed: Aug. 1, 2022

(65) Prior Publication Data

US 2024/0002366 A1 Jan. 4, 2024

(30) Foreign Application Priority Data

Aug. 2, 2021 (KR) ........................ 10-2021-0101527

(51) Int. Cl.
*C07D 403/04* (2006.01)
*C07D 403/14* (2006.01)
(Continued)

(52) U.S. Cl.
CPC ......... *C07D 403/04* (2013.01); *C07D 403/14* (2013.01); *C07D 405/14* (2013.01);
(Continued)

(58) Field of Classification Search
CPC ............. H10K 85/657; H10K 85/6572; H10K 85/6574; H10K 85/6576; H10K 85/631
See application file for complete search history.

(56) References Cited

U.S. PATENT DOCUMENTS 4,720,432 A 1/1988 VanSlyke et al.
5,061,569 A 10/1991 VanSlyke et al.
(Continued)

FOREIGN PATENT DOCUMENTS

JP 1999-144873 A 5/1999
JP 2000-302756 A 10/2000
(Continued)

OTHER PUBLICATIONS

KR-20150000967-A—translation (Year: 2015).*
(Continued)

*Primary Examiner* — Rachel Simbana
(74) *Attorney, Agent, or Firm* — Womble Bond Dickinson (US) LLP

(57) ABSTRACT

A light-emitting device includes: a first electrode; a second electrode facing the first electrode; an interlayer between the first electrode and the second electrode, the interlayer including an emission layer; and a heterocyclic compound represented by Formula 1:

Formula 1

(Continued)

Formula 1 may be understood by referring to the description of Formula 1 provided herein. An electronic apparatus may include the light-emitting device.

20 Claims, 3 Drawing Sheets

(51) Int. Cl.

| | |
|---|---|
| ***C07D 405/14*** | (2006.01) |
| ***C07D 409/14*** | (2006.01) |
| ***C07D 471/08*** | (2006.01) |
| ***C07D 491/08*** | (2006.01) |
| ***C07D 495/08*** | (2006.01) |
| ***H10K 50/11*** | (2023.01) |
| ***H10K 50/15*** | (2023.01) |
| ***H10K 50/17*** | (2023.01) |
| ***H10K 50/86*** | (2023.01) |
| ***H10K 59/123*** | (2023.01) |
| ***H10K 59/38*** | (2023.01) |
| ***H10K 59/40*** | (2023.01) |
| ***H10K 85/60*** | (2023.01) |

(52) U.S. Cl.

CPC ......... *C07D 409/14* (2013.01); *C07D 471/08* (2013.01); *C07D 491/08* (2013.01); *C07D 495/08* (2013.01); *H10K 50/15* (2023.02); *H10K 50/17* (2023.02); *H10K 85/657* (2023.02); *H10K 85/6572* (2023.02); *H10K 85/6574* (2023.02); *H10K 85/6576* (2023.02); *C07B 2200/05* (2013.01)

(56) References Cited

U.S. PATENT DOCUMENTS

| | | | | |
|---|---|---|---|---|
| 6,242,115 | B1 | 6/2001 | Thomson et al. | |
| 9,054,321 | B2 | 6/2015 | Park et al. | |
| 10,930,858 | B2 | 2/2021 | Miyazaki | |
| 2005/0236970 | A1* | 10/2005 | Matsudate ........... | H10K 59/131 313/500 |
| 2018/0166647 | A1* | 6/2018 | Shin ....................... | H10K 50/16 |
| 2020/0152884 | A1 | 5/2020 | Hwang et al. | |

FOREIGN PATENT DOCUMENTS

| | | | | | |
|---|---|---|---|---|---|
| JP | 2003-133075 | A | | 5/2003 | |
| JP | 2004-079265 | A | | 3/2004 | |
| JP | 2006-151979 | A | | 6/2006 | |
| KR | 10-2013-0042368 | A | | 4/2013 | |
| KR | 10-2015-0000967 | A | | 1/2015 | |
| KR | 20150000967 | A | * | 1/2015 | ......... H10K 85/6572 |
| KR | 10-1891773 | B1 | | 8/2018 | |
| KR | 10-2019-0049984 | A | | 5/2019 | |

OTHER PUBLICATIONS

Sabbatini et al., "*Lanthanide luminescence in supramolecular species*", Journal of Luminescence, (1991) vol. 48-49, pp. 463-468 (6 pages).

* cited by examiner

LIGHT-EMITTING DEVICE INCLUDING HETEROCYCLIC COMPOUND AND ELECTRONIC APPARATUS INCLUDING LIGHT-EMITTING DEVICE

CROSS-REFERENCE TO RELATED APPLICATION

This application claims priority to and the benefit of Korean Patent Application No. 10-2021-0101527, filed on Aug. 2, 2021, in the Korean Intellectual Property Office, the entire content of which is incorporated herein by reference.

BACKGROUND

1. Field

One or more aspects of embodiments of the present disclosure relate to a light-emitting device including a heterocyclic compound and an electronic apparatus including the light-emitting device.

2. Description of the Related Art

Light-emitting devices are self-emissive devices that have wide viewing angles, high contrast ratios, short response times, and excellent characteristics in terms of brightness, driving voltage, and/or response speed.

Light-emitting devices may include a first electrode on a substrate, and a hole transport region, an emission layer, an electron transport region, and a second electrode sequentially stacked on the first electrode. Holes provided from the first electrode may move toward the emission layer through the hole transport region, and electrons provided from the second electrode may move toward the emission layer through the electron transport region. Carriers, such as holes and electrons, recombine in the emission layer to produce excitons. These excitons transition from an excited state to a ground state to thereby generate light.

SUMMARY

One or more aspects of embodiments of the present disclosure are directed toward a light-emitting device including a heterocyclic compound and an electronic apparatus including the light-emitting device.

Additional aspects will be set forth in part in the description which follows and, in part, will be apparent from the description, or may be learned by practice of the presented embodiments of the disclosure.

According to one or more embodiments, a light-emitting device may include:

a first electrode, a second electrode facing the first electrode, an interlayer between the first electrode and the second electrode, the interlayer including an emission layer, and a heterocyclic compound represented by Formula 1:

Formula 1

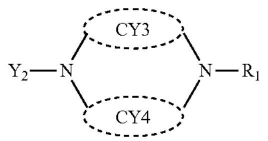

-continued

Formula 2

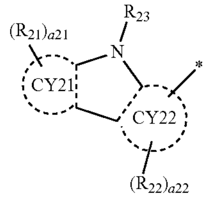

Formula 3

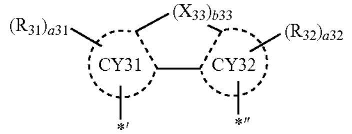

Formula 4

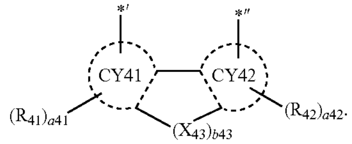

In Formulae 1 to 4, $Y_2$ may be a group represented by Formula 2, ring CY3 may be a group represented by Formula 3, ring CY4 may be a group represented by Formula 4, ring CY21, ring CY22, ring CY31, ring CY32, ring CY41, and ring CY42 may each independently be a $C_3$-$C_{60}$ carbocyclic group or a $C_1$-$C_{60}$ heterocyclic group, $X_{33}$ may be a single bond, O, S, $B(R_{33})$, $N(R_{33})$, $C(R_{33})(R_{34})$, $Si(R_{33})(R_{34})$, or $C(R_{33}){=}C(R_{34})$, $b_{33}$ may be an integer selected from 0 to 3, when $b_{33}$ is 0, $X_{33}$ may not be present, $X_{43}$ may be a single bond, O, S, $B(R_{43})$, $N(R_{43})$, $C(R_{43})(R_{44})$, $Si(R_{43})(R_{44})$, or $C(R_{43}){=}C(R_{44})$, $b_{43}$ may be an integer selected from 0 to 3, when $b_{43}$ is 0, $X_{43}$ may not be present, $R_1$, $R_{21}$ to $R_{23}$, $R_{31}$ to $R_{34}$, and $R_{41}$ to $R_{44}$ may each independently be hydrogen, deuterium, —F, —Cl, —Br, —I, a hydroxyl group, a cyano group, a nitro group, a $C_1$-$C_{60}$ alkyl group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, a $C_6$-$C_{60}$ aryloxy group unsubstituted or substituted with at least one $R_{10a}$, a $C_6$-$C_{60}$ arylthio group unsubstituted or substituted with at least one $R_{10a}$, a $C_7$-$C_{60}$ aryl alkyl group unsubstituted or substituted with at least one $R_{10a}$, a $C_2$-$C_{60}$ heteroaryl alkyl group unsubstituted or substituted with at least one $R_{10a}$, $—Si(Q_1)(Q_2)(Q_3)$, $—N(Q_1)(Q_2)$, $—B(Q_1)(Q_2)$, $—C(=O)(Q_1)$, $—S(=O)_2(Q_1)$, or $—P(=O)(Q_1)(Q_2)$, a21, a22, a31, a32, a41, and a42 may each independently be an integer selected from 0 to 10, wherein, in Formula 2,

* indicates a binding site to nitrogen (N) bound to $Y_2$ in Formula 1, wherein, in Formulae 3 and 4,

*' indicates a binding site to nitrogen (N) bound to $Y_2$ in Formula 1,

*" indicates a binding site to nitrogen (N) bound to $R_1$ in Formula 1, and $R_{10a}$ may be:

deuterium, —F, —Cl, —Br, —I, a hydroxyl group, a cyano group, or a nitro group, a $C_1$-$C_{60}$ alkyl group, a $C_2$-$C_{60}$ alkenyl group, a $C_2$-$C_{60}$ alkynyl group, or a $C_1$-$C_{60}$ alkoxy group, each unsubstituted or substituted with deuterium, —F, —Cl, —Br, —I, a hydroxyl group, a cyano group, a nitro group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, a $C_7$-$C_{60}$ aryl alkyl group, a $C_2$-$C_{60}$ heteroaryl alkyl group, —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$), —P(=O)($Q_{11}$)($Q_{12}$), or any combination thereof, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, a $C_7$-$C_{60}$ aryl alkyl group, or a $C_2$-$C_{60}$ heteroaryl alkyl group, each unsubstituted or substituted with deuterium, —F, —Cl, —Br, —I, a hydroxyl group, a cyano group, a nitro group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, a $C_7$-$C_{60}$ aryl alkyl group, a $C_2$-$C_{60}$ heteroaryl alkyl group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), —P(=O)($Q_{21}$)($Q_{22}$), or any combination thereof, or —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), or —P(=O)($Q_{31}$)($Q_{32}$), wherein $Q_1$ to $Q_3$, $Q_{11}$ to $Q_{13}$, $Q_{21}$ to $Q_{23}$, and $Q_{31}$ to $Q_{33}$ may each independently be hydrogen, deuterium, —F, —Cl, —Br, —I, a hydroxyl group, a cyano group, a nitro group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ carbocyclic group, or a $C_1$-$C_{60}$ heterocyclic group (each unsubstituted or substituted with deuterium, —F, a cyano group, a $C_1$-$C_{60}$ alkyl group, a $C_1$-$C_{60}$ alkoxy group, a phenyl group, a biphenyl group, a $C_1$-$C_{60}$ heterocyclic group, or any combination thereof), a $C_7$-$C_{60}$ aryl alkyl group, or a $C_2$-$C_{60}$ heteroaryl alkyl group.

According to one or more embodiments, an electronic apparatus may include the light-emitting device.

BRIEF DESCRIPTION OF THE DRAWINGS

The above and other aspects, features, and advantages of certain embodiments of the disclosure will be more apparent from the following description taken in conjunction with the accompanying drawings, in which.

DETAILED DESCRIPTION

Figure 1:
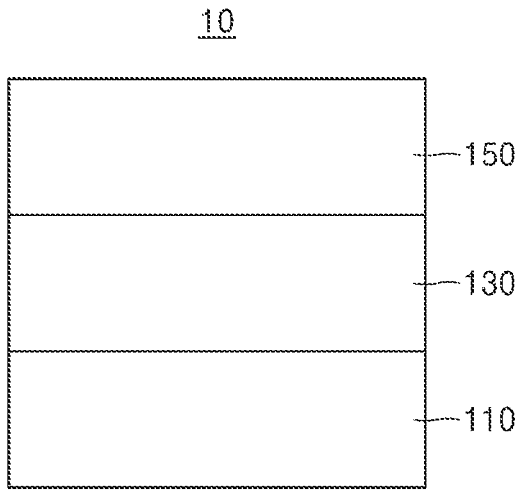
FIG. 1 is a schematic cross-sectional view of a light-emitting device according to one or more embodiments.

Reference will now be made in more detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Throughout the disclosure, expressions such as "at least one of", "one of", and "selected from", when preceding a list of elements, modify the entire list of elements and do not modify the individual elements of the list. For example, "at least one of a, b and c", "at least one of a, b or c", and "at least one of a, b and/or c" may indicate only a, only b, only c, both (e.g., simultaneously) a and b, both (e.g., simultaneously) a and c, both (e.g., simultaneously) b and c, all of a, b, and c, or variations thereof.

Further, the use of "may" when describing embodiments of the present disclosure refers to "one or more embodiments of the present disclosure".

As used herein, the singular forms "a," "an," and "the" are intended to include the plural forms as well, unless the context clearly indicates otherwise.

It will be further understood that the terms "includes," "including," "comprises," and/or "comprising," when used in this specification, specify the presence of stated features, steps, operations, elements, and/or components, but do not preclude the presence or addition of one or more other features, steps, operations, elements, components, and/or groups thereof.

As used herein, the terms "use," "using," and "used" may be considered synonymous with the terms "utilize," "utilizing," and "utilized," respectively.

As used herein, the terms "substantially", "about", and similar terms are used as terms of approximation and not as terms of degree, and are intended to account for the inherent deviations in measured or calculated values that would be recognized by those of ordinary skill in the art. "About" or "approximately," as used herein, is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" may mean within one or more standard deviations, or within ±30%, 20%, 10%, 5% of the stated value.

Any numerical range recited herein is intended to include all sub-ranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein.

A light-emitting device may include: a first electrode; a second electrode facing the first electrode; an interlayer between the first electrode and the second electrode and including an emission layer; and a heterocyclic compound represented by Formula 1:

Formula 1

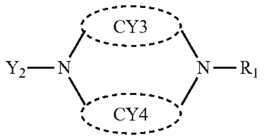

Formula 2

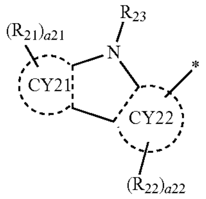

Formula 3

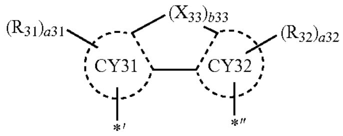

Formula 4

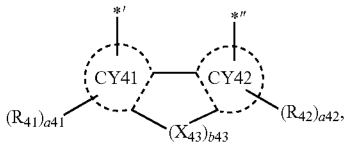

wherein, in Formulae 1 to 4, $Y_2$ may be a group represented by Formula 2, ring CY3 may be a group represented by Formula 3, and ring CY4 may be a group represented by Formula 4.

ring CY21, ring CY22, ring CY31, ring CY32, ring CY41, and ring CY42 may each independently be a $C_3$-$C_{60}$ carbocyclic group or a $C_1$-$C_{60}$ heterocyclic group.

In some embodiments, ring CY21, ring CY22, ring CY31, ring CY32, ring CY41, and ring CY42 may each independently be a benzene group, a naphthalene group, an anthracene group, a dibenzofuran group, a dibenzothiophene group, a carbazole group, a fluorene group, or a dibenzosilole group.

In one or more embodiments, ring CY21, ring CY22, ring CY31, ring CY32, ring CY41, and ring CY42 may each independently be a benzene group or a naphthalene group.

In one or more embodiments, in Formula 2, at least one of ring CY21 and/or ring CY22 may be a benzene group.

In one or more embodiments, in Formula 2, ring CY21 and ring CY22 may be identical to each other. In one or more embodiments, in Formula 2, ring CY21 and ring CY22 may be different from each other.

In one or more embodiments, in Formula 2, ring CY21 and ring CY22 may each be a benzene group.

In one or more embodiments, in Formula 2, ring CY22 may be represented by one of ring CY22-1 to ring CY22-4:

CY22-1

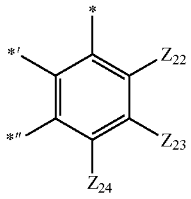

-continued

CY22-2

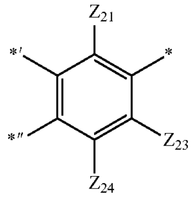

CY22-3

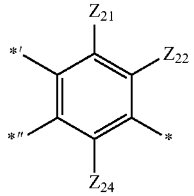

CY22-4

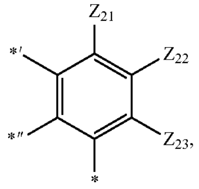

wherein, in ring CY22-1 to ring CY22-4, $Z_{21}$ to $Z_{24}$ may each be understood by referring to the description of $R_{22}$ provided herein, * indicates a binding site to nitrogen (N) bound to $Y_2$ in Formula 1, *' indicates a binding site to nitrogen (N) bound to $R_{23}$ in Formula 2, and *" indicates a binding site to ring CY21 in Formula 2.

In Formula 3, $X_{33}$ may be a single bond, O, S, $B(R_{33})$, $N(R_{33})$, $C(R_{33})(R_{34})$, $Si(R_{33})(R_{34})$, or $C(R_{33}){=}C(R_{34})$.

In one or more embodiments, in Formula 3, $X_{33}$ may be O, S, $N(R_{33})$, $C(R_{33})(R_{34})$, or $C(R_{33}){=}C(R_{34})$.

In Formula 3, $b_{33}$ may be an integer selected from 0 to 3. b33 may indicate the number of $X_{33}$(s).

When b33 is an integer of 2 or greater, at least two $X_{33}$(s) may be identical to or different from each other. When b33 is 0, $X_{33}$ may not be present.

When $X_{33}$ is not present, the group represented by Formula 3 may be represented by Formula 3(a):

Formula 3(a)

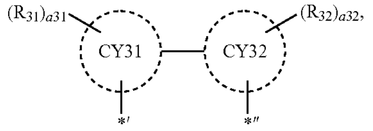

wherein, in Formula 3(a), CY31, CY32, $R_{31}$, $R_{32}$, a31, and a32 may respectively be understood by referring to the description of CY31, CY32, $R_{31}$, $R_{32}$, a31, and a32 provided herein. *' indicates a binding site to nitrogen (N) bound to $Y_2$ in Formula 1, and *" indicates a binding site to nitrogen (N) bound to $R_1$ in Formula 1.

In one or more embodiments, in Formula 3, $b_{33}$ may be 0 or 1.

In one or more embodiments, in Formula 3, ring CY31 and ring CY32 may each independently be a benzene group or a naphthalene group.

In one or more embodiments, in Formula 3, at least one of ring CY31 and/or ring CY32 may be a benzene group.

In one or more embodiments, in Formula 3, ring CY31 and ring CY32 may be identical to each other. In one or more embodiments, in Formula 3, ring CY31 and ring CY32 may be different from each other.

In one or more embodiments, in Formula 3, ring CY31 and ring CY32 may each be a benzene group.

In one or more embodiments, the group represented by Formula 3 may be represented by one of Formulae 3-1 to 3-9:

3-1

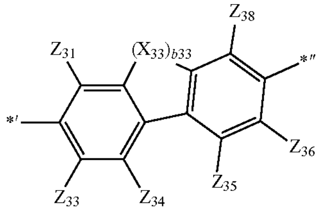

3-2

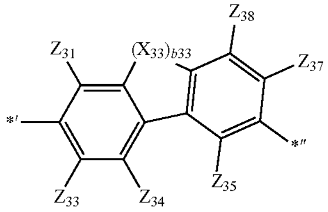

3-3

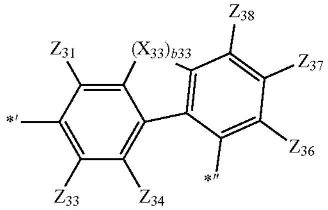

3-4

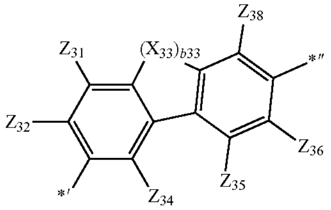

3-5

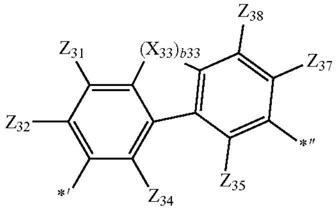

3-6

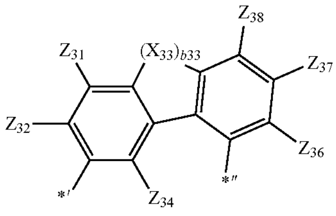

-continued 3-7

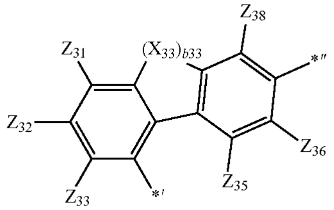

3-8

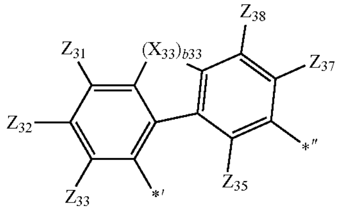

3-9

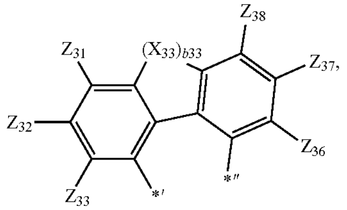

wherein, in Formulae 3-1 to 3-9, $Z_{31}$ to $Z_{38}$ may each independently be understood by referring to the description of $R_{31}$ provided herein, and $X_{33}$ and b33 may respectively be understood by referring to the descriptions of $X_{33}$ and b33 provided herein. *' indicates a binding site to nitrogen (N) bound to $Y_2$ in Formula 1, and *" indicates a binding site to nitrogen (N) bound to $R_1$ in Formula 1.

In one or more embodiments, the group represented by Formula 3 may be represented by Formula 3-5.

In Formula 4, $X_{43}$ may be a single bond, O, S, $B(R_{43})$, $N(R_{43})$, $C(R_{43})(R_{44})$, $Si(R_{43})(R_{44})$, or $C(R_{43}){=}C(R_{44})$.

In one or more embodiments, in Formula 4, $X_{43}$ may be O, S, $N(R_{43})$, $C(R_{43})(R_{44})$, or $C(R_{43}){=}C(R_{44})$.

In Formula 4, $b_{43}$ may be an integer from 0 to 3. b43 may indicate the number of $X_{43}$(s).

When b43 is an integer of 2 or greater, at least two $X_{43}$(s) may be identical to or different from each other. When b43 is 0, $X_{43}$ may not be present.

In one or more embodiments, in Formula 4, $b_{43}$ may be 0, and $X_{43}$ may not be present.

For example, when $X_{43}$ is not present, the group represented by Formula 4 may be represented by Formula 4(a):

Formula 4(a)

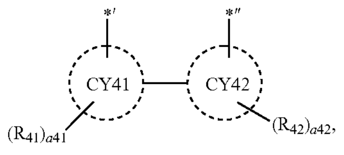

wherein, in Formula 4(a), CY41, CY42, $R_{41}$, $R_{42}$, a41, and a42 may respectively be understood by referring to the descriptions of CY41, CY42, $R_{41}$, $R_{42}$, a41, and a42 provided herein. *' indicates a binding site to nitrogen (N) bound to $Y_2$ in Formula 1, and *" indicates a binding site to nitrogen (N) bound to $R_1$ in Formula 1.

In one or more embodiments, in Formula 4, $b_{43}$ may be 0 or 1.

In one or more embodiments, in Formula 4, ring CY41 and ring CY42 may each independently be a benzene group or a naphthalene group.

In one or more embodiments, in Formula 4, at least one of ring CY41 and/or ring CY42 may be a benzene group.

In one or more embodiments, in Formula 4, ring CY41 and ring CY42 may be identical to each other. In one or more embodiments, in Formula 4, ring CY41 and ring CY42 may be different from each other.

In one or more embodiments, in Formula 4, ring CY41 and ring CY42 may each be a benzene group.

In one or more embodiments, the group represented by Formula 4 may be represented by one of Formulae 4-1 to 4-9:

4-1

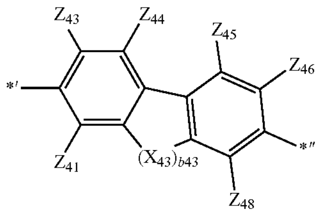

4-2

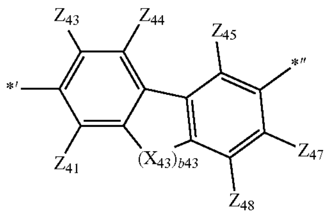

4-3

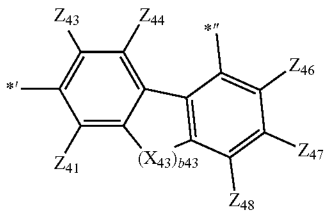

4-4

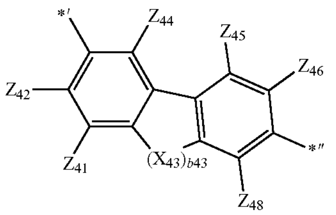

4-5

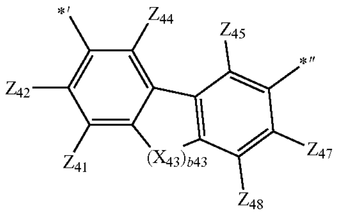

-continued 4-6

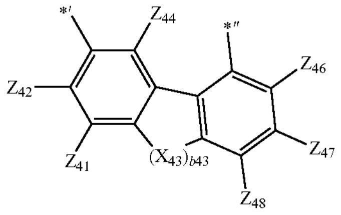

4-7

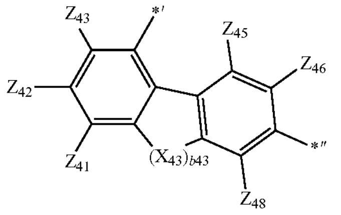

4-8

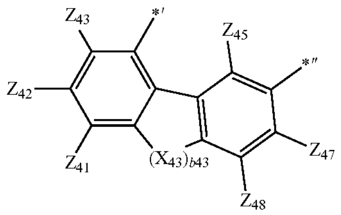

4-9

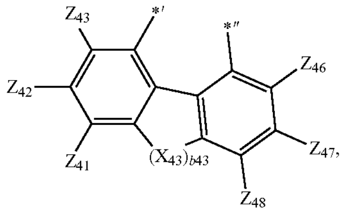

wherein, in Formulae 4-1 to 4-9, $Z_{41}$ to $Z_{48}$ may each independently be understood by referring to the description of $R_{41}$ provided herein, and $X_{43}$ and b43 may respectively be understood by referring to the descriptions of $X_{43}$ and b43 provided herein. *' indicates a binding site to nitrogen (N) bound to $Y_2$ in Formula 1, and indicates a binding site to nitrogen (N) bound to $R_1$ in Formula 1.

In one or more embodiments, the group represented by Formula 4 may be represented by Formula 4-5.

In Formulae 1 to 4, $R_1$, $R_{21}$ to $R_{23}$, $R_{31}$ to $R_{34}$, and $R_{41}$ to $R_{44}$ may each independently be hydrogen, deuterium, —F, —Cl, —Br, —I, a hydroxyl group, a cyano group, a nitro group, a $C_1$-$C_{60}$ alkyl group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, a $C_6$-$C_{60}$ aryloxy group unsubstituted or substituted with at least one $R_{10a}$, a $C_6$-$C_{60}$ arylthio group unsubstituted or substituted with at least one $R_{10a}$, a $C_7$-$C_{60}$ aryl alkyl group unsubstituted or substituted with at least one $R_{10a}$, a $C_2$-$C_{60}$ heteroaryl alkyl group unsubstituted or substituted with at least one $R_{10a}$, —$Si(Q_1)(Q_2)(Q_3)$, —$N(Q_1)(Q_2)$, —$B(Q_1)(Q_2)$, —$C(=O)(Q_1)$, —$S(=O)_2(Q_1)$, or —$P(=O)(Q_1)(Q_2)$, In some embodiments, in Formulae 1 to 4, $R_1$, $R_{21}$ to $R_{23}$, $R_{31}$ to $R_{34}$, and $R_{41}$ to $R_{44}$ may each independently be:

hydrogen, deuterium, —F, —Cl, —Br, —I, a hydroxyl group, a cyano group, a nitro group, a $C_1$-$C_{20}$ alkyl group, or a $C_1$-$C_{20}$ alkoxy group;

a $C_1$-$C_{20}$ alkyl group or a $C_1$-$C_{20}$ alkoxy group, each substituted with deuterium, —F, —Cl, —Br, —I, —CDs, —$CD_2H$, —$CDH_2$, —$CF_3$, —$CF_2H$, —$CFH_2$, a hydroxyl group, a cyano group, a nitro group, a $C_1$-$C_{20}$ alkyl group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a biphenyl group, a terphenyl group, a naphthyl group, a pyridinyl group, a pyrimidinyl group, or any combination thereof;

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a biphenyl group, a terphenyl group, a $C_1$-$C_{20}$ alkyl phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indenyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, a benzosilolyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a benzofluorenyl group, a benzocarbazolyl group, a naphthobenzofuranyl group, a naphthobenzothiophenyl group, a naphthobenzosilolyl group, a dibenzofluorenyl group, a dibenzocarbazolyl group, a dinaphthofuranyl group, a dinaphthothiophenyl group, a dinaphthosilolyl group, an indenocarbazolyl group, an indolocarbazolyl group, a benzofuranocarbazolyl group, a benzothienocarbazolyl group, a benzosilolocarbazolyl group, an imidazopyridinyl group, an imidazopyrimidinyl group, an azafluorenyl group, an azacarbazolyl group, an azadibenzofuranyl group, an azadibenzothiophenyl group, or an azadibenzosilolyl group, each unsubstituted or substituted with deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, a $C_1$-$C_{20}$ alkyl group, a $C_1$-$C_{20}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a biphenyl group, a terphenyl group, a $C_1$-$C_{20}$ alkyl phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indenyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, a benzosilolyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a benzofluorenyl group, a benzocarbazolyl group, a naphthobenzofuranyl group, a naphthobenzothiophenyl group, a naphthobenzosilolyl group, a dibenzofluorenyl group, a dibenzocarbazolyl group, a dinaphthofuranyl group, a dinaphthothiophenyl group, a dinaphthosilolyl group, an indenocarbazolyl group, an indolocarbazolyl group, a benzofuranocarbazolyl group, a benzothienocarbazolyl group, a benzosilolocarbazolyl group, an imidazopyridinyl group, an imidazopyrimidinyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), —P(=O)($Q_{31}$)($Q_{32}$), or any combination thereof; or —Si($Q_1$)($Q_2$)($Q_3$), —N($Q_1$)($Q_2$), —B($Q_1$)($Q_2$), —C(=O)($Q_1$), —S(=O)$_2$($Q_1$), or —P(=O)($Q_1$)($Q_2$), wherein $Q_1$ to $Q_3$ and $Q_{31}$ to $Q_{33}$ may each independently be: —$CH_3$, —$CD_3$, —$CD_2H$, —$CDH_2$, —$CH_2CH_3$, —$CH_2CD_3$, —$CH_2CD_2H$, —$CH_2CDH_2$, —$CHDCH_3$, —$CHDCD_2H$, —$CHDCDH_2$, —$CHDCD_3$, —$CD_2CD_3$, —$CD_2CD_2H$, or —$CD_2CDH_2$; or an n-propyl group, an iso-propyl group, an n-butyl group, an isobutyl group, a sec-butyl group, a tert-butyl group, an n-pentyl group, an isopentyl group, a sec-pentyl group, a tert-pentyl group, a phenyl group, a naphthyl group, a pyridinyl group, a pyrimidinyl group, a pyridazinyl group, a pyrazinyl group, a triazinyl group, a fluorenyl group, a carbazolyl group, a dibenzofuranyl group, or a dibenzothiophenyl group, each unsubstituted or substituted with deuterium, a $C_1$-$C_{20}$ alkyl group, a phenyl group, a biphenyl group, a pyridinyl group, a pyrimidinyl group, a pyridazinyl group, a pyrazinyl group, a triazinyl group, or any combination thereof.

In one or more embodiments, in Formulae 1 to 4, $R_1$, $R_{21}$ to $R_{23}$, $R_{31}$ to $R_{34}$, and $R_{41}$ to $R_{44}$ may each independently be: hydrogen, deuterium, —F, a cyano group, a $C_1$-$C_{20}$ alkyl group, or a $C_1$-$C_{20}$ alkoxy group;

a $C_1$-$C_{20}$ alkyl group or a $C_1$-$C_{20}$ alkoxy group, each substituted with deuterium, —F, —$CD_3$, —$CD_2H$, —$CDH_2$, —$CF_3$, —$CF_2H$, —$CFH_2$, a cyano group, or any combination thereof;

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a biphenyl group, a terphenyl group, a $C_1$-$C_{20}$ alkyl phenyl group, a naphthyl group, a fluorenyl group, a phenanthrenyl group, an anthracenyl group, a thiophenyl group, a furanyl group, an indenyl group, an isoindolyl group, an indolyl group, a carbazolyl group, a benzofuranyl group, a benzothiophenyl group, a benzosilolyl group, a dibenzofuranyl group, a dibenzothiophenyl group, a dibenzosilolyl group, a benzofluorenyl group, a benzocarbazolyl group, a naphthobenzofuranyl group, a naphthobenzothiophenyl group, a naphthobenzosilolyl group, a dibenzofluorenyl group, a dibenzocarbazolyl group, a dinaphthofuranyl group, a dinaphthothiophenyl group, a dinaphthosilolyl group, an indenocarbazolyl group, an indolocarbazolyl group, a benzofuranocarbazolyl group, a benzothienocarbazolyl group, or benzosilolocarbazolyl group, each unsubstituted or substituted with deuterium, —F, —$CD_3$, —$CD_2H$, —$CDH_2$, —$CF_3$, —$CF_2H$, —$CFH_2$, a cyano group, a $C_1$-$C_{20}$ alkyl group, a $C_1$-$C_{20}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a biphenyl group, a terphenyl group, a $C_1$-$C_{20}$ alkyl phenyl group, a naphthyl group, a fluorenyl group, a phenanthrenyl group, an anthracenyl group, a thiophenyl group, a furanyl group, an indenyl group, an isoindolyl group, an indolyl group, a carbazolyl group, a benzofuranyl group, a benzothiophenyl group, a benzosilolyl group, a dibenzofuranyl group, a dibenzothiophenyl group, a dibenzosilolyl group, a benzofluorenyl group, a benzocarbazolyl group, a naphthobenzofuranyl group, a naphthobenzothiophenyl group, a naphthobenzosilolyl group, a dibenzofluorenyl group, a dibenzocarbazolyl group, a dinaphthofuranyl group, a dinaphthothiophenyl group, a dinaphthosilolyl group, an indenocarbazolyl group, an indolocarbazolyl group, a benzofuranocarbazolyl group, a benzothienocarbazolyl group, a benzosilolocarbazolyl group, or any combination thereof.

In one or more embodiments, in Formulae 1 to 4, $R_1$, $R_{21}$ to $R_{23}$, $R_{31}$ to $R_{34}$, and $R_{41}$ to $R_{44}$ may each independently be: hydrogen, deuterium, —F, or a cyano group; or a phenyl group, a biphenyl group, a naphthyl group, a fluorenyl group, a carbazolyl group, a dibenzofuranyl group, or a dibenzothiophenyl group, each unsubstituted or substituted with deuterium, —F, a cyano group, a $C_1$-$C_{20}$ alkyl group, a phenyl group, a biphenyl group, a naphthyl group, a $C_1$-$C_{20}$ alkyl phenyl group, a fluorenyl group, a carbazolyl group, a dibenzofuranyl group, a dibenzothiophenyl group, or any combination thereof.

In Formulae 1 to 4, a21, a22, a31, a32, a41, and a42 may each independently be an integer selected from 0 to 10.

In one or more embodiments, in Formulae 1 to 4, a21, a22, a31, a32, a41, and a42 may each independently be an integer selected from 0 to 4.

In one or more embodiments, in Formulae 1 to 4, a21, a41, and a42 may each independently be an integer selected from 0 to 4, and a22, a31, and a32 may each independently be an integer selected from 0 to 3.

In one or more embodiments, in Formulae 1 to 4, CY21, CY22, CY31, CY32, CY41, and CY42 may each be a benzene group, b33 may be 1, and when b43 is 0, a21, a41, and a42 may each independently be an integer selected from 0 to 4, and a22, a31, and a32 may each independently be an integer selected from 0 to 3.

In Formula 2, *' indicates a binding site to nitrogen (N) bound to $Y_2$ in Formula 1.

In Formulae 3 and 4, *' indicates a binding site to nitrogen (N) bound to $Y_2$ in Formula 1, and *" indicates a binding site to nitrogen (N) bound to $R_1$ in Formula 1.

In one or more embodiments, in Formula 1, $R_1$ may be: hydrogen, deuterium, or a cyano group; or a group represented by one of Formulae 1-1 to 1-57:

1-1

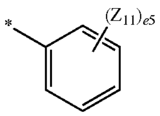

1-2

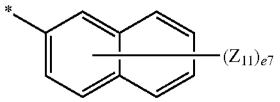

1-3

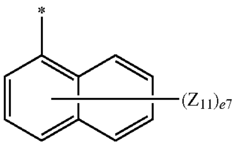

1-4

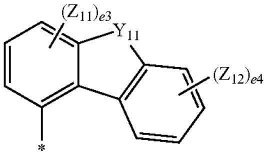

1-5

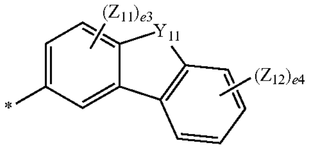

1-6

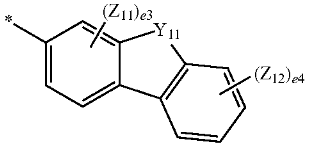

1-7

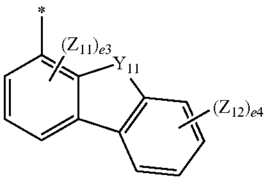

1-8

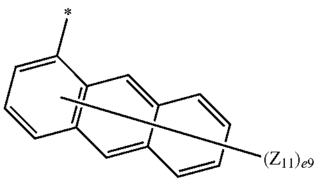

1-9

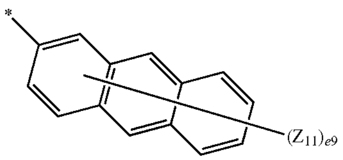

1-10

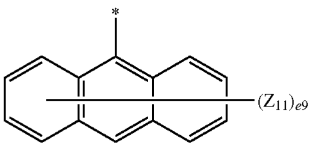

-continued
1-11
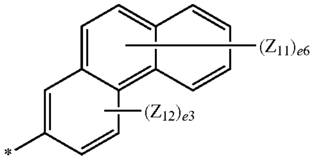
1-12
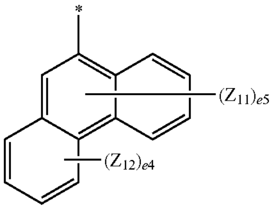
1-13
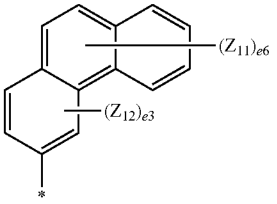
1-14
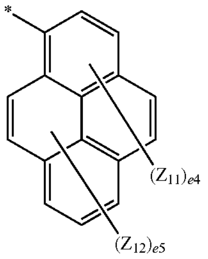
1-15
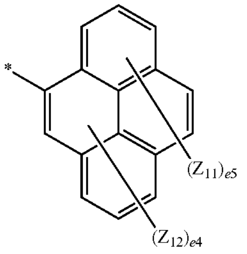
1-16
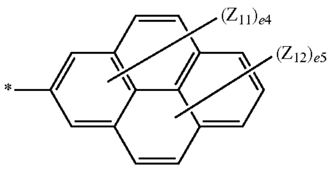
1-17
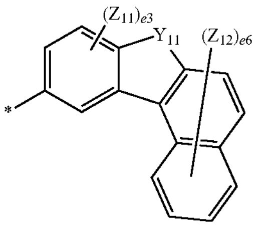
-continued
1-18
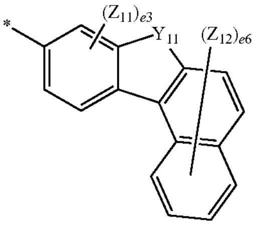
1-19
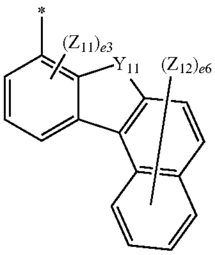
1-20
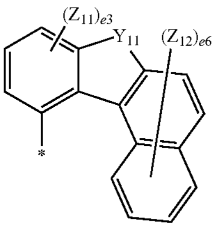
1-21
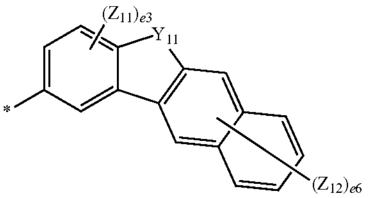
1-22
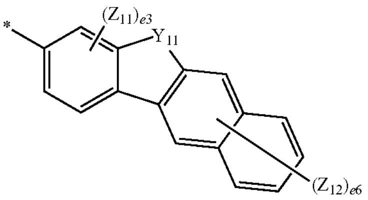
1-23
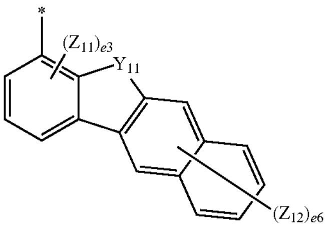
1-24
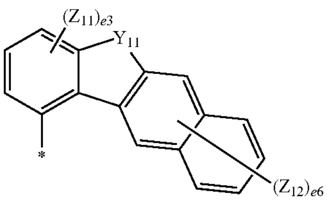

-continued
1-25
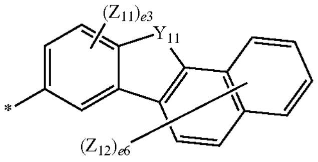
1-26
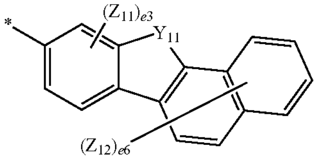
1-27
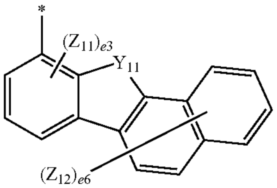
1-28
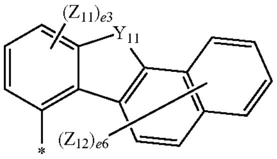
1-29
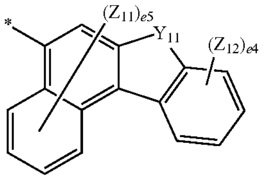
1-30
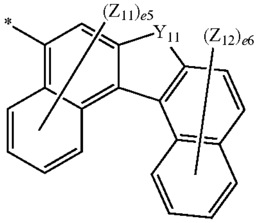
1-31
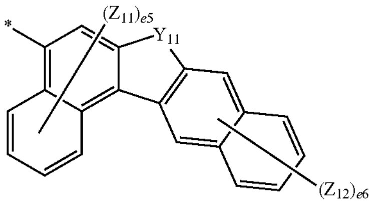
1-32
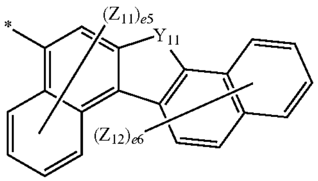
-continued
1-33
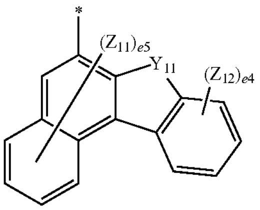
1-34
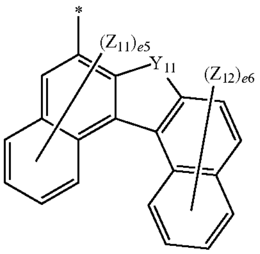
1-35
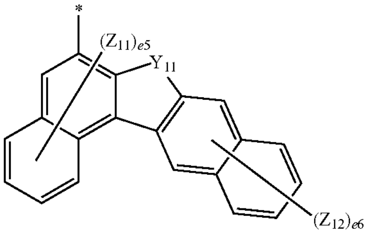
1-36
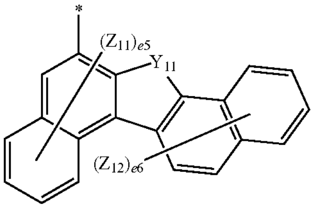
1-37
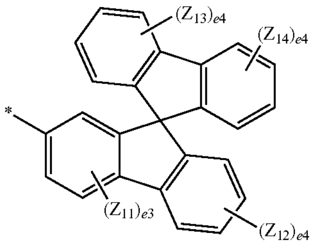
1-38
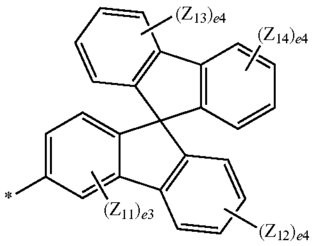

-continued
1-39
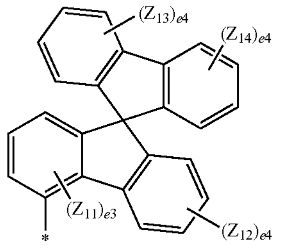
1-40
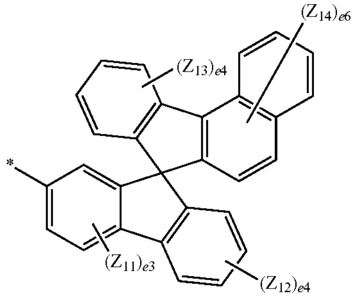
1-41
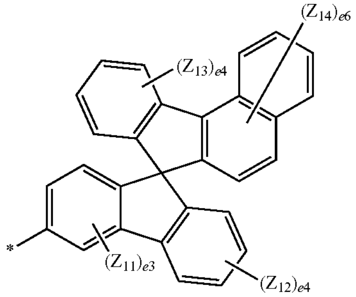
1-42
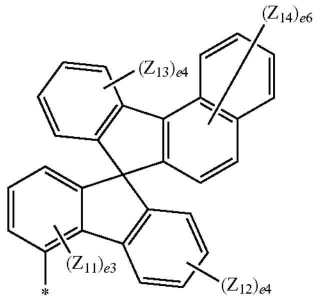
1-43
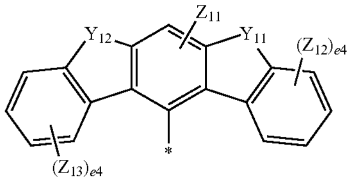
1-44
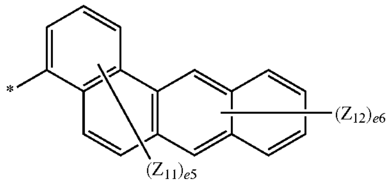
-continued
1-45
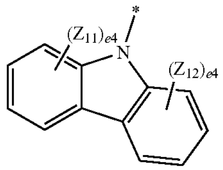
1-46
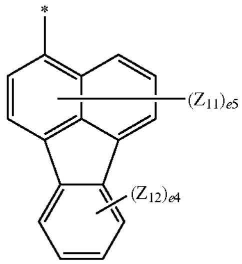
1-47
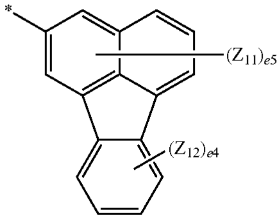
1-48
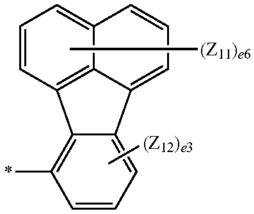
1-49
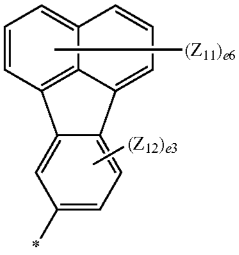
1-50
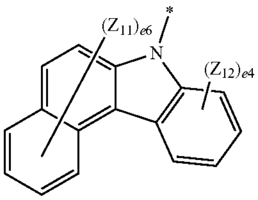
1-51
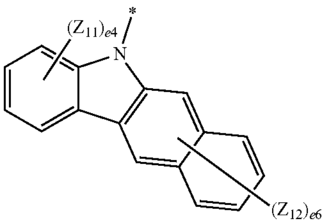

-continued 1-52

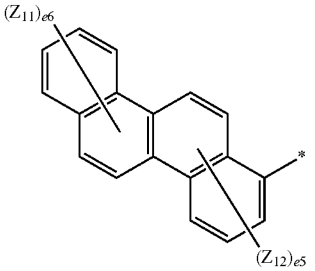

1-53

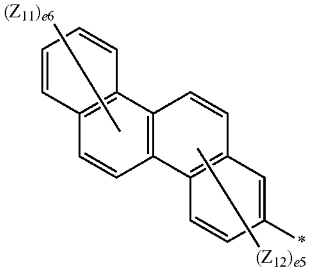

1-54

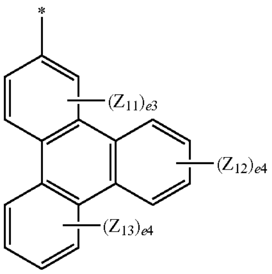

1-55

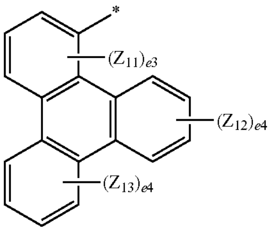

1-56

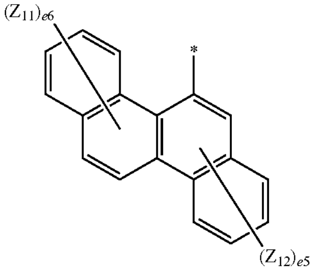

-continued 1-57

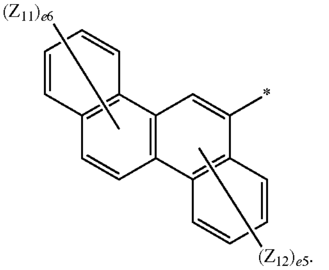

$Y_{11}$ may be O, S, $B(R_{11})$, $N(R_{11})$, $C(R_{11})(R_{12})$, or $Si(R_{11})(R_{12})$; $Y_{12}$ may be O, S, $B(R_{21})$, $N(R_{21})$, $C(R_{21})(R_{22})$, or $Si(R_{21})(R_{22})$; and $Z_{11}$, $Z_{12}$, $Z_{13}$, $Z_{14}$, $R_{11}$, $R_{12}$, $R_{21}$, and $R_{22}$ may each be understood by referring to the description of $R_{10a}$ provided herein, e3 may be an integer selected from 0 to 3, e4 may be an integer selected from 0 to 4, e5 may be an integer selected from 0 to 5, e6 may be an integer selected from 0 to 6, e7 may be an integer selected from 0 to 7, e9 may be an integer selected from 0 to 9, and * indicates a binding site to an adjacent atom.

In one or more embodiments, in Formula 1, $R_1$ may be a group represented by one of Formulae 1-1 to 1-7.

In one or more embodiments, the heterocyclic compound may be represented by one of Compounds 1 to 408.

1

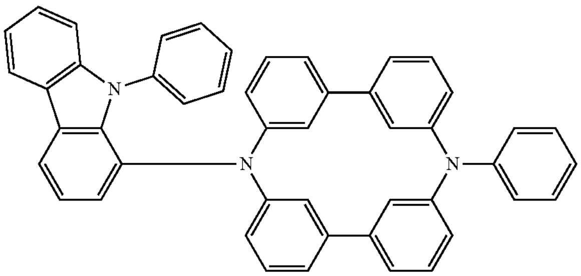

2

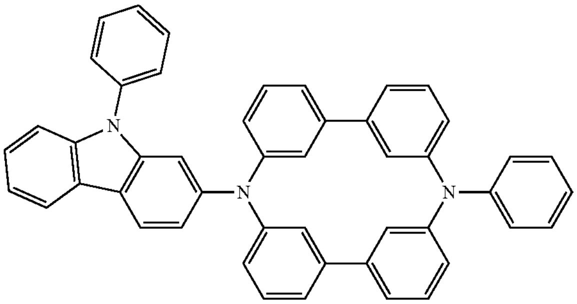

3

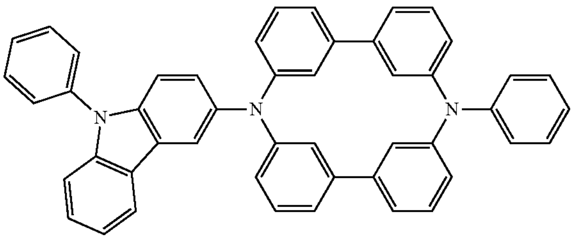

-continued
4
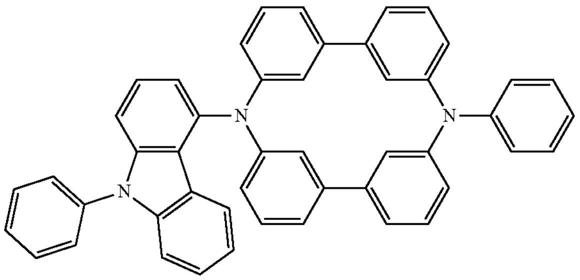
5
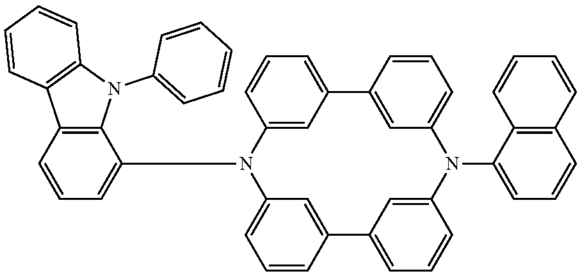
6
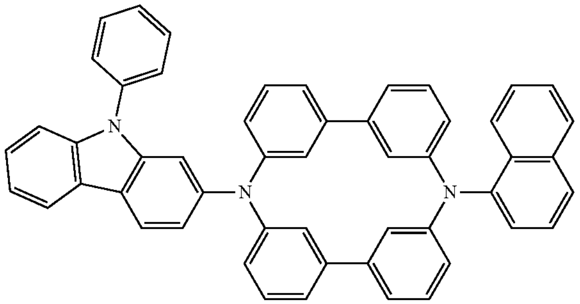
7
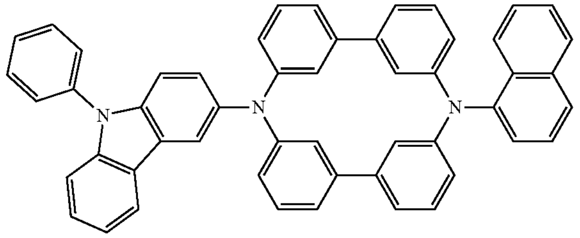
8
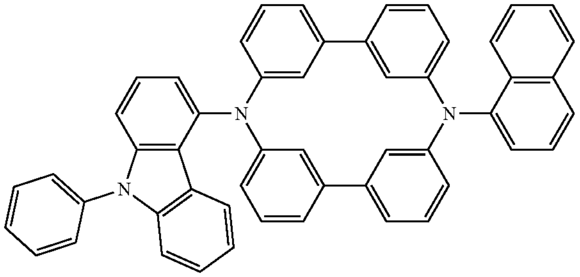
-continued
9
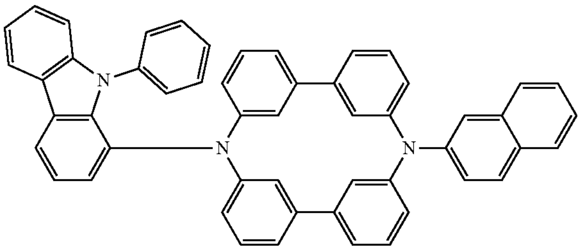
10
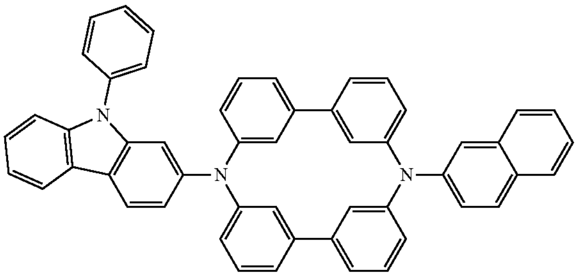
11
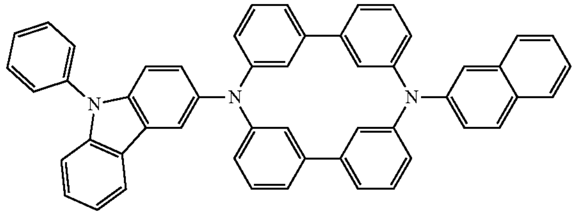
12
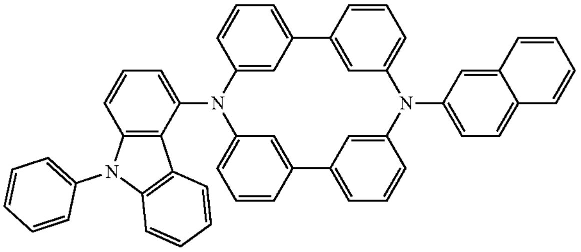
13
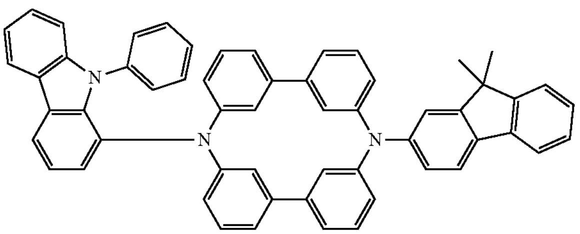
14
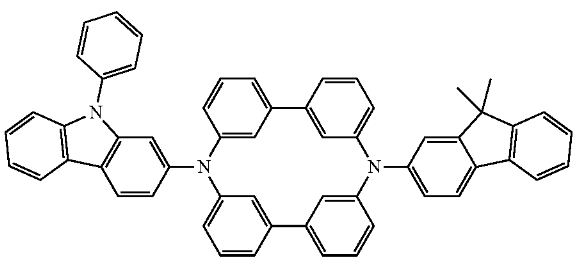

-continued
15
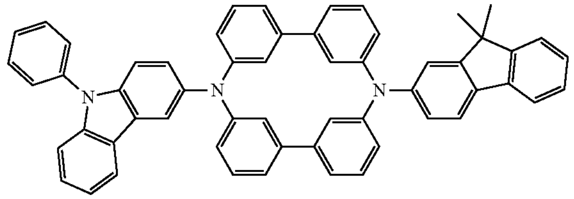
16
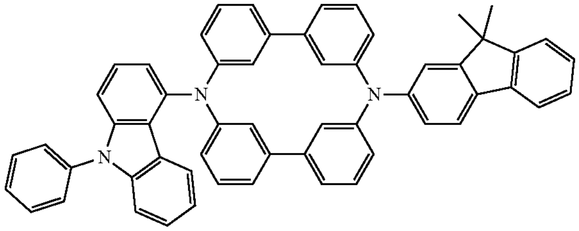
17
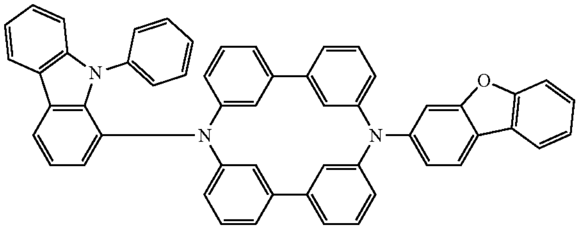
18
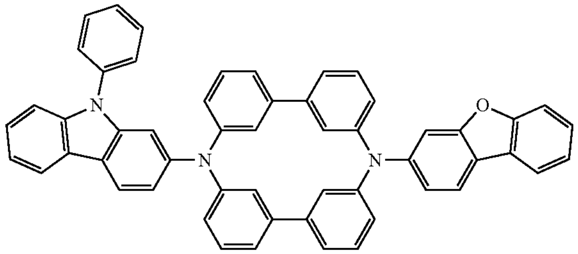
19
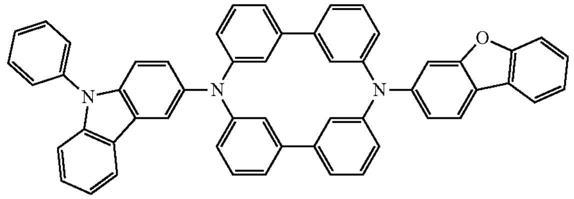
20
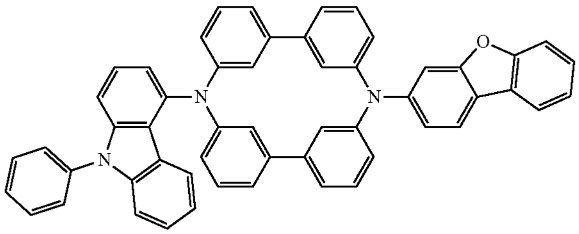
-continued
21
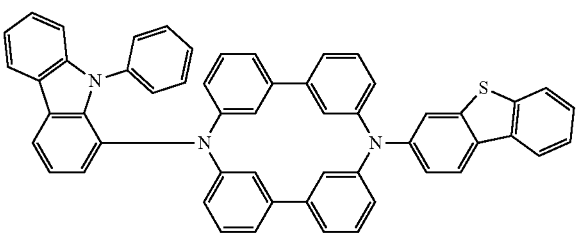
22
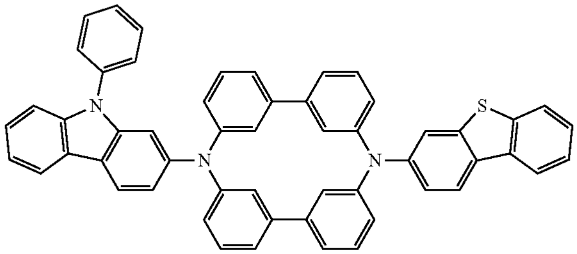
23
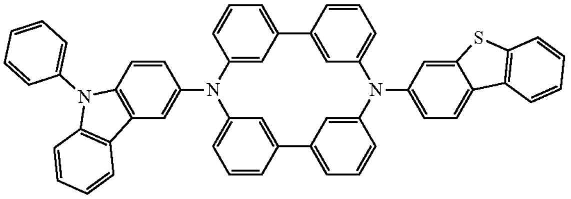
24
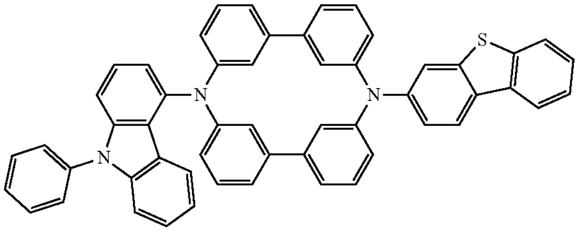
25
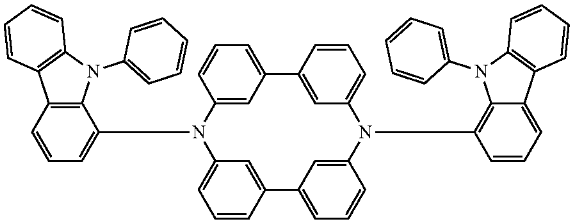
26
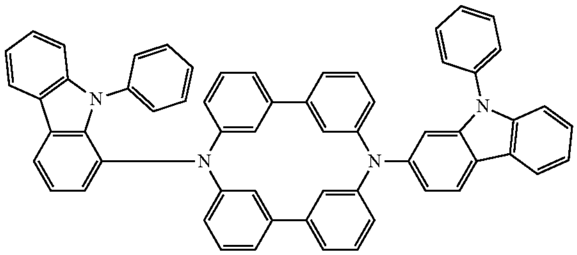

-continued
27
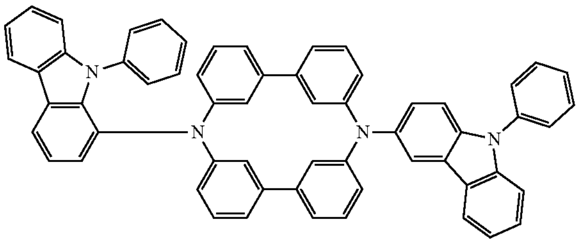
28
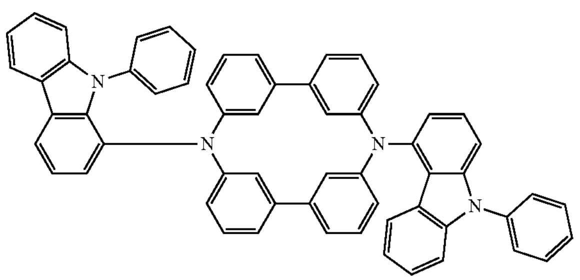
29
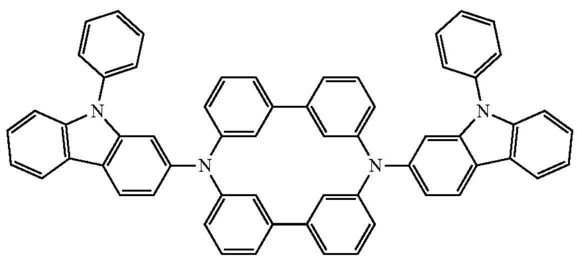
30
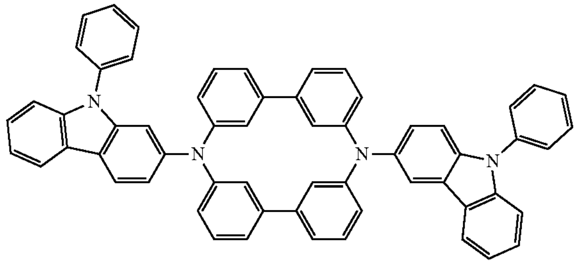
31
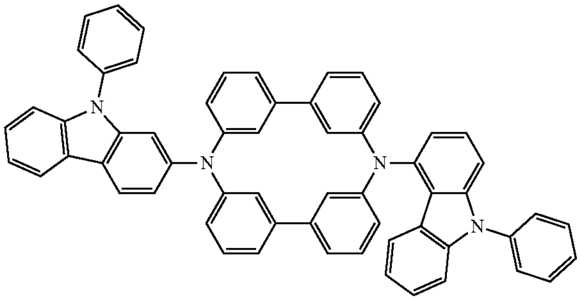
-continued
32
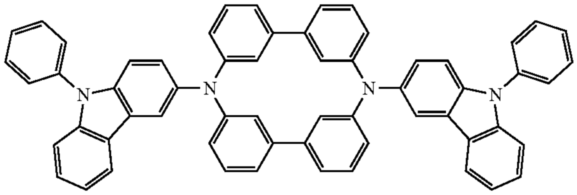
33
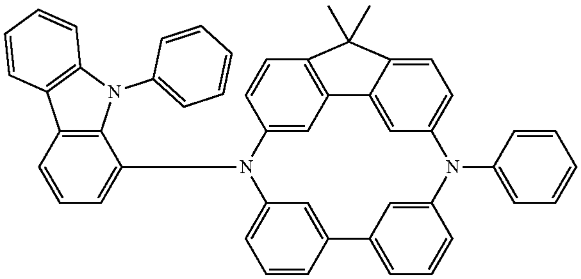
34
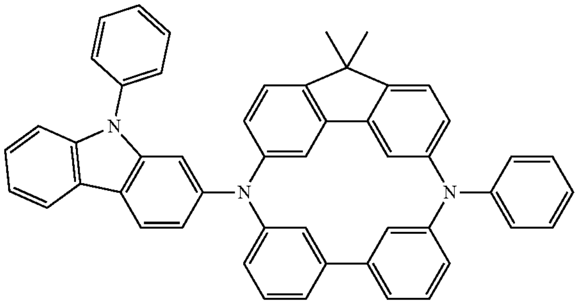
35
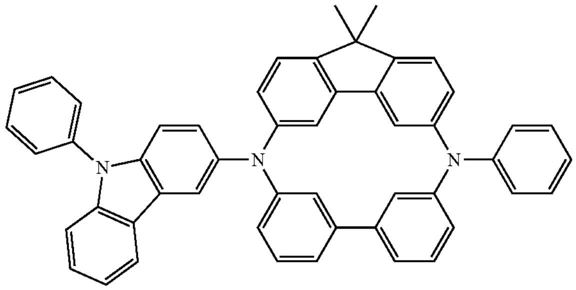
36
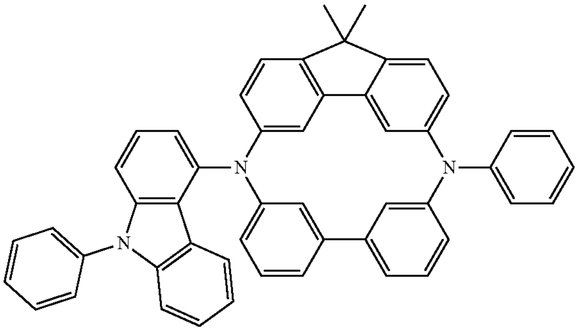

-continued
37
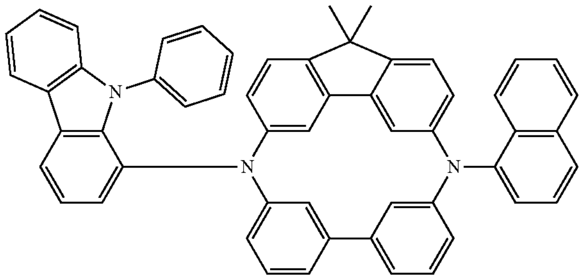
38
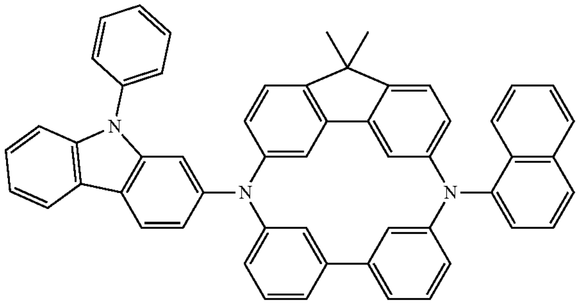
39
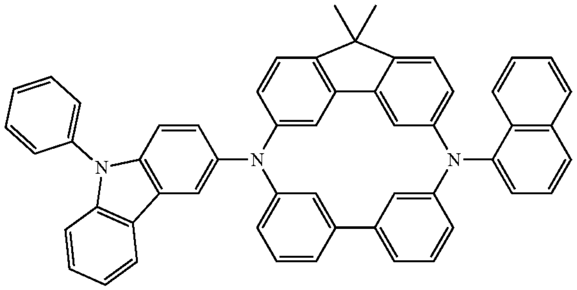
40
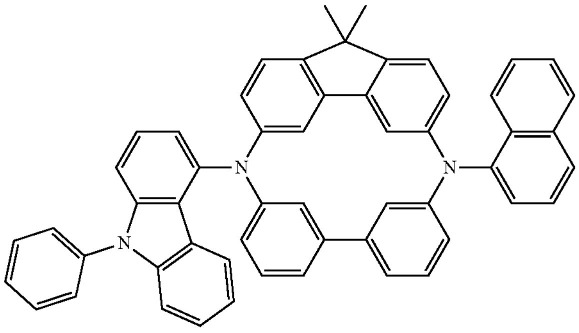
41
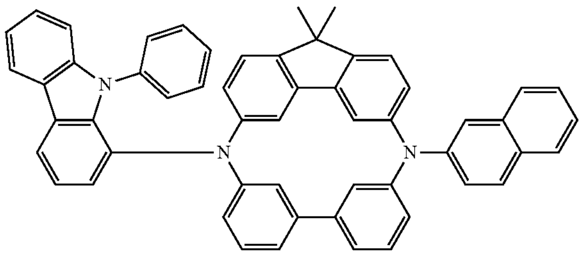
-continued
42
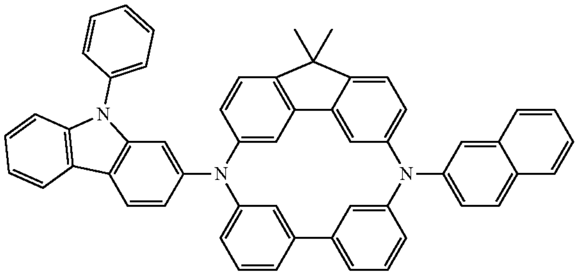
43
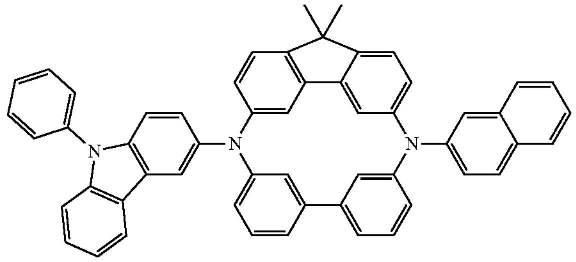
44
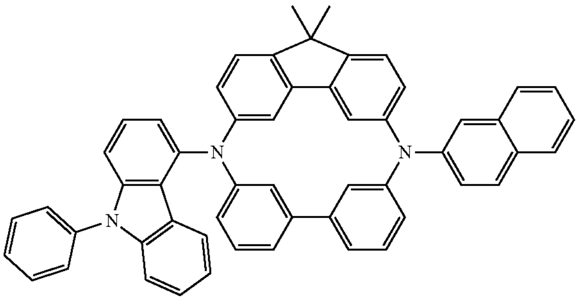
45
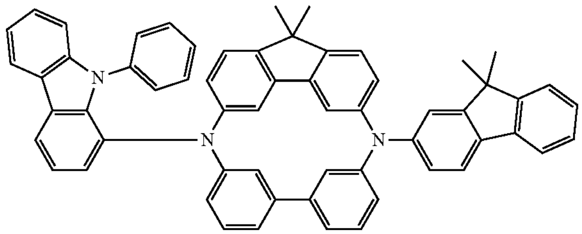
46
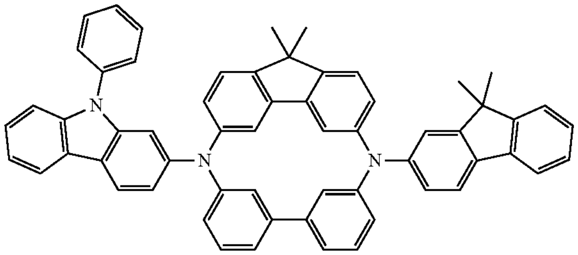

-continued
47
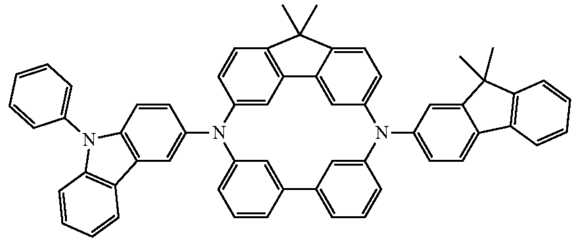
48
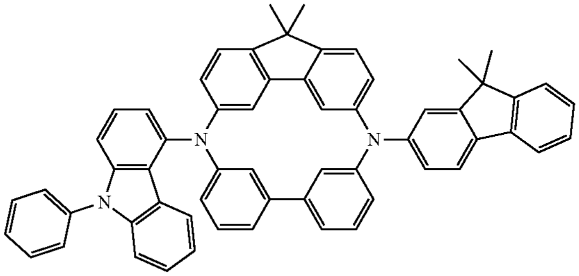
49
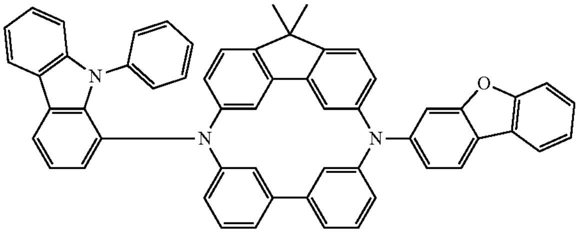
50
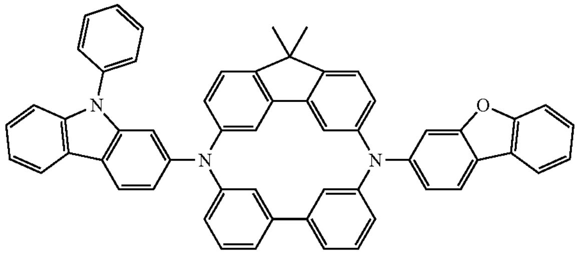
51
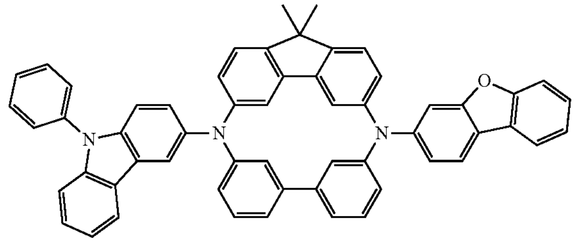
-continued
52
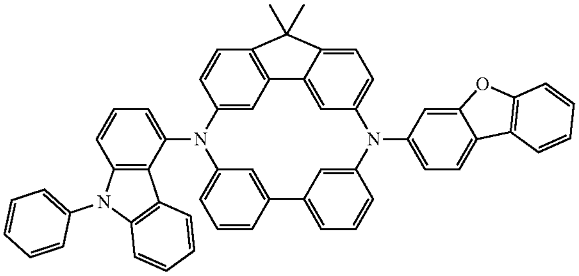
53
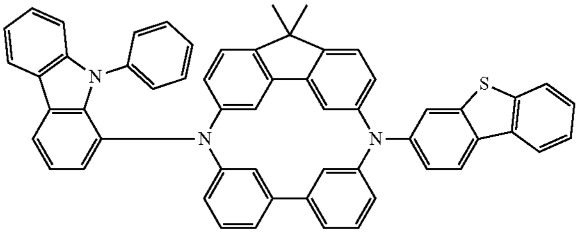
54
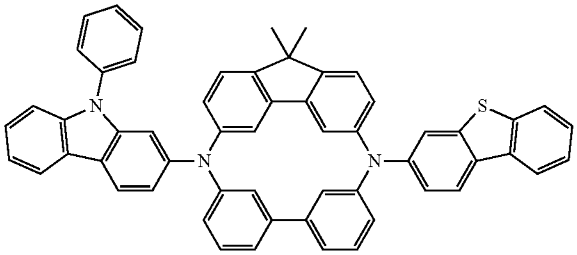
55
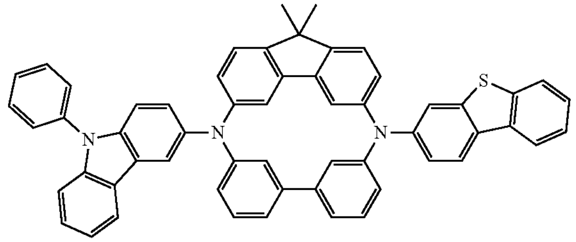
56
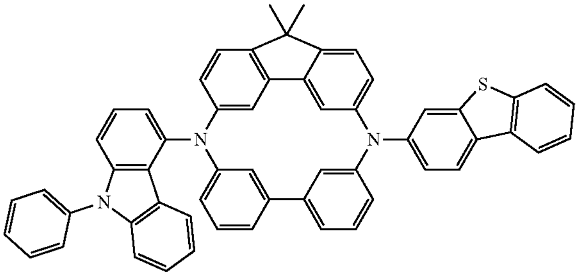

-continued
57
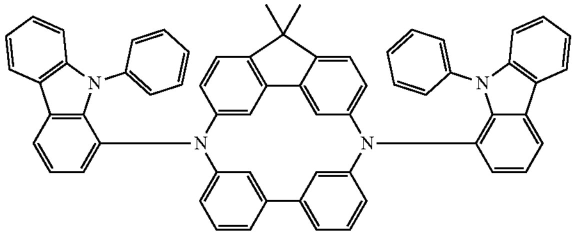
58
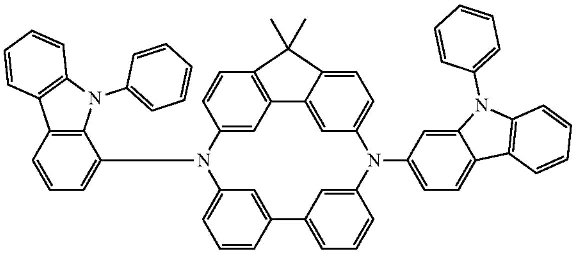
59
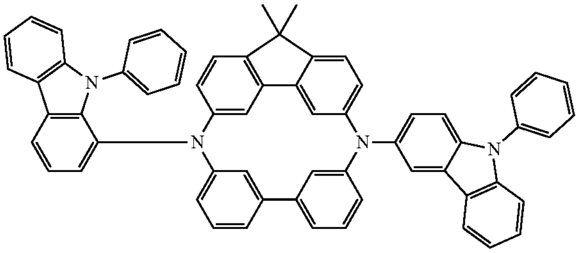
60
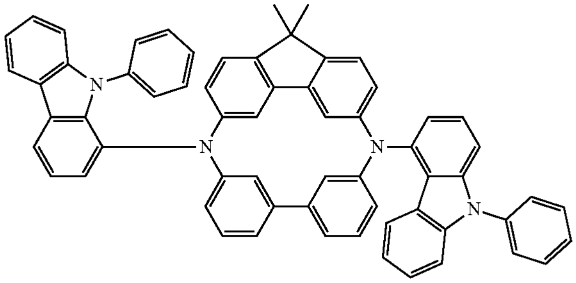
61
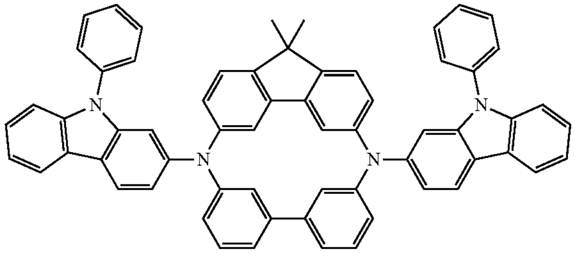
-continued
62
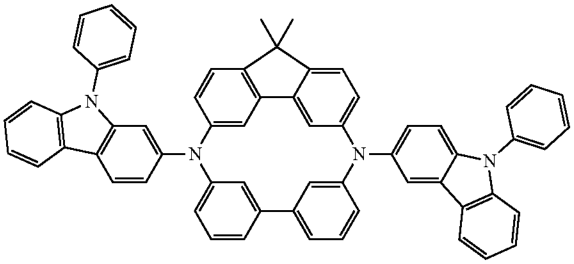
63
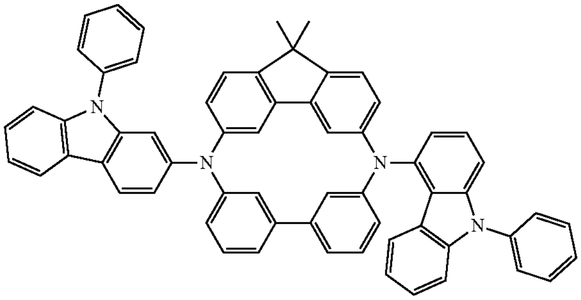
64
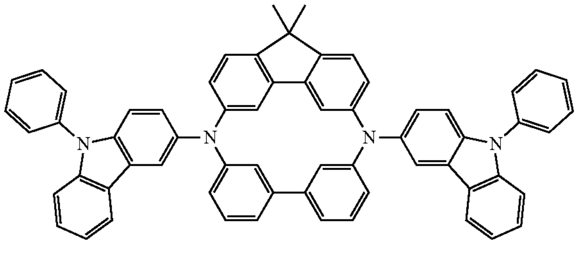
65
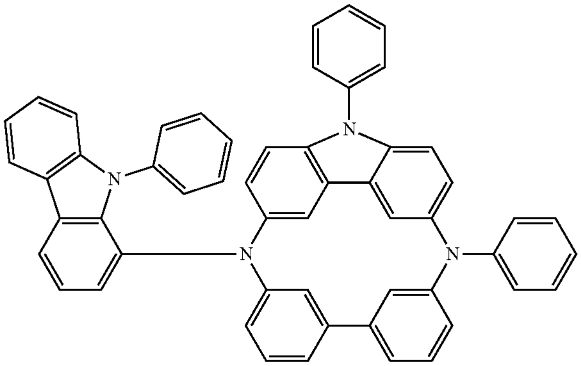

-continued
66
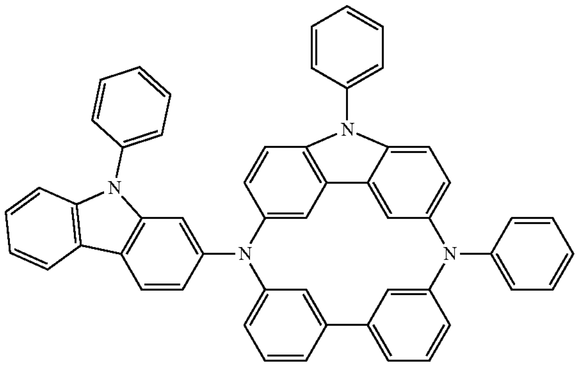
67
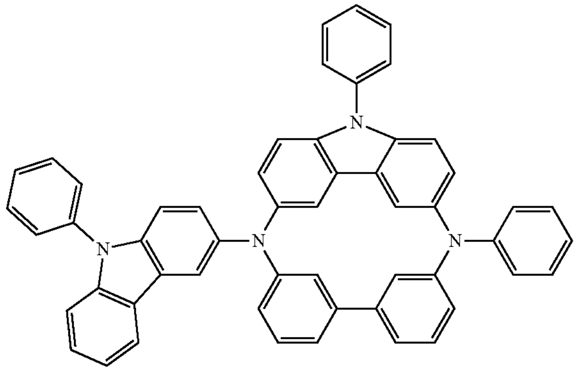
68
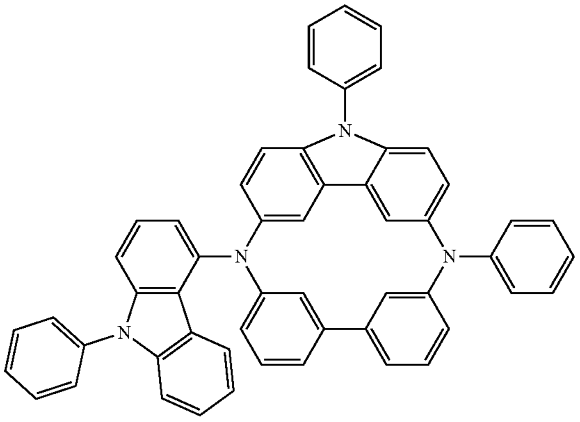
69
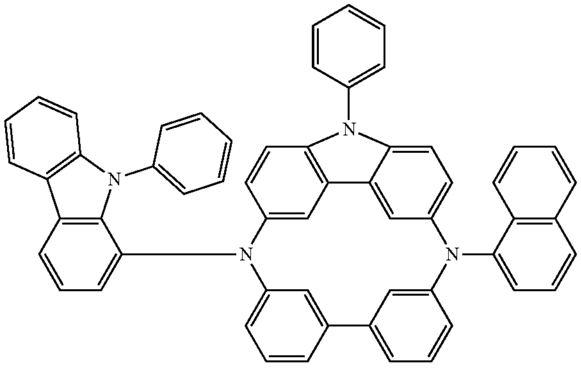
-continued
70
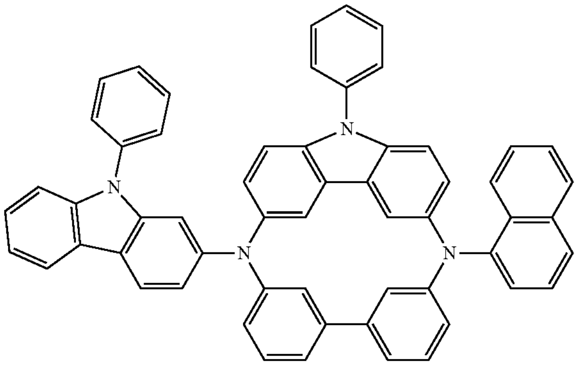
71
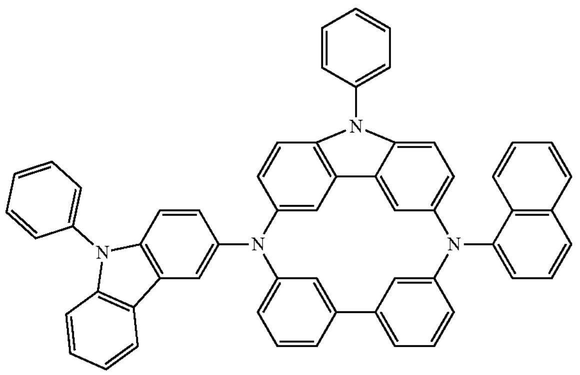
72
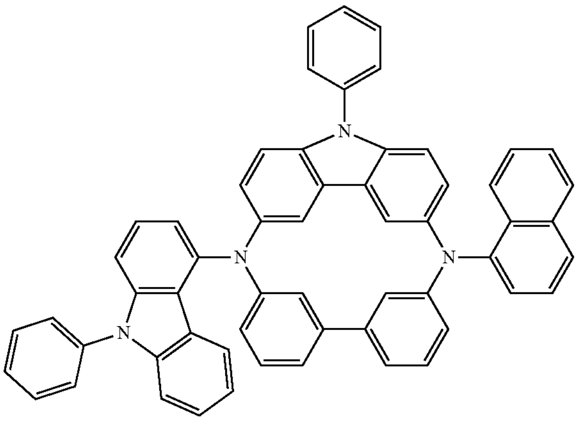
73
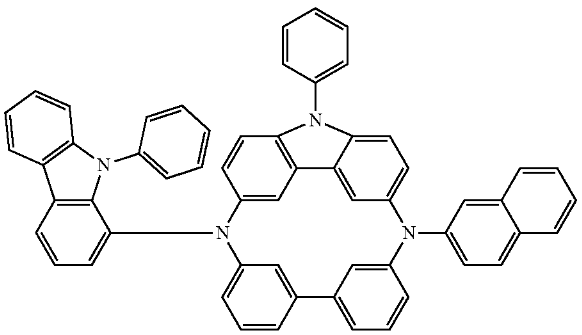

-continued
74
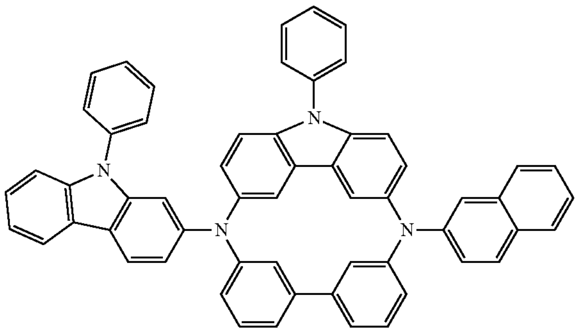
75
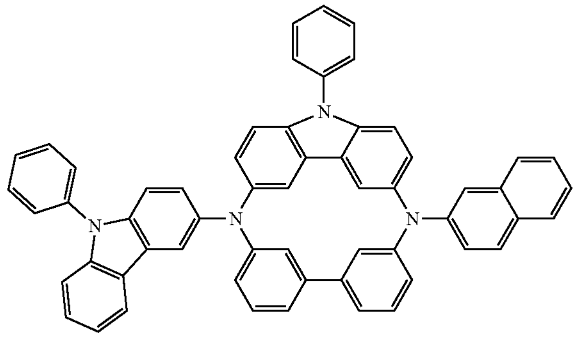
76
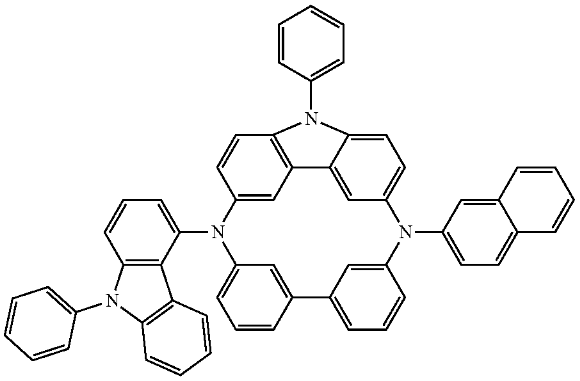
77
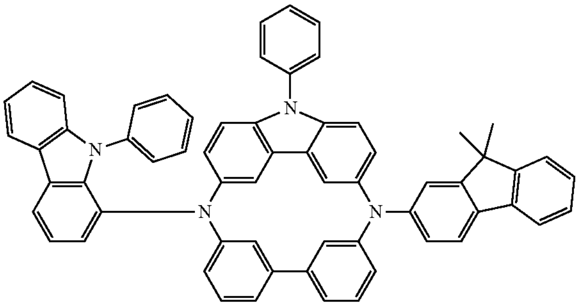
-continued
78
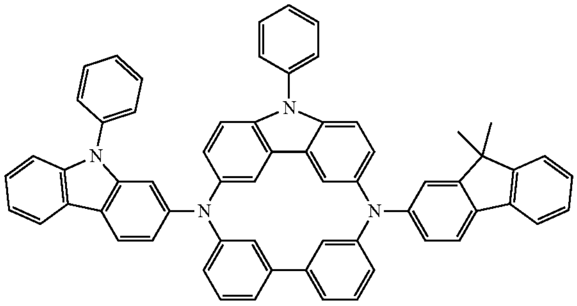
79
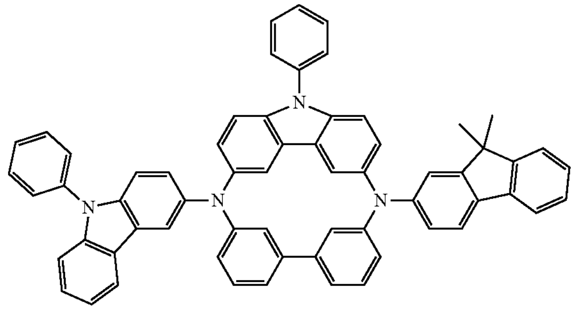
80
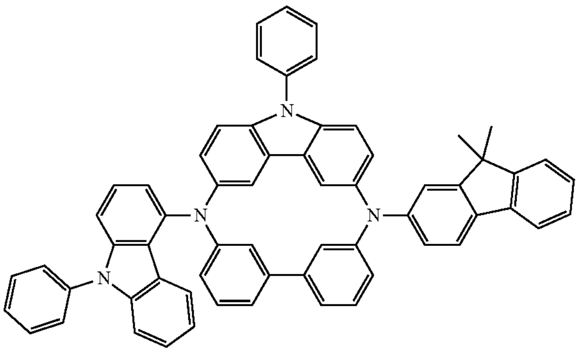
81
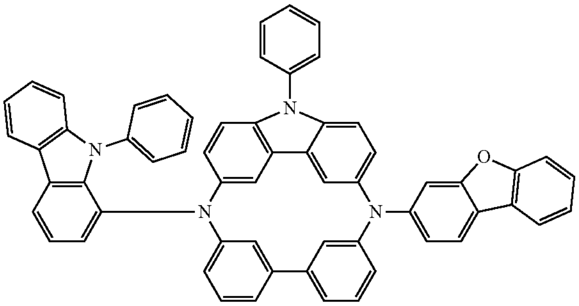

-continued
82
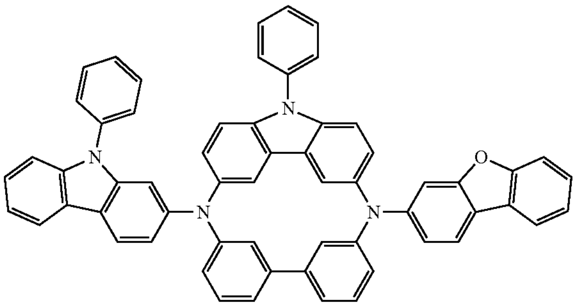
83
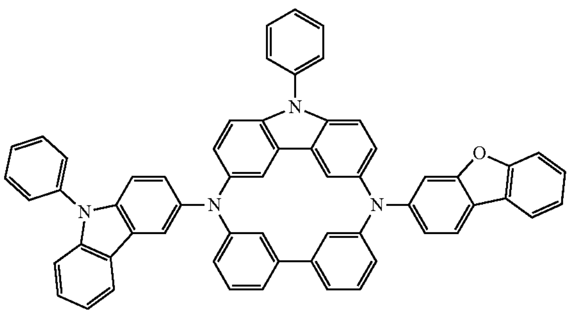
84
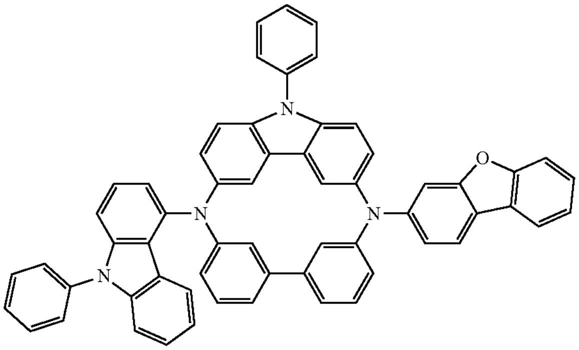
85
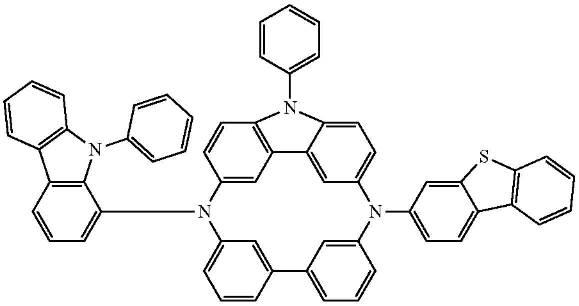
-continued
86
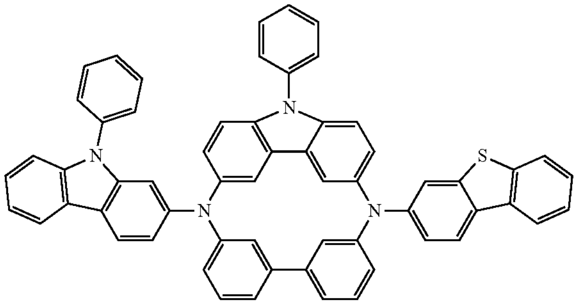
87
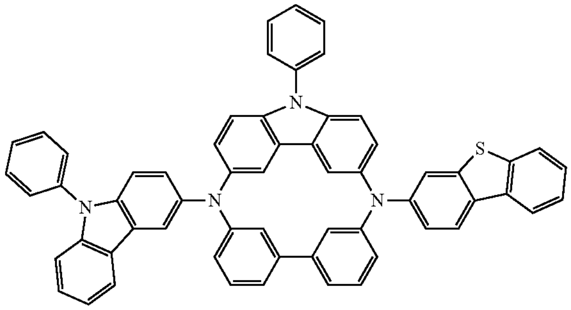
88
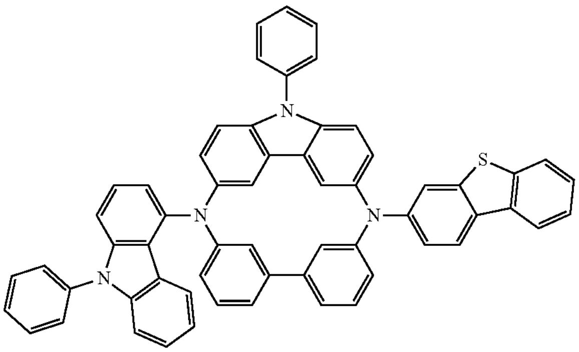
89
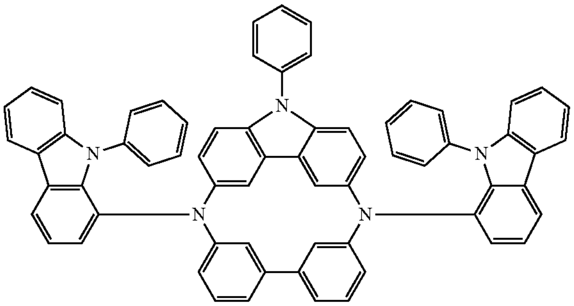

90
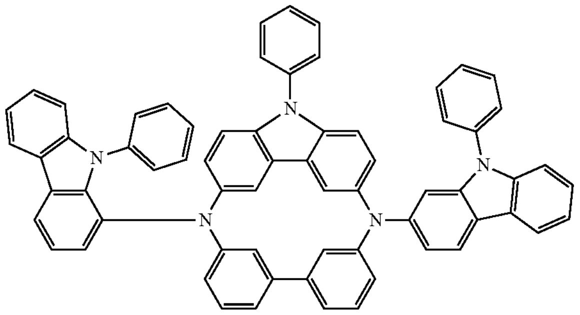
91
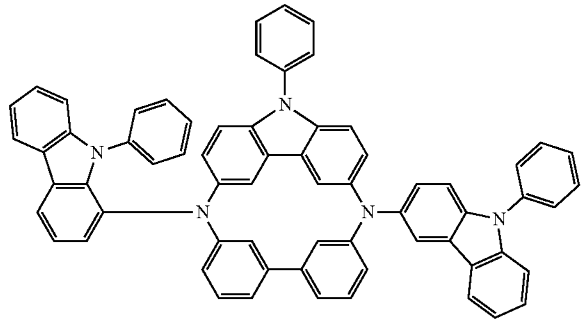
92
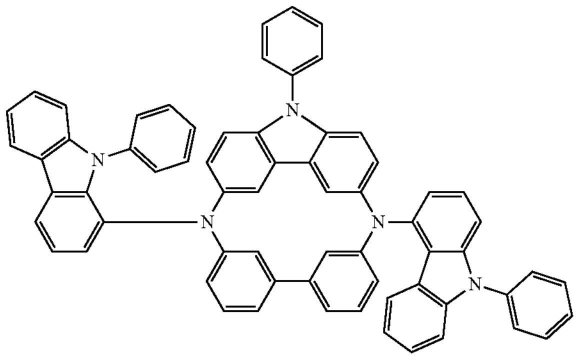
93
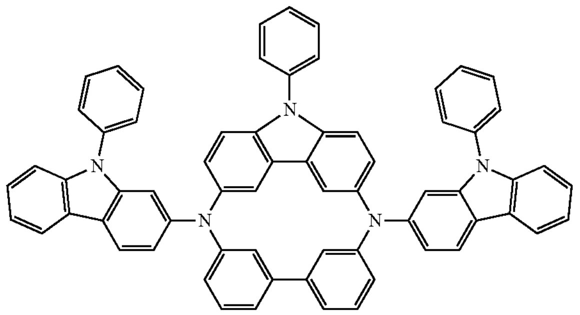
94
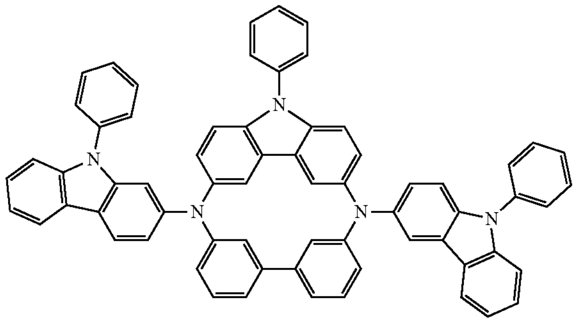
95
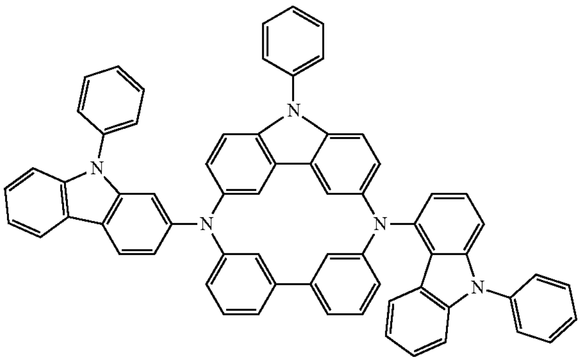
96
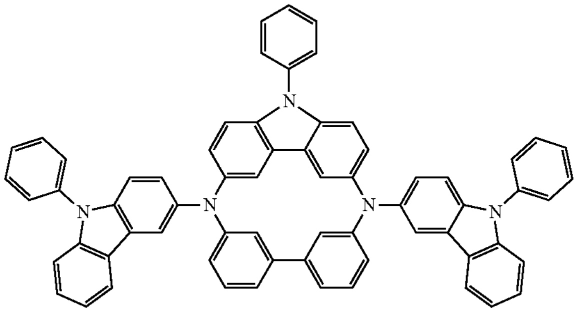
97
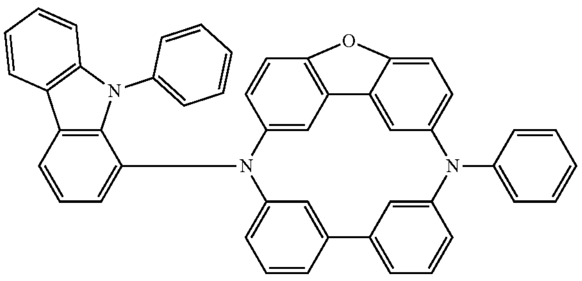

-continued
98
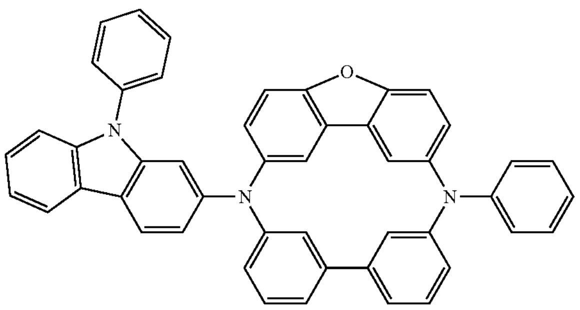
99
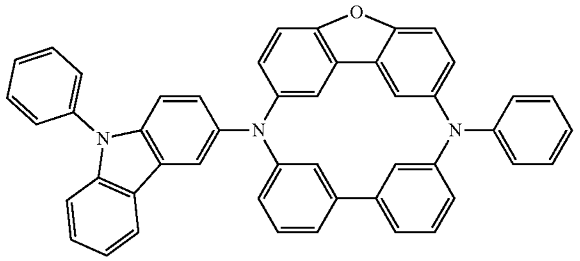
100
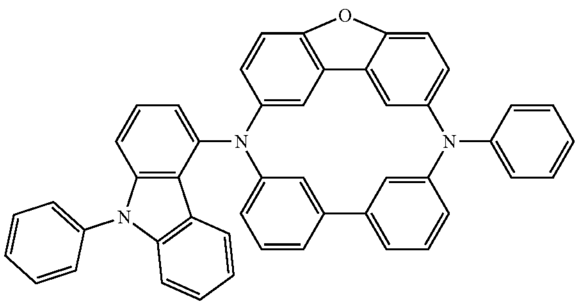
101
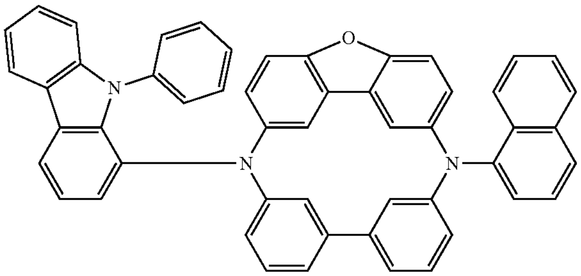
102
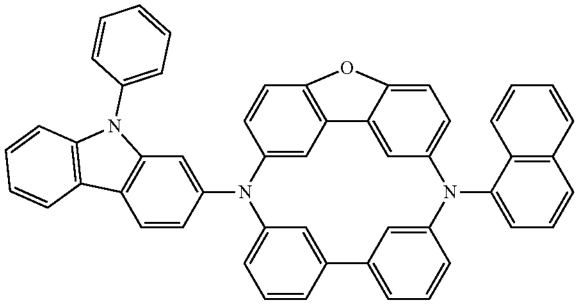
-continued
103
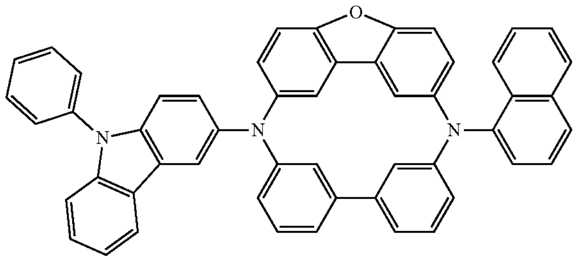
104
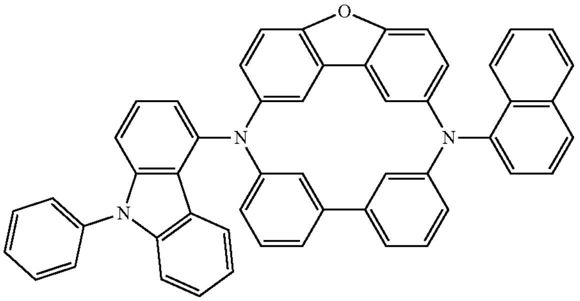
105
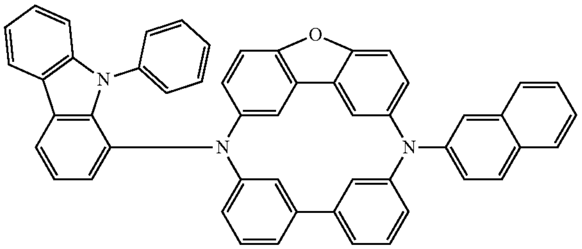
106
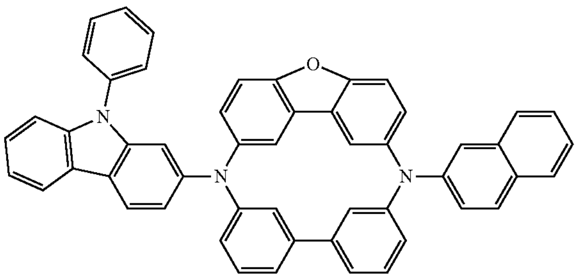
107
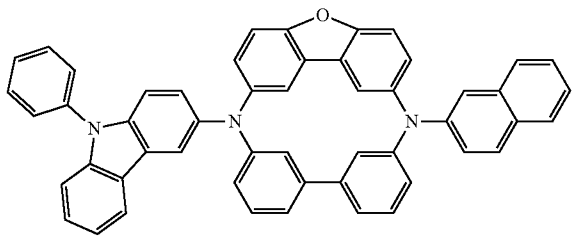

-continued
108
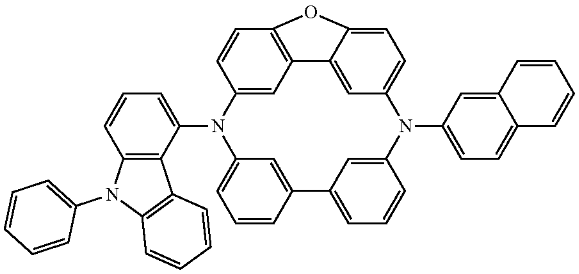
109
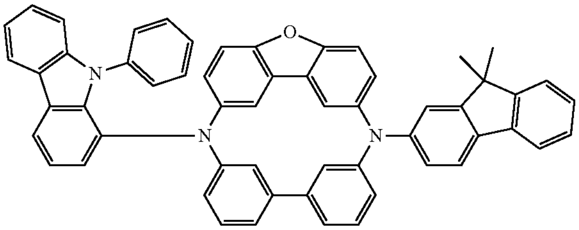
110
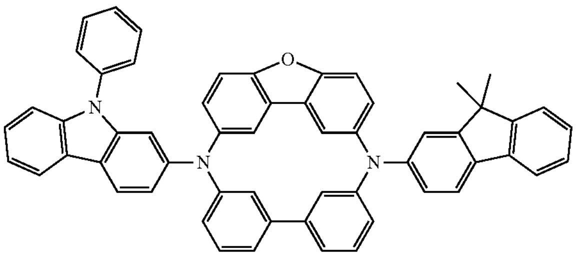
111
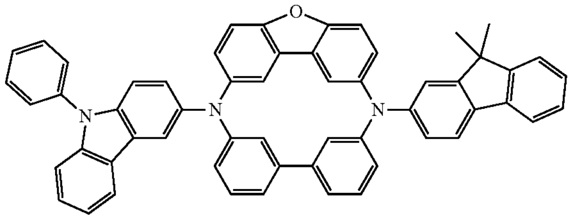
112
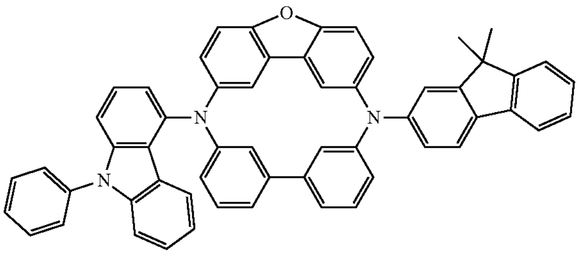
113
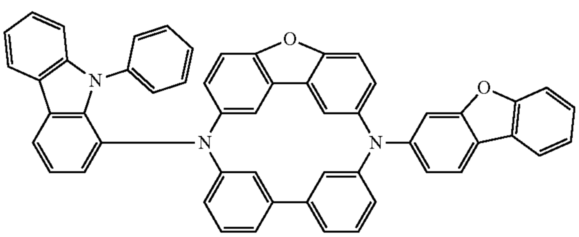
-continued
114
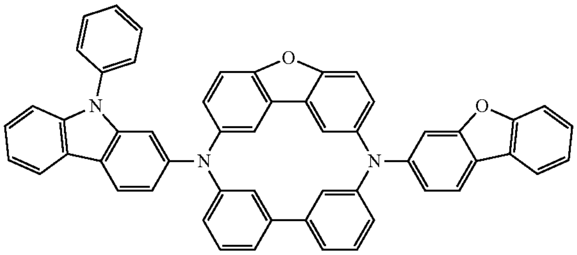
115
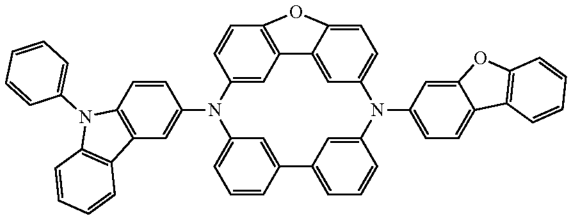
116
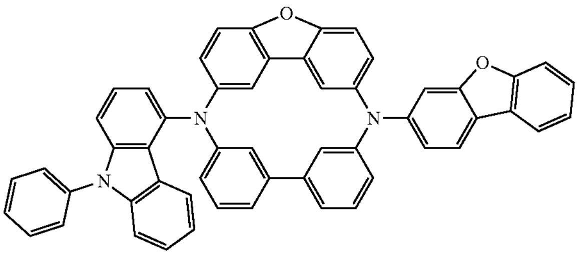
117
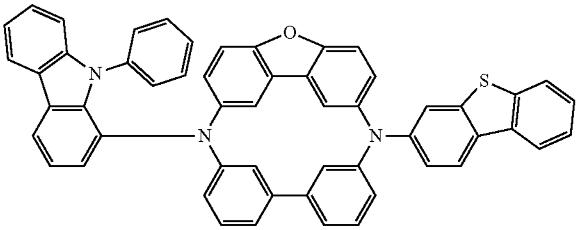
118
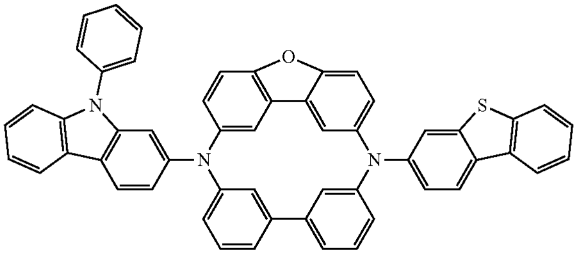
119
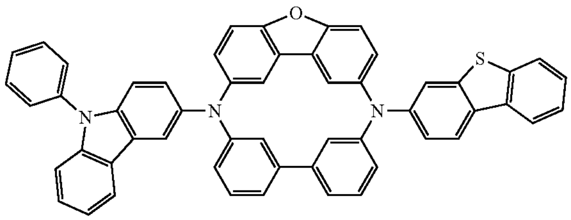

-continued
120
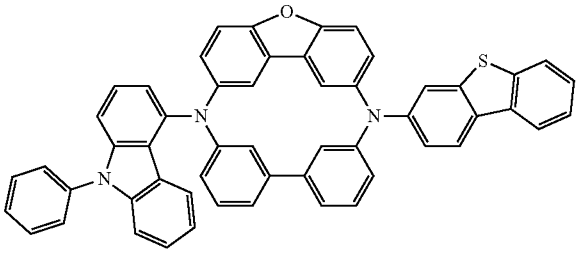
121
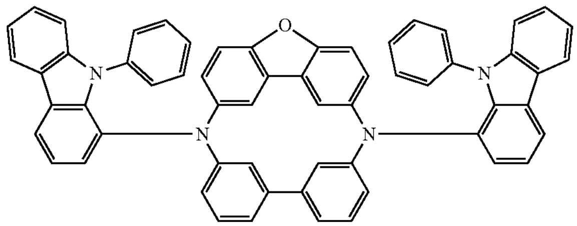
122
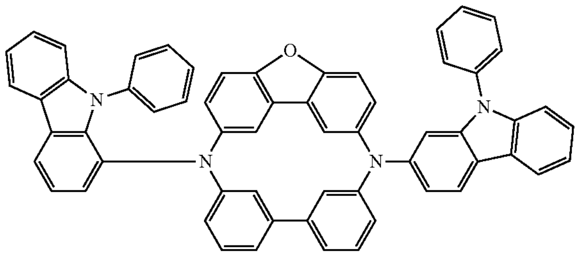
123
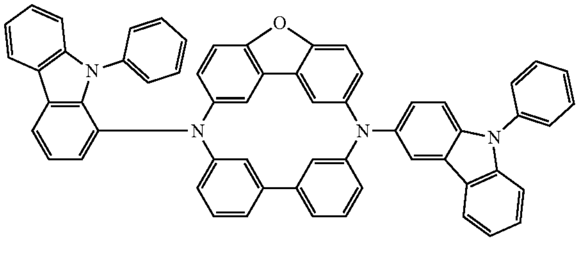
124
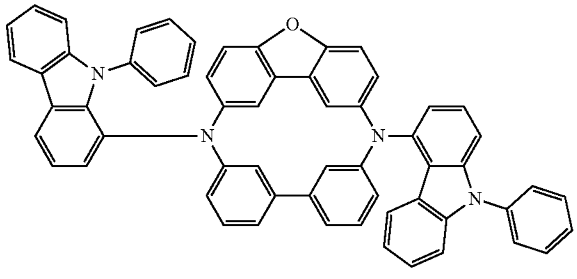
-continued
125
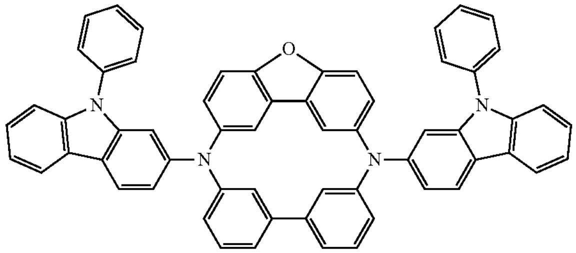
126
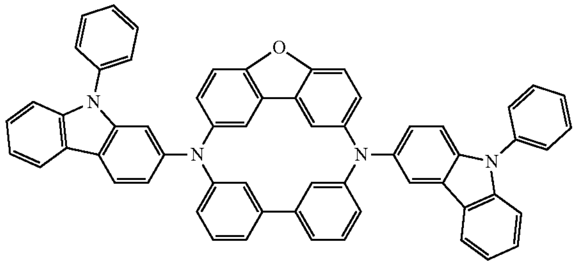
127
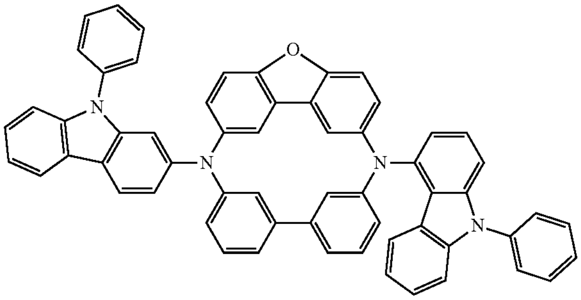
128
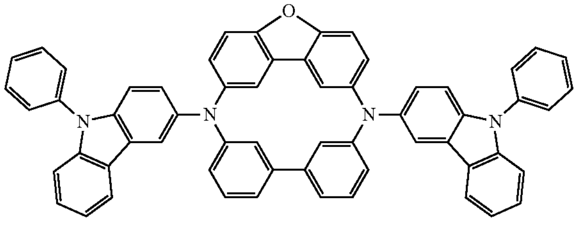
129
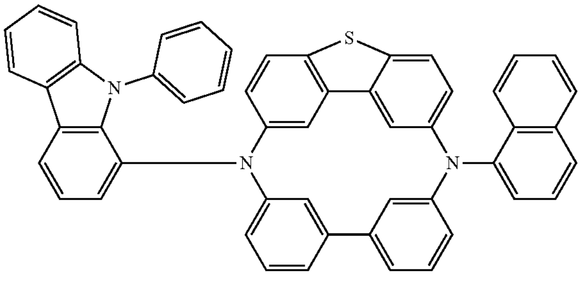

-continued
130
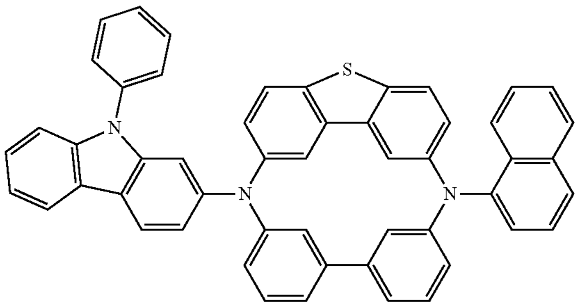
131
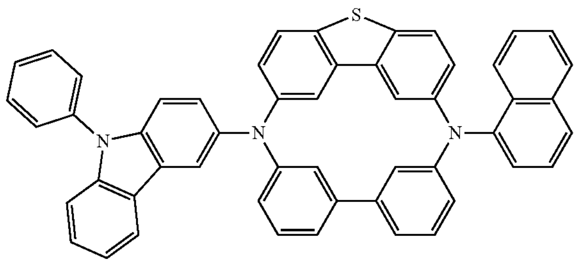
132
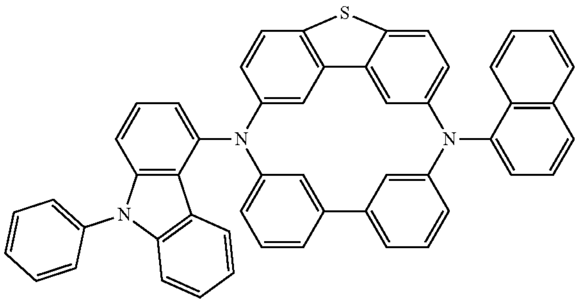
133
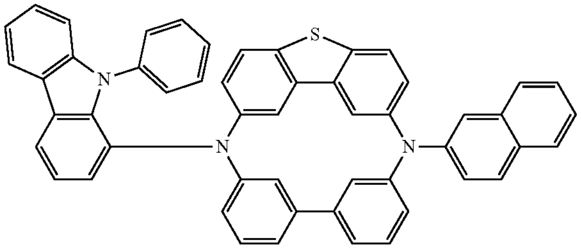
134
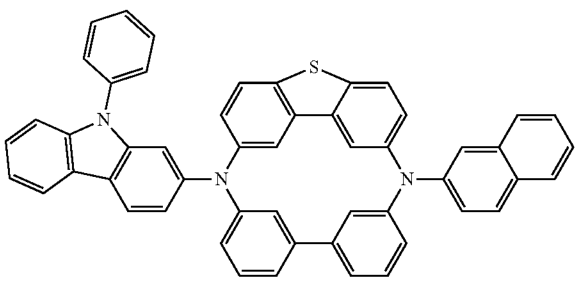
-continued
135
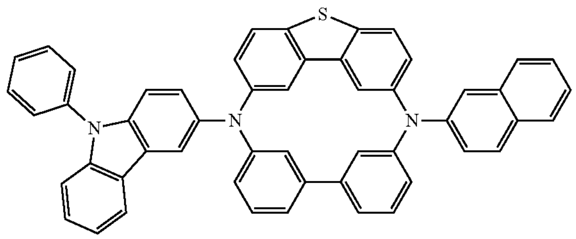
136
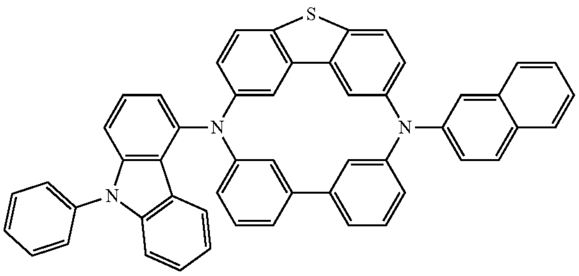
137
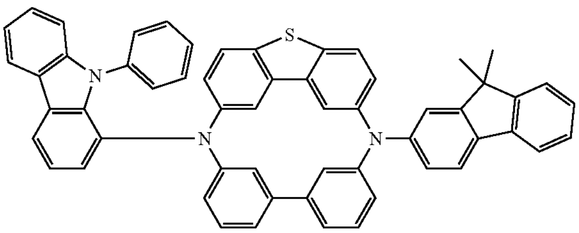
138
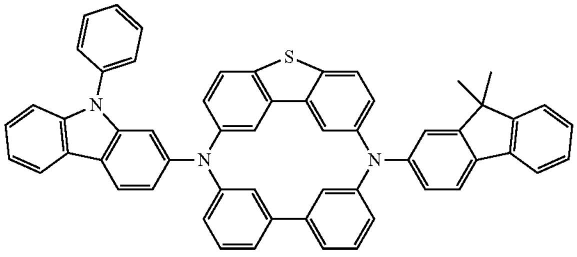
139
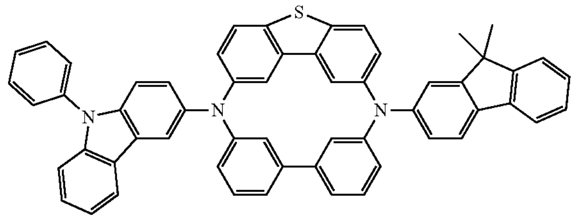
140
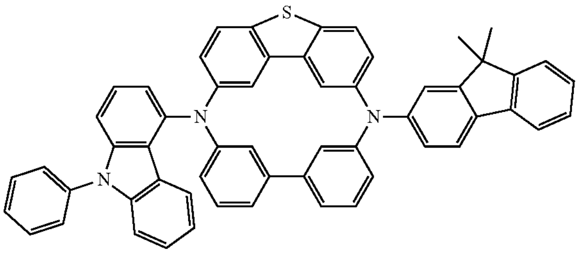

-continued
141
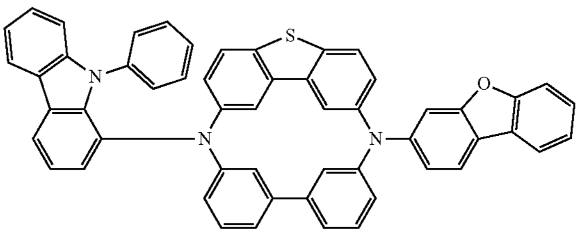
142
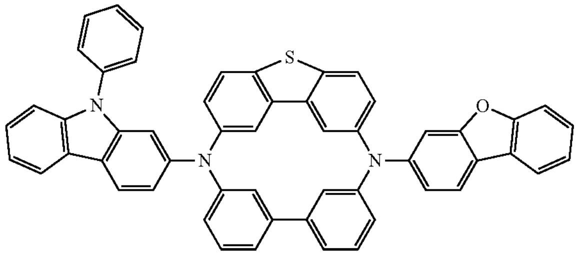
143
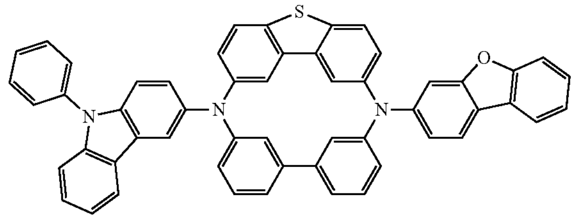
144
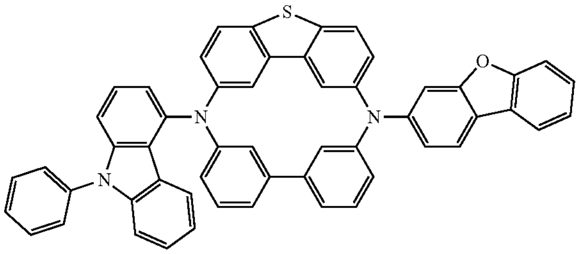
145
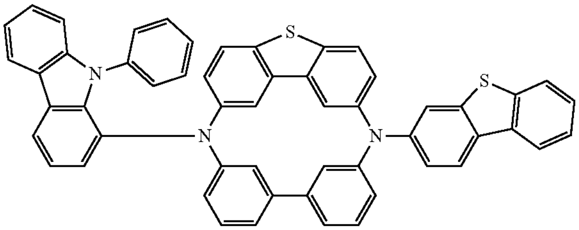
146
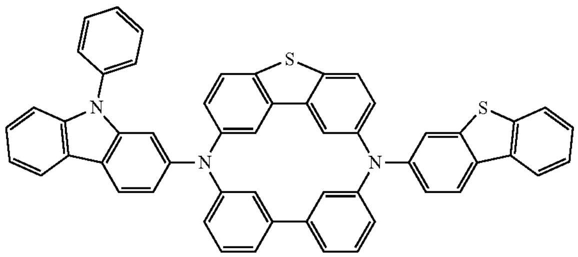
-continued
147
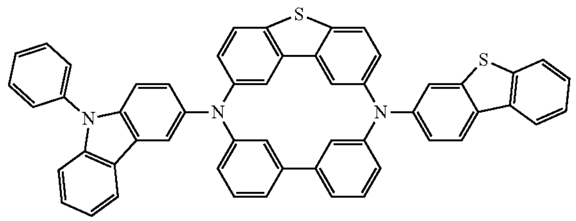
148
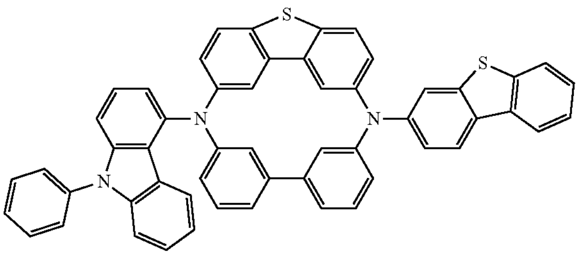
149
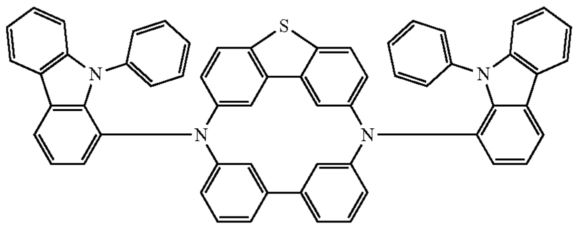
150
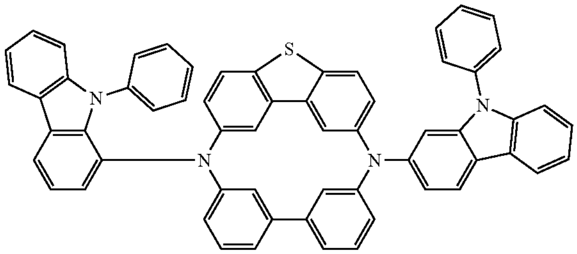
151
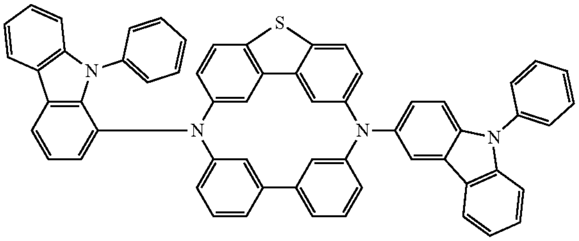
152
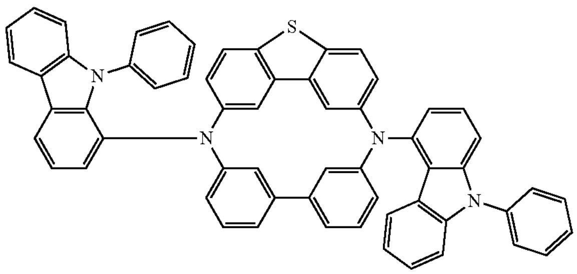

153
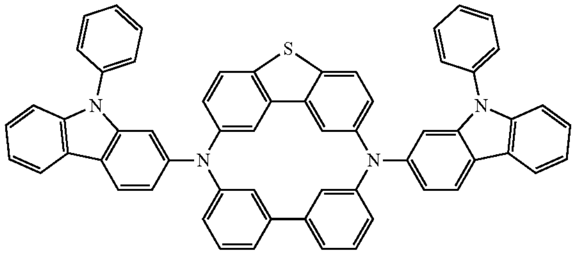
154
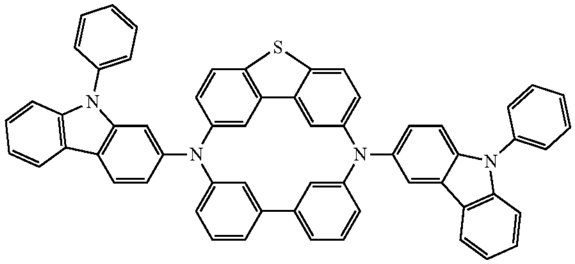
155
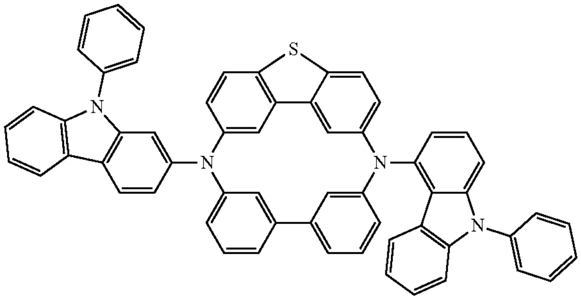
156
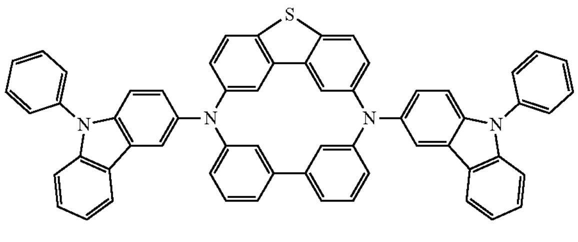
157
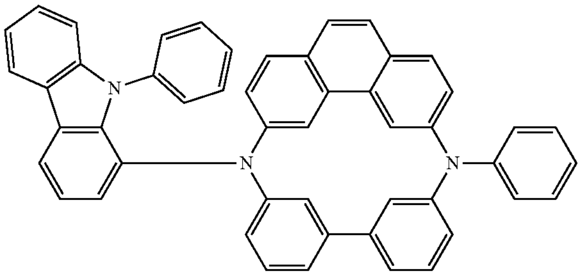
158
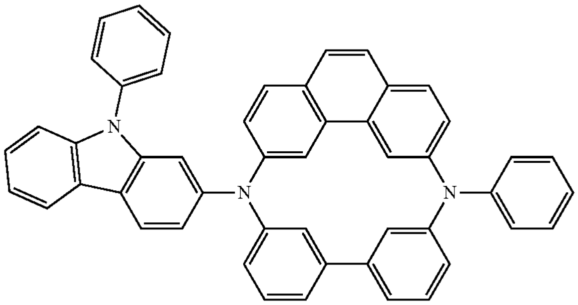
159
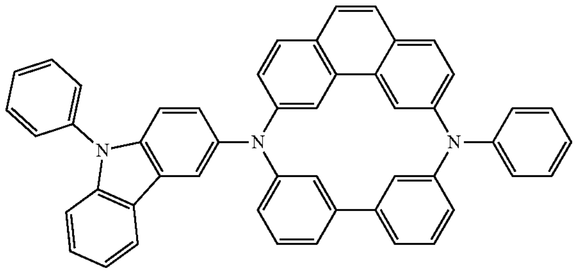
160
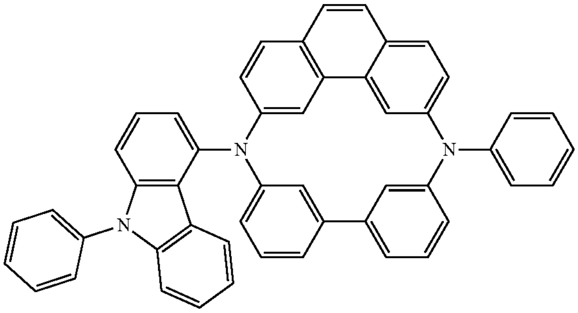
161
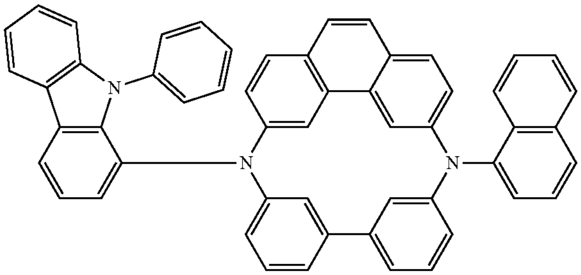
162
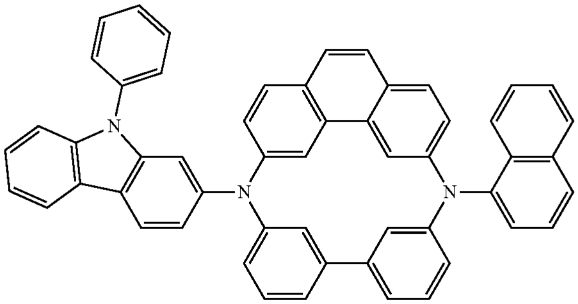

-continued
163
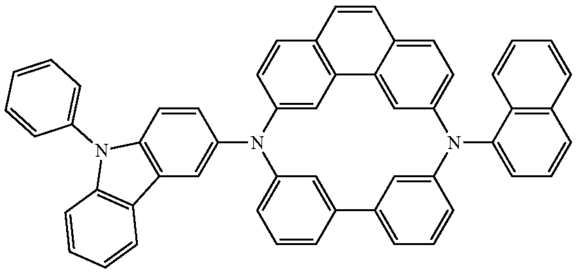
164
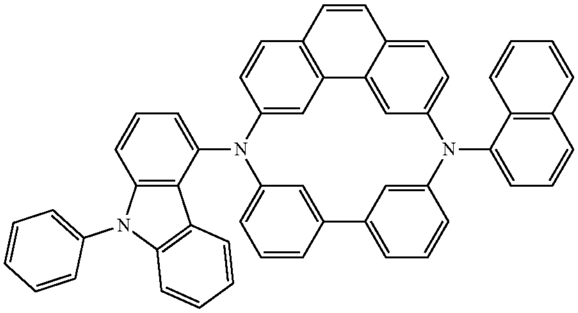
165
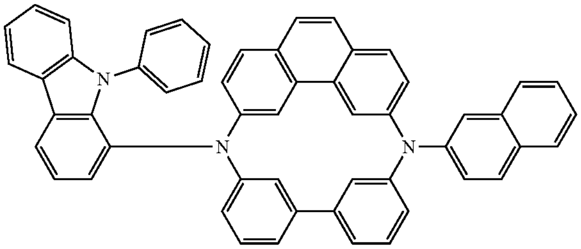
166
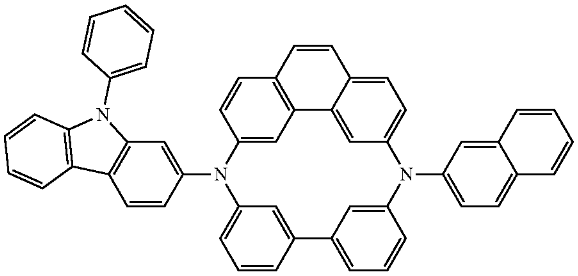
167
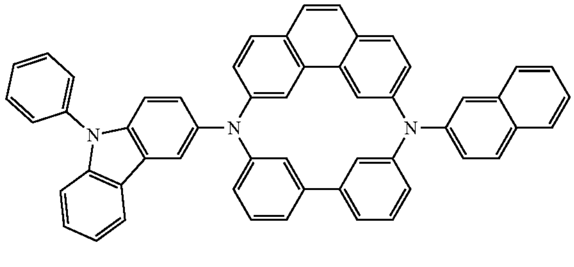
-continued
168
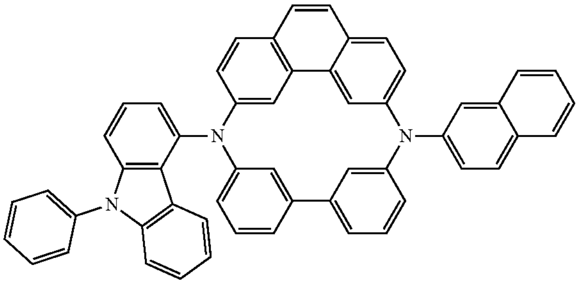
169
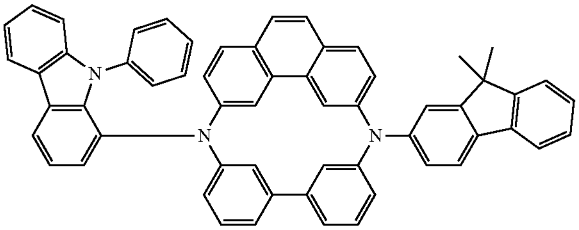
170
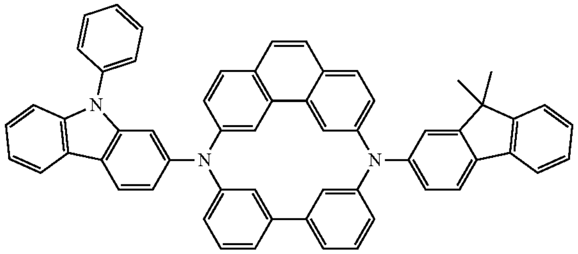
171
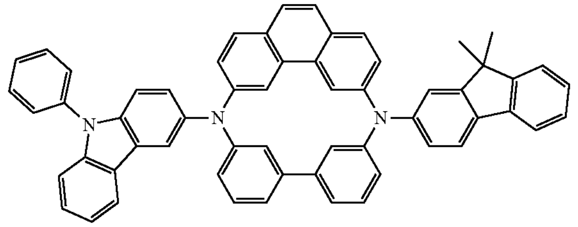
172
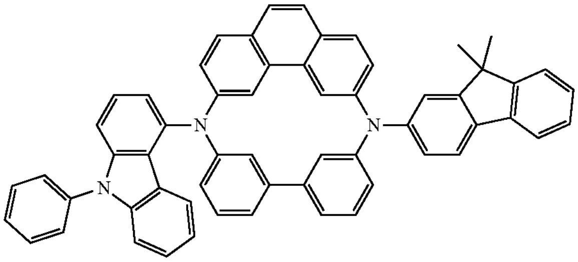
173
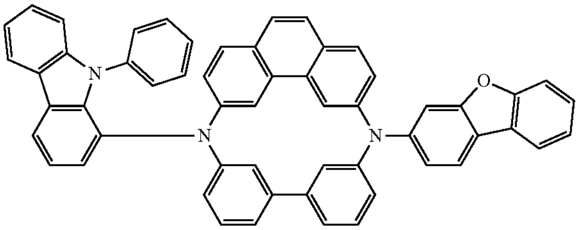

174
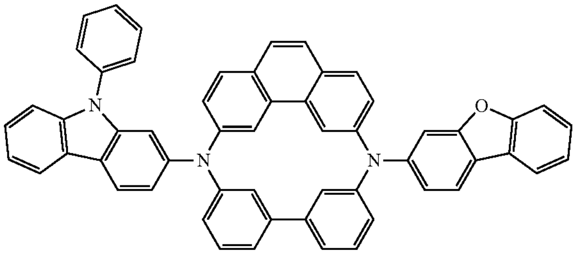
175
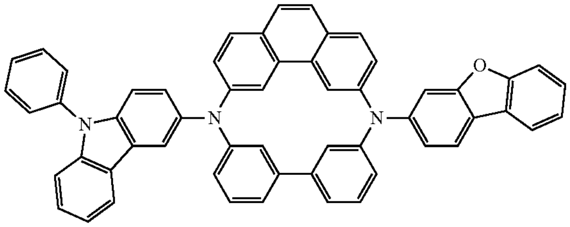
176
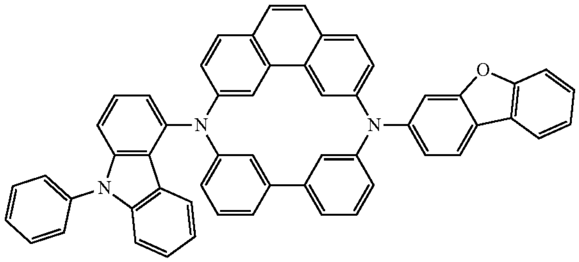
177
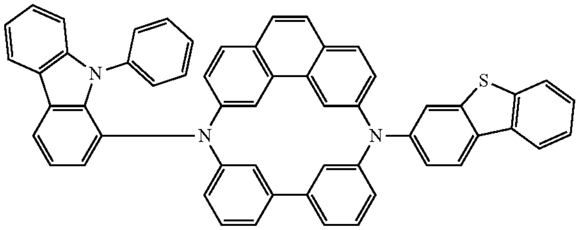
178
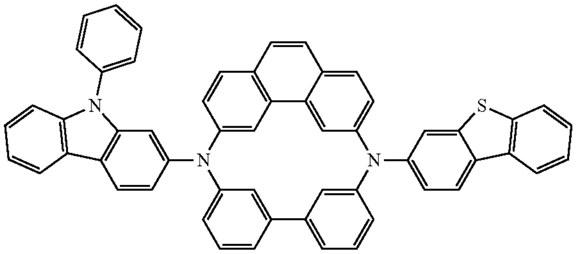
179
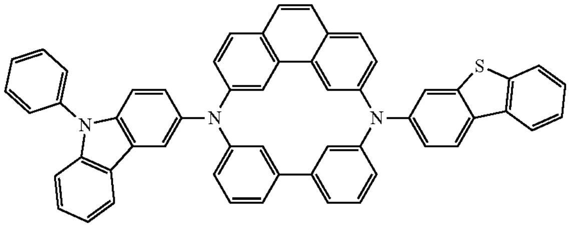
180
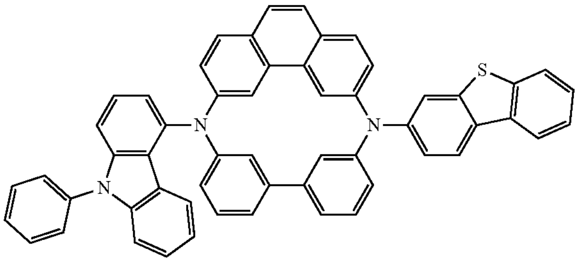
181
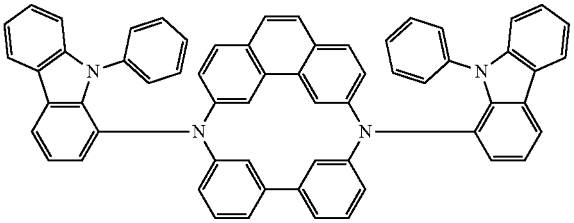
182
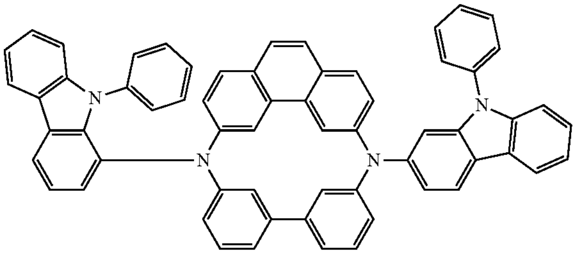
183
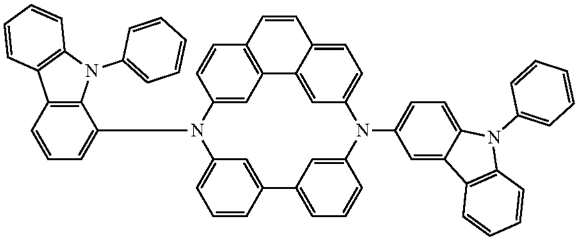
184
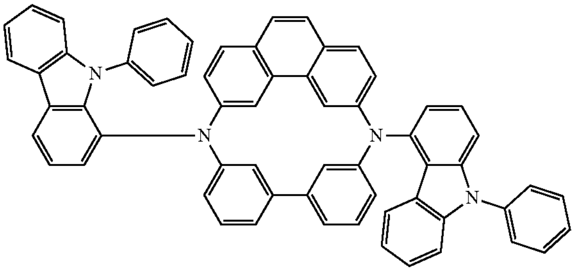

-continued
185
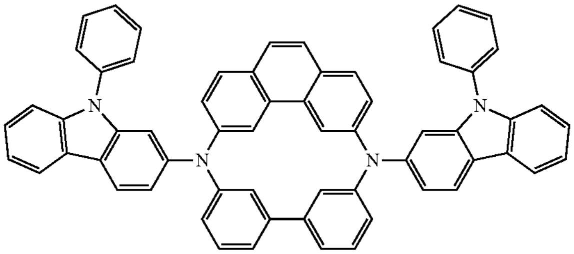
186
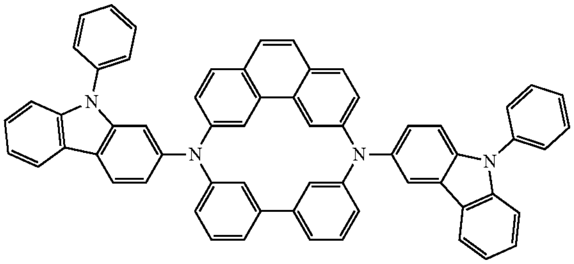
187
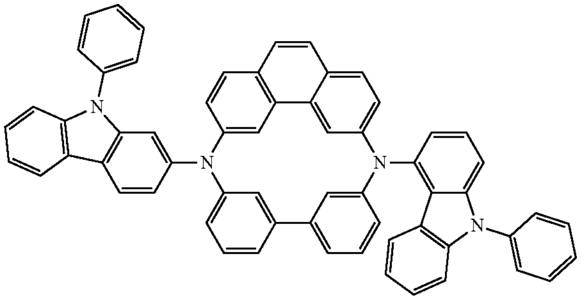
188
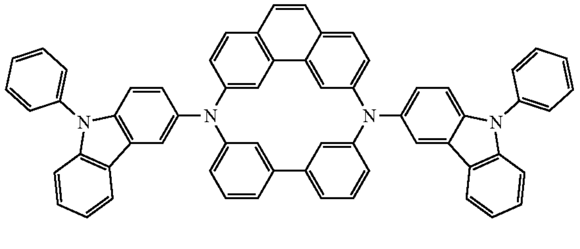
189
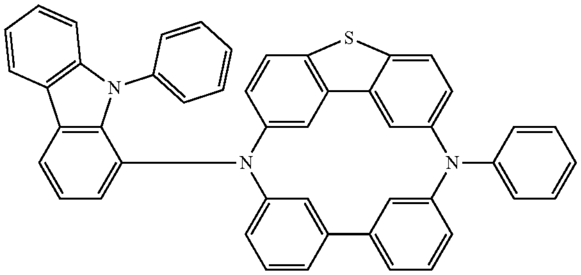
-continued
190
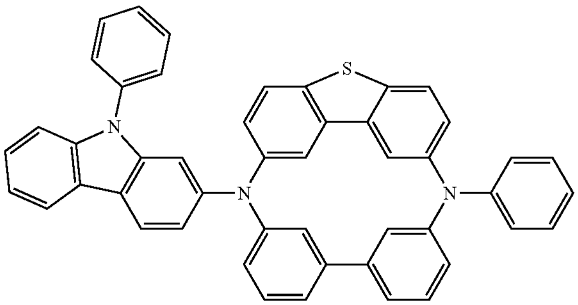
191
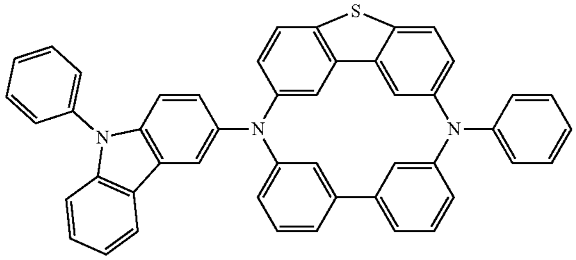
192
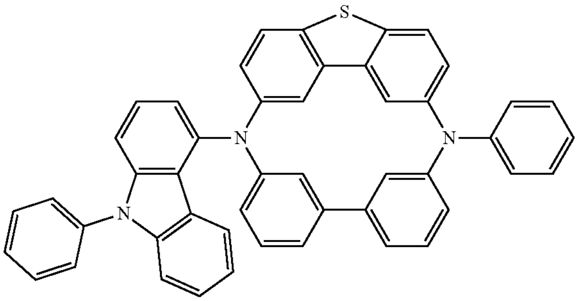
193
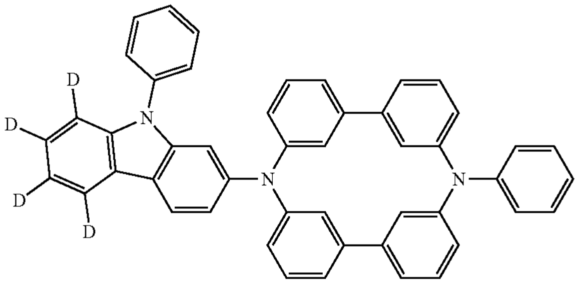
194
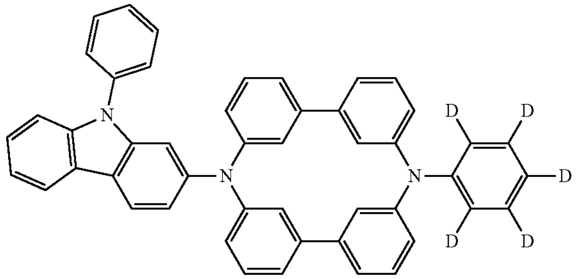

195
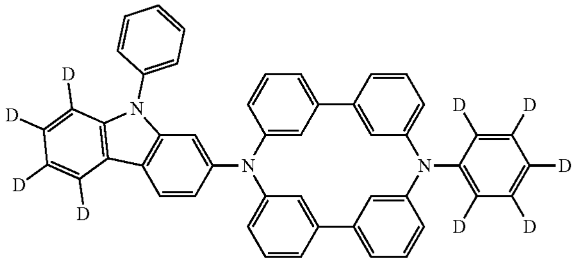
196
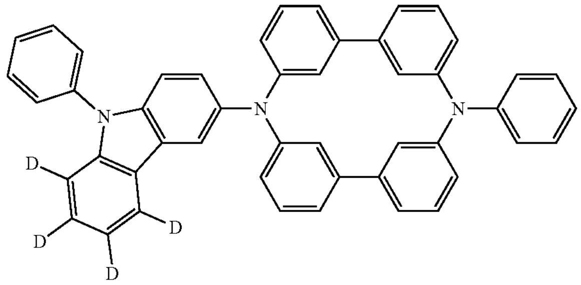
197
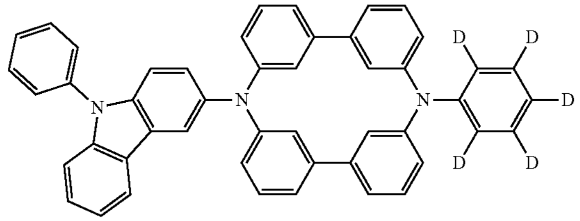
198
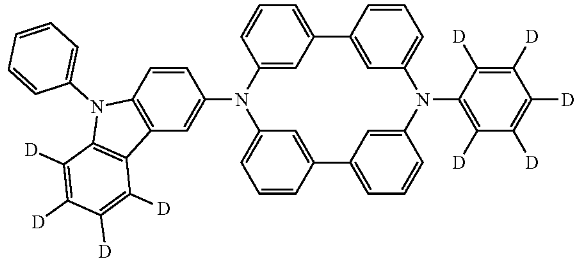
199
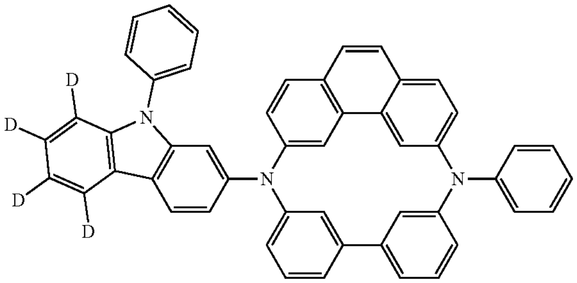
200
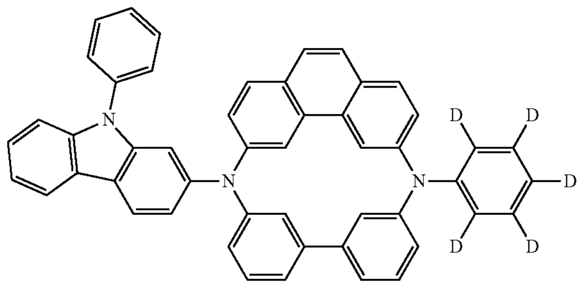
201
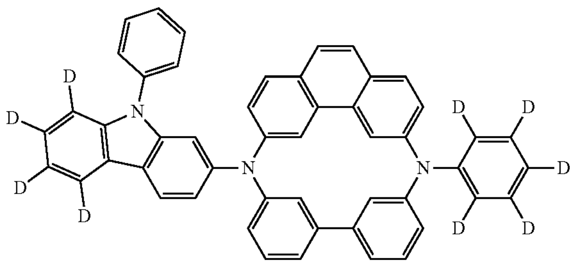
202
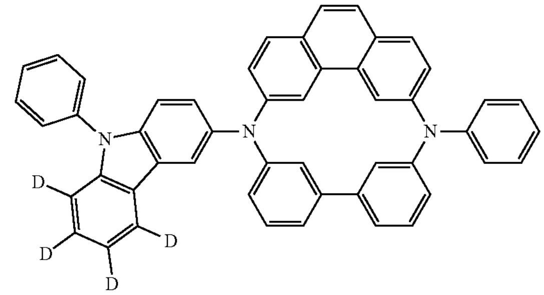
203
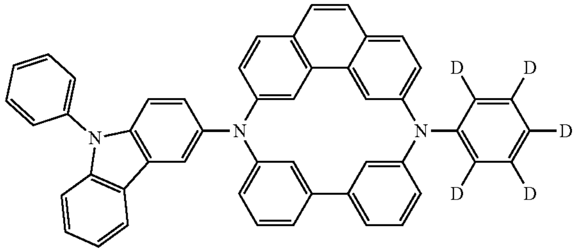
204
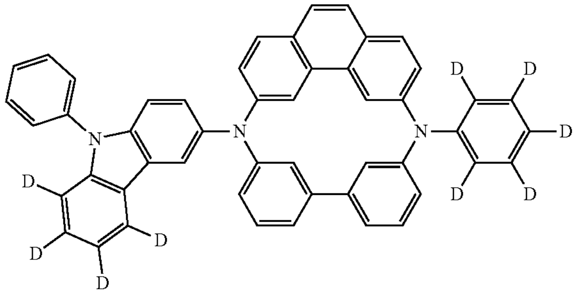

-continued
205
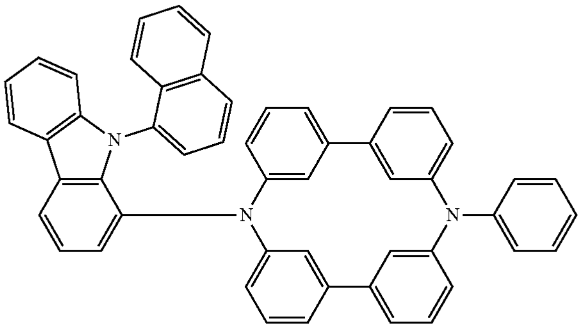
206
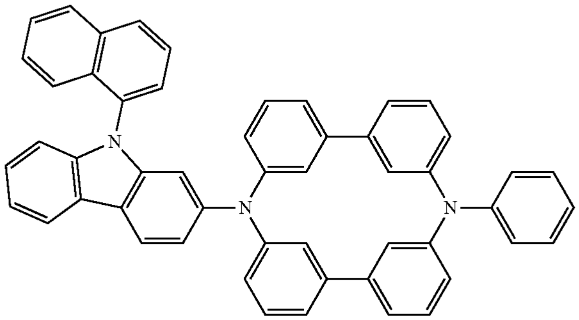
207
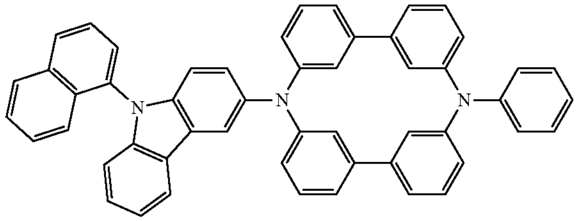
208
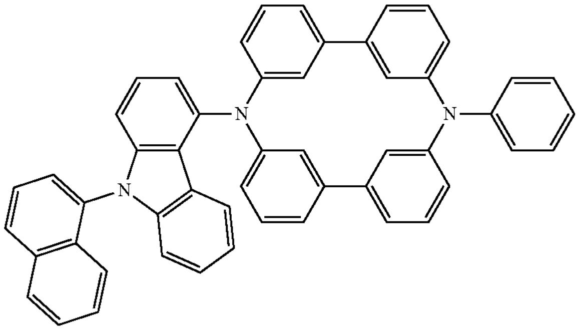
209
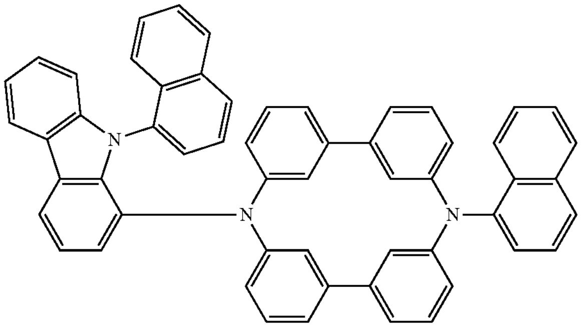
-continued
210
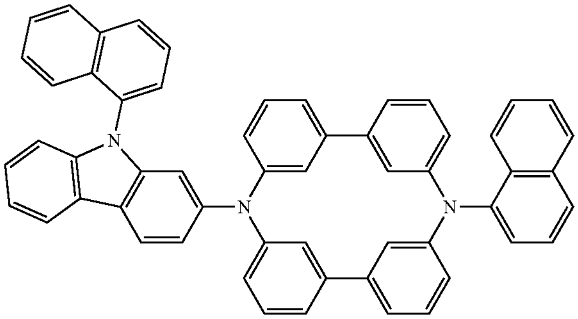
211
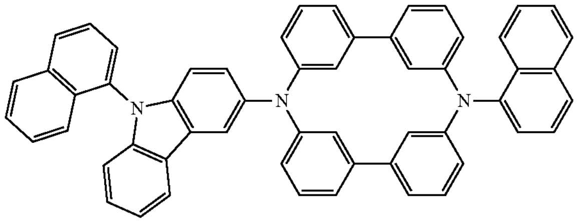
212
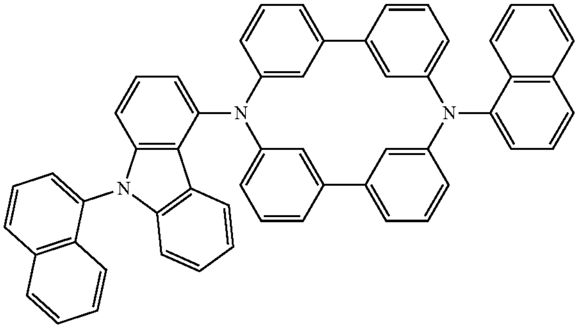
213
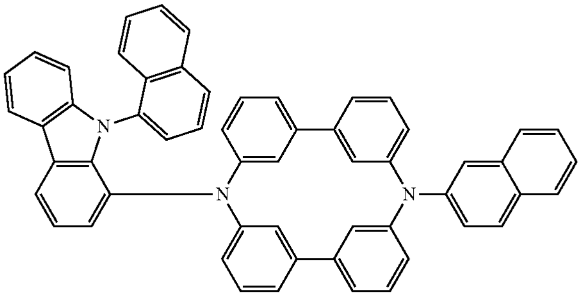
214
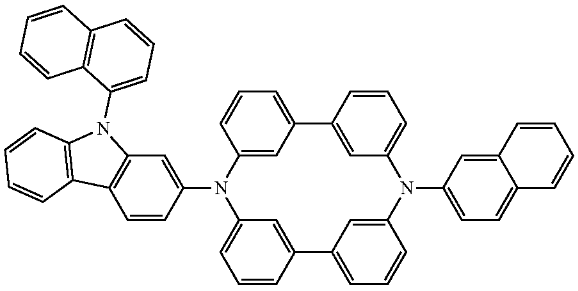

-continued
215
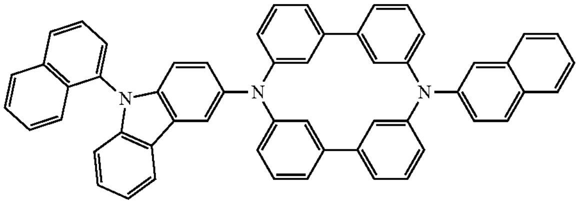
216
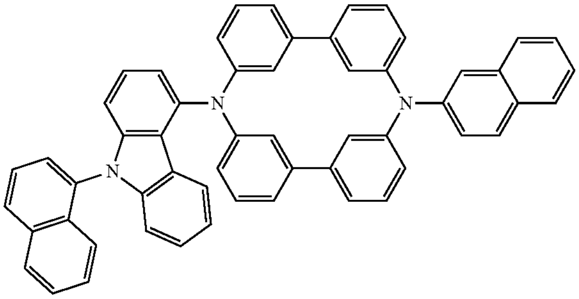
217
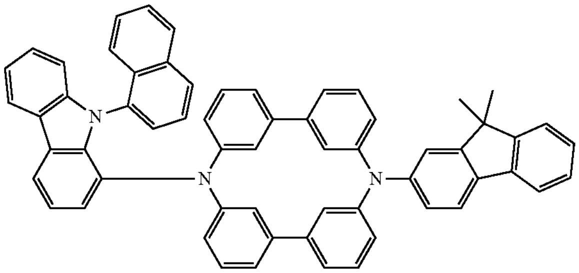
218
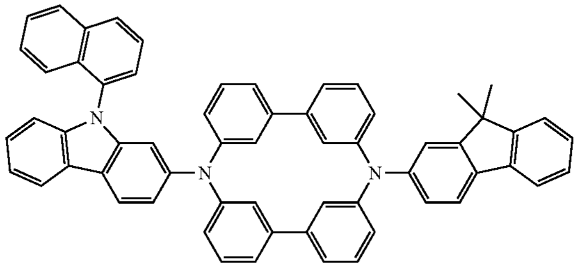
219
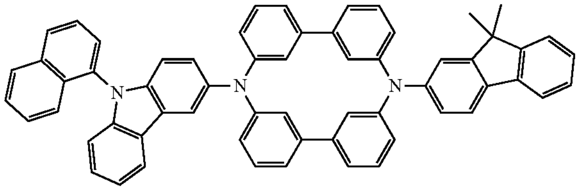
-continued
220
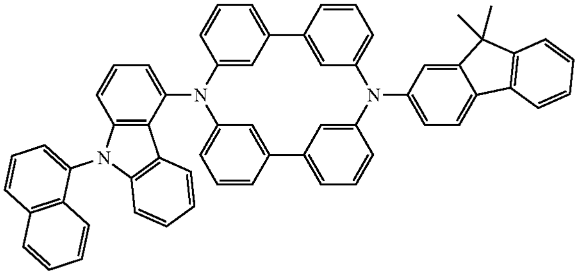
221
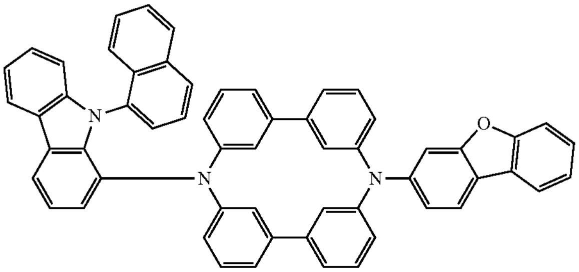
222
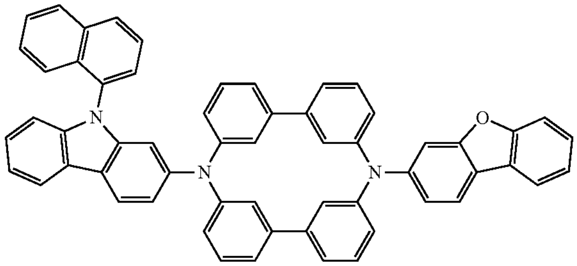
223
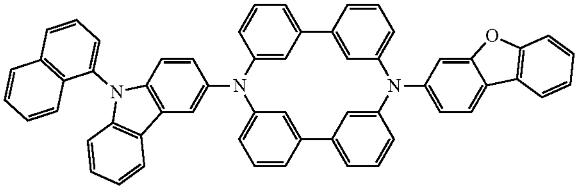
224
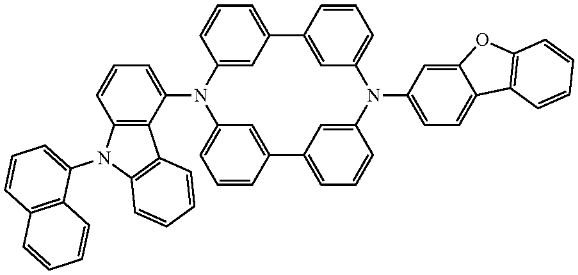

-continued
225
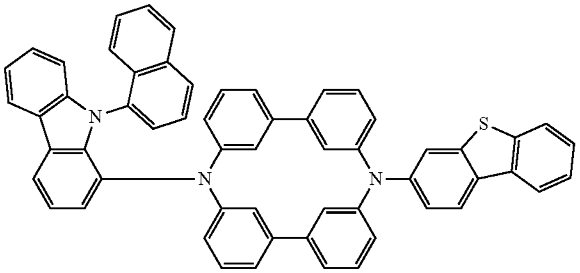
226
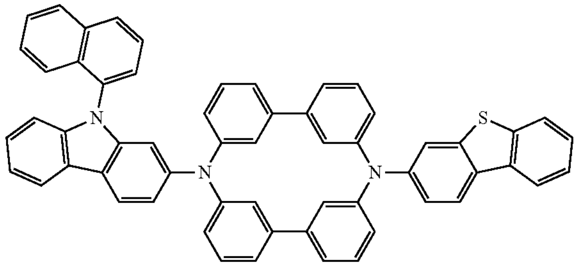
227
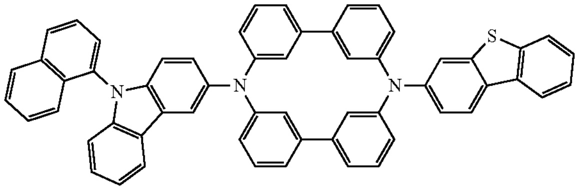
228
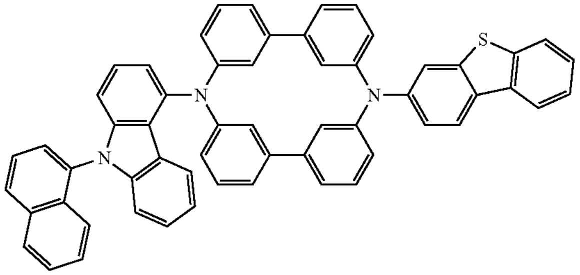
229
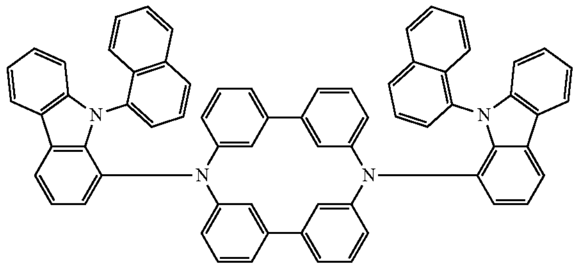
-continued
230
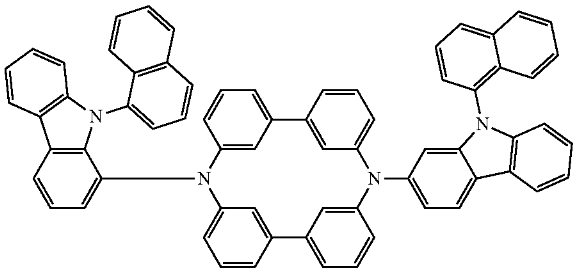
231
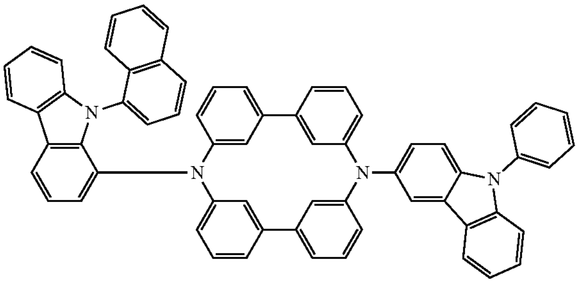
232
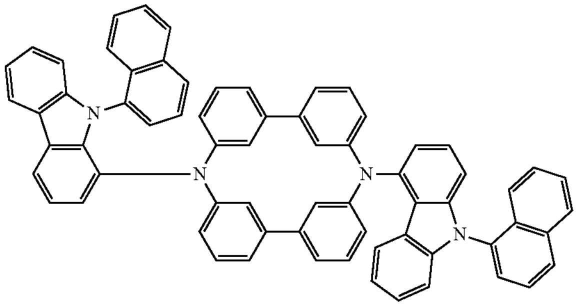
233
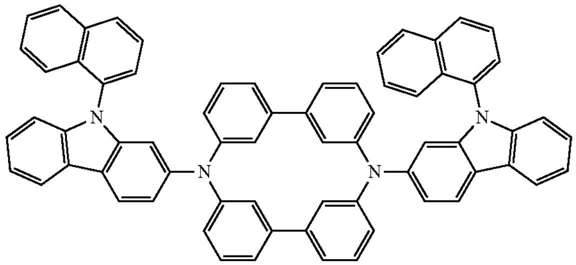
234
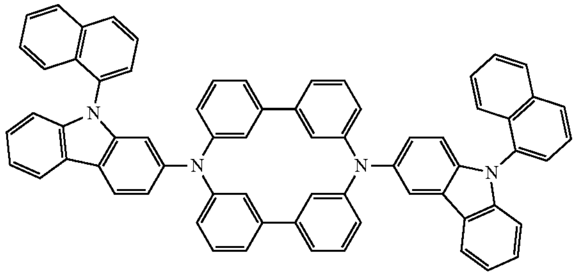

-continued
235
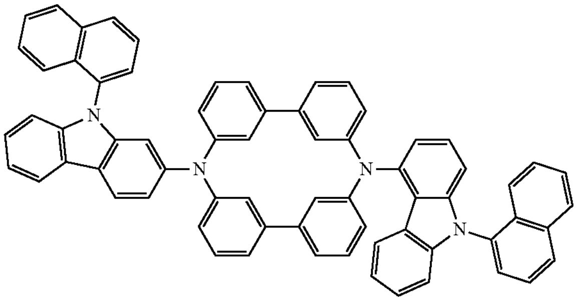
236
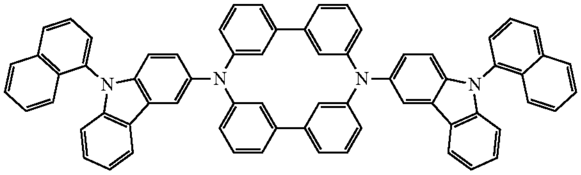
237
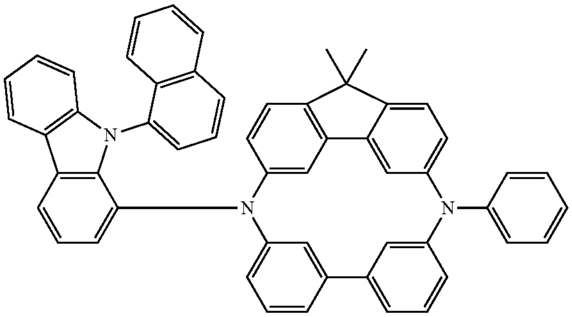
238
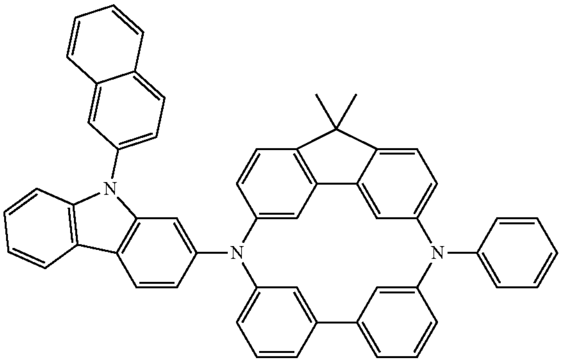
239
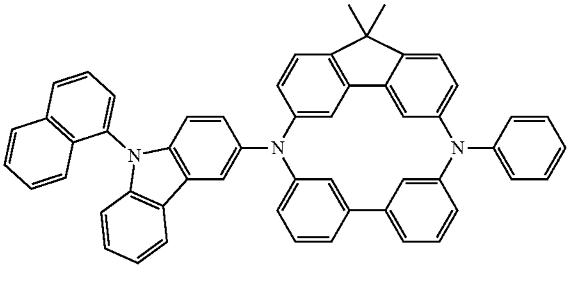
-continued
240
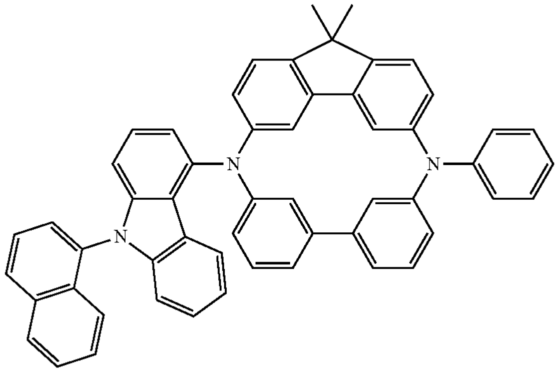
241
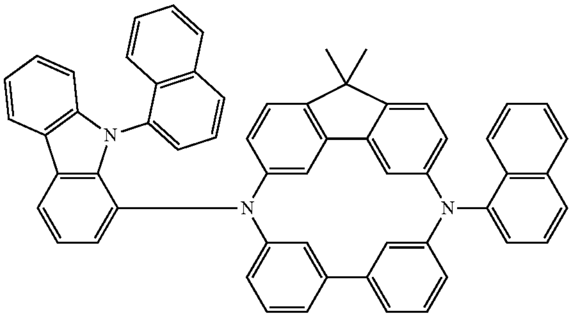
242
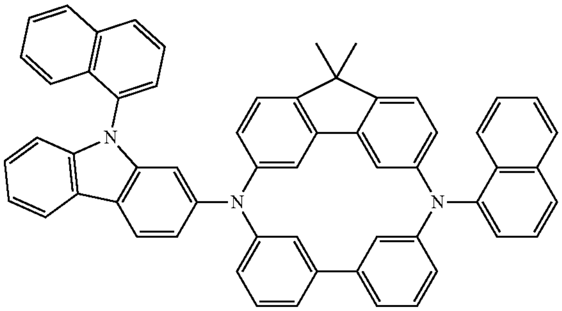
243
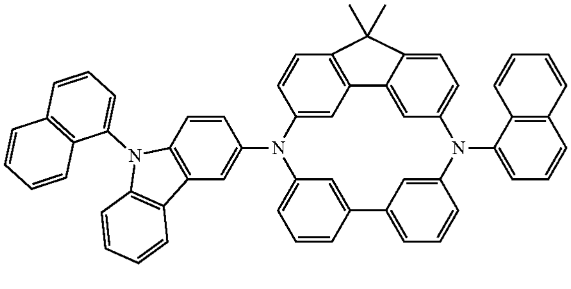

-continued
244
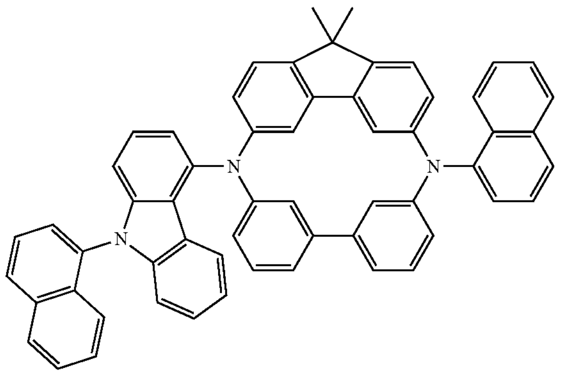
245
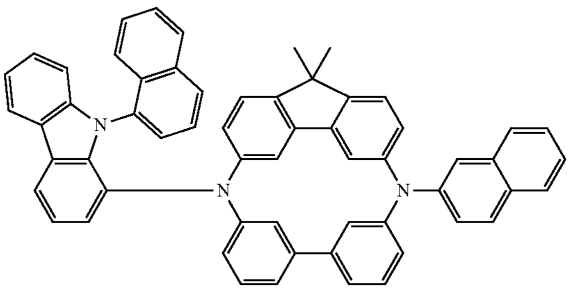
246
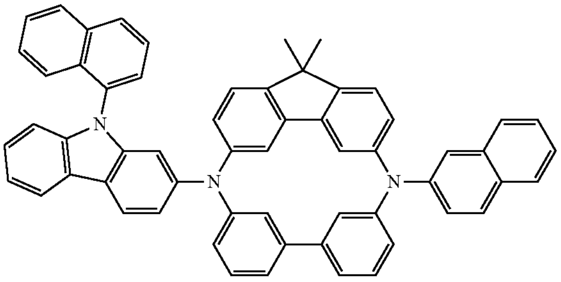
247
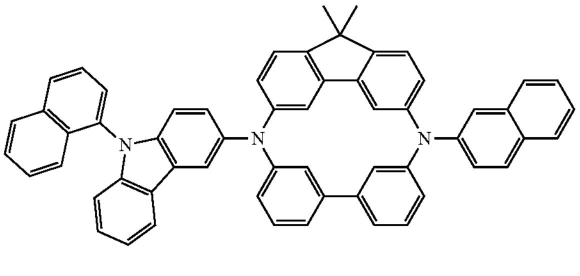
-continued
248
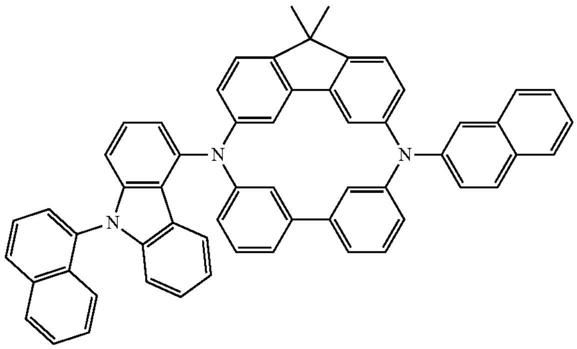
249
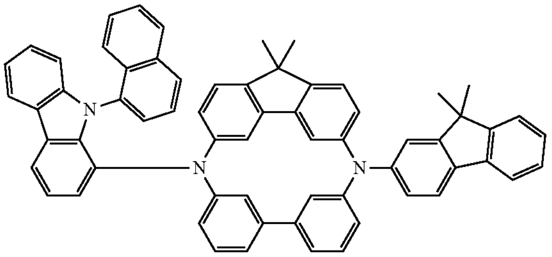
250
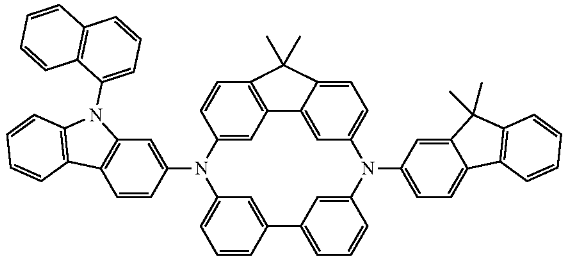
251
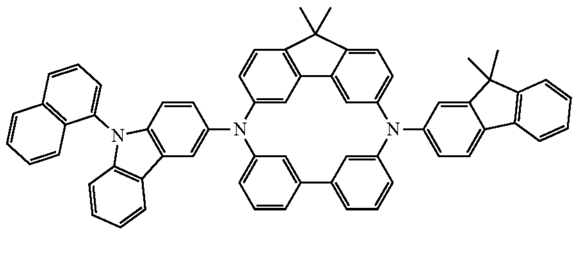
252
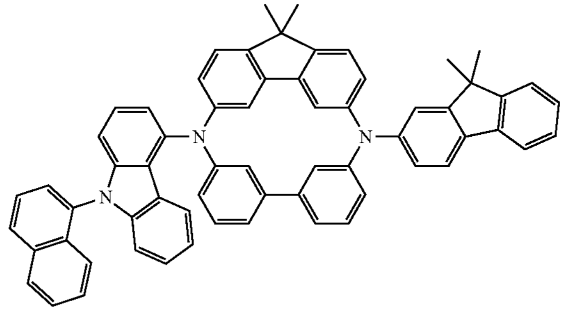

-continued
253
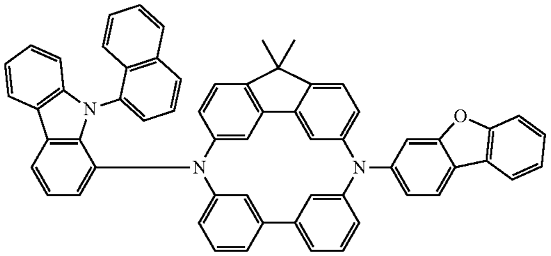
254
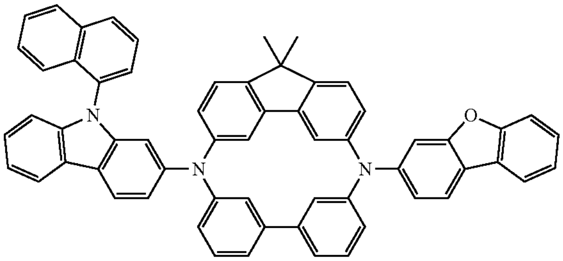
255
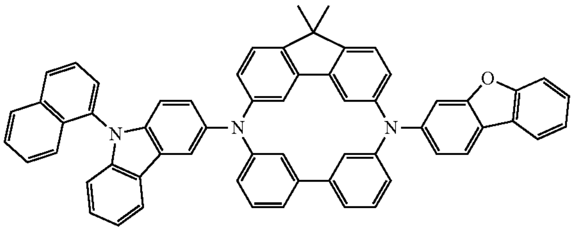
256
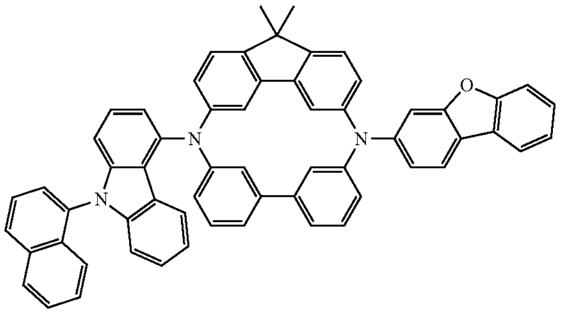
257
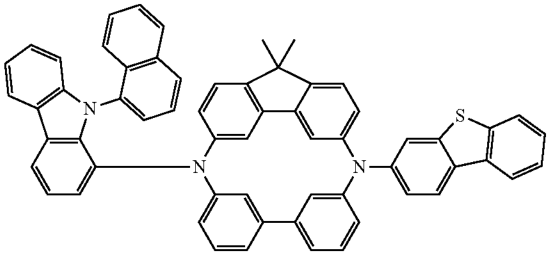
-continued
258
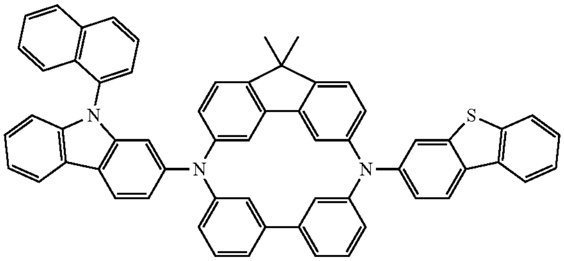
259
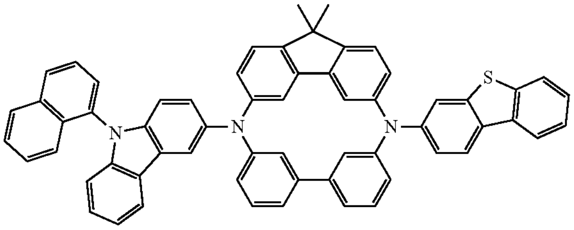
260
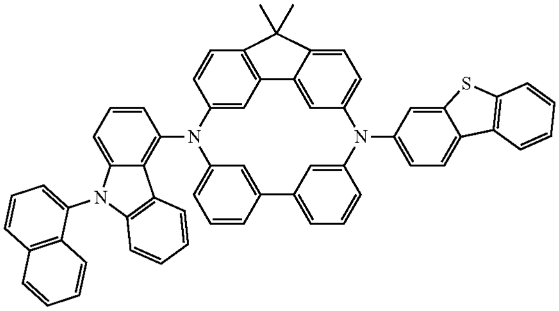
261
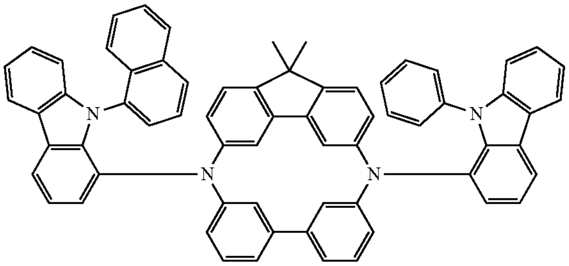
262
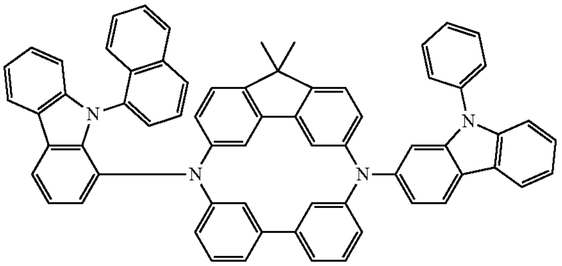

-continued
263
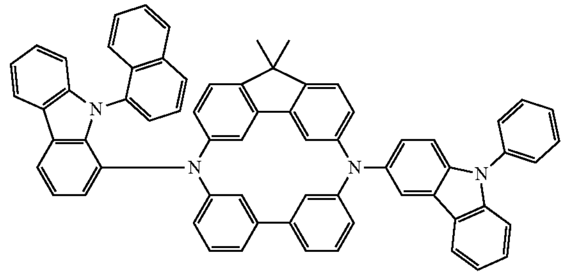
264
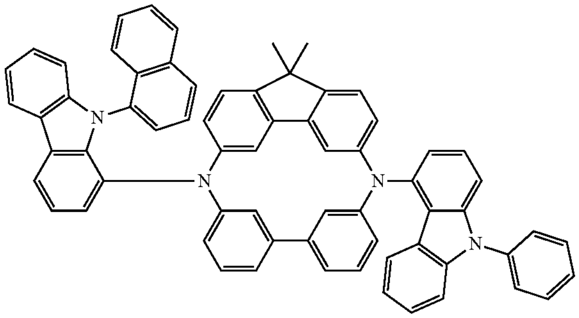
265
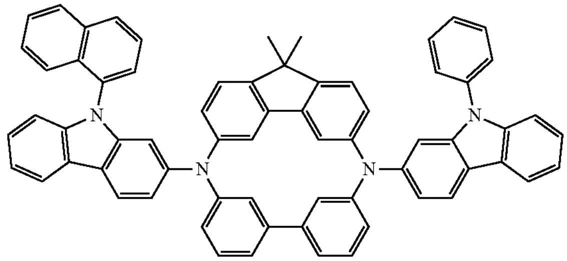
266
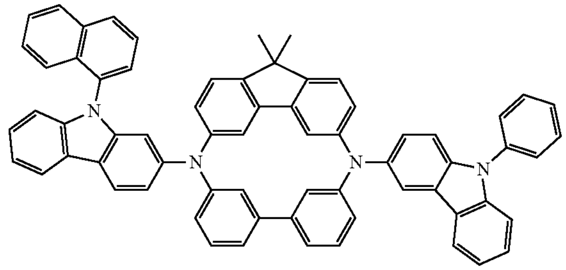
267
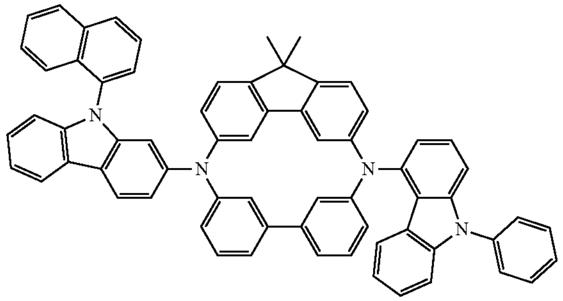
-continued
268
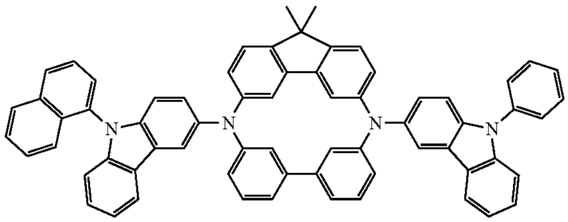
269
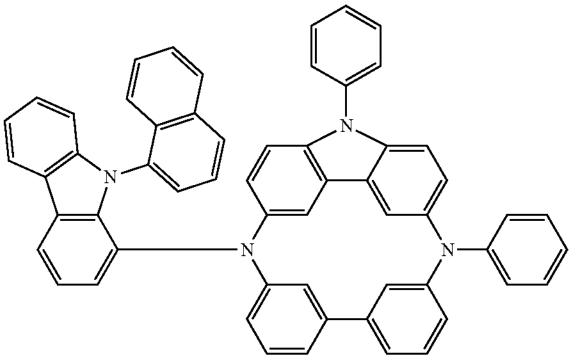
270
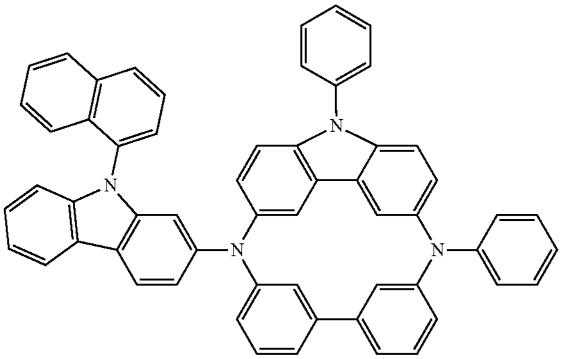
271
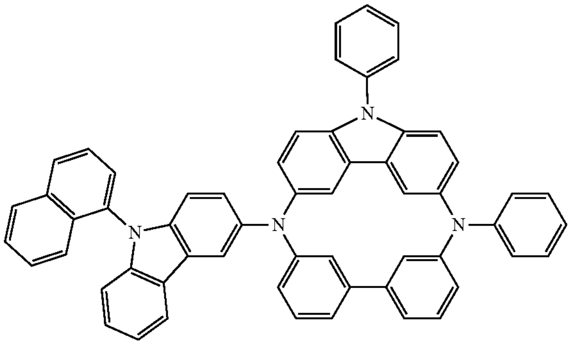

-continued
272
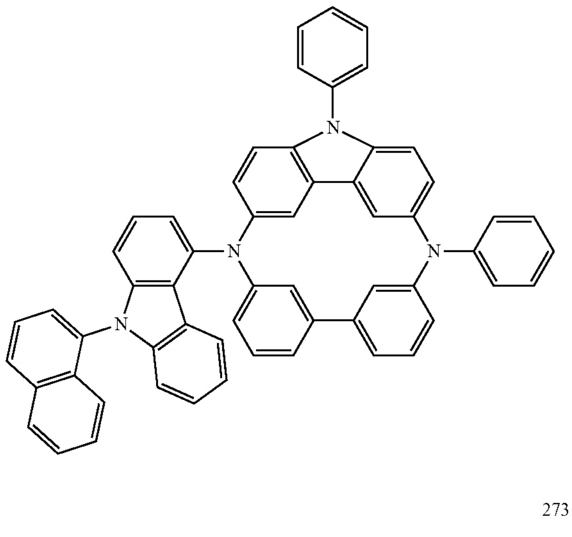
273
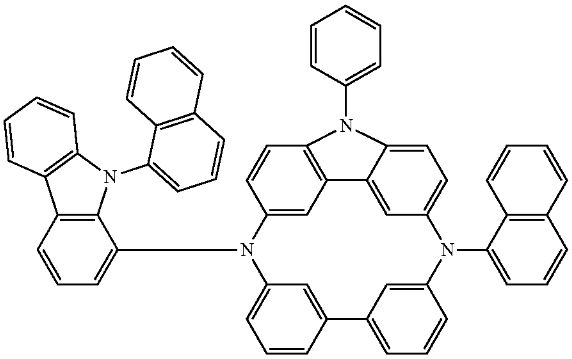
274
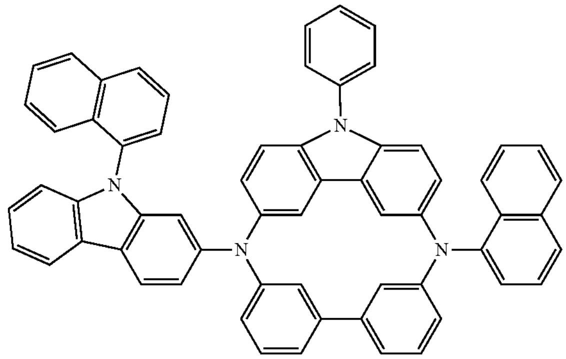
275
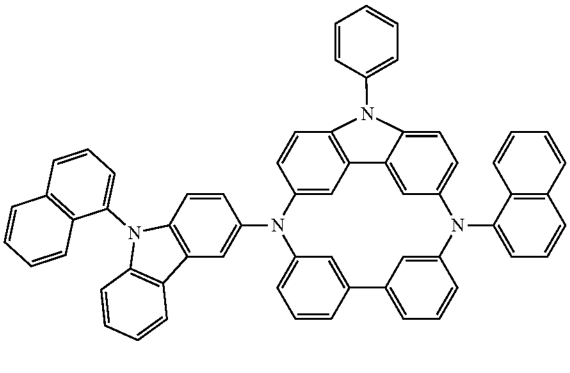
-continued
276
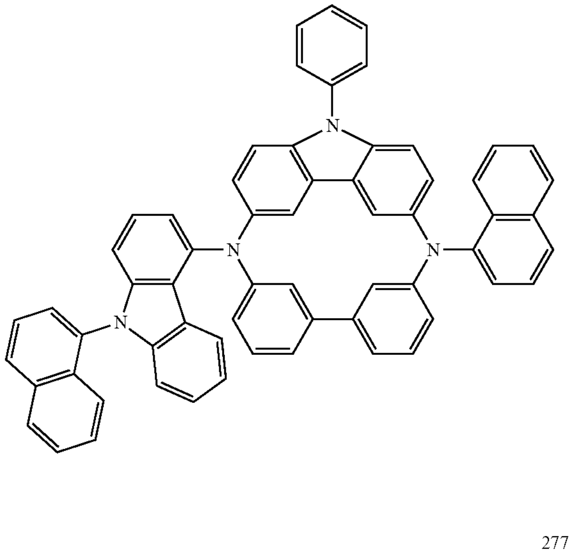
277
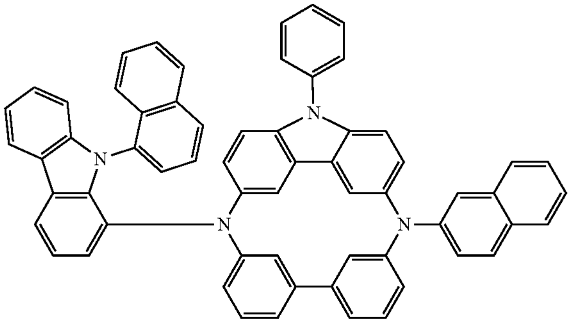
278
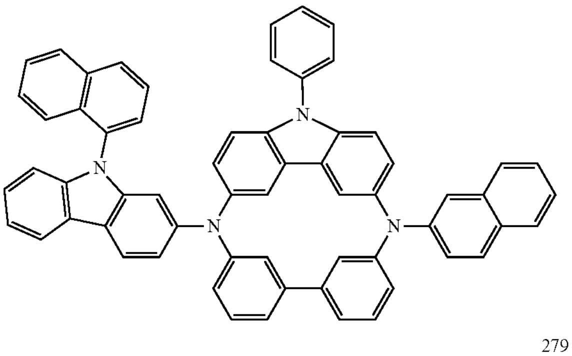
279
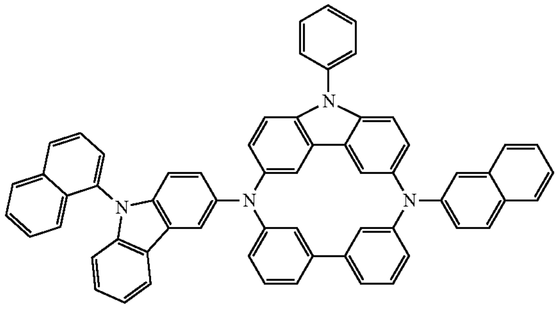

-continued
280
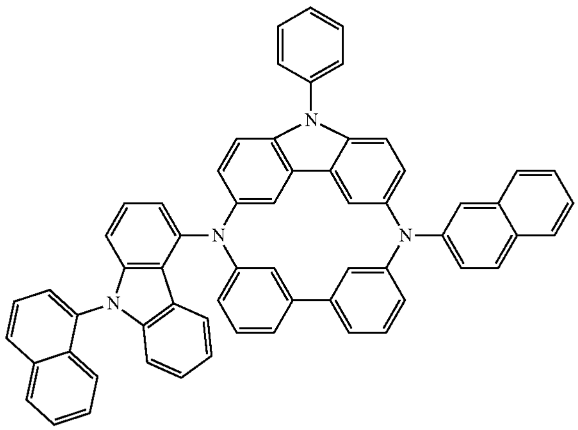
281
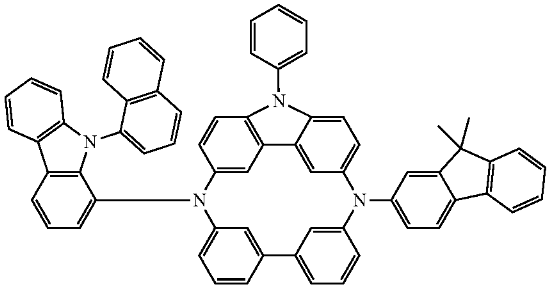
282
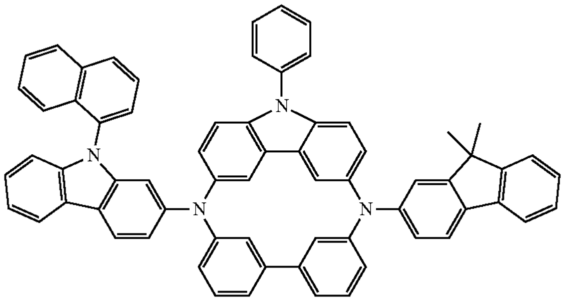
283
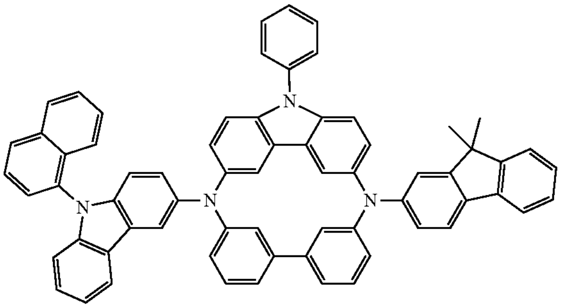
-continued
284
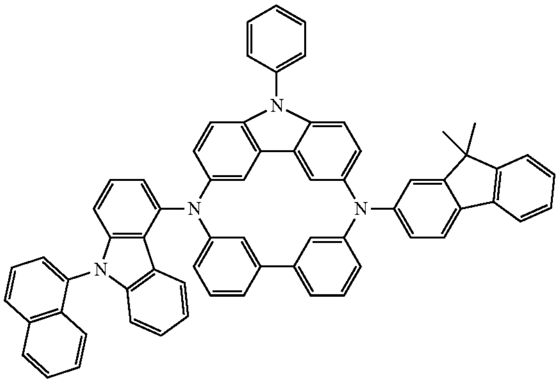
285
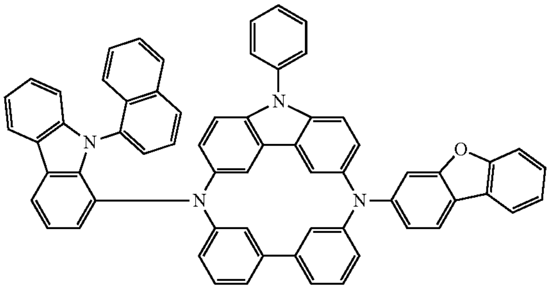
286
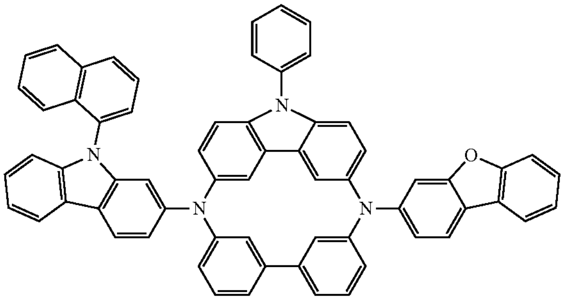
287
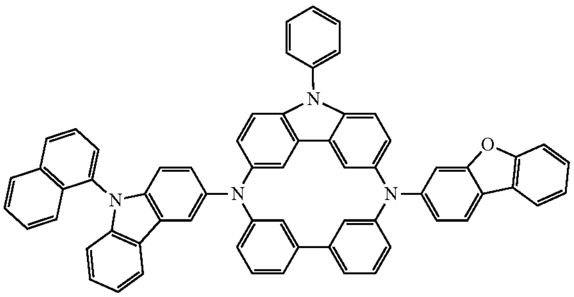

288
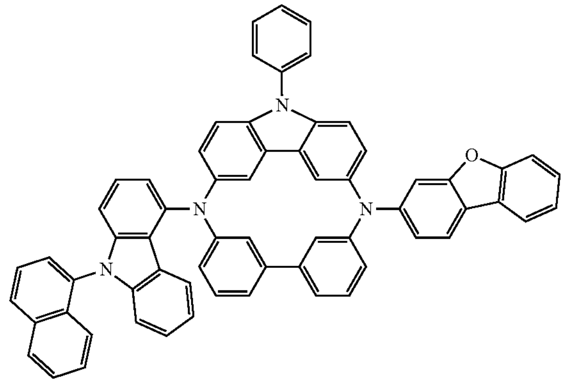
289
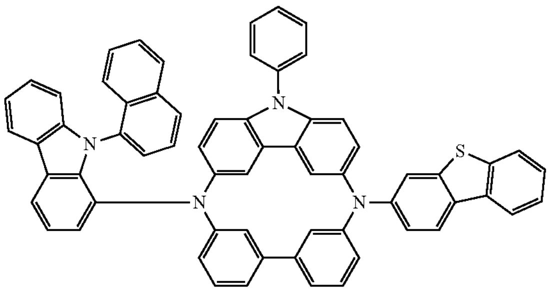
290
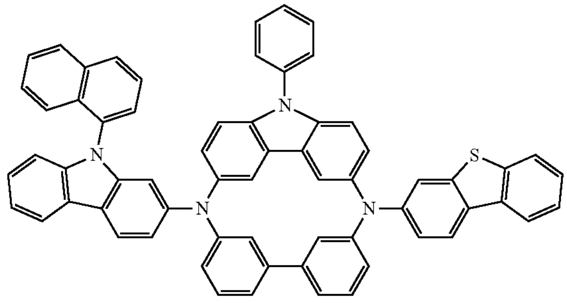
291
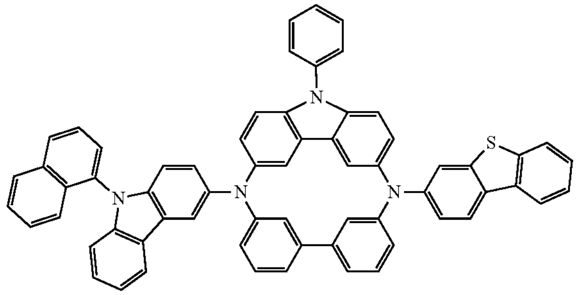
292
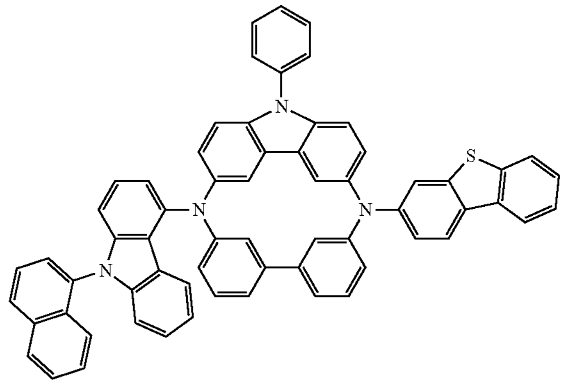
293
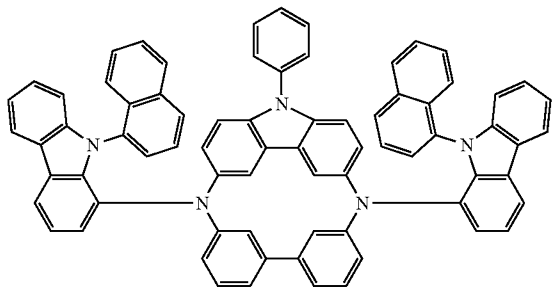
294
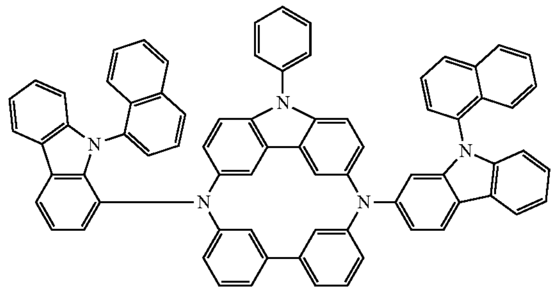
295
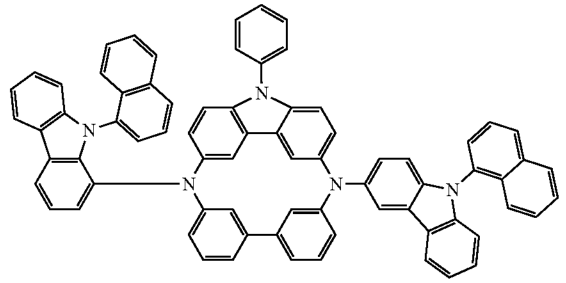

296
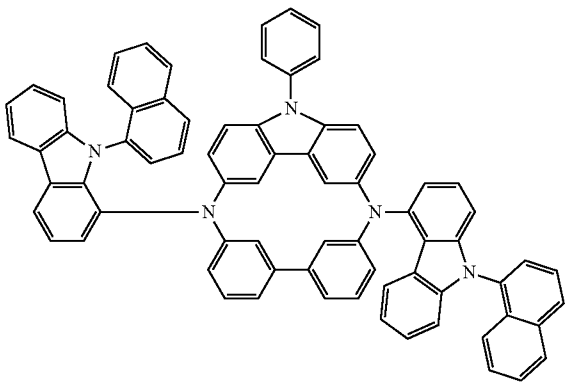
297
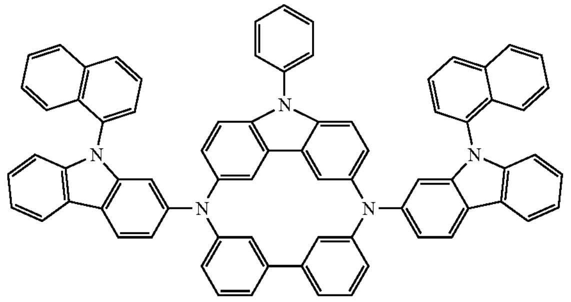
298
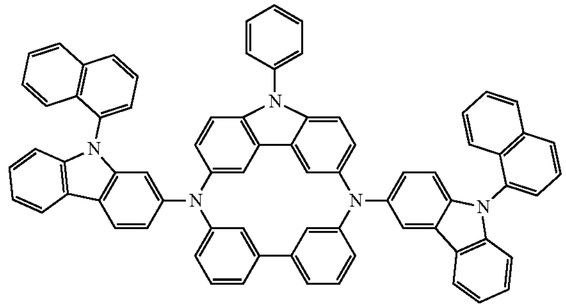
299
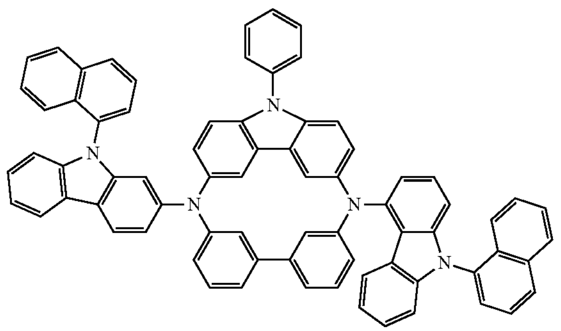
300
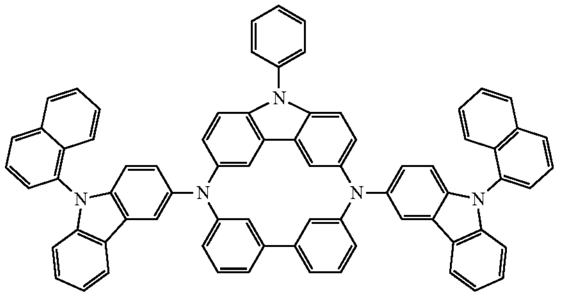
301
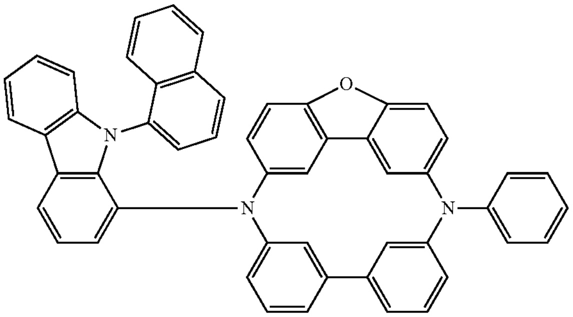
302
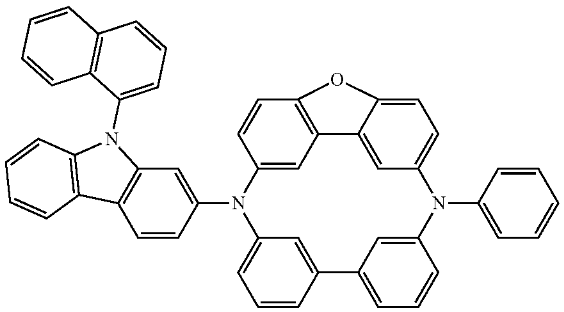
303
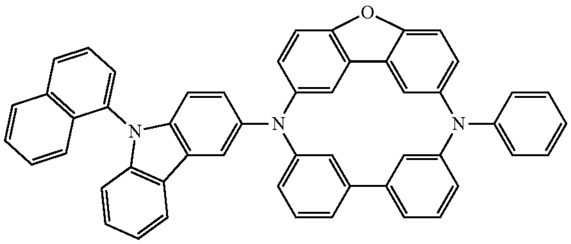
304
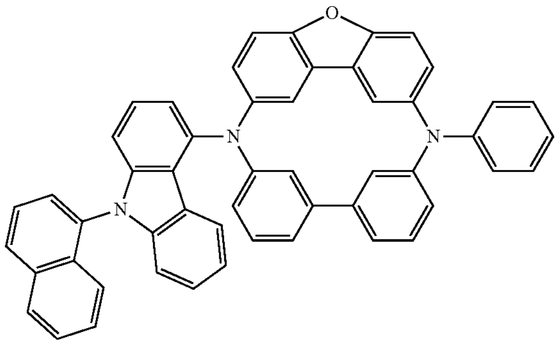

-continued
305
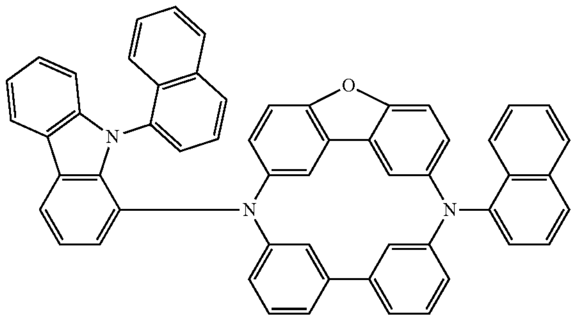
306
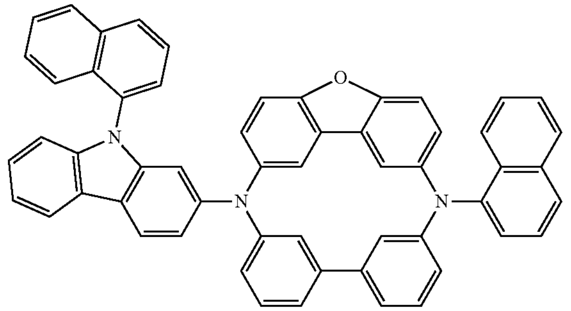
307
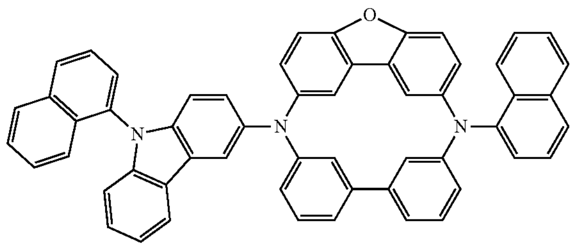
308
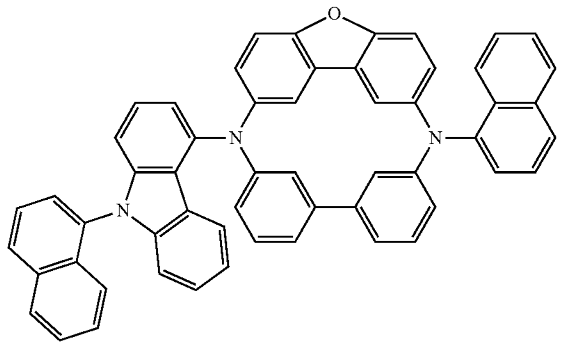
309
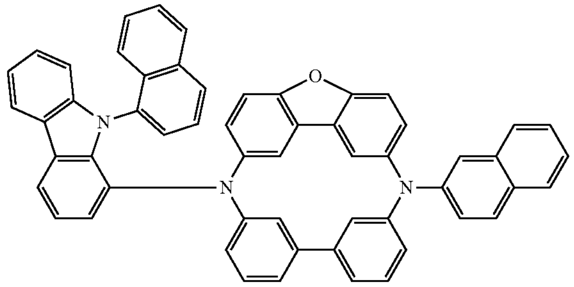
-continued
310
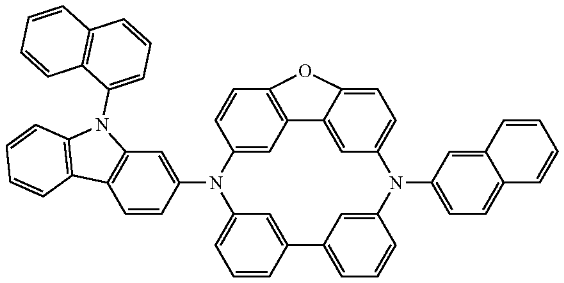
311
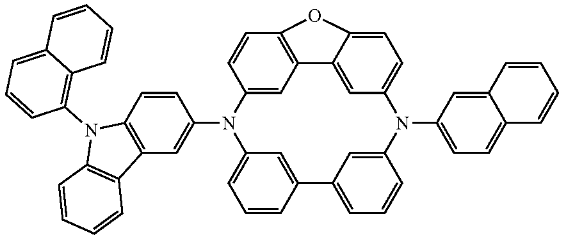
312
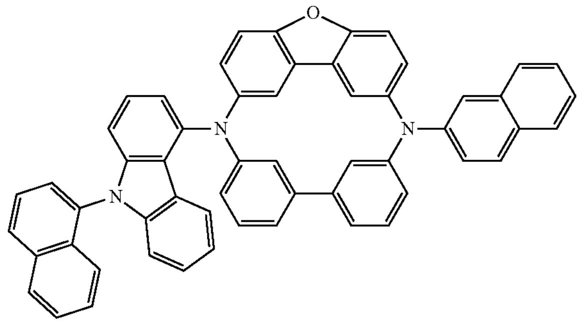
313
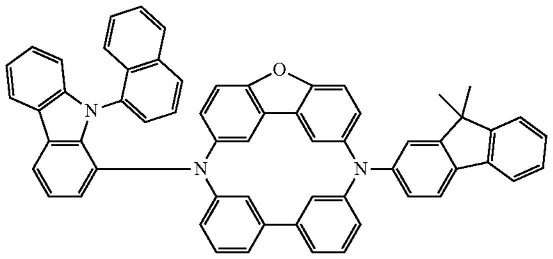
314
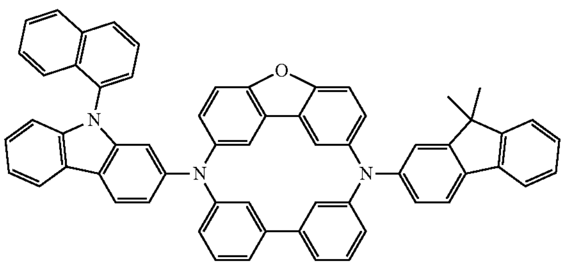

-continued
315
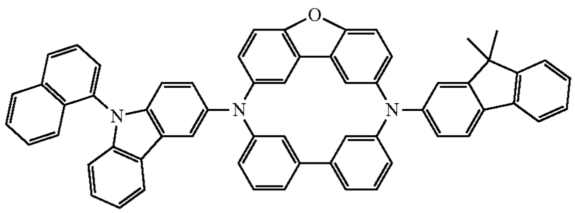
316
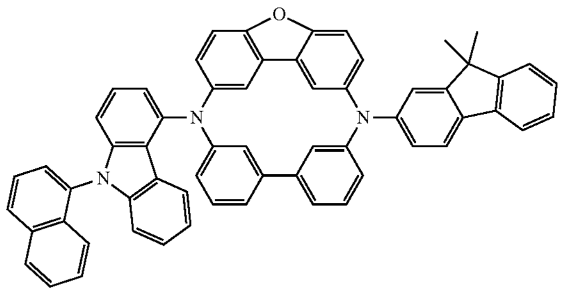
317
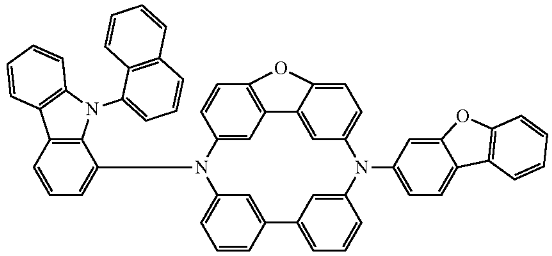
318
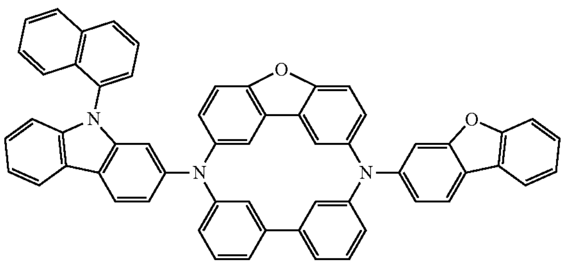
319
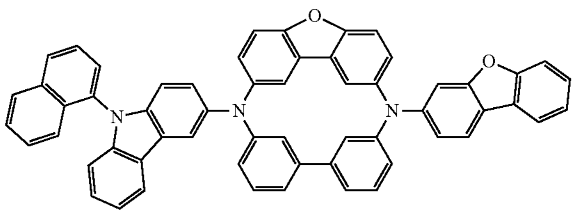
-continued
320
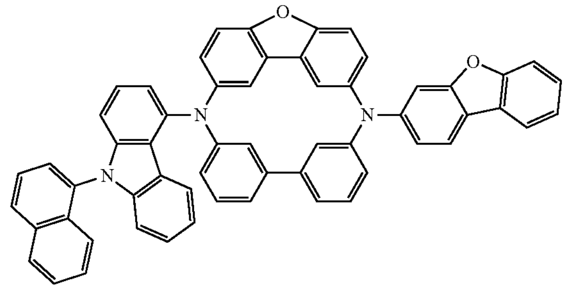
321
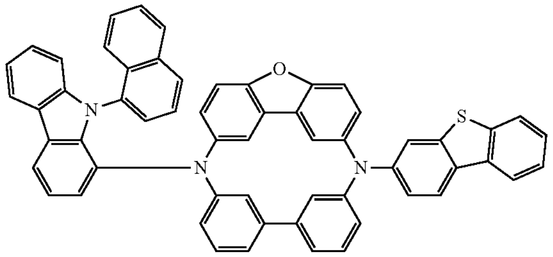
322
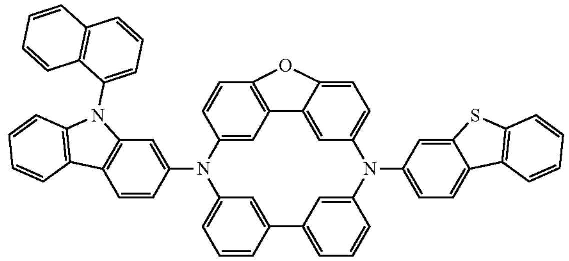
323
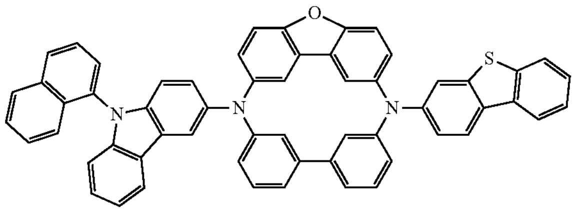
324
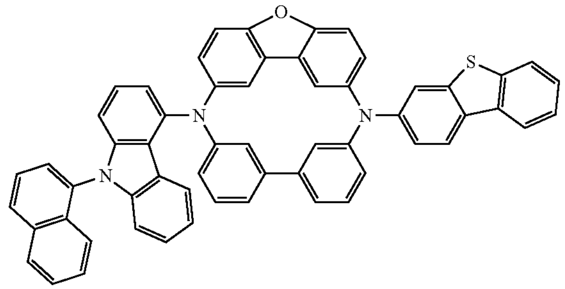

-continued
325
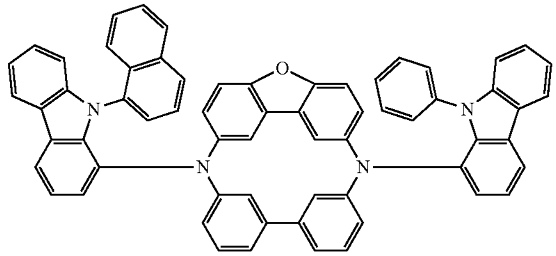
326
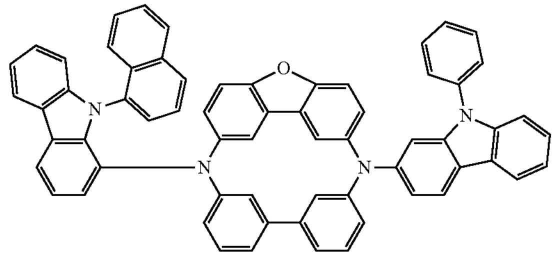
327
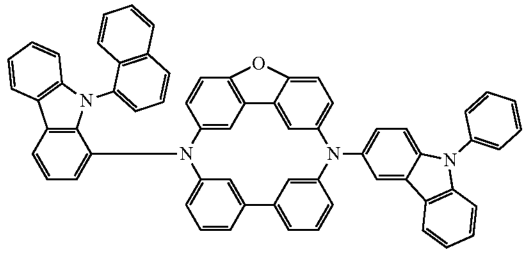
328
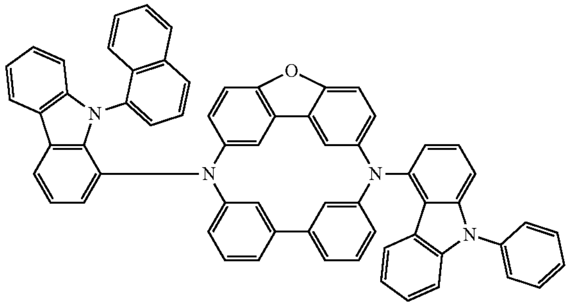
329
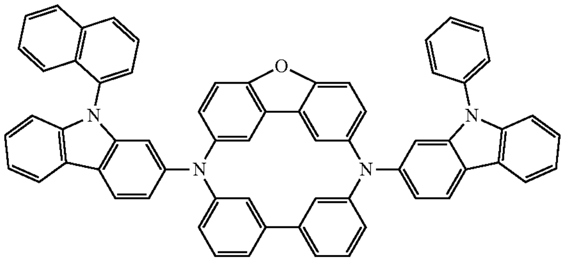
-continued
330
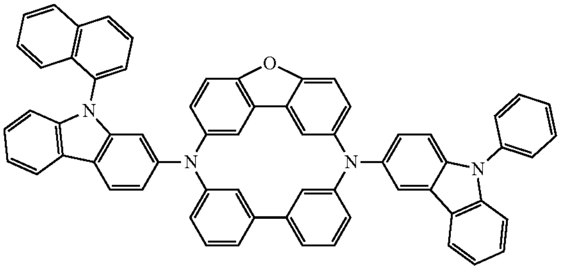
331
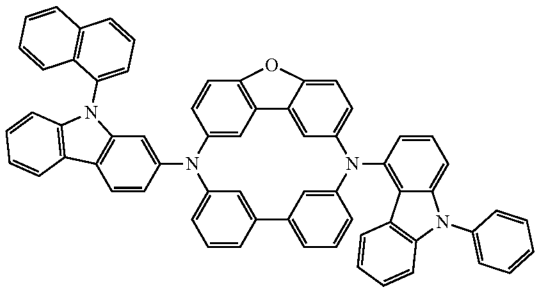
332
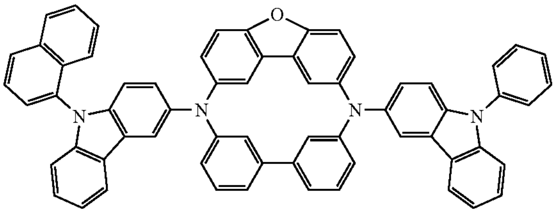
333
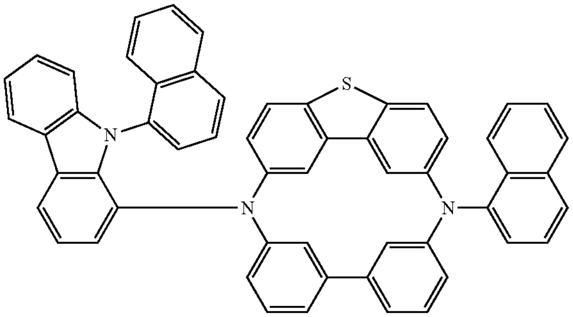
334
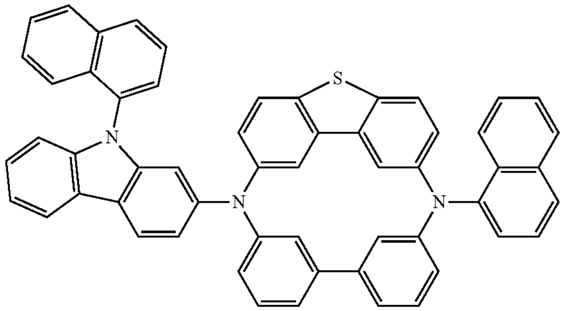

-continued
335
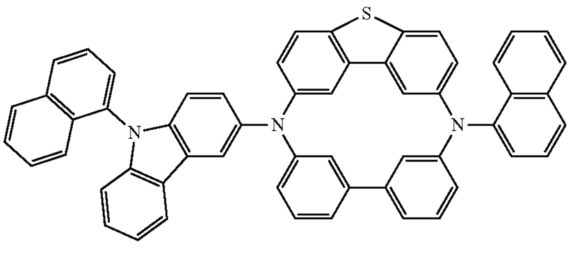
336
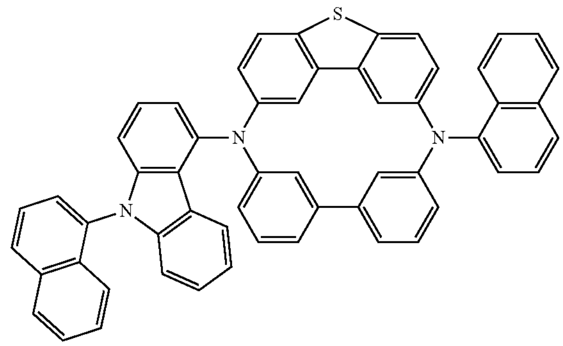
337
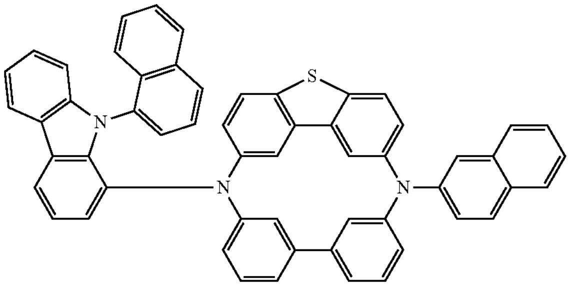
338
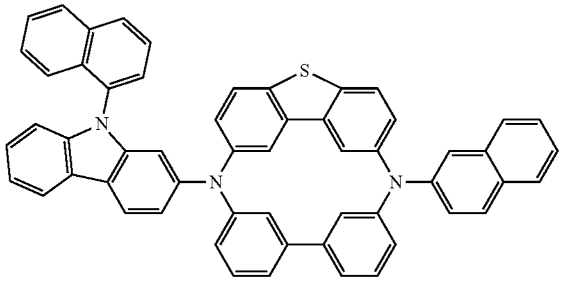
339
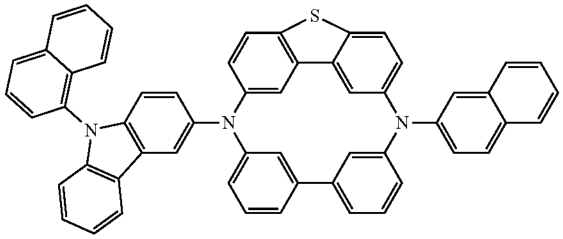
-continued
340
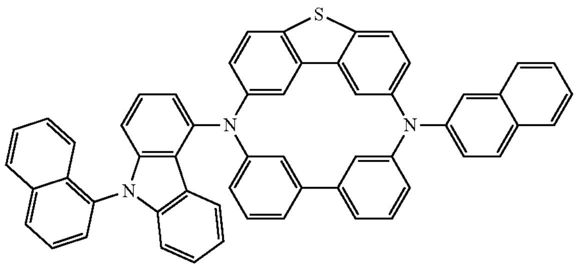
341
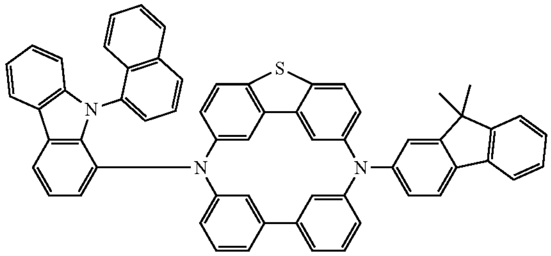
342
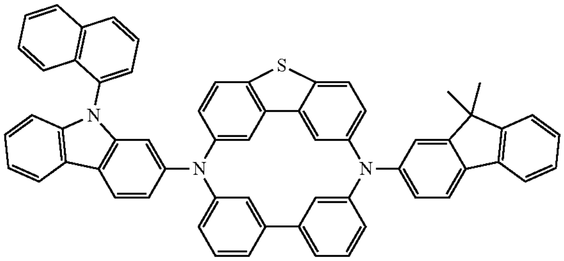
343
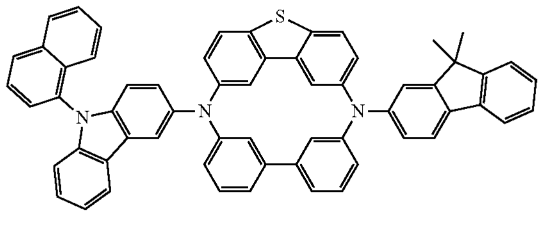
344
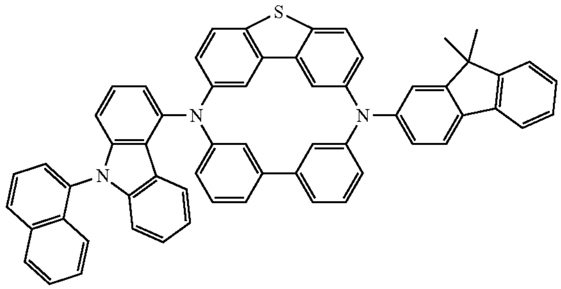

345
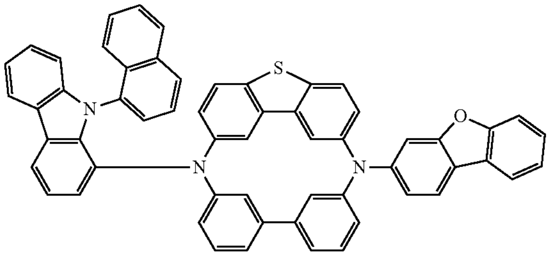
346
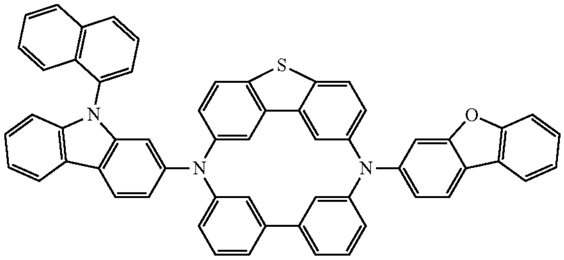
347
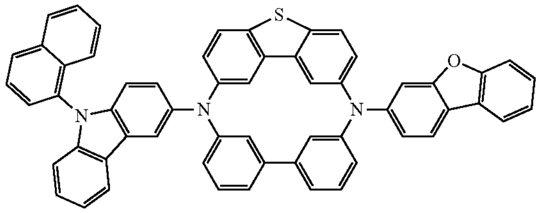
348
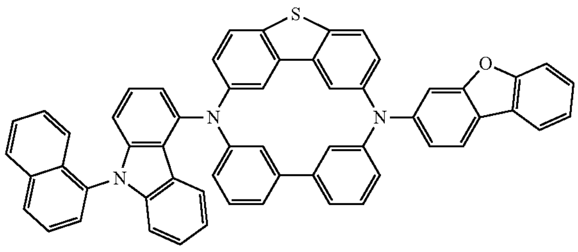
349
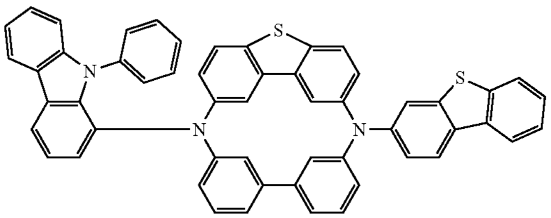
350
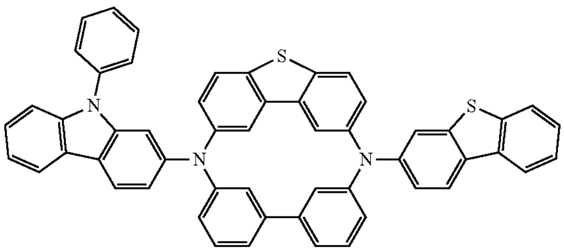
351
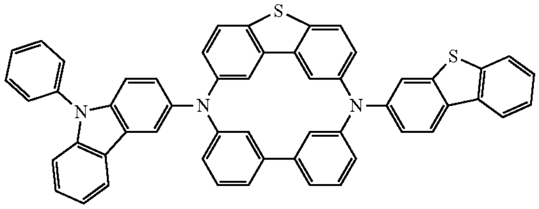
352
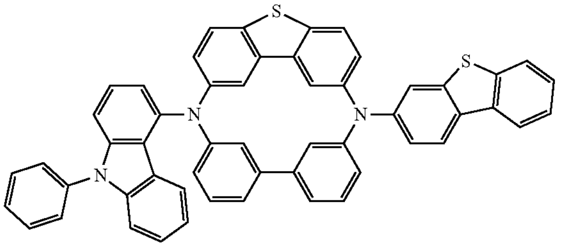
353
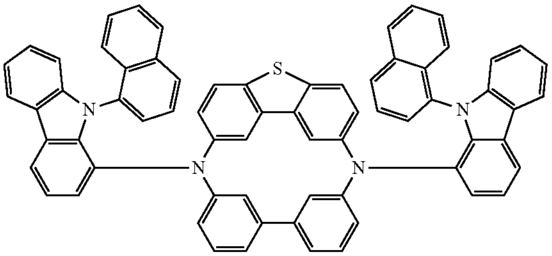
354
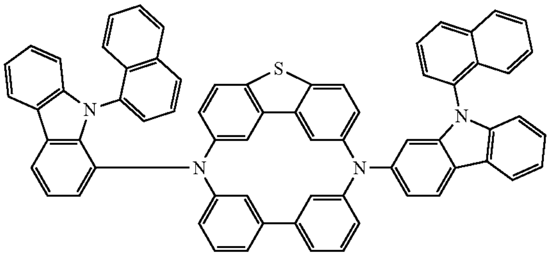
355
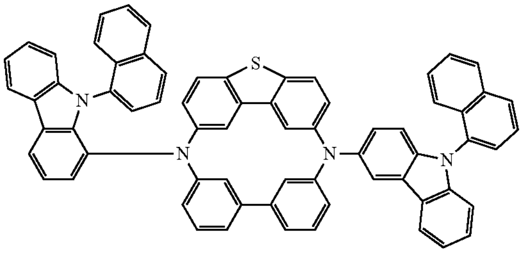

-continued
356
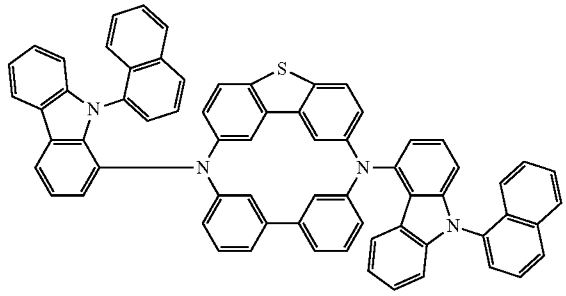
357
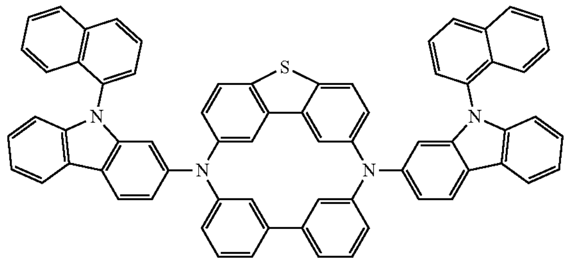
358
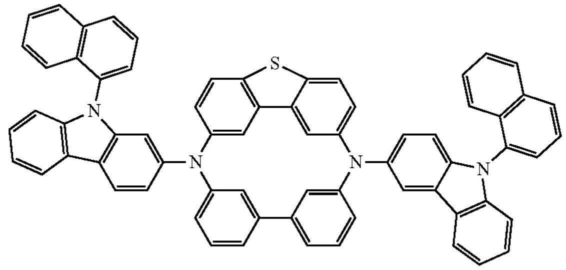
359
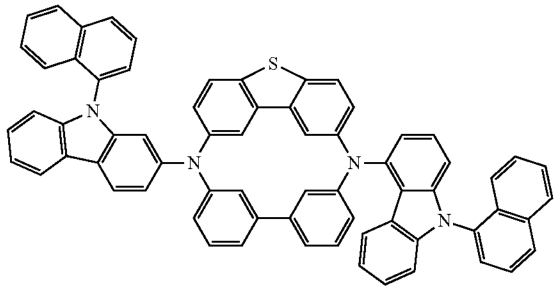
360
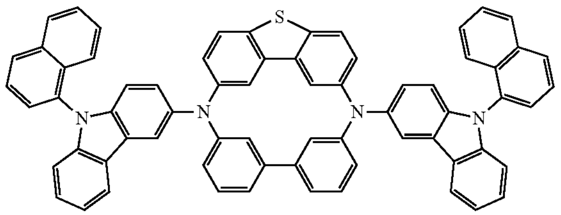
-continued
361
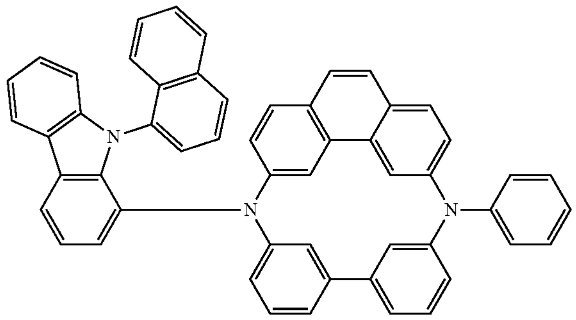
362
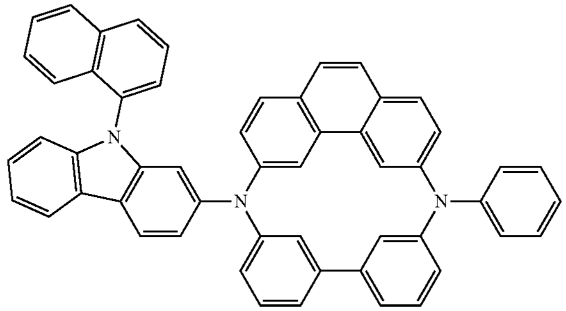
363
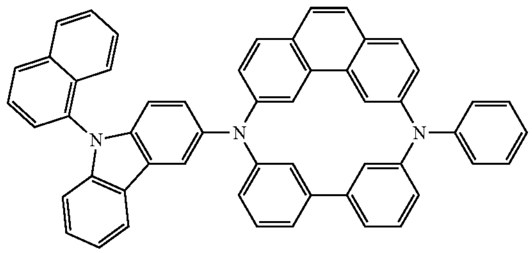
364
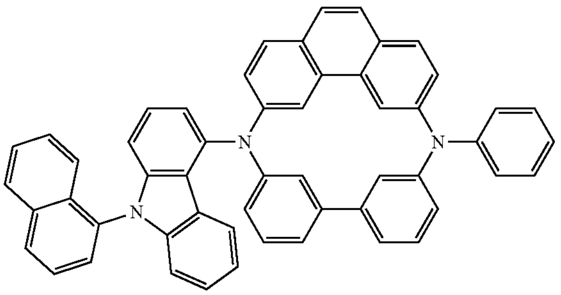
365
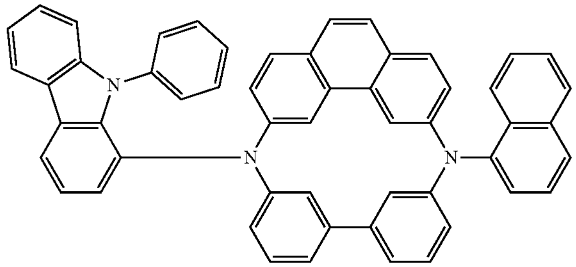

-continued
366
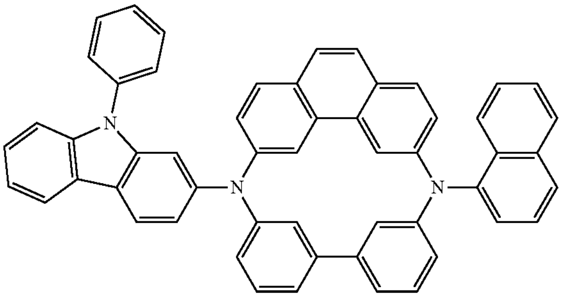
367
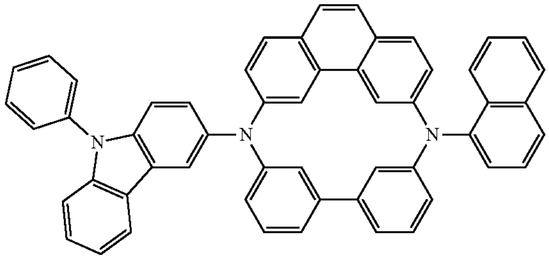
368
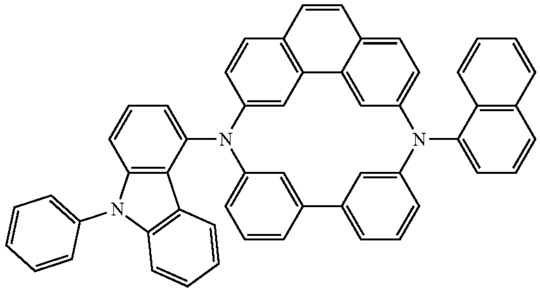
369
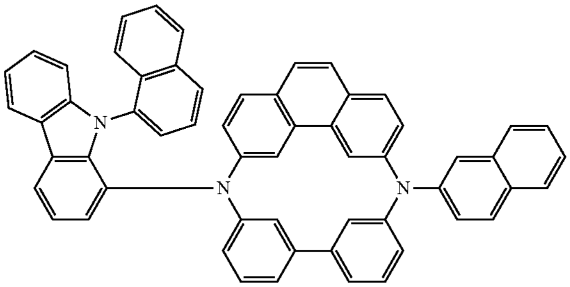
370
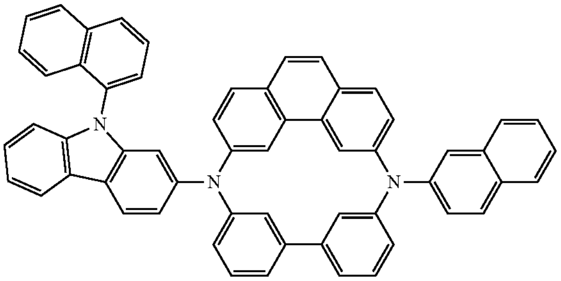
-continued
371
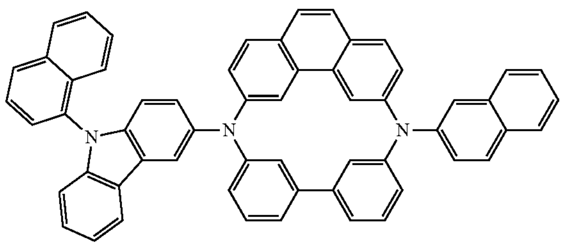
372
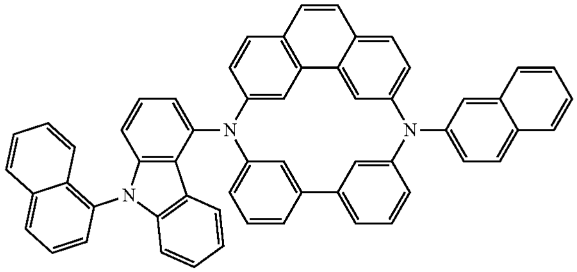
373
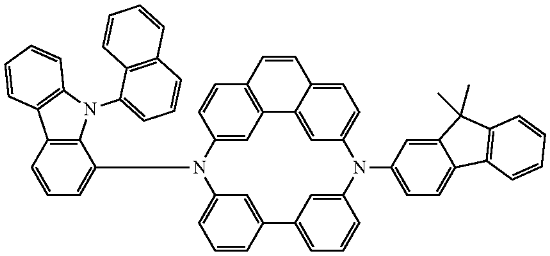
374
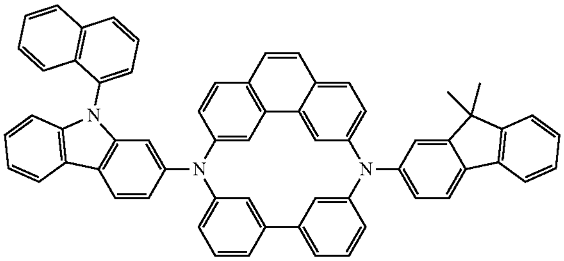
375
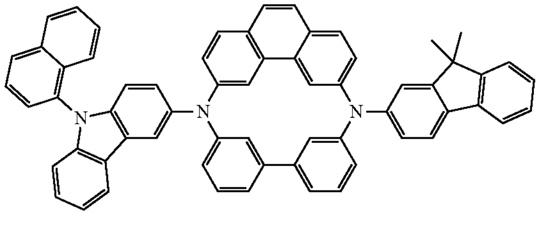

-continued
376
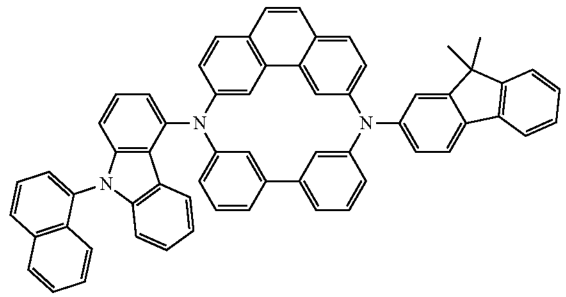
377
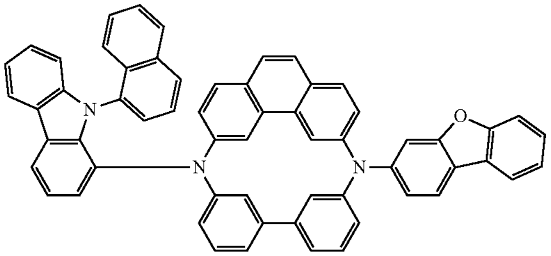
378
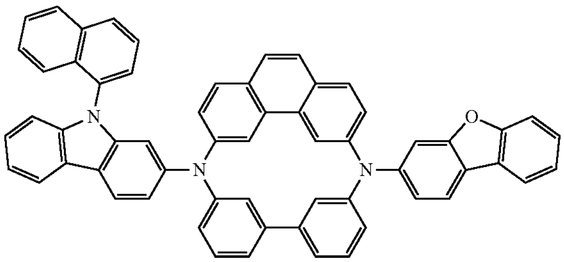
379
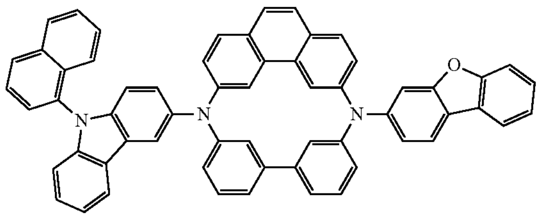
380
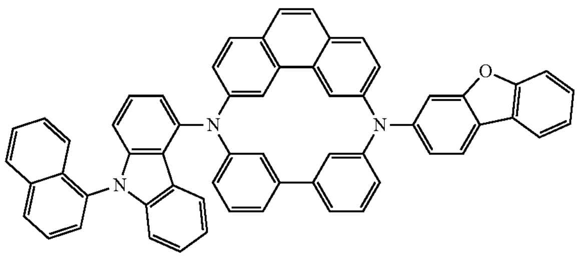
-continued
381
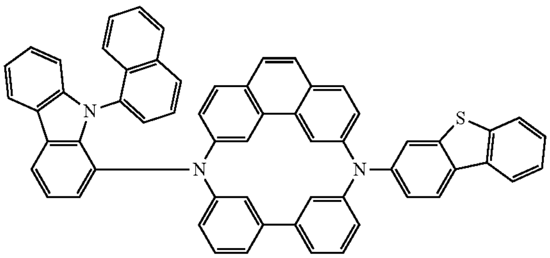
382
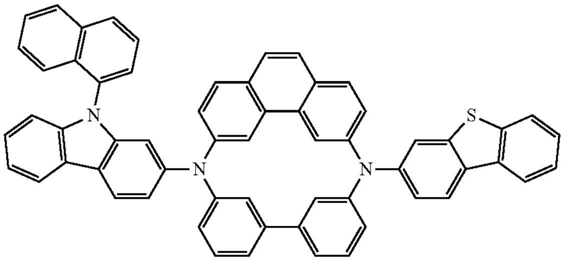
383
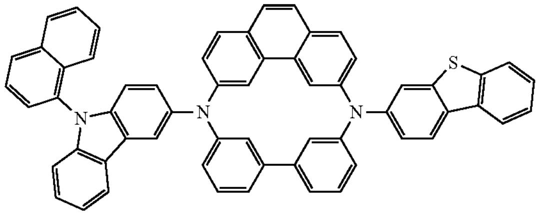
384
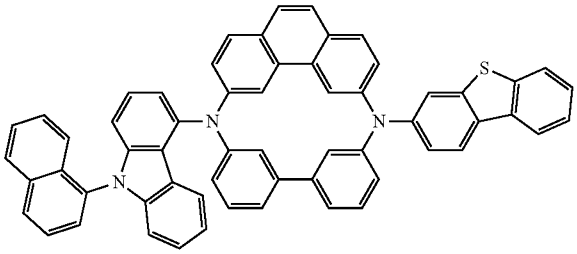
385
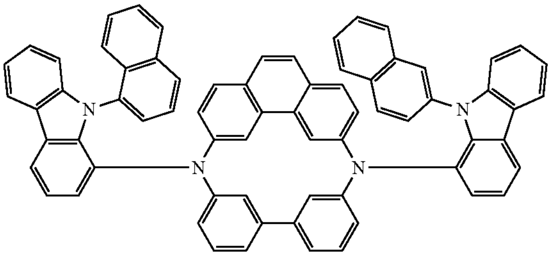

-continued
386
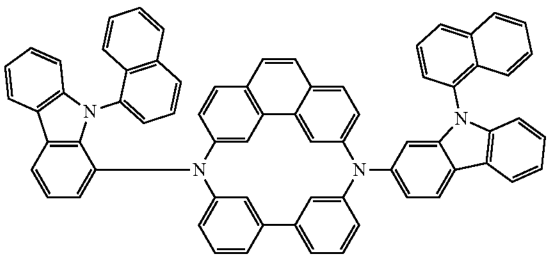
387
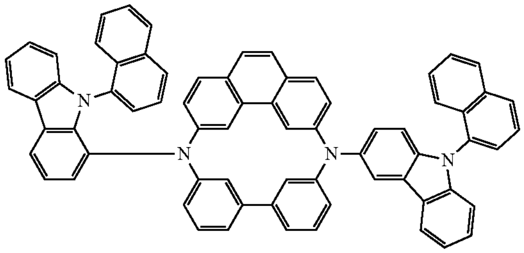
388
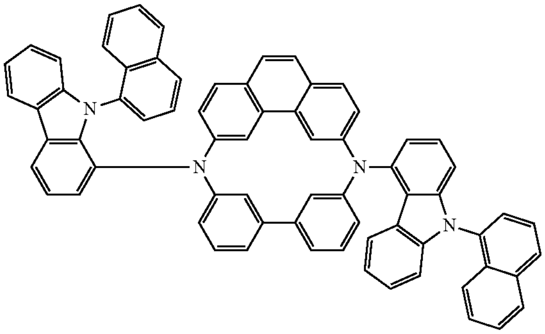
389
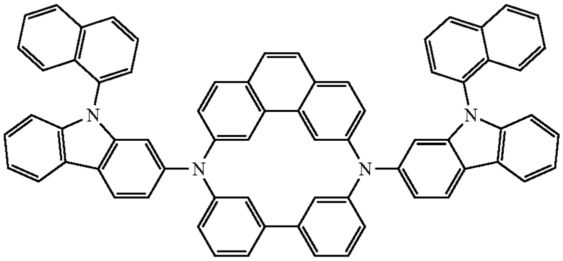
390
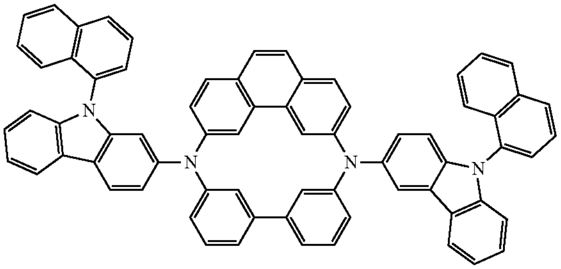
-continued
391
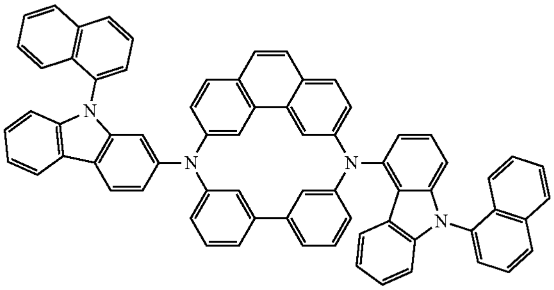
392
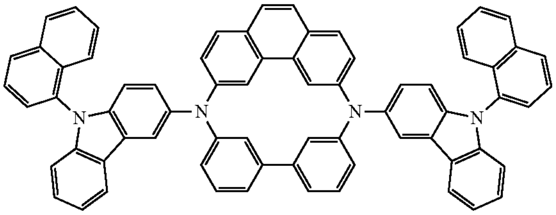
393
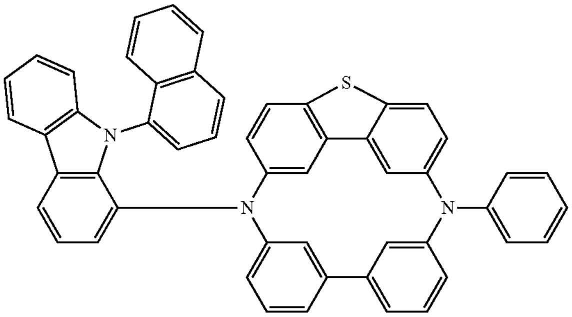
394
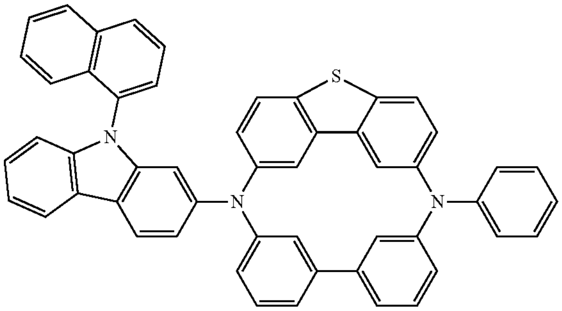
395
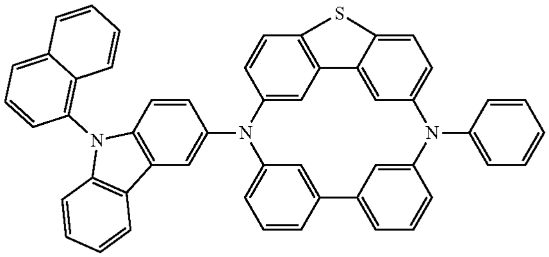

396
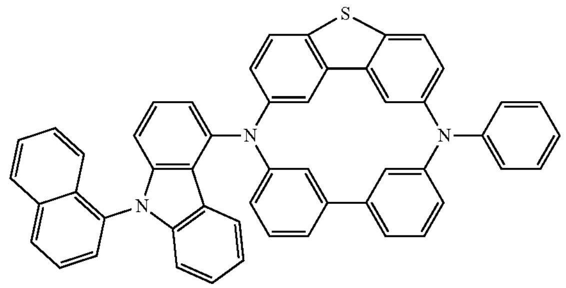
397
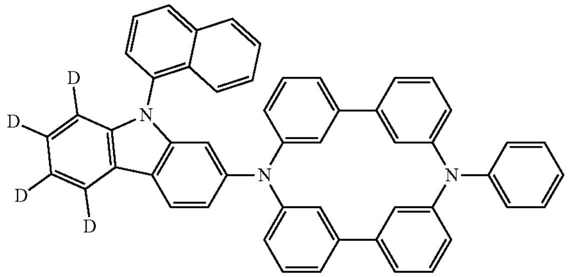
398
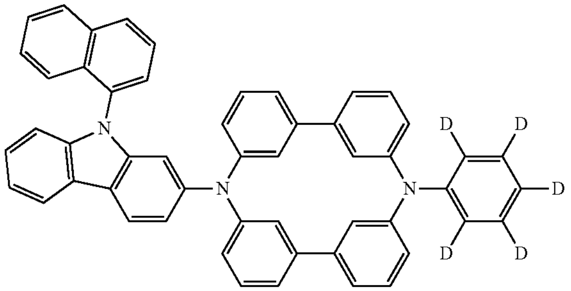
399
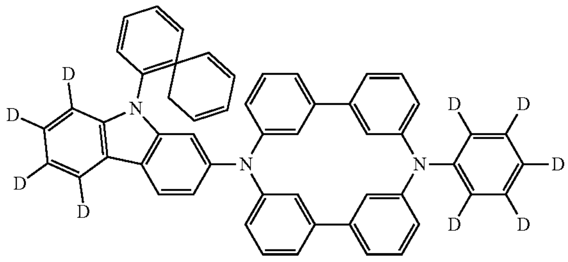
400
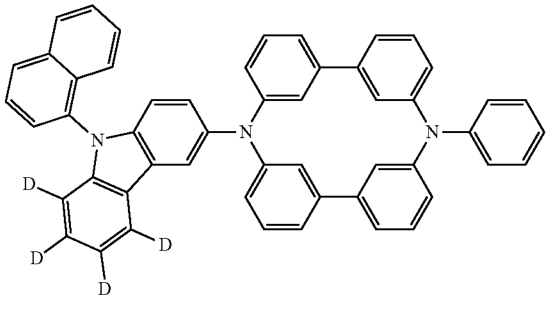
401
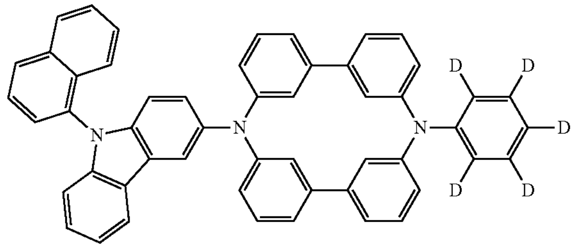
402
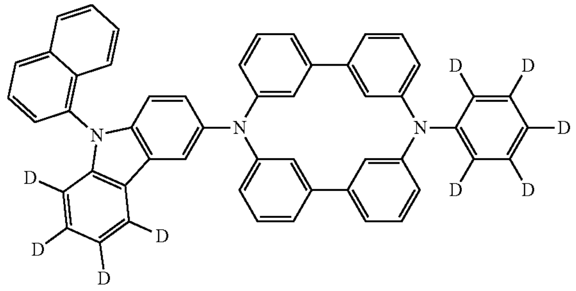
403
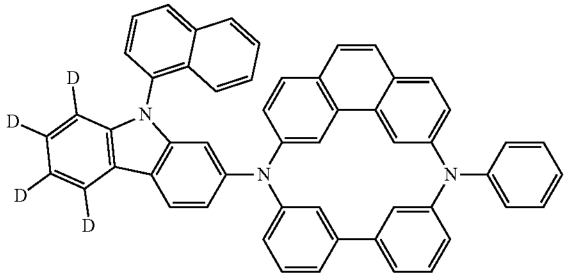
404
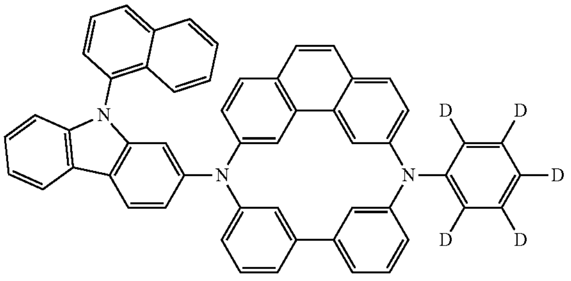
405
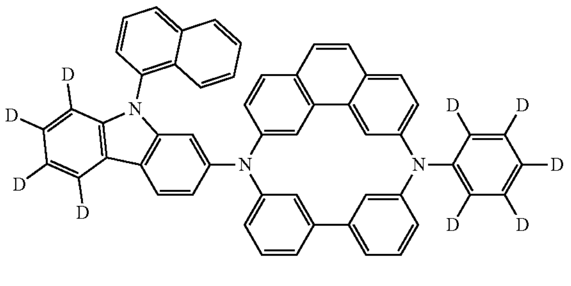

-continued

406

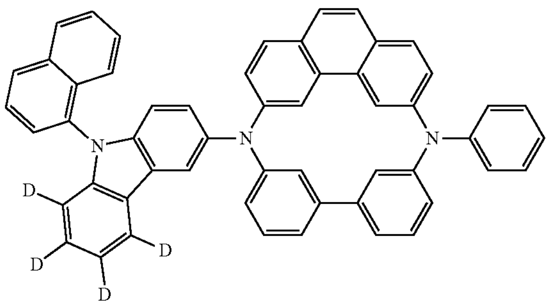

407

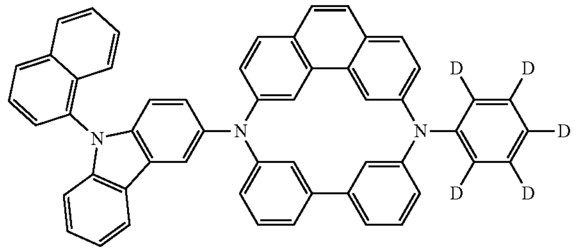

408

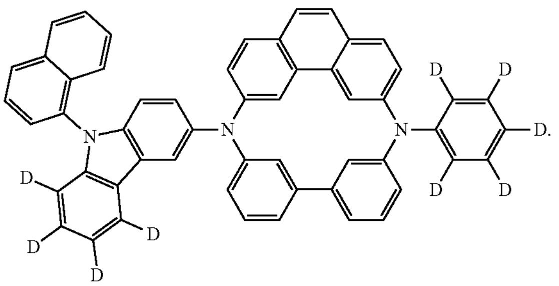

The light-emitting device may include the heterocyclic compound represented by Formula 1.

While not being bound by theory, as the light-emitting device includes the heterocyclic compound represented by Formula 1, due to excellent or suitable hole transportability of the heterocyclic compound represented by Formula 1, the light-emitting device may have a high efficiency, a low voltage, a high luminance, and long lifespan characteristics.

For example, in the heterocyclic compound represented by Formula 1, two amine groups may be bound to groups represented by CY3 and CY4, and the group represented by Formula 2 may be included as a substituent. Thus, as compared with a heterocyclic compound that may not satisfy such conditions, the heterocyclic compound represented by Formula 1 may easily (or more easily) form a resonance structure, and improved hole transportability may be realized due to the resonance structure.

Thus, an electronic device, e.g., a light-emitting device, including the heterocyclic compound represented by Formula 1 may have a low driving voltage, improved luminance, improved luminescence efficiency, and/or improved lifespan.

Methods of synthesizing the heterocyclic compound represented by Formula 1 may be easily understood by those of ordinary skill in the art by referring to Synthesis Examples and Examples described herein.

At least one of the heterocyclic compounds represented by Formula 1 may be used in a light-emitting device (e.g., an organic light-emitting device). According to one or more embodiments, a light-emitting device may include: a first electrode; a second electrode facing the first electrode; an interlayer located between the first electrode and the second electrode and including an emission layer; and the heterocyclic compound represented by Formula 1.

In some embodiments, the first electrode of the light-emitting device may be an anode, the second electrode of the light-emitting device may be a cathode, the interlayer may further include a hole transport region between the first electrode and the emission layer, and an electron transport region between the emission layer and the second electrode, the hole transport region may include a hole injection layer, a hole transport layer, an emission auxiliary layer, an electron blocking layer, or any combination thereof, and the electron transport region may include a buffer layer, a hole blocking layer, an electron control layer, an electron transport layer, an electron injection layer, or any combination thereof.

In one or more embodiments, the heterocyclic compound represented by Formula 1 may be included between the first electrode and the second electrode of the light-emitting device. For example, the heterocyclic compound represented by Formula 1 may be included in the interlayer. For example, the heterocyclic compound represented by Formula 1 may be included in the hole transport region.

In one or more embodiments, the heterocyclic compound represented by Formula 1 may be included in the hole injection layer, the hole transport layer, the emission auxiliary layer, the electron blocking layer, or any combination thereof.

In one or more embodiments, the heterocyclic compound represented by Formula 1 may be included in the hole transport layer.

The emission layer may emit red light, green light, blue light, and/or white light.

In some embodiments, the emission layer may emit blue light. The blue light may have a maximum emission wavelength in a range of about 400 nanometers (nm) to about 490 nm.

In some embodiments, the emission layer may include a host. For example, a host included in the emission layer may include at least two different hosts.

In some embodiments, the emission layer may further include a dopant. In some embodiments, the dopant may include a phosphorescent dopant, a fluorescent dopant, a delayed fluorescence material, or a combination thereof.

In some embodiments, the emission layer may include a phosphorescent dopant, a delayed fluorescence material, or a combination thereof.

In some embodiments, the dopant may include a transition metal and ligand(s) in the number of m, m may be an integer selected from 1 to 6, the ligand(s) in the number of m may be identical to or different from each other, at least one of the ligand(s) in the number of m may be bound to the transition metal via a carbon-transition metal bond, and the carbon-transition metal bond may be a coordinate bond. For example, at least one of the ligand(s) in the number of m may be a carbene ligand (e.g., $Ir(pmp)_3$ and/or the like). The transition metal may be, for example, iridium, platinum, osmium, palladium, rhodium, and/or gold. The emission layer and the dopant may respectively be understood by referring to the descriptions of the emission layer and the dopant provided herein:

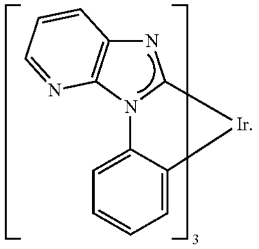

Ir(pmp)$_3$

In one or more embodiments, the light-emitting device may include a capping layer located outside the first electrode or the second electrode. For example, the heterocyclic compound represented by Formula 1 may be included in the capping layer.

In one or more embodiments, the light-emitting device may further include at least one of a first capping layer located outside a first electrode and/or a second capping layer located outside a second electrode, and at least one of the first capping layer and/or the second capping layer may include the heterocyclic compound represented by Formula 1. The first capping layer and the second capping layer may respectively be understood by referring to the descriptions of the first capping layer and the second capping layer provided herein.

The expression that an "(interlayer and/or a capping layer) includes a heterocyclic compound represented by Formula 1" as used herein may be construed as meaning that the "(interlayer and/or the capping layer) may include one identical heterocyclic compounds of Formula 1 or two or more different heterocyclic compounds of Formula 1".

For example, the interlayer and/or capping layer may include the heterocyclic compound represented by Formula 1.

In one or more embodiments, the heterocyclic compound represented by Formula 1 may be included in the interlayer. For example, the heterocyclic compound represented by Formula 1 may be present in the hole transport region. For example, the heterocyclic compound represented by Formula 1 may be present in the hole transport layer.

The term "interlayer" as used herein refers to a single layer and/or a plurality of all layers located between a first electrode and a second electrode in a light-emitting device.

According to one or more embodiments, an electronic apparatus may include the light-emitting device. The electronic apparatus may further include a thin-film transistor. In some embodiments, the electronic apparatus may further include a thin-film transistor including a source electrode and drain electrode, and a first electrode of the light-emitting device may be electrically connected (e.g., electrically coupled) to the source electrode or the drain electrode. The electronic apparatus may further include a color filter, a color-conversion layer, a touchscreen layer, a polarizing layer, or any combination thereof. The electronic apparatus may be understood by referring to the description of the electronic apparatus provided herein.

Description of FIG. 1

FIG. 1 is a schematic view of a light-emitting device 10 according to one or more embodiments. The light-emitting device 10 may include a first electrode 110, an interlayer 130, and a second electrode 150.

Hereinafter, the structure of the light-emitting device 10 according to one or more embodiments and a method of manufacturing the light-emitting device 10 according to one or more embodiments will be described in connection with FIG. 1.

First Electrode 110

In FIG. 1, a substrate may be additionally located under the first electrode 110 or above the second electrode 150. The substrate may be a glass substrate and/or a plastic substrate. The substrate may be a flexible substrate including plastic having excellent or suitable heat resistance and/or durability, for example, polyimide, polyethylene terephthalate (PET), polycarbonate, polyethylene naphthalate, polyarylate (PAR), polyetherimide, or any combination thereof.

The first electrode 110 may be formed by depositing or sputtering, on the substrate, a material for forming the first electrode 110. When the first electrode 110 is an anode, a high work function material that may easily (or suitably) inject holes may be used as a material for a first electrode.

The first electrode 110 may be a reflective electrode, a semi-transmissive electrode, or a transmissive electrode. When the first electrode 110 is a transmissive electrode, a material for forming the first electrode 110 may be indium tin oxide (ITO), indium zinc oxide (IZO), tin oxide ($SnO_2$), zinc oxide (ZnO), or any combination thereof.

In some embodiments, when the first electrode 110 is a semi-transmissive electrode or a reflective electrode, magnesium (Mg), silver (Ag), aluminum (Al), aluminum-lithium (Al—Li), calcium (Ca), magnesium-indium (Mg—In), magnesium-silver (Mg—Ag), or any combination thereof may be used as a material for forming the first electrode 110.

The first electrode 110 may have a single-layered structure including (e.g., consisting of) a single layer or a multi-layered structure including two or more layers. In some embodiments, the first electrode 110 may have a triple-layered structure of ITO/Ag/ITO.

Interlayer 130

The interlayer 130 may be on the first electrode 110. The interlayer 130 may include an emission layer.

The interlayer 130 may further include a hole transport region between the first electrode 110 and the emission layer, and an electron transport region between the emission layer and the second electrode 150.

The interlayer 130 may further include metal-containing compounds such as organometallic compounds, inorganic materials such as quantum dots, and/or the like, in addition to various suitable organic materials.

The interlayer 130 may include: i) at least two emitting units sequentially stacked between the first electrode 110 and the second electrode 150; and ii) a charge generation layer located between the at least two emitting units. When the interlayer 130 includes the at least two emitting units and a charge generation layer, the light-emitting device 10 may be a tandem light-emitting device.

Hole Transport Region in Interlayer 130

The hole transport region may have i) a single-layered structure including (e.g., consisting of) a single layer including (e.g., consisting of) a single material, ii) a single-layered structure including (e.g., consisting of) a single layer including a plurality of different materials, or iii) a multi-layered structure having a plurality of layers including a plurality of different materials.

The hole transport region may include a hole injection layer, a hole transport layer, an emission auxiliary layer, an electron blocking layer, or a combination thereof.

For example, the hole transport region may have a multi-layered structure, e.g., a hole injection layer/hole transport layer structure, a hole injection layer/hole transport layer/emission auxiliary layer structure, a hole injection layer/emission auxiliary layer structure, a hole transport layer/emission auxiliary layer structure, or a hole injection layer/hole transport layer/electron blocking layer structure, wherein layers of each structure are sequentially stacked on the first electrode 110 in each stated order.

In some embodiments, the hole transport region may include the heterocyclic compound represented by Formula 1.

The hole transport region may further include a compound represented by Formula 201, a compound represented by Formula 202, or any combination thereof:

Formula 201

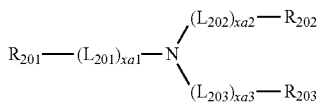

Formula 20x2

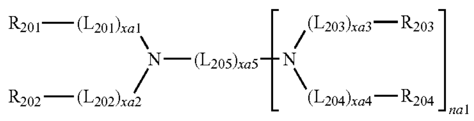

wherein, in Formulae 201 and 202, $L_{201}$ to $L_{204}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, $L_{205}$ may be *—O—*', *—S—*', *—N($Q_{201}$)-*', a $C_1$-$C_{20}$ alkylene group unsubstituted or substituted with at least one $R_{10a}$, a $C_2$-$C_{20}$ alkenylene group unsubstituted or substituted with at least one $R_{10a}$, a $C_3$-$C_{60}$ carbocyclic group unsubstituted or substituted with at least one $R_{10a}$, or a $C_1$-$C_{60}$ heterocyclic group unsubstituted or substituted with at least one $R_{10a}$, xa1 to xa4 may each independently be an integer selected from 0 to 5, xa5 may be an integer selected from 1 to 10, $R_{201}$ to $R_{204}$ and $Q_{201}$ may each independently be a $C_3$-$C_{60}$ carbocyclic group unsubstituted or substituted with at least one $R_{10a}$, or a $C_1$-$C_{60}$ heterocyclic group unsubstituted or substituted with at least one $R_{10a}$, $R_{201}$ and $R_{202}$ may optionally be bound to each other via a single bond, a $C_1$-$C_5$ alkylene group unsubstituted or substituted with at least one $R_{10a}$, or a $C_2$-$C_5$ alkenylene group unsubstituted or substituted with at least one $R_{10a}$ to form a $C_8$-$C_{60}$ polycyclic group (e.g., a carbazole group and/or the like) unsubstituted or substituted with at least one $R_{10a}$ (e.g., Compound HT16 described herein), $R_{203}$ and $R_{204}$ may optionally be bound to each other via a single bond, a $C_1$-$C_5$ alkylene group unsubstituted or substituted with at least one $R_{10a}$ or a $C_2$-$C_5$ alkenylene group unsubstituted or substituted with at least one $R_{10a}$ to form a $C_8$-$C_{60}$ polycyclic group unsubstituted or substituted with at least one $R_{10a}$, and na1 may be an integer selected from 1 to 4.

In some embodiments, Formulae 201 and 202 may each include at least one of groups represented by Formulae CY201 to CY217:

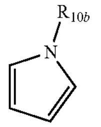

CY201

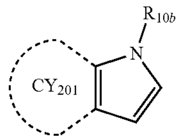

CY202

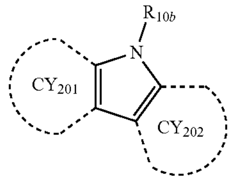

CY203

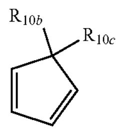

CY204

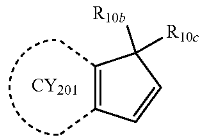

CY205

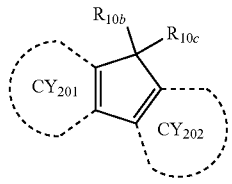

CY206

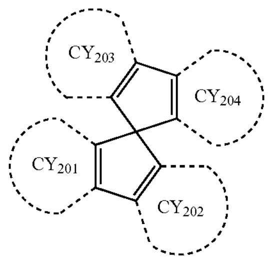

CY207

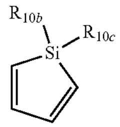

CY208

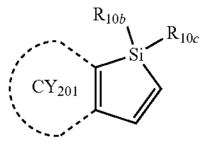

CY209

-continued

CY210

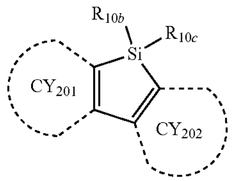

CY211

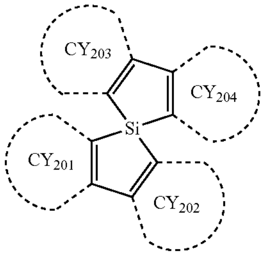

CY212

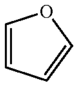

CY213

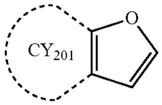

CY214

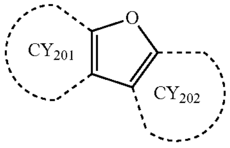

CY215

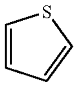

CY216

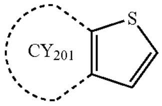

-continued

CY217

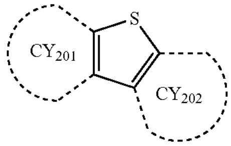

, wherein, in Formulae CY201 to CY217, $R_{10b}$ and $R_{10c}$ may each be understood by referring to the descriptions of $R_{10a}$, ring CY201 to ring CY204 may each independently be a $C_3$-$C_{20}$ carbocyclic group or a $C_1$-$C_{20}$ heterocyclic group, and in some embodiments, at least one hydrogen in Formulae CY201 to CY217 may be substituted with $R_{10a}$.

In one or more embodiments, in Formulae CY201 to CY217, ring $CY_{201}$ to ring $CY_{204}$ may each independently be a benzene group, a naphthalene group, a phenanthrene group, or an anthracene group.

In one or more embodiments, Formulae 201 and 202 may each include at least one of groups represented by Formulae CY201 to CY203.

In one or more embodiments, Formula 201 may include at least one of groups represented by Formulae CY201 to CY203 and at least one of groups represented by Formulae CY204 to CY217.

In one or more embodiments, in Formula 201, xa1 may be 1, $R_{201}$ may be represented by one of Formulae CY201 to CY203, xa2 may be 0, and $R_{202}$ may be represented by one of Formulae CY204 to CY207.

In one or more embodiments, Formulae 201 and 202 may each not include groups represented by Formulae CY201 to CY203.

In one or more embodiments, Formulae 201 and 202 may each not include groups represented by Formulae CY201 to CY203, and include at least one of groups represented by Formulae CY204 to CY217.

In one or more embodiments, Formulae 201 and 202 may each not include groups represented by Formulae CY201 to CY217.

In some embodiments, the hole transport region may include one compound selected from Compounds HT1 to HT46, m-MTDATA, TDATA, 2-TNATA, NPB (NPD), β-NPB, TPD, spiro-TPD, spiro-NPB, methylated-NPB, TAPC, HMTPD, 4,4',4"-tris(N-carbazolyl)triphenylamine (TCTA), polyaniline/dodecylbenzenesulfonic acid (PANI/DBSA), poly(3,4-ethylenedioxythiophene)/poly(4-styrenesulfonate) (PEDOT/PSS), polyaniline/camphorsulfonic acid (PANI/CSA), polyaniline/poly(4-styrenesulfonate (PANI/PSS), and combinations thereof:

HT1
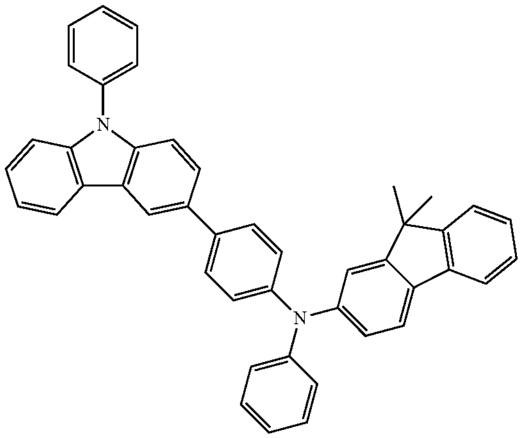
HT2
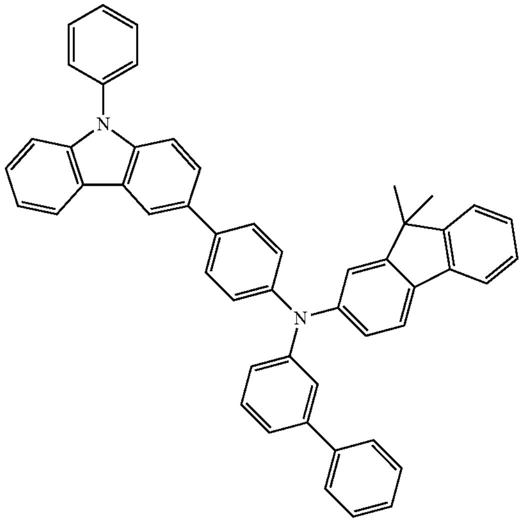
HT3
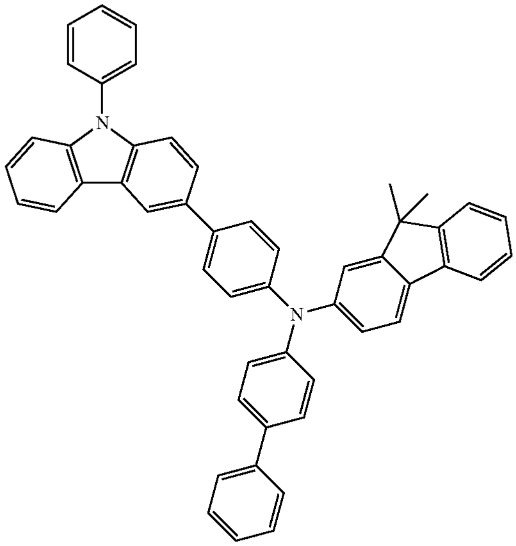
HT4
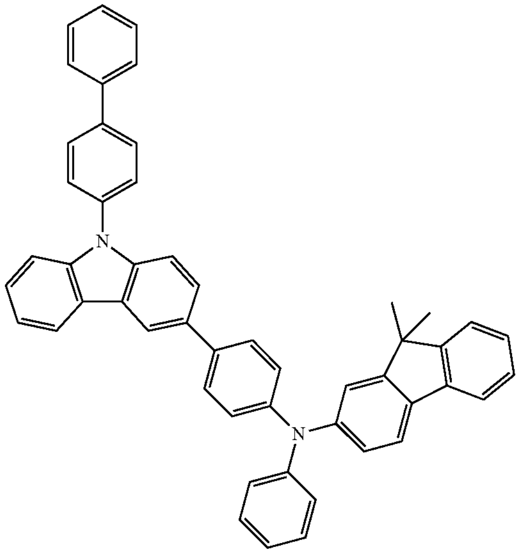
HT5
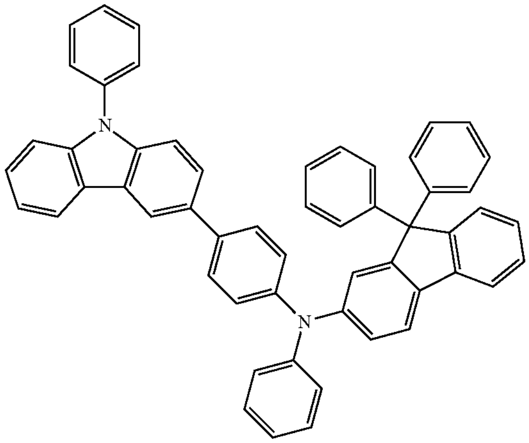
HT6
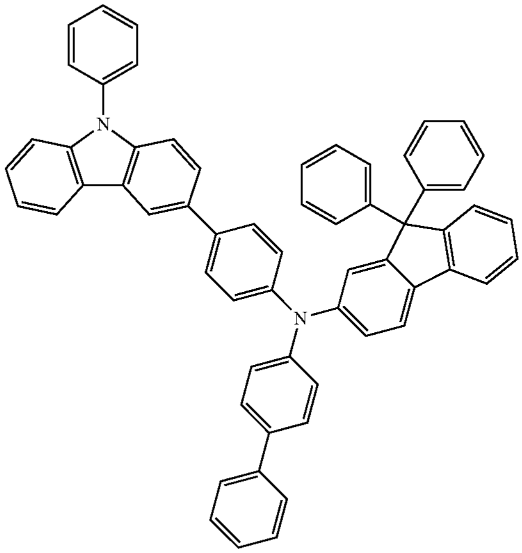

-continued
HT7
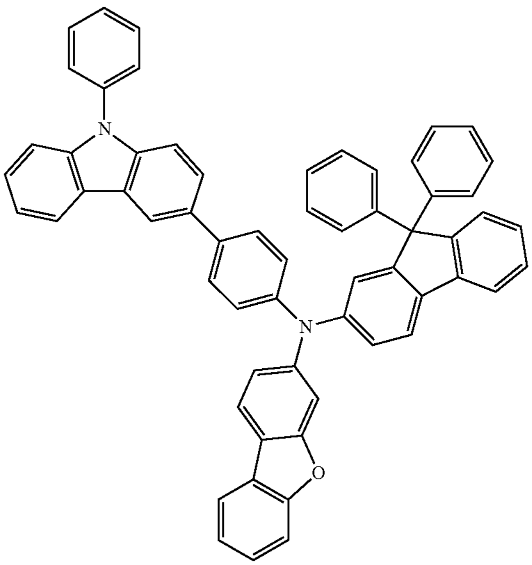
HT8
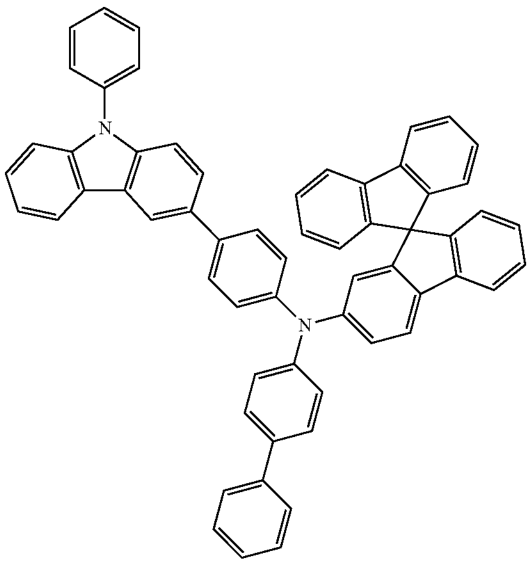
HT9
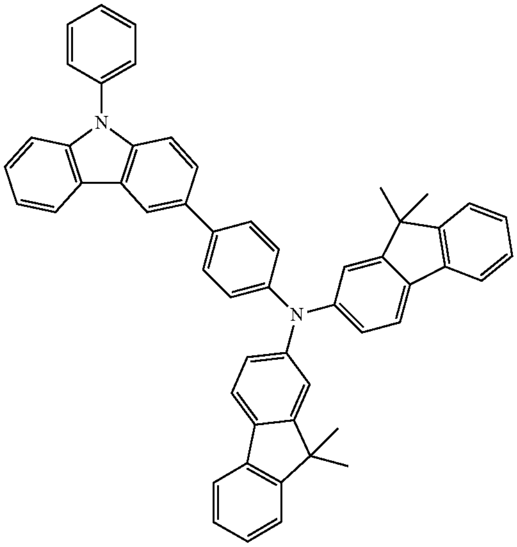
HT10
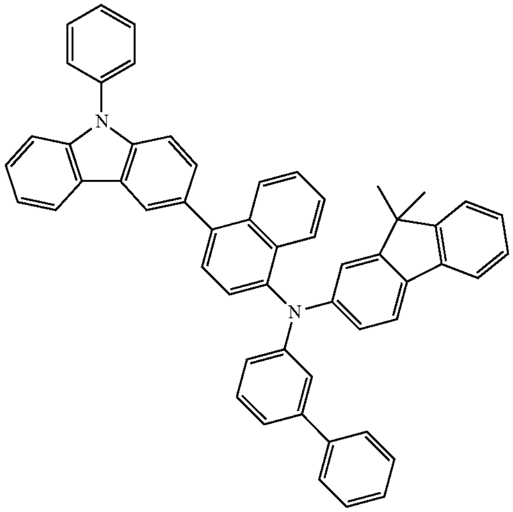
HT11
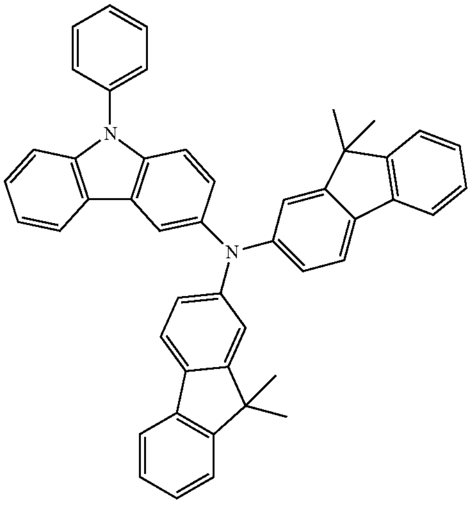
HT12
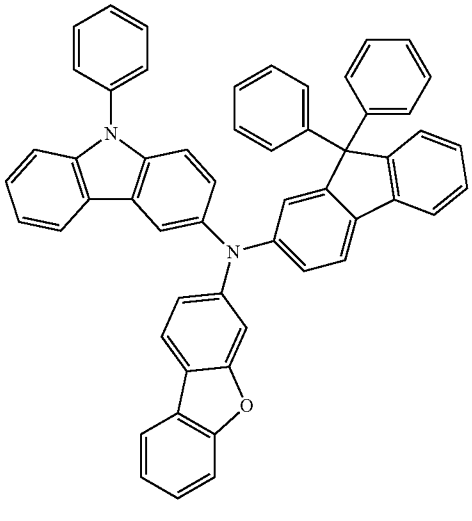

-continued
HT13
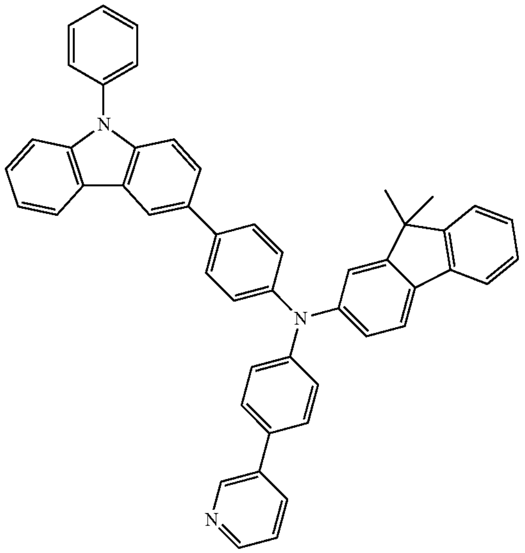
HT14
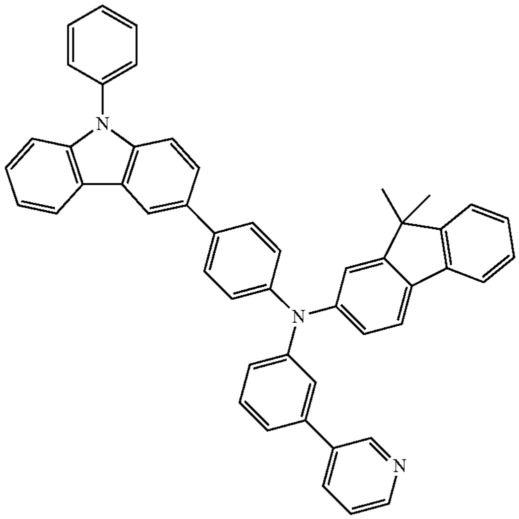
HT15
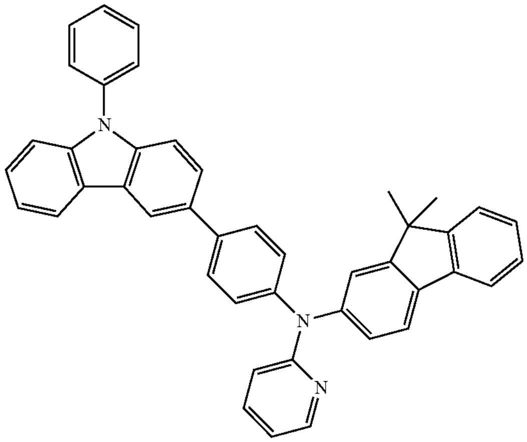
HT16
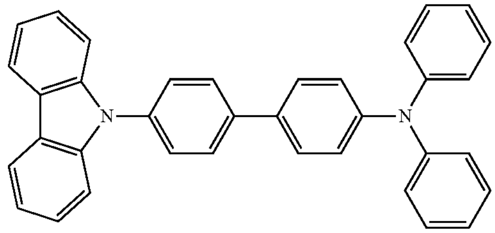
HT17
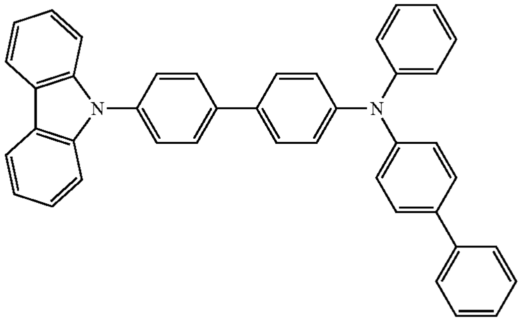
HT18
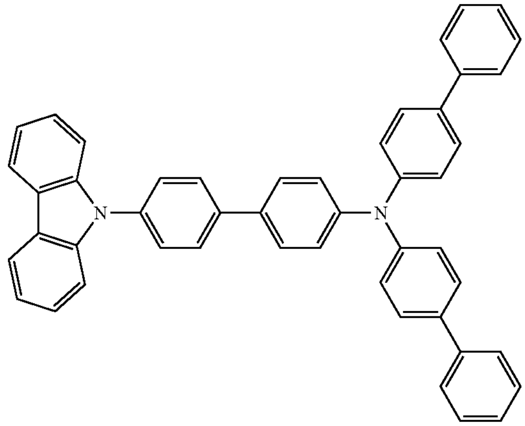

-continued
HT19
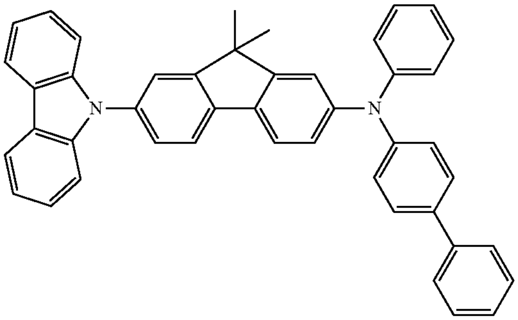
HT20
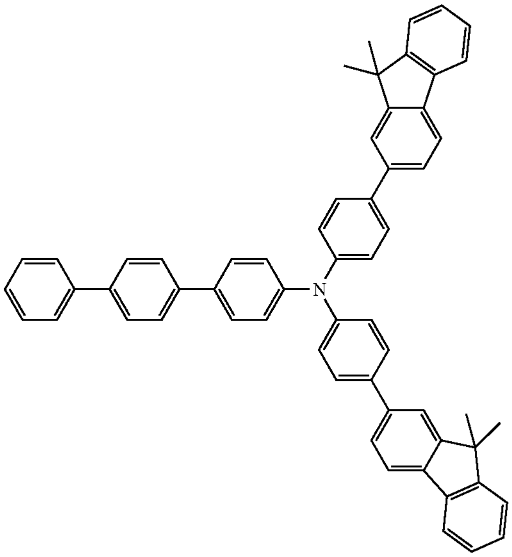
HT21
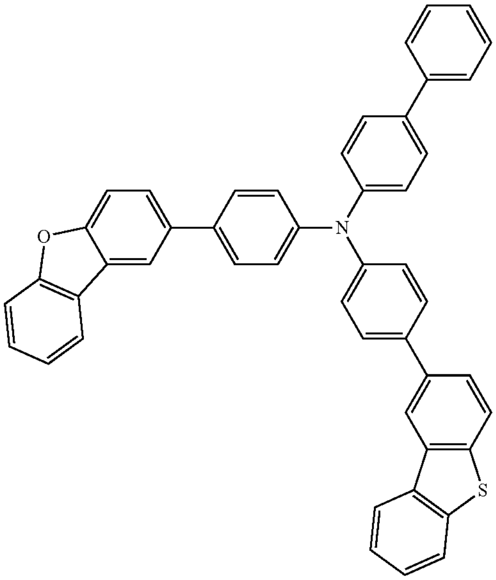
HT22
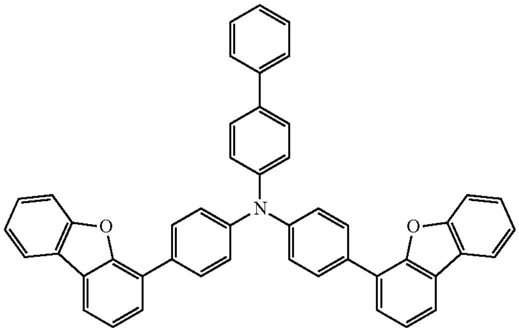
HT23
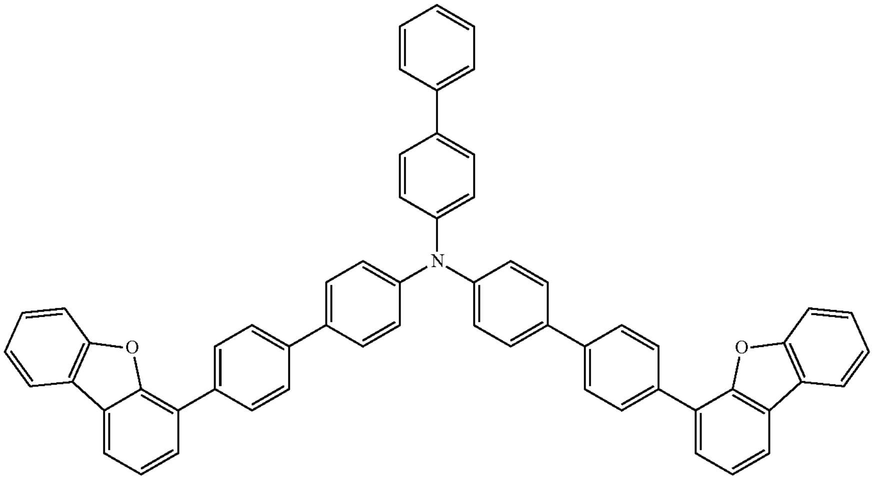

-continued
HT24
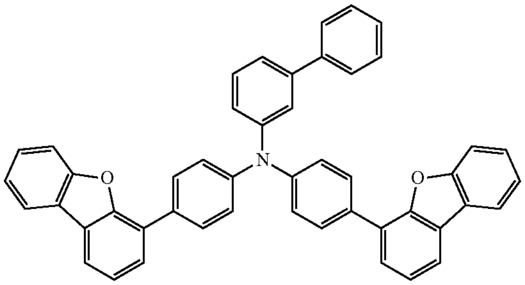
HT25
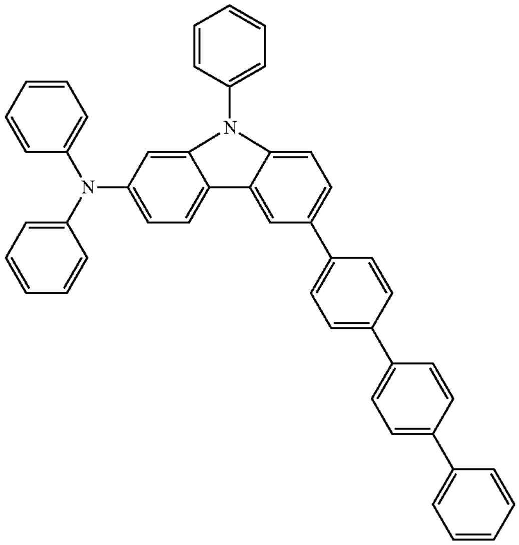
HT26
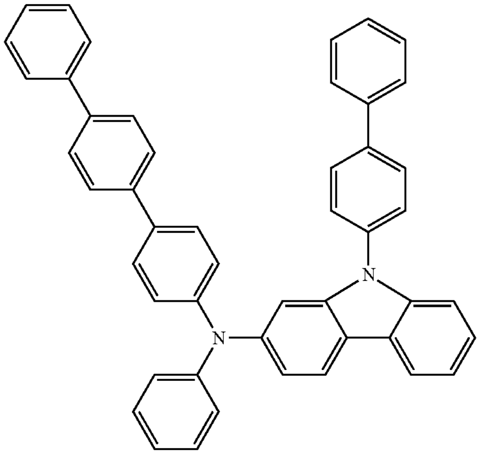
HT27
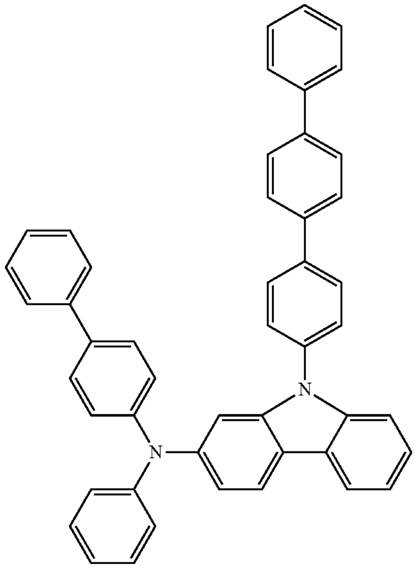
HT28
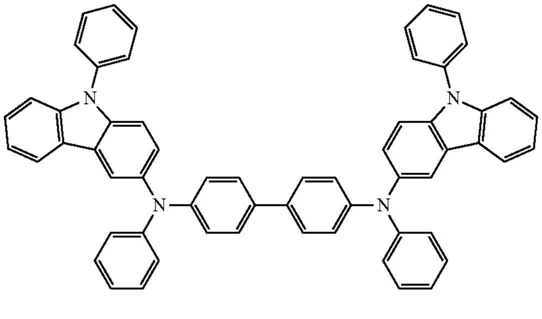
HT29
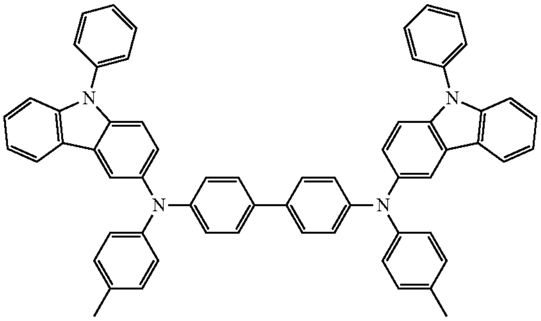

-continued
HT30
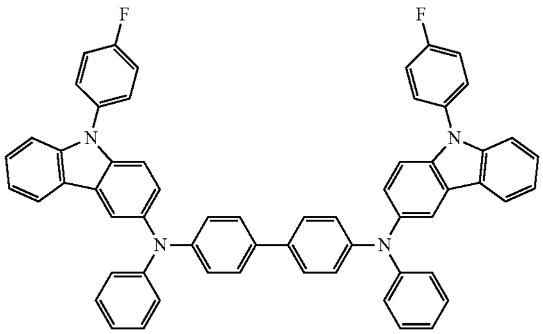
HT31
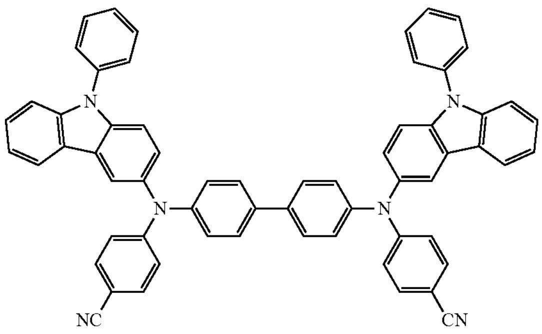
HT32
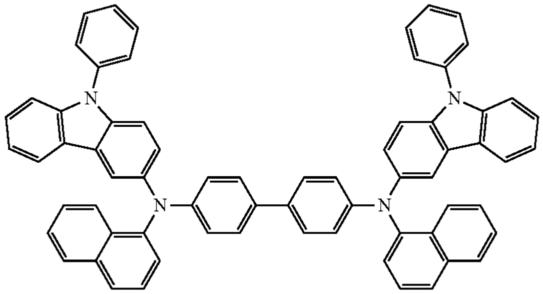
HT33
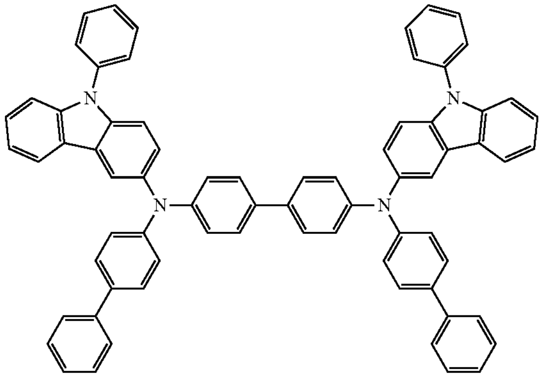
HT34
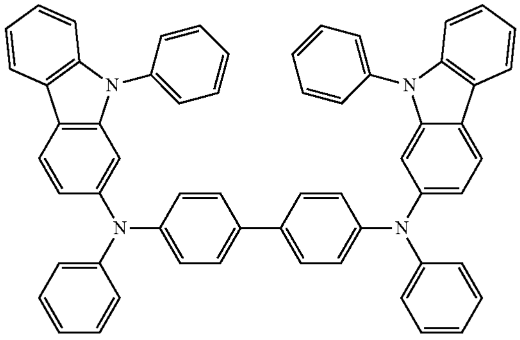
HT35
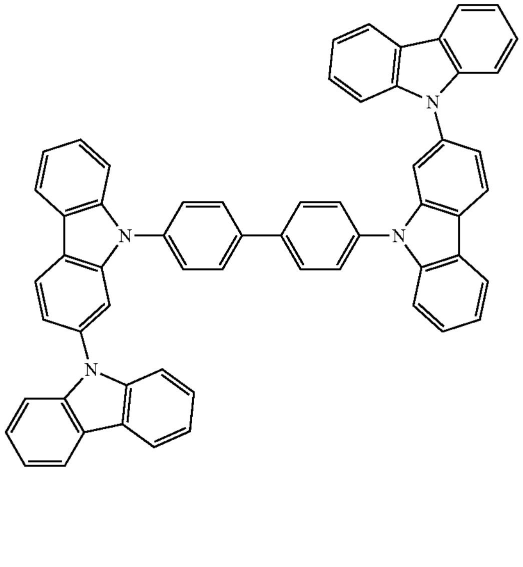

-continued
HT36
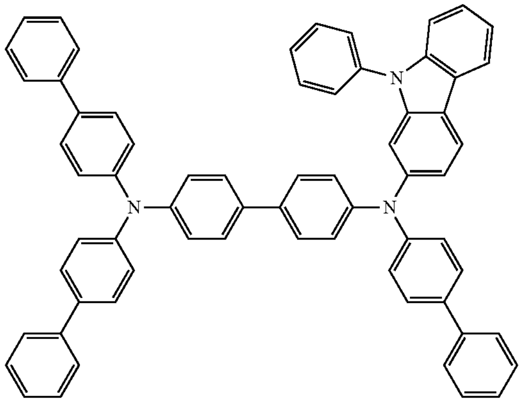
HT37
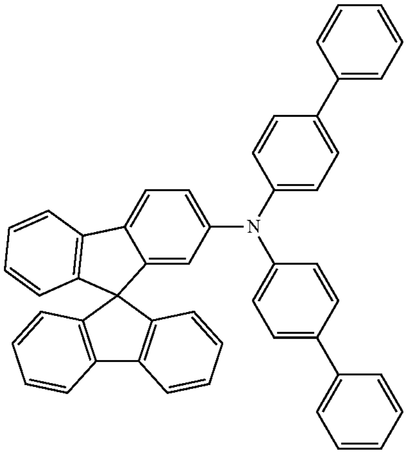
HT38
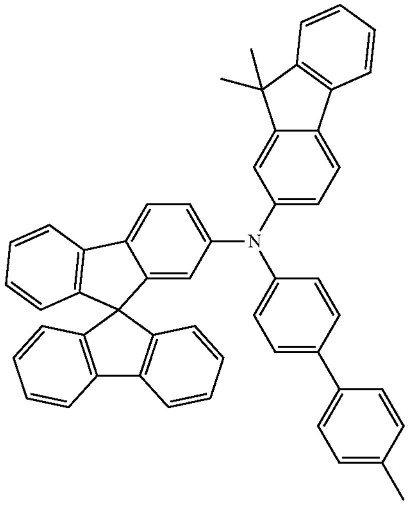
HT39
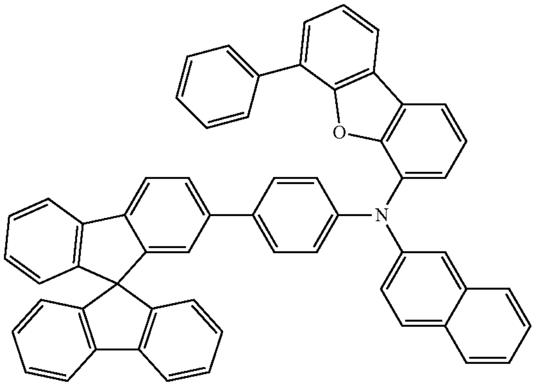
HT40
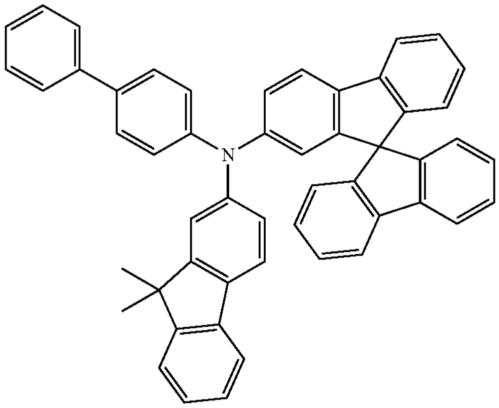
HT41
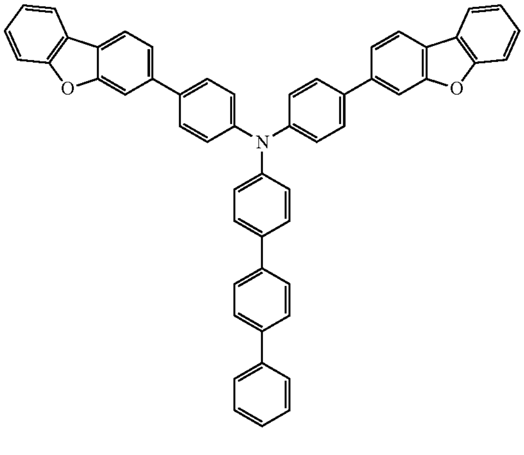

-continued
HT42
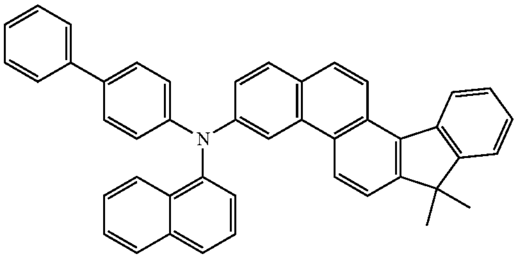
HT43
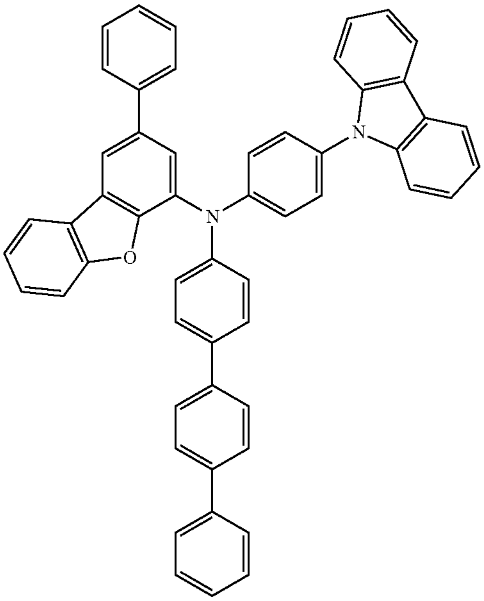
HT44
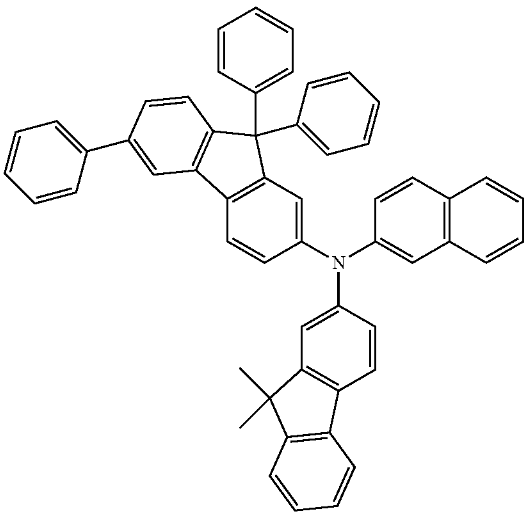
HT45
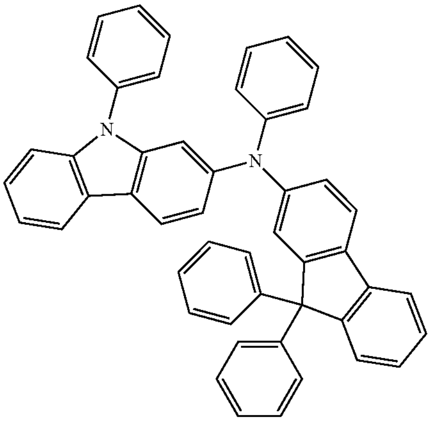
HT46
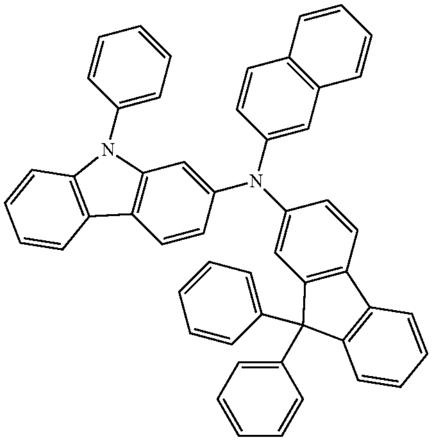

-continued
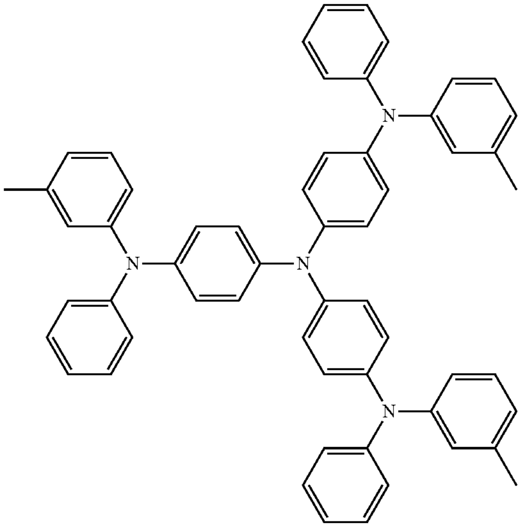
m-MTDATA
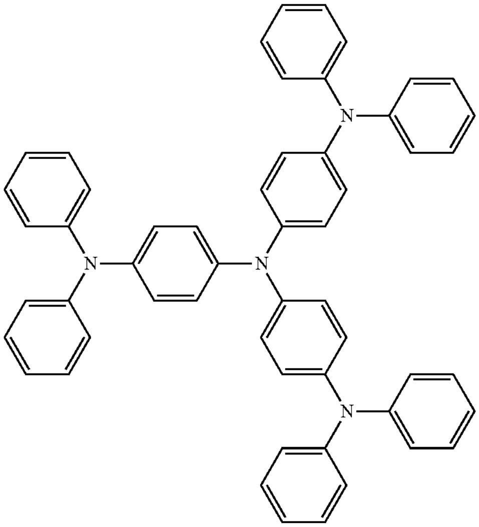
TDATA
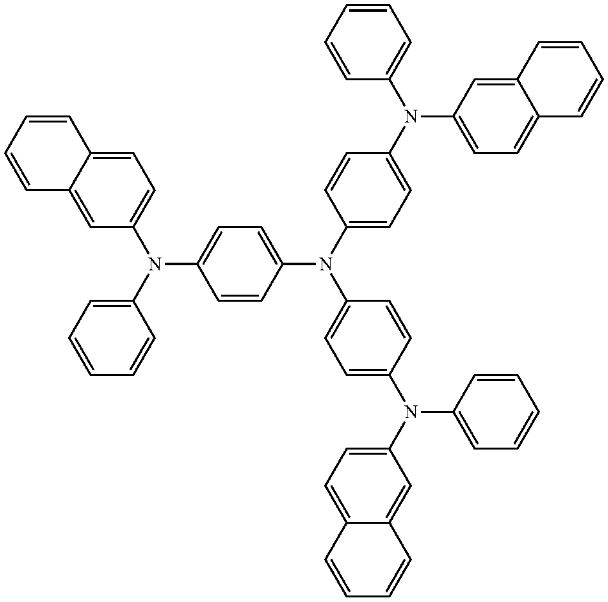
2-TNATA
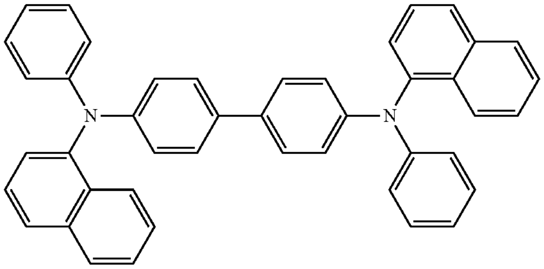
NPB -continued
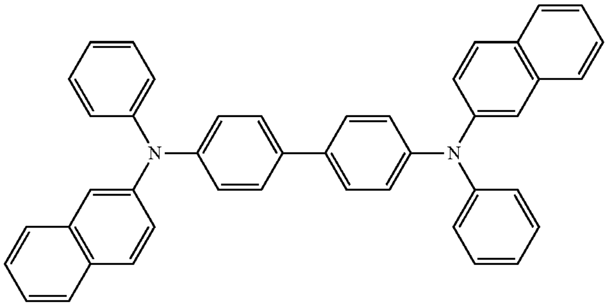
β-NPB
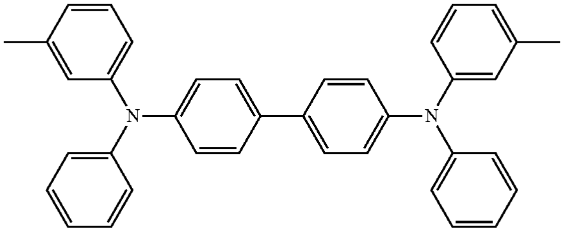
TPD
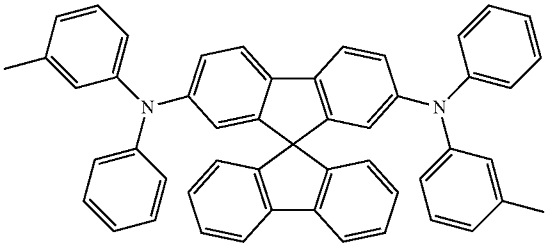
Spiro-TPD
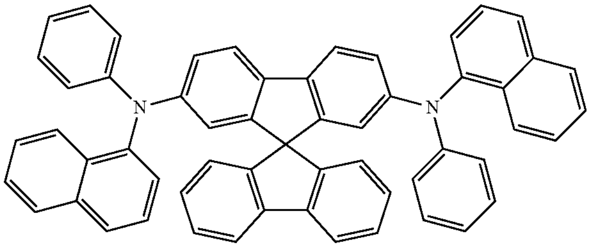
Spiro-NPB
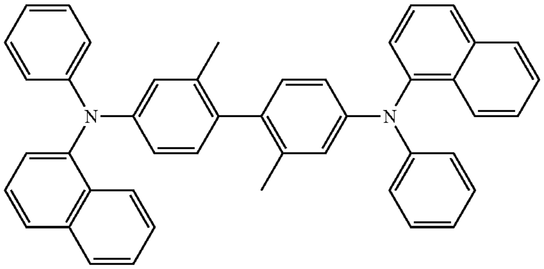
methylated-NPB
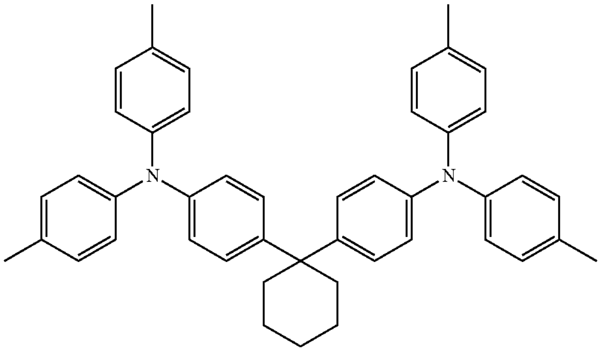
TAPC -continued

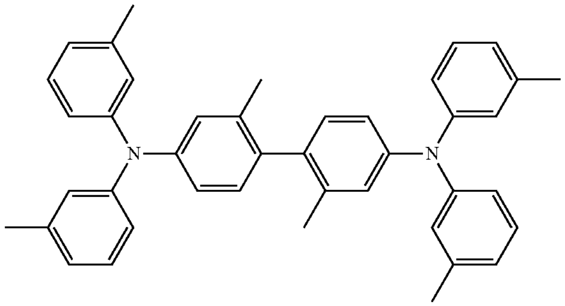

HMTPD

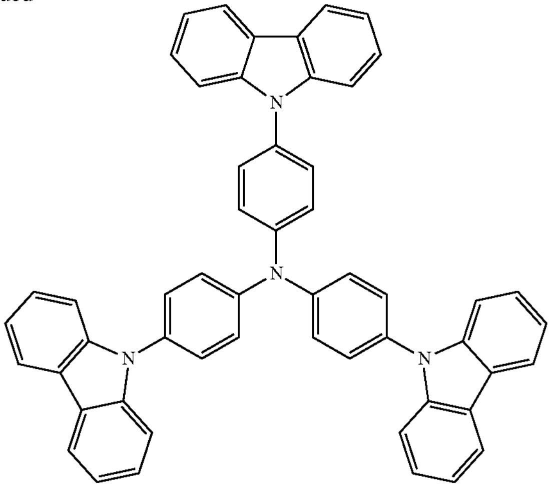

TCTA

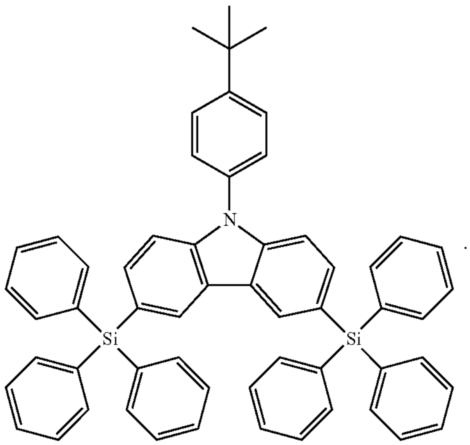

CzSi

The thickness of the hole transport region may be in a range of about 50 Angstroms (Å) to about 10,000 Å, for example, about 100 Å to about 4,000 Å. When the hole transport region includes a hole injection layer, a hole transport layer, and any combination thereof, the thickness of the hole injection layer may be in a range of about 100 Å to about 9,000 Å, for example, about 100 Å to about 1,000 Å, and the thickness of the hole transport layer may be in a range of about 50 Å to about 2,000 Å, for example, about 100 Å to about 1,500 Å. When the thicknesses of the hole transport region, the hole injection layer, and the hole transport layer are within any of these ranges, excellent (or improved) hole transport characteristics may be obtained without a substantial increase in driving voltage.

The emission auxiliary layer may increase light emission efficiency by compensating for an optical resonance distance according to the wavelength of light emitted by an emission layer. The electron blocking layer may prevent or reduce leakage of electrons to a hole transport region from the emission layer. Materials that may be included in the hole transport region may also be included in an emission auxiliary layer and/or an electron blocking layer.

p-Dopant

The hole transport region may include a charge generating material, as well as the aforementioned materials, to improve conductive properties of the hole transport region. The charge generating material may be substantially homogeneously or non-homogeneously dispersed (for example, as a single layer including (e.g., consisting of) charge generating material) in the hole transport region.

The charge generating material may include, for example, a p-dopant.

In some embodiments, a lowest unoccupied molecular orbital (LUMO) energy level of the p-dopant may be −3.5 eV or less.

In some embodiments, the p-dopant may include a quinone derivative, a compound containing a cyano group, a compound containing element EL1 and element EL2, or any combination thereof.

Examples of the quinone derivative may include TCNQ, F4-TCNQ, and the like.

Examples of the compound containing a cyano group may include HAT-CN, a compound represented by Formula 221, and the like:

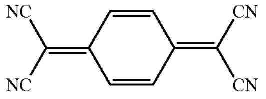

TCNQ

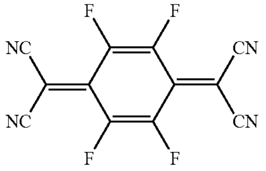

F4-TCNQ

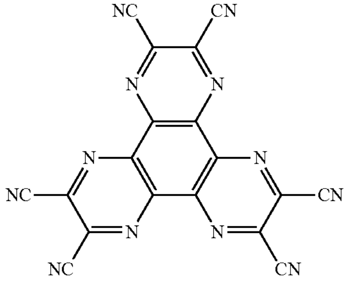

HAT-CN

Formula 221

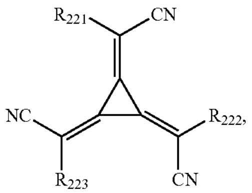

wherein, in Formula 221, $R_{221}$ to $R_{223}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, at least one of $R_{221}$ to $R_{223}$ may each independently be: a $C_3$-$C_{60}$ carbocyclic group or a $C_1$-$C_{60}$ heterocyclic group, each independently substituted with a cyano group; —F; —Cl; —Br; —I; a $C_1$-$C_{20}$ alkyl group substituted with a cyano group, —F, —Cl, —Br, —I, or any combination thereof; or any combination thereof.

In the compound containing element EL1 and element EL2, element EL1 may be a metal, a metalloid, or a combination thereof, and element EL2 may be non-metal, a metalloid, or a combination thereof.

Examples of the metal may include: an alkali metal (e.g., lithium (Li), sodium (Na), potassium (K), rubidium (Rb), cesium (Cs), and/or the like); an alkaline earth metal (e.g., beryllium (Be), magnesium (Mg), calcium (Ca), strontium (Sr), barium (Ba), and/or the like); a transition metal (e.g., titanium (Ti), zirconium (Zr), hafnium (Hf), vanadium (V), niobium (Nb), tantalum (Ta), chromium (Cr), molybdenum (Mo), tungsten (W), manganese (Mn), technetium (Tc), rhenium (Re), iron (Fe), ruthenium (Ru), osmium (Os), cobalt (Co), rhodium (Rh), iridium (Ir), nickel (Ni), palladium (Pd), platinum (Pt), copper (Cu), silver (Ag), gold (Au), and/or the like); post-transition metal (e.g., zinc (Zn), indium (In), tin (Sn), and/or the like); a lanthanide metal (e.g., lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb), lutetium (Lu), and/or the like); and the like.

Examples of the metalloid may include silicon (Si), antimony (Sb), tellurium (Te), and the like.

Examples of the non-metal may include oxygen (O), halogen (e.g., F, Cl, Br, I, and/or the like), and the like.

For example, the compound containing element EL1 and element EL2 may include a metal oxide, a metal halide (e.g., metal fluoride, metal chloride, metal bromide, metal iodide, and/or the like), a metalloid halide (e.g., a metalloid fluoride, a metalloid chloride, a metalloid bromide, a metalloid iodide, and/or the like), a metal telluride, or any combination thereof.

Examples of the metal oxide may include a tungsten oxide (e.g., WO, $W_2O_3$, $WO_2$, $WO_3$, and/or $W_2O_5$), a vanadium oxide (e.g., VO, $V_2O_3$, $VO_2$, and/or $V_2O_5$), a molybdenum oxide (MoO, $Mo_2O_3$, $MoO_2$, $MoO_3$, and/or $Mo_2O_5$), and a rhenium oxide (e.g., $ReO_3$).

Examples of the metal halide may include alkali metal halide, alkaline earth metal halide, transition metal halide, post-transition metal halide, lanthanide metal halide, and the like.

Examples of the alkali metal halide may include LiF, NaF, KF, RbF, CsF, LiCl, NaCl, KCl, RbCl, CsCl, LiBr, NaBr, KBr, RbBr, CsBr, LiI, NaI, KI, RbI, CsI, and the like.

Examples of the alkaline earth metal halide may include $BeF_2$, $MgF_2$, $CaF_2$, $SrF_2$, $BaF_2$, $BeCl_2$, $MgCl_2$, $CaCl_2$), $SrCl_2$, $BaCl_2$, $BeBr_2$, $MgBr_2$, $CaBr_2$, $SrBr_2$, $BaBr_2$, $BeI_2$, $MgI_2$, $CaI_2$, $SrI_2$, and $BaI_2$.

Examples of the transition metal halide may include a titanium halide (e.g., $TiF_4$, $TiCl_4$, $TiBr_4$, and/or $TiO_4$), a zirconium halide (e.g., $ZrF_4$, $ZrCl_4$, $ZrBr_4$, and/or $ZrI_4$), a hafnium halide (e.g., $HfF_4$, $HfCl_4$, $HfBr_4$, and/or $HfI_4$), a vanadium halide (e.g., $VF_3$, $VCl_3$, $VBr_3$, and/or $VI_3$), a niobium halide (e.g., $NbF_3$, $NbCl_3$, $NbBr_3$, and/or $NbI_3$), a tantalum halide (e.g., $TaF_3$, $TaCl_3$, $TaBr_3$, and/or $TaI_3$), a chromium halide (e.g., $CrF_3$, $CrCl_3$, $CrBr_3$, and/or $CrI_3$), a molybdenum halide (e.g., $MoF_3$, $MoCl_3$, $MoBr_3$, and/or $MoI_3$), a tungsten halide (e.g., $WF_3$, $WCl_3$, $WBr_3$, and/or $WI_3$), a manganese halide (e.g., $MnF_2$, $MnCl_2$, $MnBr_2$, and/or $MnI_2$), a technetium halide (e.g., $TcF_2$, $TcCl_2$, $TcBr_2$, and/or $TcI_2$), a rhenium halide (e.g., $ReF_2$, $ReCl_2$, $ReBr_2$, and/or $ReI_2$), an iron halide (e.g., $FeF_2$, $FeCl_2$, $FeBr_2$, and/or $FeI_2$), a ruthenium halide (e.g., $RuF_2$, $RuCl_2$, $RuBr_2$, and/or $RuI_2$), an osmium halide (e.g., $OsF_2$, $OsCl_2$, $OsBr_2$, and/or $OsI_2$), a cobalt halide (e.g., $CoF_2$, $COCl_2$, $CoBr_2$, and/or $CoI_2$), a rhodium halide (e.g., $RhF_2$, $RhCl_2$, $RhBr_2$, and/or $RhI_2$), an iridium halide (e.g., $IrF_2$, $IrCl_2$, $IrBr_2$, and/or $IrI_2$), a nickel halide (e.g., $NiF_2$, $NiCl_2$, $NiBr_2$, and/or $NiI_2$), a palladium halide (e.g., $PdF_2$, $PdCl_2$, $PdBr_2$, and/or $PdI_2$), a platinum halide (e.g., $PtF_2$, $PtCl_2$, $PtBr_2$, and/or $PtI_2$), a copper halide (e.g., CuF, CuCl, CuBr, and/or CuI), a silver halide (e.g., AgF, AgCl, AgBr, and/or AgI), and a gold halide (e.g., AuF, AuCl, AuBr, and/or AuI).

Examples of the post-transition metal halide may include a zinc halide (e.g., $ZnF_2$, $ZnCl_2$, $ZnBr_2$, and/or $ZnI_2$), an indium halide (e.g., Inks), and a tin halide (e.g., $SnI_2$).

Examples of the lanthanide metal halide may include YbF, $YbF_2$, $YbF_3$, $SmF_3$, YbCl, $YbCl_2$, $YbCl_3$ $SmCl_3$, YbBr, $YbBr_2$, $YbBr_3$ SmBrs, YbI, $YbI_2$, $YbI_3$, and $SmI_3$.

Examples of the metalloid halide may include an antimony halide (e.g., $SbCl_5$).

Examples of the metal telluride may include an alkali metal telluride (e.g., $Li_2Te$, $Na_2Te$, $K_2Te$, $Rb_2Te$, and/or $Cs_2Te$), an alkaline earth metal telluride (e.g., BeTe, MgTe, CaTe, SrTe, and/or BaTe), a transition metal telluride (e.g., $TiTe_2$, $ZrTe_2$, $HfTe_2$, $V_2Te_3$, $Nb_2Te_3$, $Ta_2Te_3$, $Cr_2Te_3$, $Mo_2Te_3$, $W_2Te_3$, MnTe, TcTe, ReTe, FeTe, RuTe, OsTe, CoTe, RhTe, IrTe, NiTe, PdTe, PtTe, $Cu_2Te$, CuTe, $Ag_2Te$, AgTe, and/or $Au_2Te$), a post-transition metal telluride (e.g., ZnTe), and a lanthanide metal telluride (e.g., LaTe, CeTe, PrTe, NdTe, PmTe, EuTe, GdTe, TbTe, DyTe, HoTe, ErTe, TmTe, YbTe, and/or LuTe).

Emission Layer in Interlayer 130

When the light-emitting device 10 is a full color light-emitting device, the emission layer may be patterned into a red emission layer, a green emission layer, and/or a blue emission layer, according to a sub-pixel. In one or more embodiments, the emission layer may have a stacked structure. The stacked structure may include two or more layers selected from a red emission layer, a green emission layer, and a blue emission layer. The two or more layers may be in direct contact with each other.

In some embodiments, the two or more layers may be separated from each other. In one or more embodiments, the emission layer may include two or more materials. The two or more materials may include a red light-emitting material, a green light-emitting material, or a blue light-emitting material. The two or more materials may be mixed with each other in a single layer. The two or more materials mixed with each other in the single layer may emit white light. In some embodiments, the emission layer may emit blue light.

The emission layer may include a host and a dopant.

In some embodiments, the dopant may include a phosphorescent dopant, a fluorescent dopant, a delayed fluorescence material, or a combination thereof.

In some embodiments, the dopant may include a phosphorescent dopant, a delayed fluorescence material, or a combination thereof.

The phosphorescent dopant or the fluorescent dopant that may be included in the emission layer may be understood by respectively referring to the descriptions of the phosphorescent dopant or the fluorescent dopant provided herein.

The amount of the dopant in the emission layer may be in a range of about 0.01 parts to about 15 parts by weight based on 100 parts by weight of the host.

In some embodiments, the emission layer may include a quantum dot.

The emission layer may include a delayed fluorescence material. The delayed fluorescence material may serve as a host or a dopant in the emission layer.

The thickness of the emission layer may be in a range of about 100 Å to about 1,000 Å, and in some embodiments, about 200 Å to about 600 Å. When the thickness of the emission layer is within any of these ranges, improved luminescence characteristics may be obtained without a substantial increase in driving voltage.

Host

The host may include a carbazole-containing compound, an anthracene-containing compound, a triazine-containing compound, or any combination thereof.

The host may include, for example, a carbazole-containing compound and a triazine-containing compound.

In some embodiments, the host may further include a compound represented by Formula 301:

$$[Ar_{301}]_{xb11}\text{-}[(L_{301})_{xb1}\text{-}R_{301}]_{xb21}, \qquad \text{Formula 301}$$

wherein, in Formula 301, $Ar_{301}$ and $L_{301}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, xb11 may be 1, 2, or 3, xb1 may be an integer selected from 0 to 5, $R_{301}$ may be hydrogen, deuterium, —F, —Cl, —Br, —I, a hydroxyl group, a cyano group, a nitro group, a $C_1$-$C_{60}$ alkyl group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, $—Si(Q_{301})(Q_{302})(Q_{303})$, $—N(Q_{301})(Q_{302})$, $—B(Q_{301})(Q_{302})$, $—C(=O)(Q_{301})$, $—S(=O)_2(Q_{301})$, or $—P(=O)(Q_{301})(Q_{302})$, xb21 may be an integer selected from 1 to 5, and $Q_{301}$ to $Q_{303}$ may each be understood by referring to the description of $Q_1$ provided herein.

In some embodiments, when xb11 in Formula 301 is 2 or greater, at least two $Ar_{301}$(s) may be bound via a single bond.

In some embodiments, the host may include a compound represented by Formula 301-1, a compound represented by Formula 301-2, or any combination thereof:

Formula 301-1

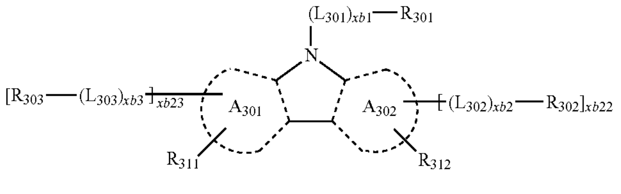

Formula 301-2

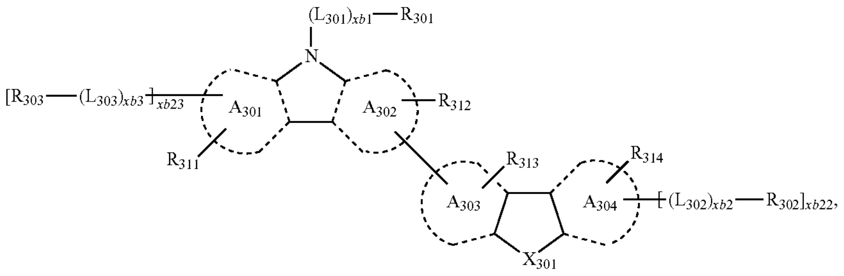

wherein, in Formulae 301-1 to 301-2, ring $A_{301}$ to ring $A_{304}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, $X_{301}$ may be O, S, N-[$(L_{304})_{xb4}$-$R_{304}$], $C(R_{304})(R_{305})$, or $Si(R_{304})(R_{305})$, xb22 and xb23 may each independently be 0, 1, or 2, $L_{301}$, xb1, and $R_{301}$ may respectively be understood by referring to the descriptions of $L_{301}$, xb1, and $R_{301}$ provided herein, $L_{302}$ to $L_{304}$ may each be understood by referring to the description of $L_{301}$ provided herein, xb2 to xb4 may each be understood by referring to the description of xb1 provided herein, and $R_{302}$ to $R_{305}$ and $R_{311}$ to $R_{314}$ may each be understood by referring to the description of $R_{301}$ provided herein.

In some embodiments, the host may include an alkaline earth-metal complex, a post-transitional metal complex, or any combination thereof. For example, the host may include a Be complex (e.g., Compound H55), a Mg complex, a Zn complex, or any combination thereof.

In some embodiments, the host may include at least one compound selected from Compounds H1 to H124, 9,10-di (2-naphthyl)anthracene (DNA), 2-methyl-9,10-bis(naphthalen-2-yl)anthracene (MADN), 9,10-di-(2-naphthyl)-2-t-butyl-anthracene (TBADN), 4,4'-bis(N-carbazolyl)-1,1'-biphenyl (CBP), 1,3-di-9-carbazolylbenzene (mCP), 1,3,5-tri(carbazol-9-yl)benzene (TCP), or any combination thereof:

H1

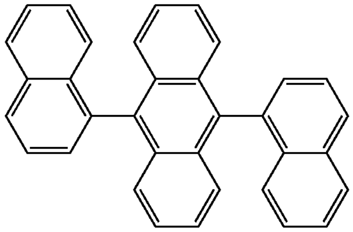

H2

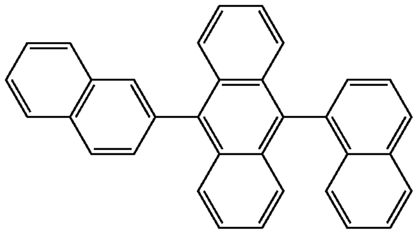

H3

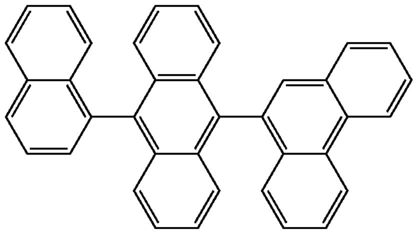

-continued

H4

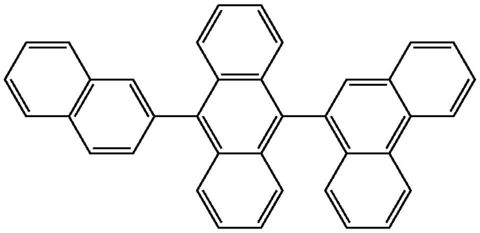

H5

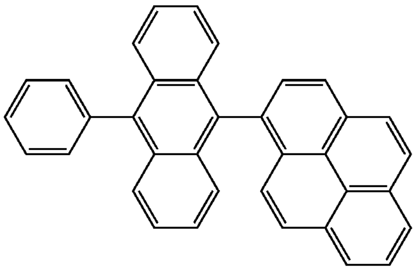

H6

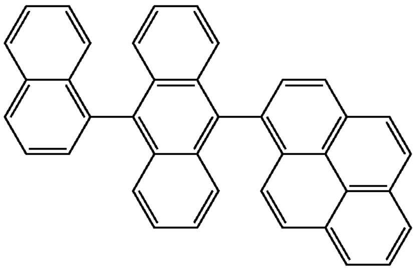

H7

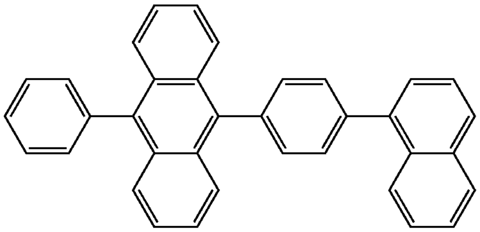

H8

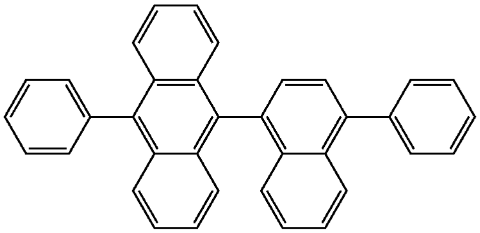

H9

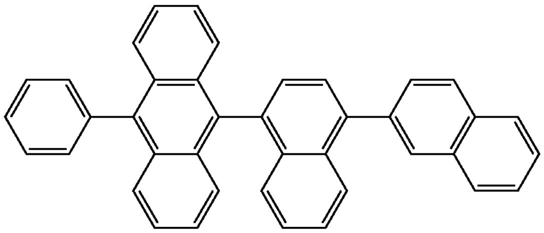

-continued
H10
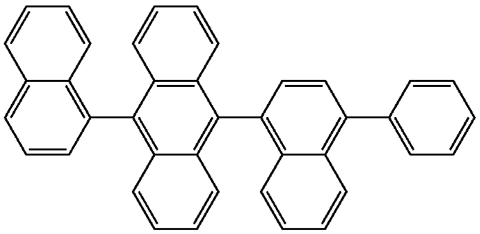
H11
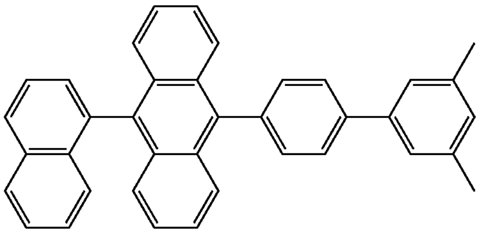
H12
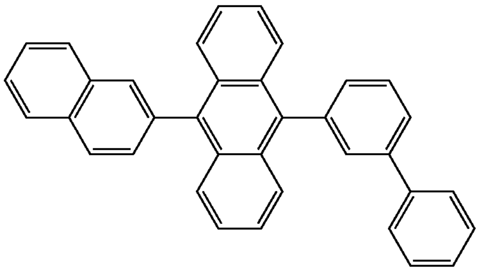
H13
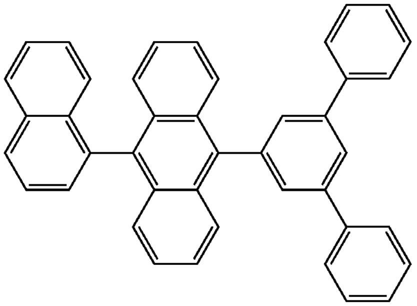
H14
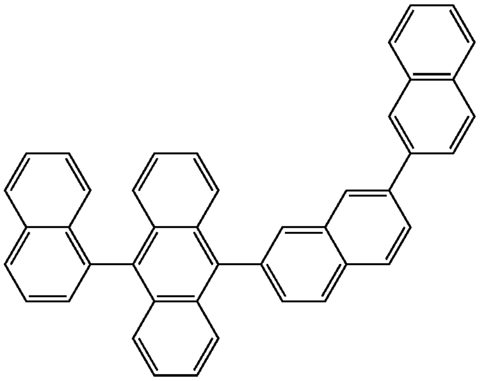
-continued
H15
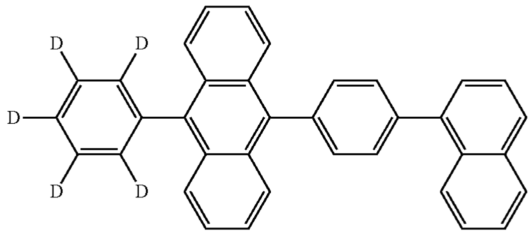
H16
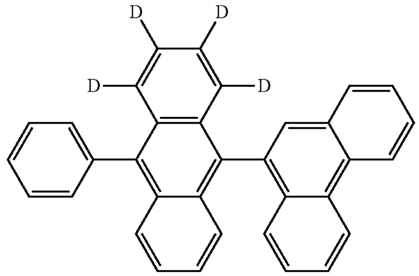
H17
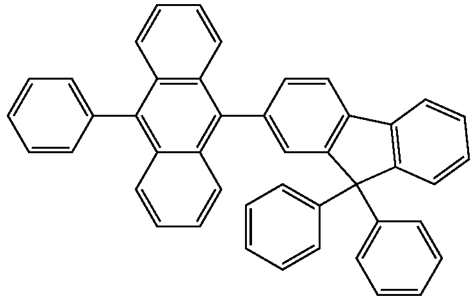
H18
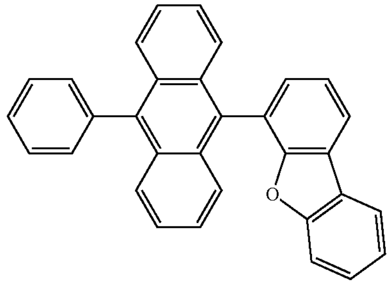
H19
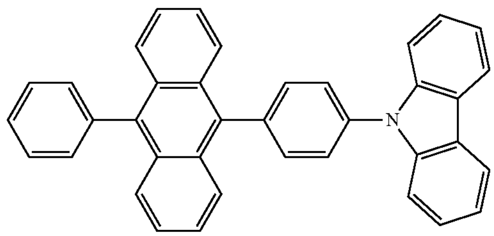

-continued
H20
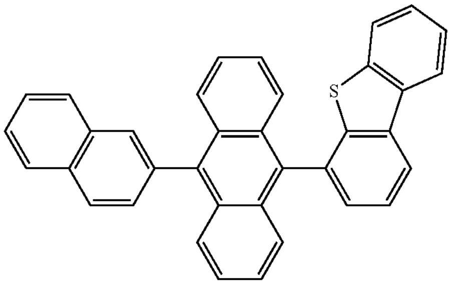
H21
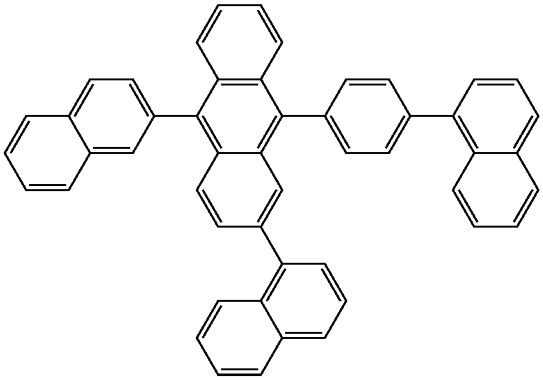
H22
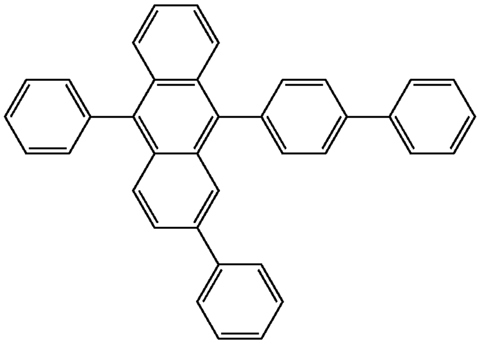
H23
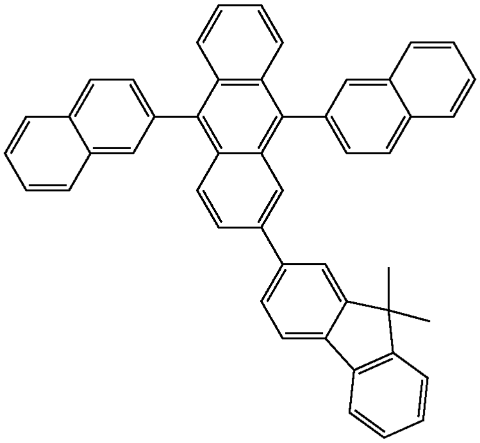
-continued
H24
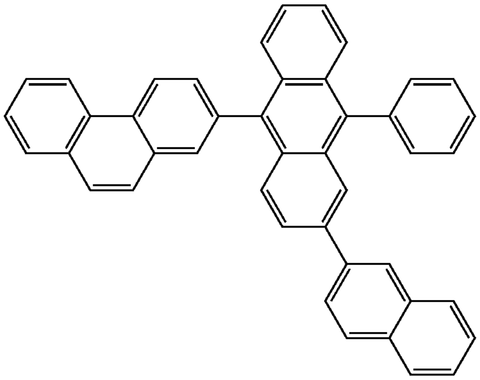
H25
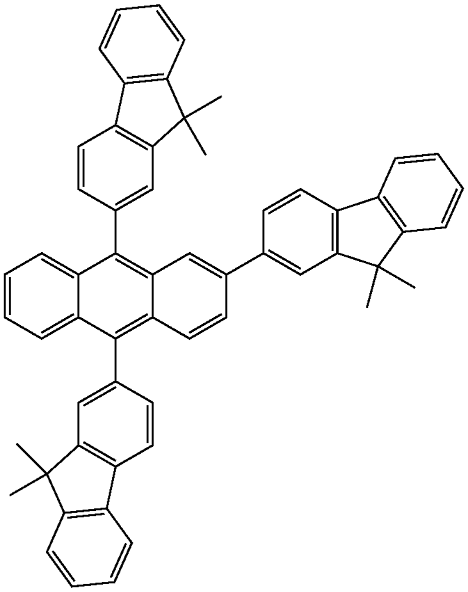
H26
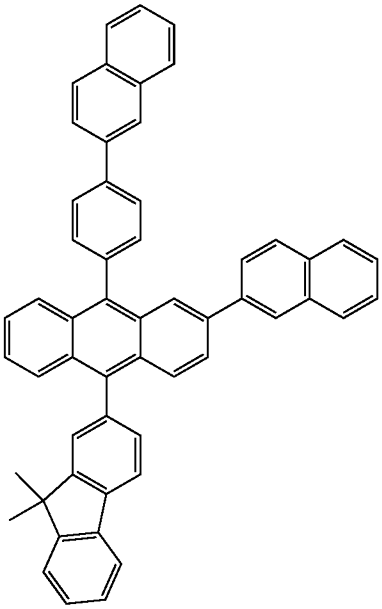

-continued
H27
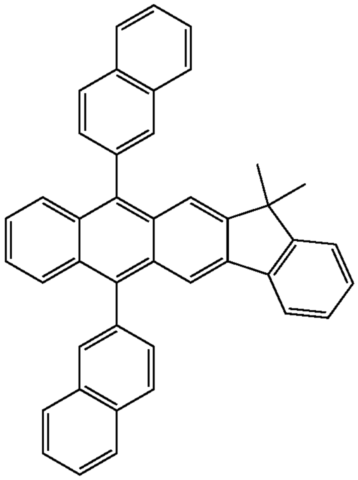
H28
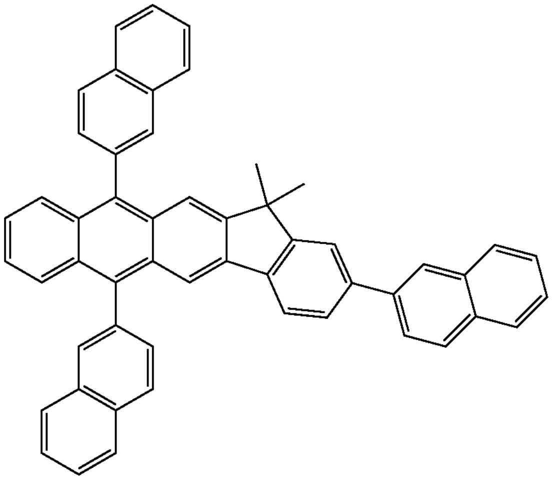
H29
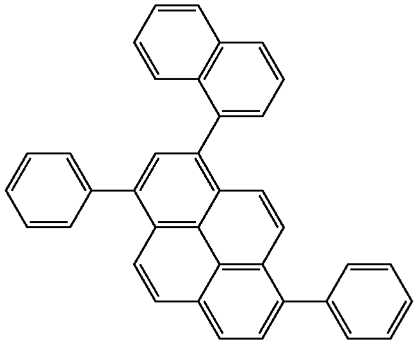
-continued
H30
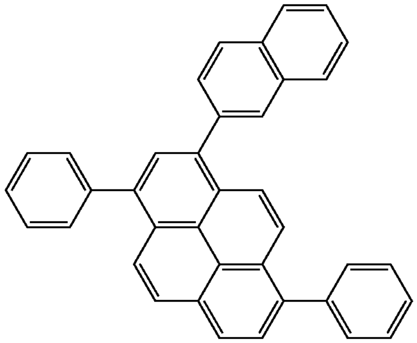
H31
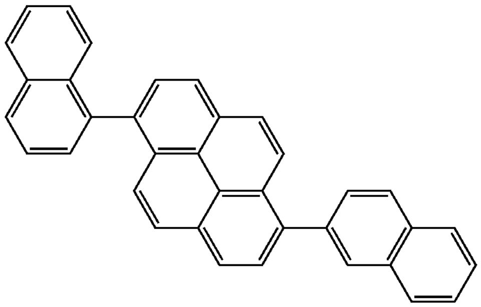
H32
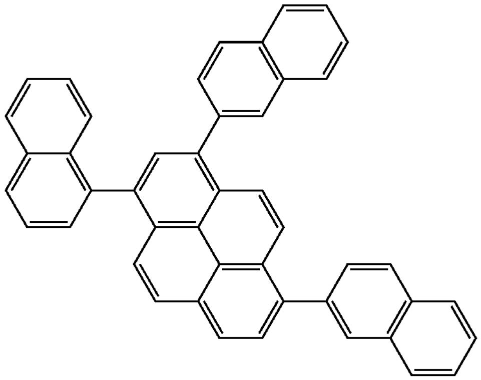
H33
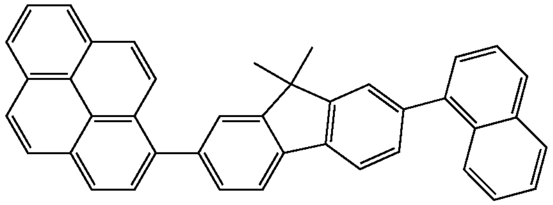
H34
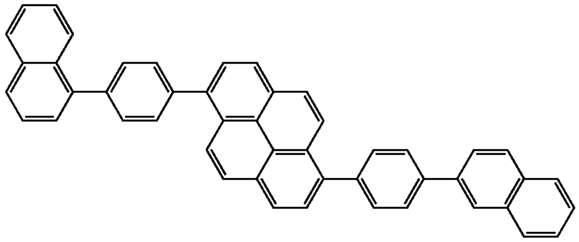

-continued
H35
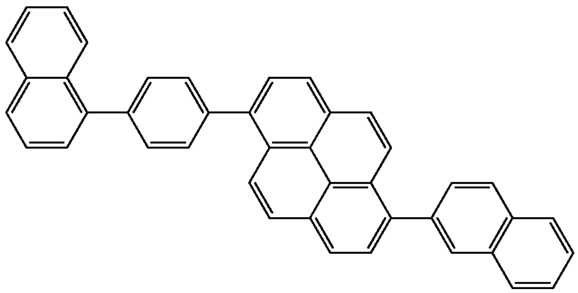
H36
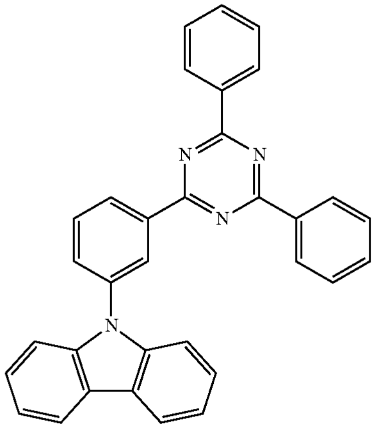
H37
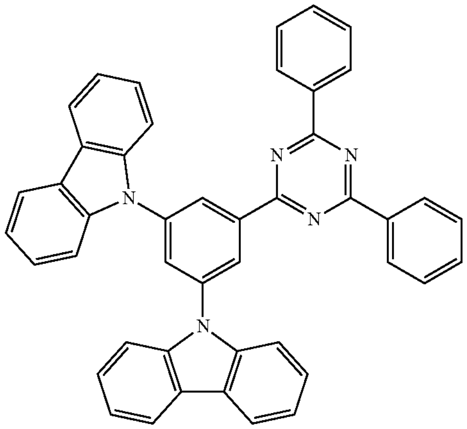
H38
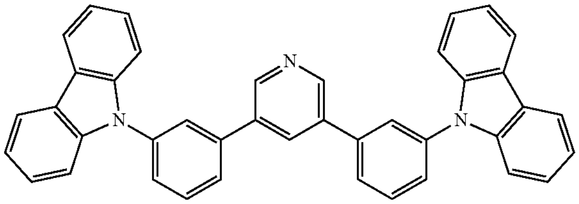
-continued
H39
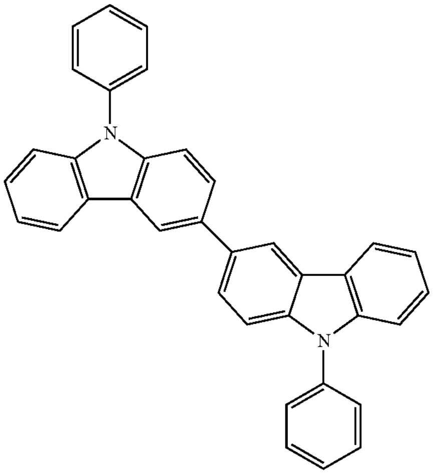
H40
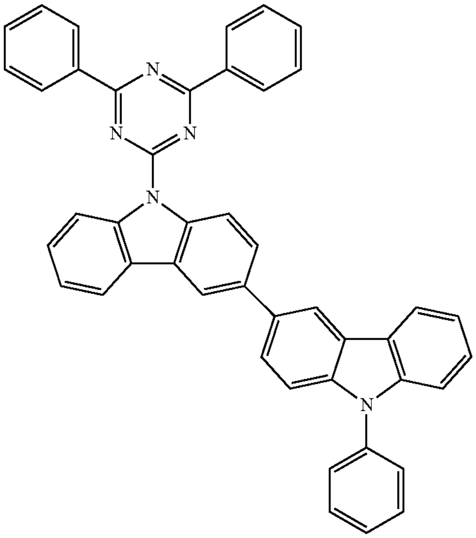
H41
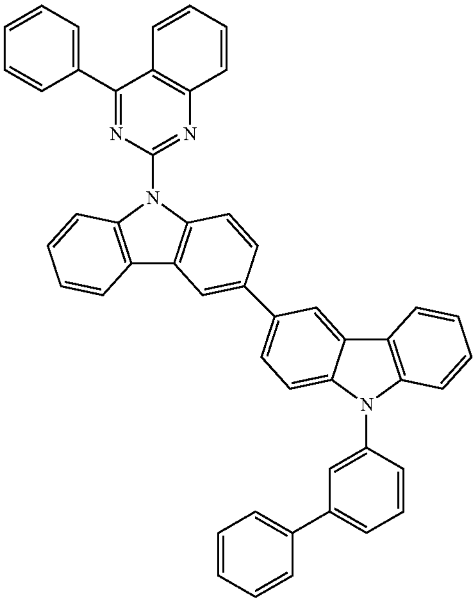

-continued
H42
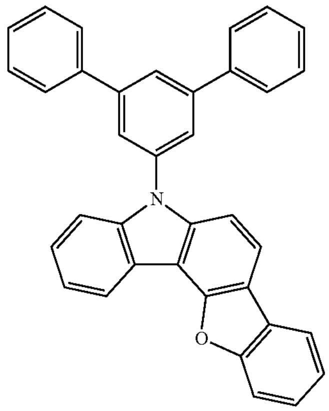
H43
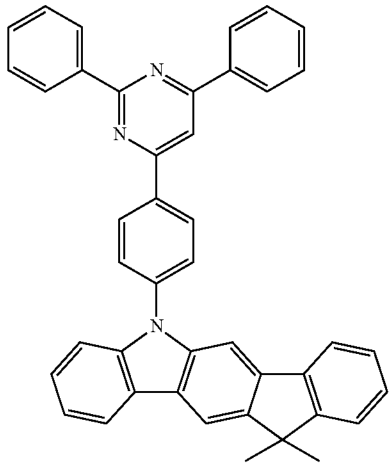
H44
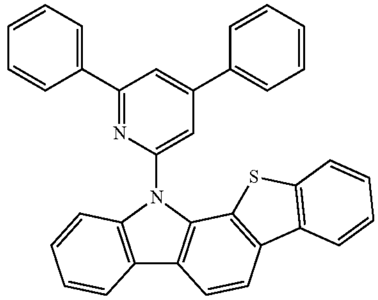
H45
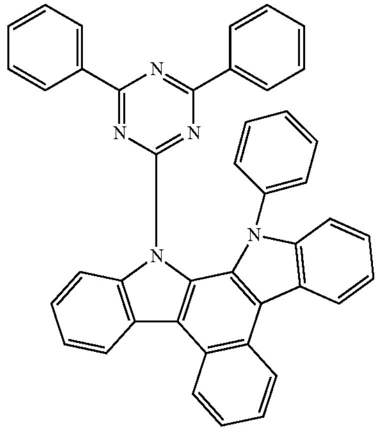
-continued
H46
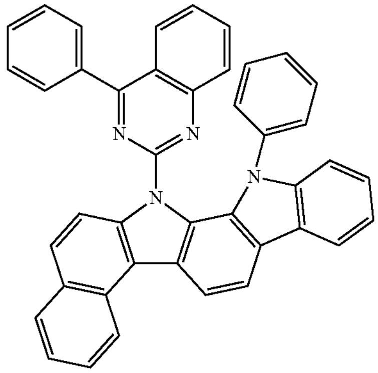
H47
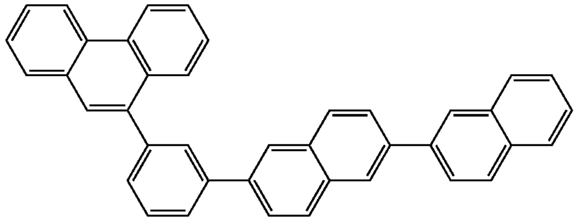
H48
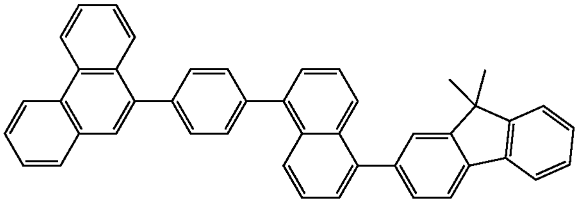
H49
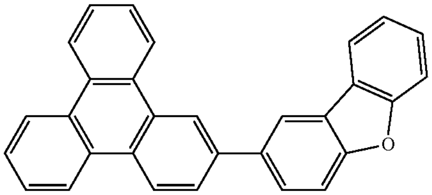
H50
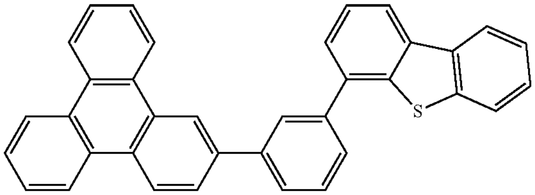
H51
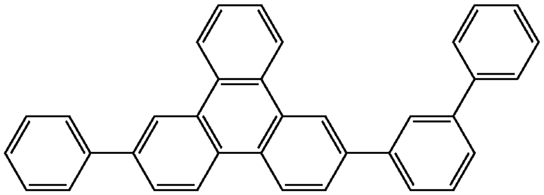

-continued
H52
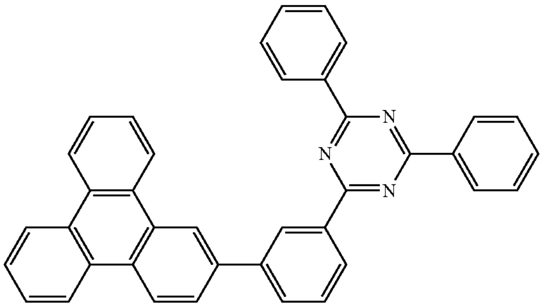
H53
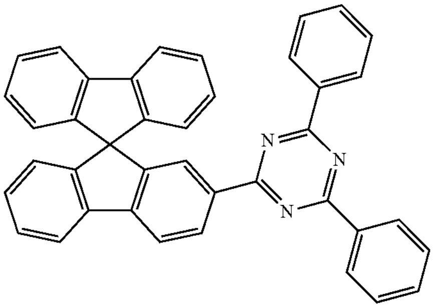
H54
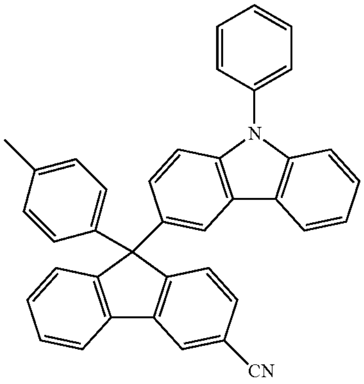
H55
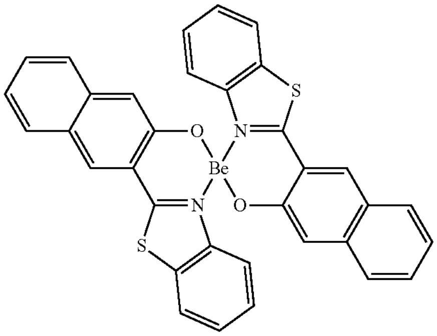
.
-continued
H56
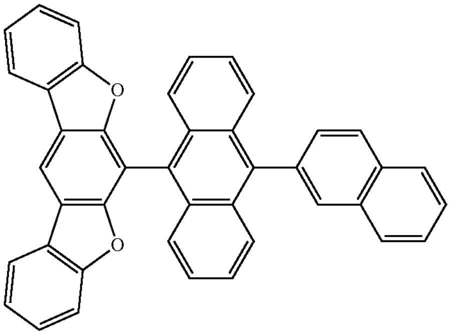
H57
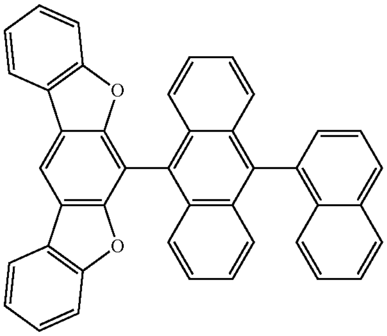
H58
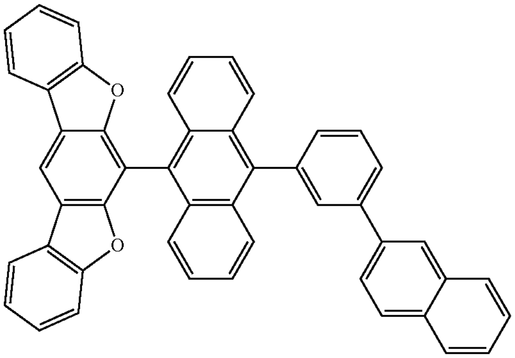
H59
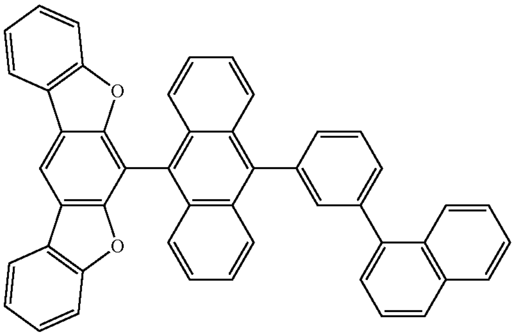

-continued
H60
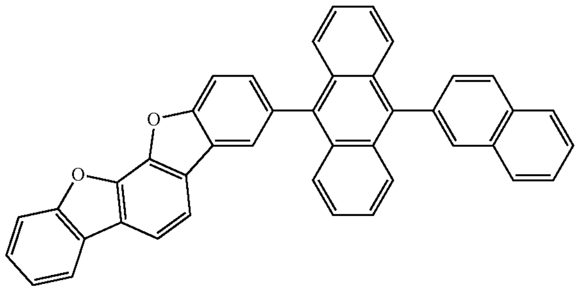
H61
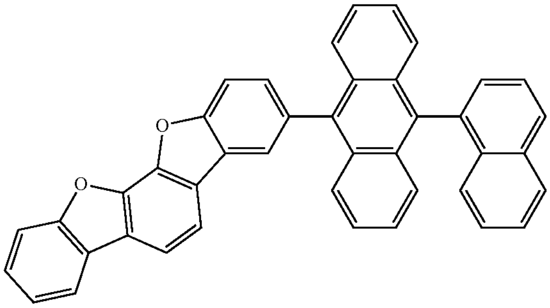
H62
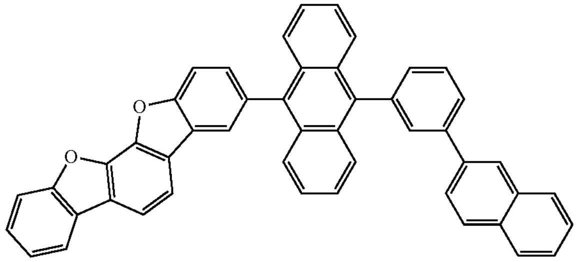
H63
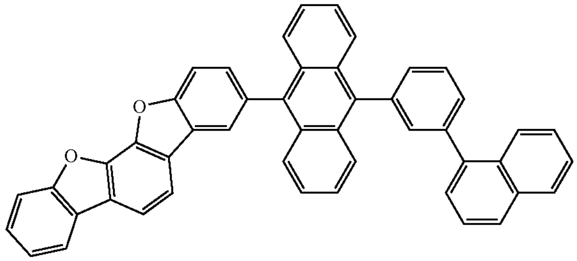
H64
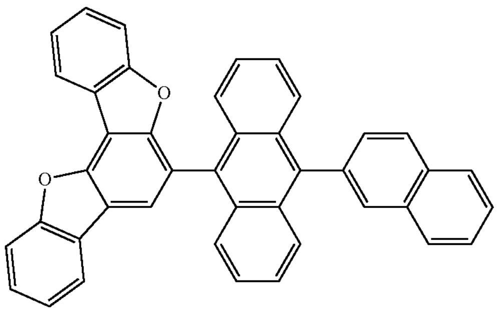
-continued
H65
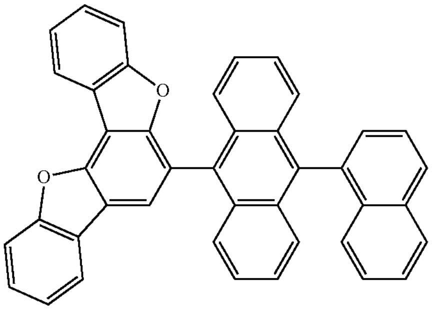
H66
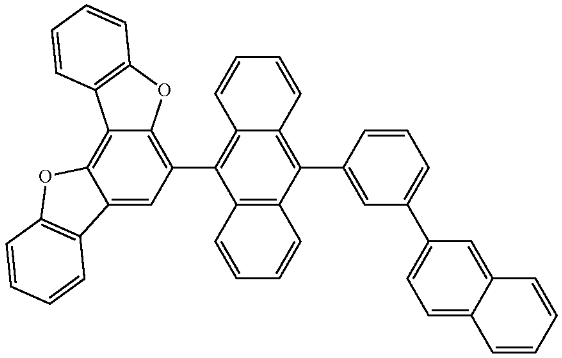
H67
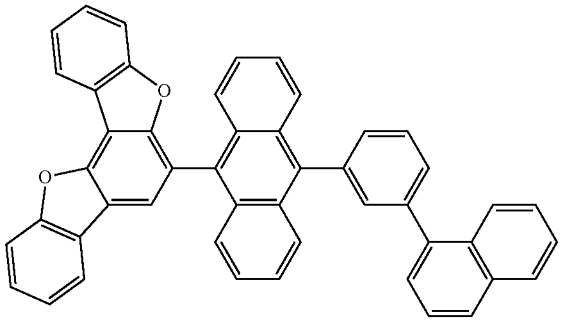
H68
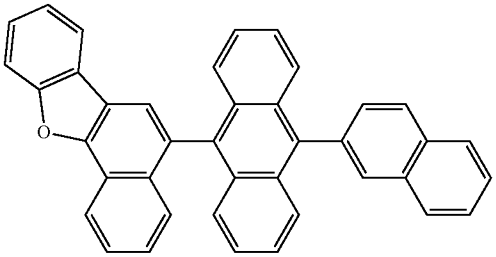
H69
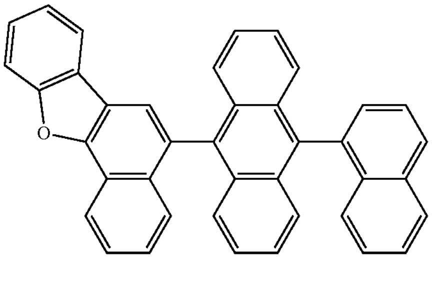

-continued
H70
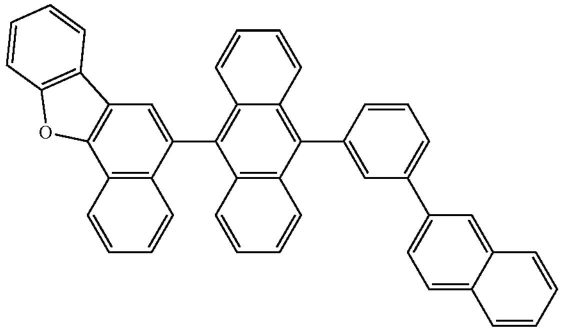
H71
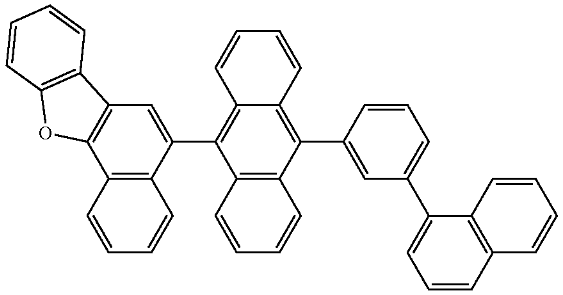
H72
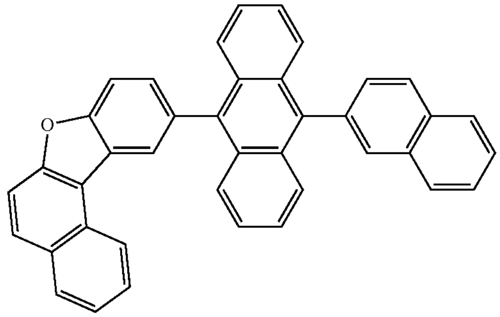
H73
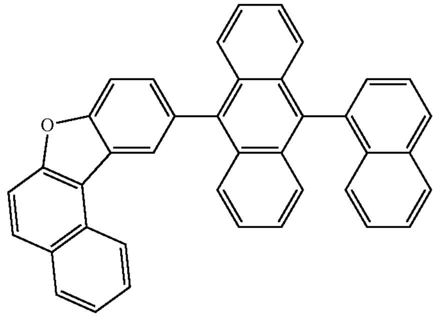
-continued
H74
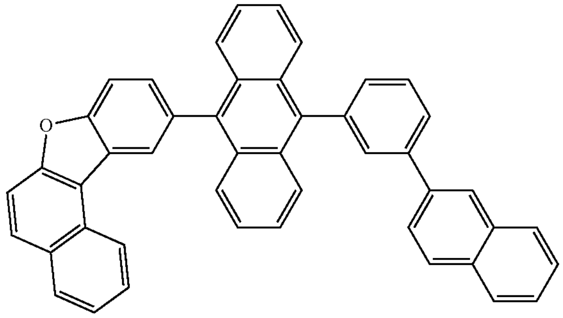
H75
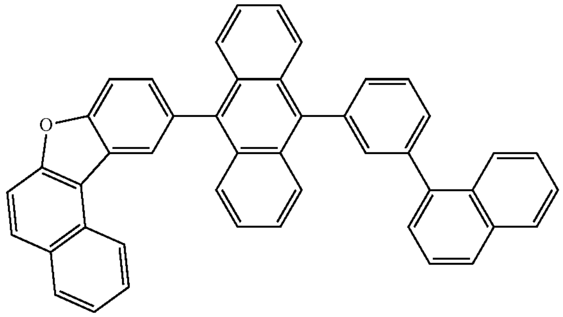
H76
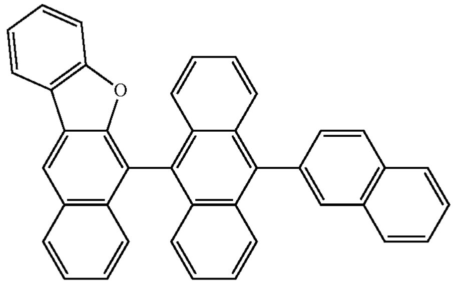
H77
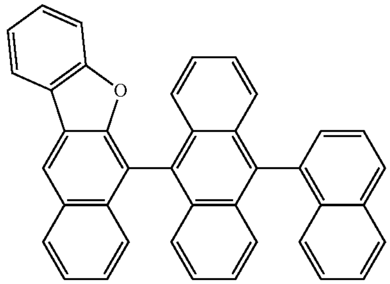
H78
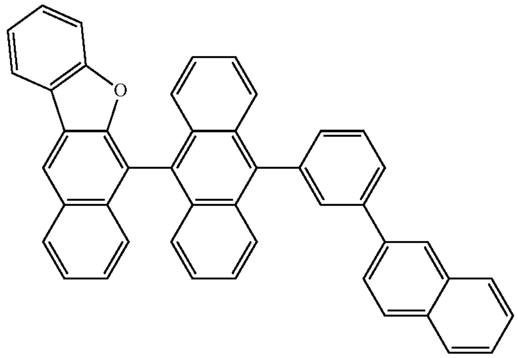

-continued
H79
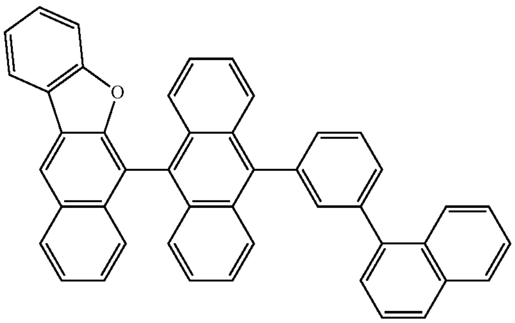
H80
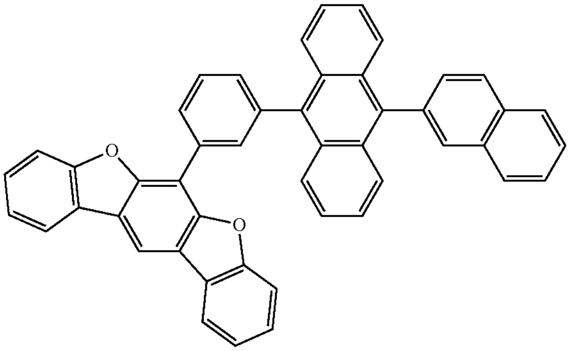
H81
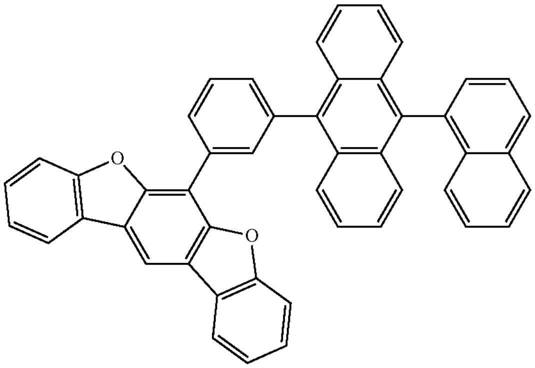
H82
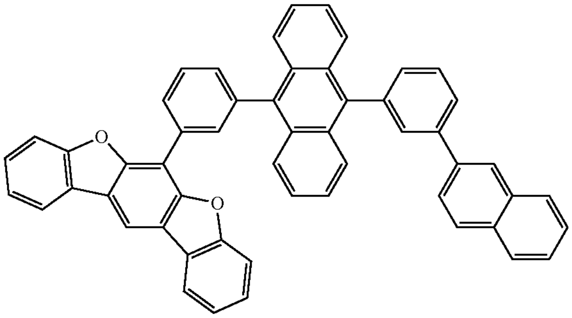
-continued
H83
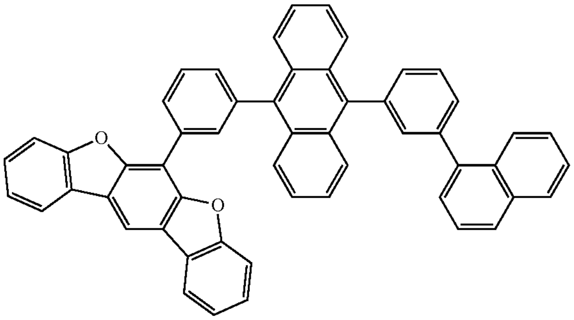
H84
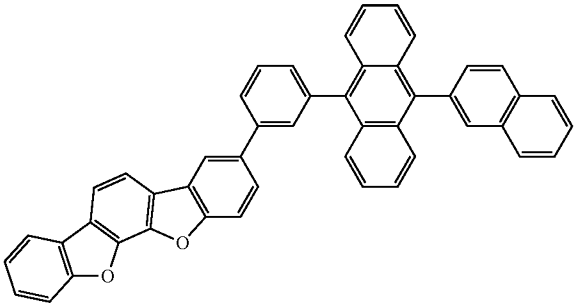
H85
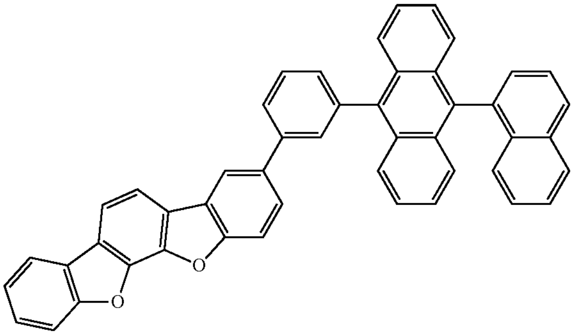
H86
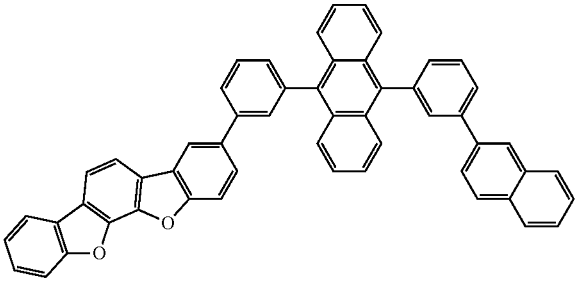
H87
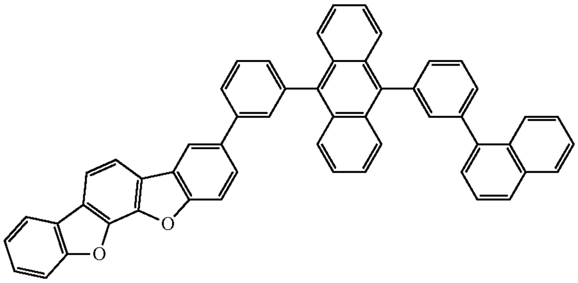

-continued
H88
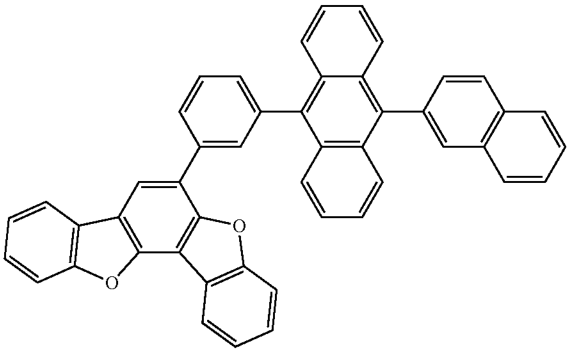
H89
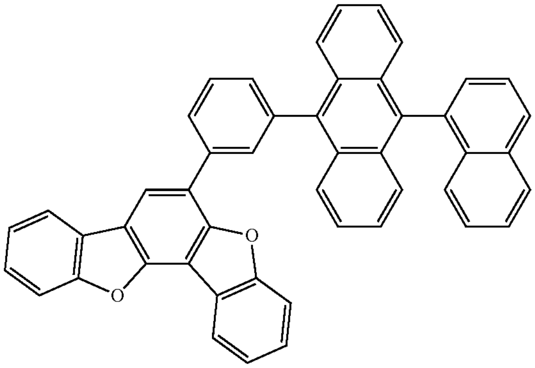
H90
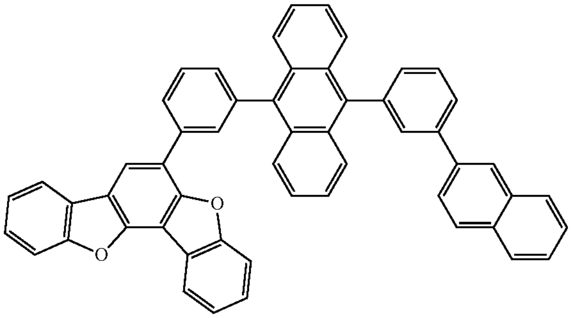
H91
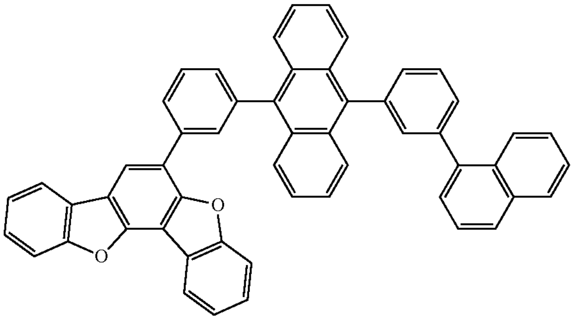
-continued
H92
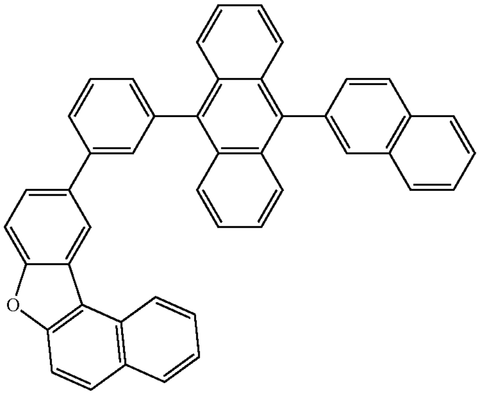
H93
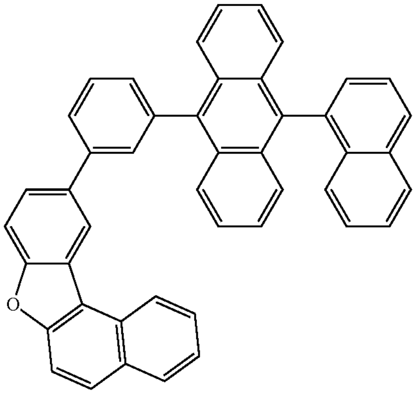
H94
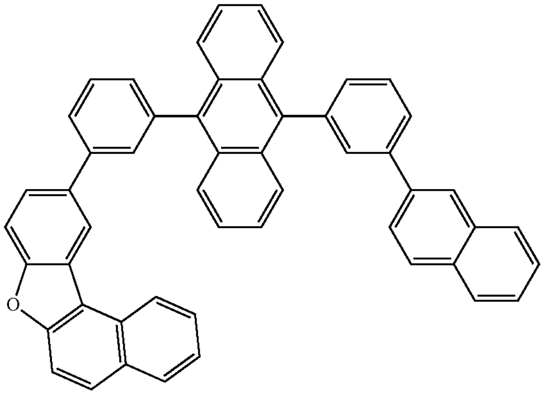
H95
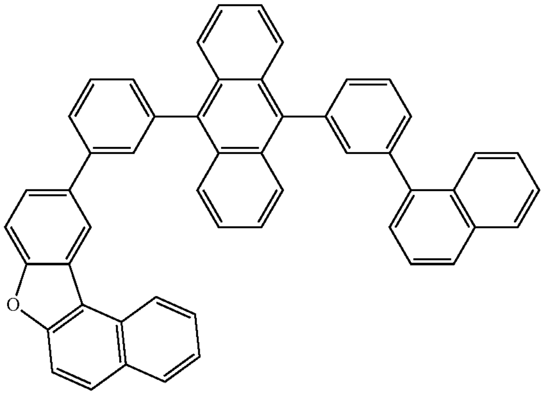

H96
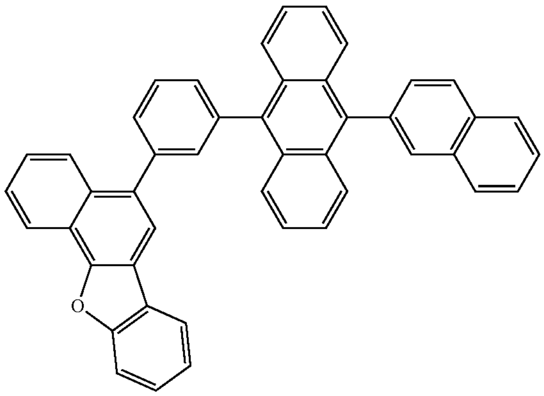
H97
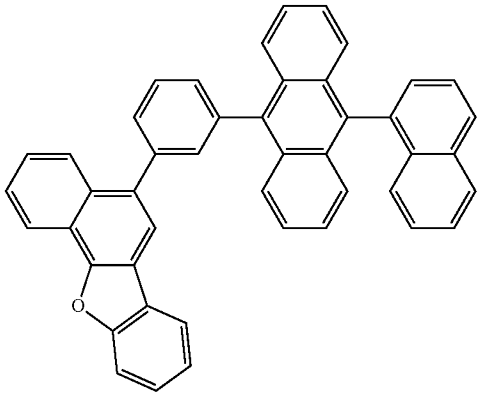
H98
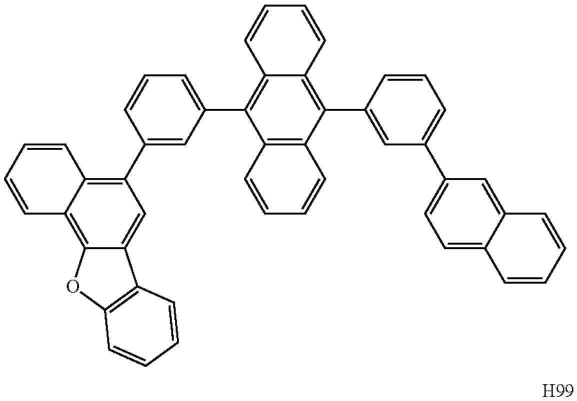
H99
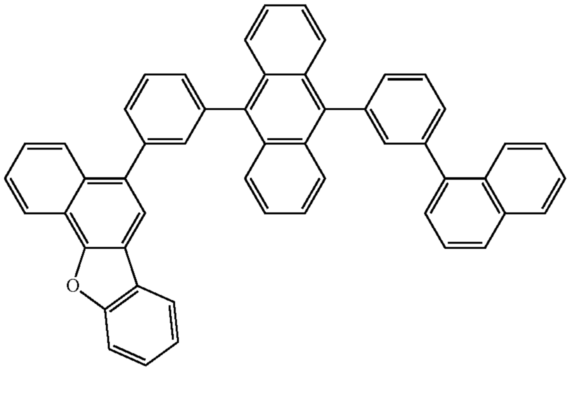
H100
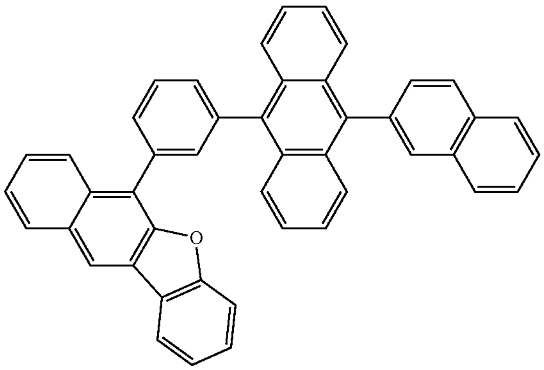
H101
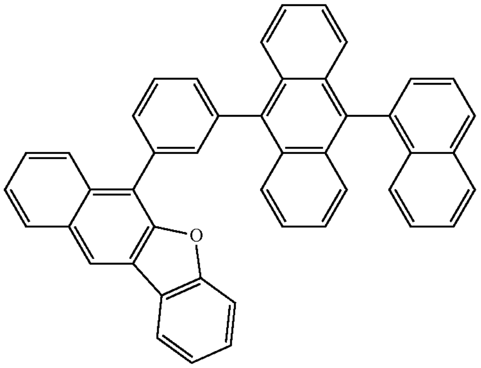
H102
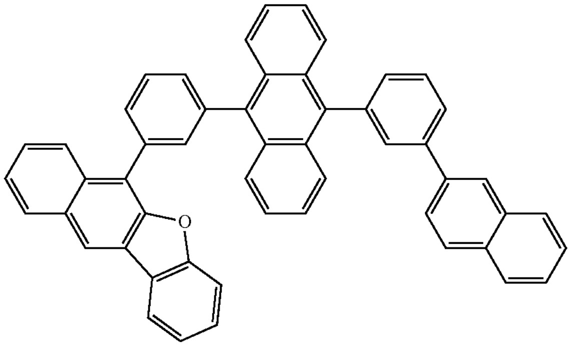
H103
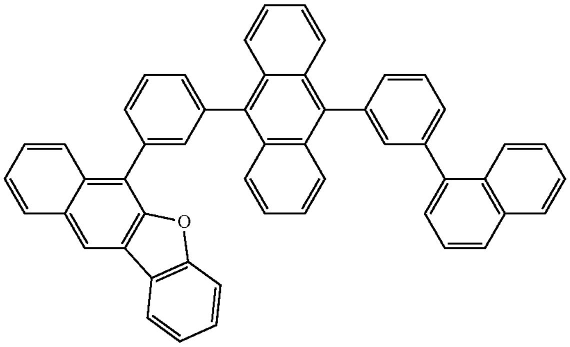

-continued
H104
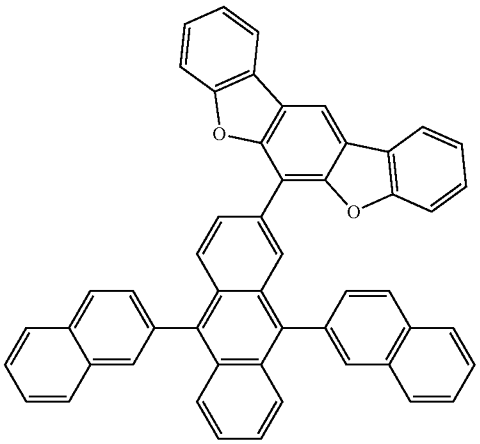
H105
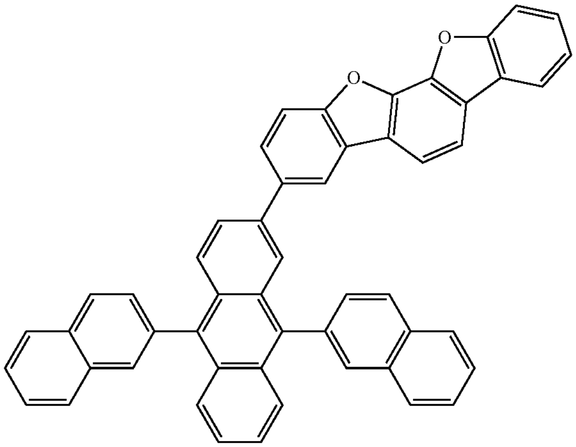
H106
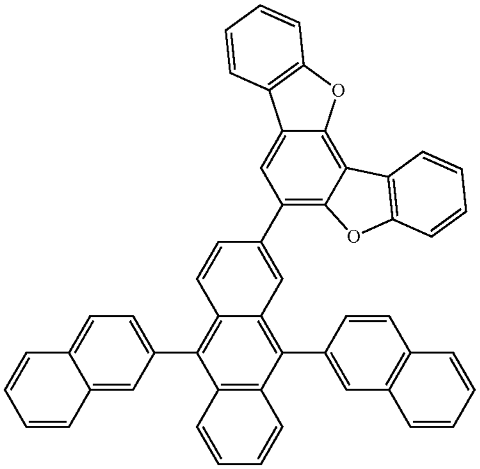
-continued
H107
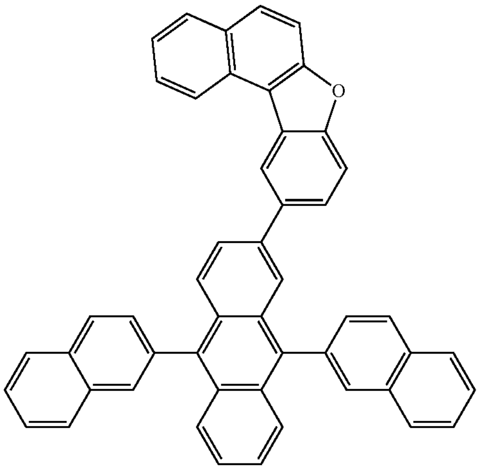
H108
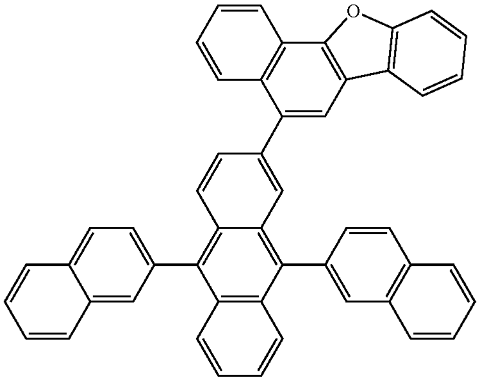
H109
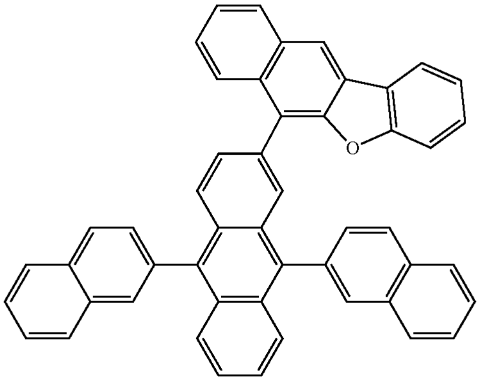
H110
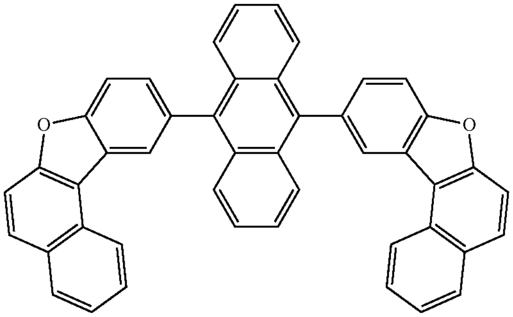

-continued
H111
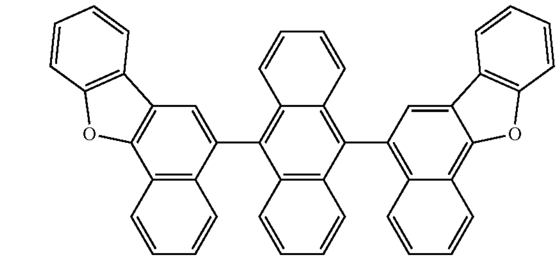
H112
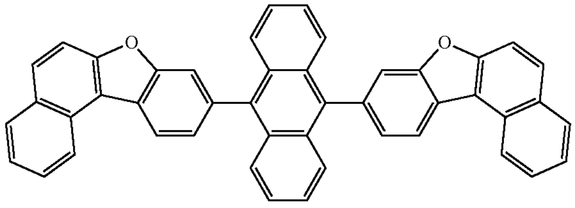
H113
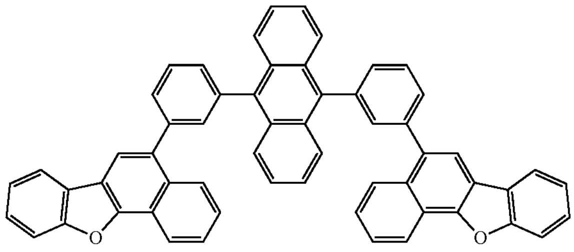
H114
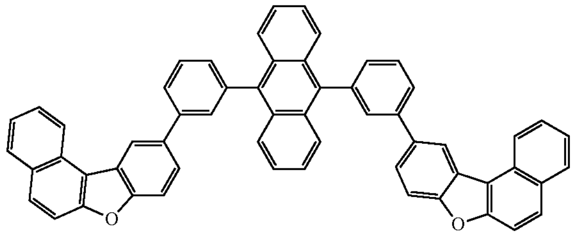
H115
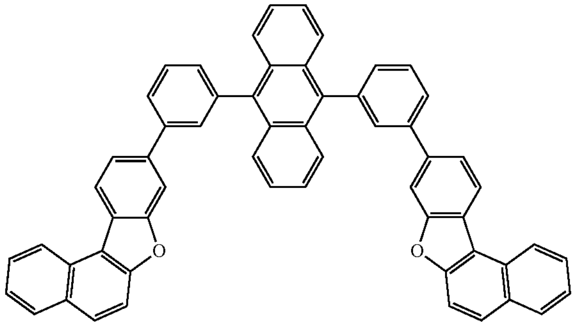
-continued
H116
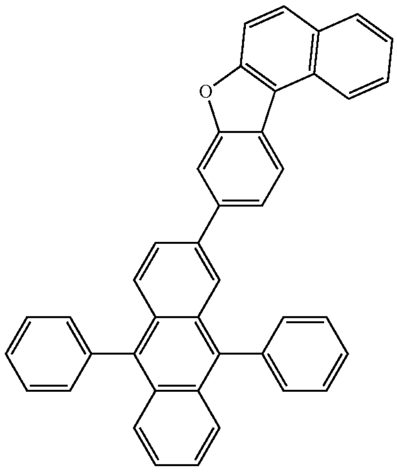
H117
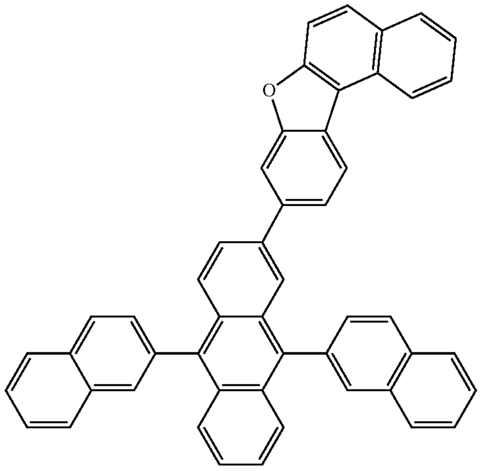
H118
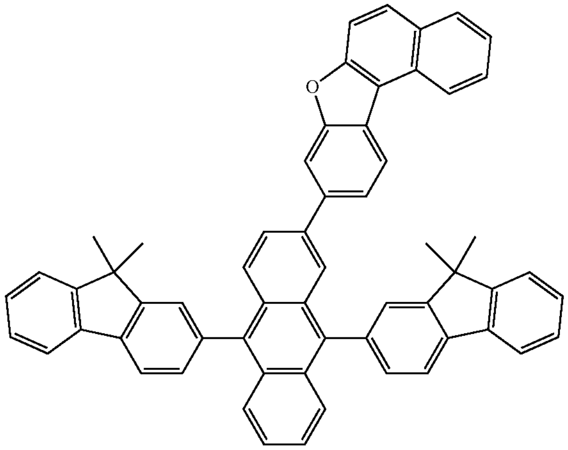

-continued
H119
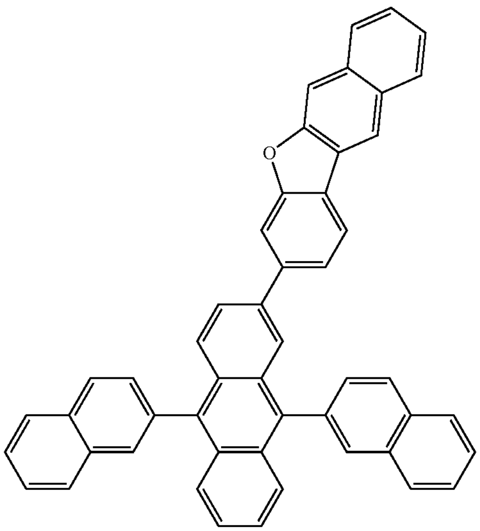
H120
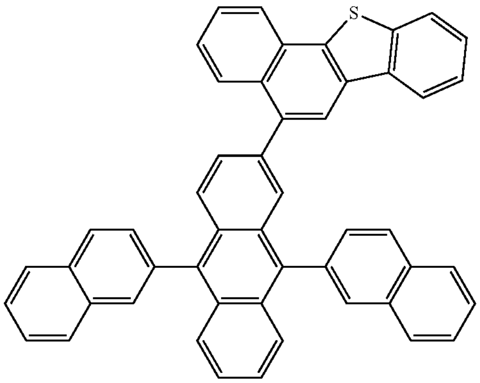
H121
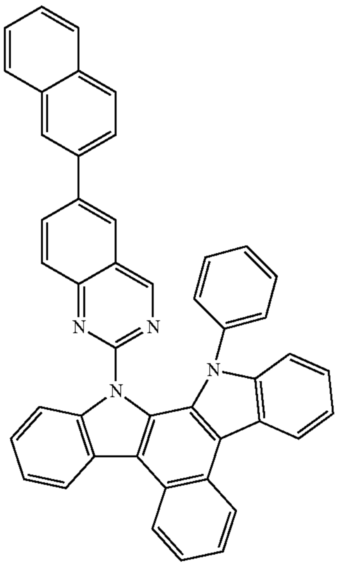
-continued
H122
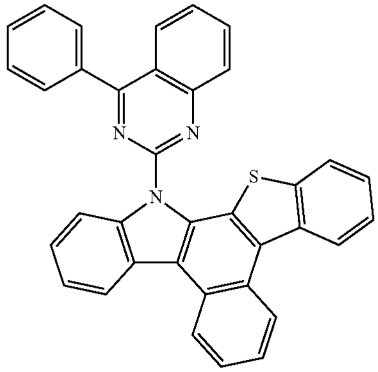
H123
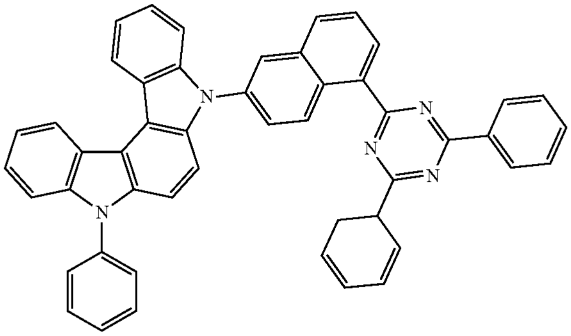
H124
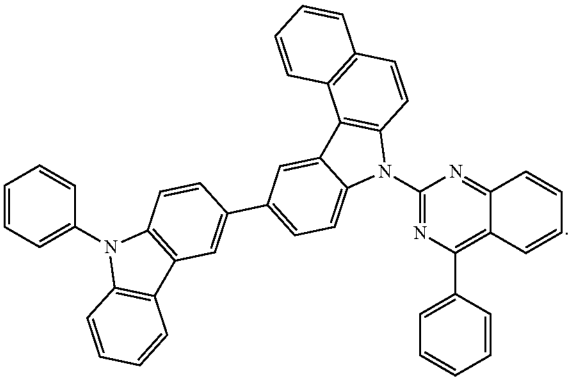
Phosphorescent Dopant
The phosphorescent dopant may include at least one transition metal as a center metal.
The phosphorescent dopant may include a monodentate ligand, a bidentate ligand, a tridentate ligand, a tetradentate ligand, a pentadentate ligand, a hexadentate ligand, or any combination thereof.

The phosphorescent dopant may be electrically neutral.

In some embodiments, the phosphorescent dopant may include an organometallic complex represented by Formula 401:

Formula 401

$M(L_{401})_{xc1}(L_{402})_{xc2}$

Formula 402

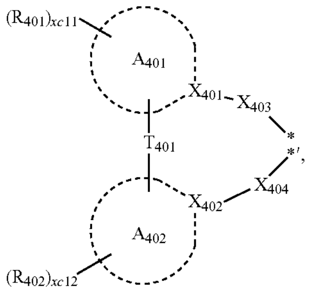

wherein, in Formulae 401 and 402,

M may be a transition metal (e.g., iridium (Ir), platinum (Pt), palladium (Pd), osmium (Os), titanium (Ti), gold (Au), hafnium (Hf), europium (Eu), terbium (Tb), rhodium (Rh), rhenium (Re), or thulium (Tm)), $L_{401}$ may be a ligand represented by Formula 402, and xc1 may be 1, 2, or 3, and when xc1 is 2 or greater, at least two $L_{401}$ (s) may be identical to or different from each other, $L_{402}$ may be an organic ligand, and xc2 may be an integer selected from 0 to 4, and when xc2 is 2 or greater, at least two $L_{402}$(s) may be identical to or different from each other, $X_{401}$ and $X_{402}$ may each independently be nitrogen or carbon, ring $A_{401}$ and ring $A_{402}$ may each independently be a $C_3$-$C_{60}$ carbocyclic group or a $C_1$-$C_{60}$ heterocyclic group, $T_{401}$ may be a single bond, *—O—*', *—S—*', *—C(=O)—*', *—N($Q_{411}$)-*', *—C($Q_{411}$)($Q_{412}$)-*', *—C($Q_{411}$)=C($Q_{412}$)-*', *—C($Q_{411}$)=*', or *=C=*', $X_{403}$ and $X_{404}$ may each independently be a chemical bond (e.g., a covalent bond or a coordinate bond), O, S, N($Q_{413}$), B($Q_{413}$), P($Q_{413}$), C($Q_{413}$)($Q_{414}$), or Si($Q_{413}$)($Q_{414}$), wherein $Q_{411}$ to $Q_{414}$ may each be understood by referring to the description of $Q_1$ provided herein, $R_{401}$ and $R_{402}$ may each independently be hydrogen, deuterium, —F, —Cl, —Br, —I, a hydroxyl group, a cyano group, a nitro group, a $C_1$-$C_{20}$ alkyl group unsubstituted or substituted with at least one $R_{10a}$, a $C_1$-$C_{20}$ alkoxy group unsubstituted or substituted with at least one $R_{10a}$, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, —Si($Q_{401}$)($Q_{402}$)($Q_{403}$), —N($Q_{401}$)($Q_{402}$), —B($Q_{401}$)($Q_{402}$), —C(=O)($Q_{401}$), —S(=O)$_2$($Q_{401}$), or —P(=O)($Q_{401}$)($Q_{402}$), wherein $Q_{401}$ to $Q_{403}$ may each be understood by referring to the description of $Q_1$ provided herein, xc11 and xc12 may each independently be an integer selected from 0 to 10, and

* and *' in Formula 402 each indicate a binding site to M in Formula 401.

For example, in Formula 402, i) $X_{401}$ may be nitrogen, and $X_{402}$ may be carbon, or ii) $X_{401}$ and $X_{402}$ may each be nitrogen.

In one or more embodiments, when xc1 in Formula 401 is 2 or greater, two ring $A_{401}$(s) of at least two $L_{401}$(s) may optionally be bound via $T_{402}$ as a linking group, or two ring $A_{402}$(s) may optionally be bound via $T_{403}$ as a linking group (see e.g., Compounds PD1 to PD4 and PD7). $T_{402}$ and $T_{403}$ may each be understood by referring to the description of $T_{401}$ provided herein.

In Formula 401, $L_{402}$ may be any suitable organic ligand. For example, $L_{402}$ may be a halogen group, a diketone group (e.g., an acetylacetonate group), a carboxylic acid group (e.g., a picolinate group), —C(=O), an isonitrile group, —CN, or a phosphorus group (e.g., a phosphine group or a phosphite group).

The phosphorescent dopant may be, for example, one compound selected from Compounds PD1 to PD39, Dopant-2, or any combination thereof:

PD1

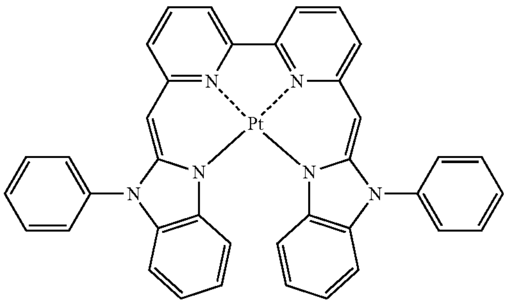

PD2

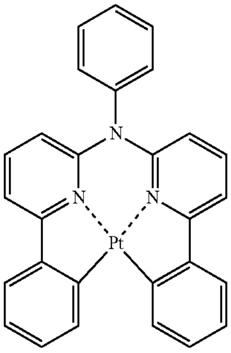

PD3

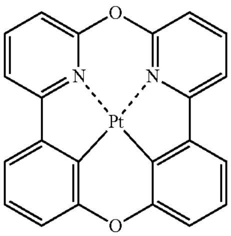

-continued
PD4
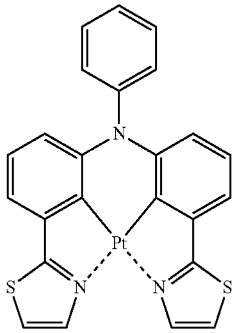
PD5
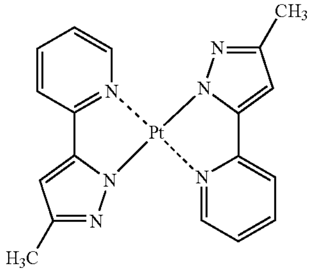
PD6
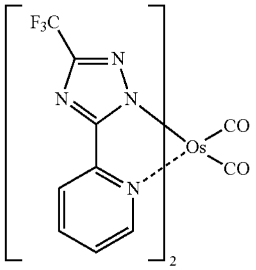
PD7
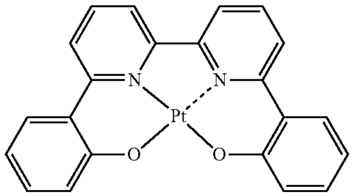
PD8
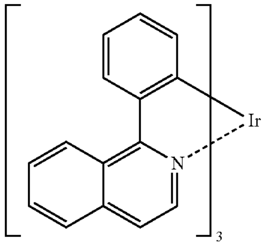
PD9
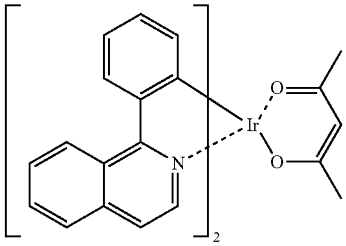
-continued
PD10
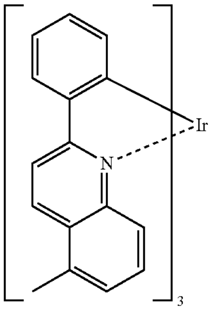
PD11
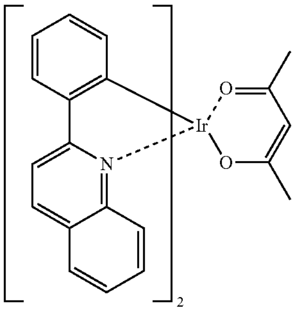
PD12
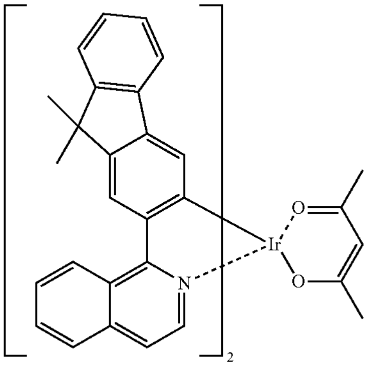
PD13
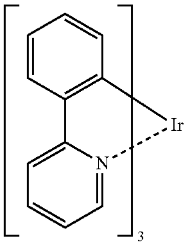
PD14
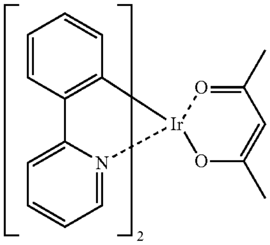

-continued
PD15
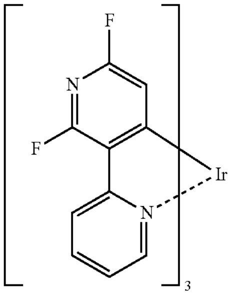
PD16
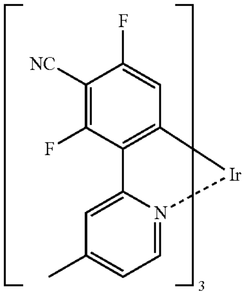
PD17
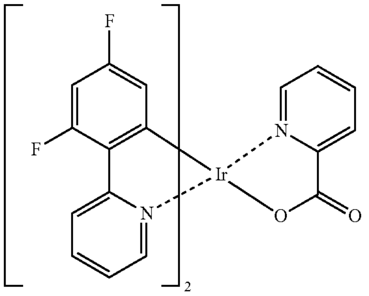
PD18
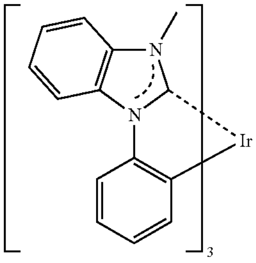
PD19
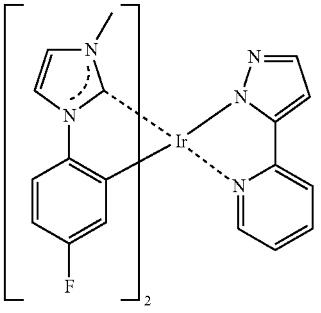
-continued
PD20
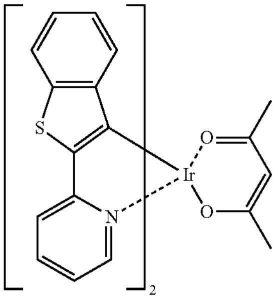
PD21
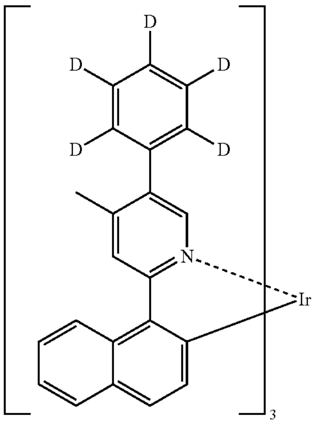
PD22
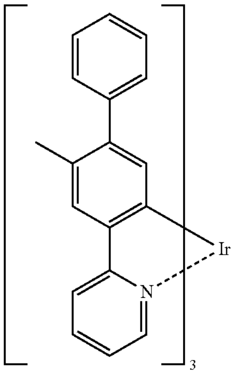
PD23
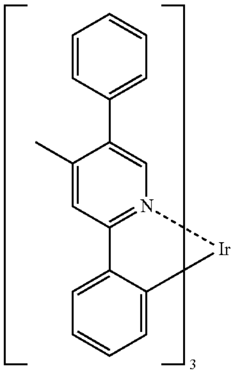

-continued
PD24
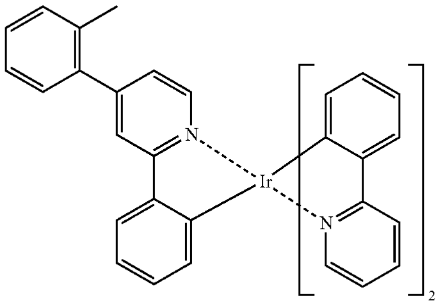
PD25
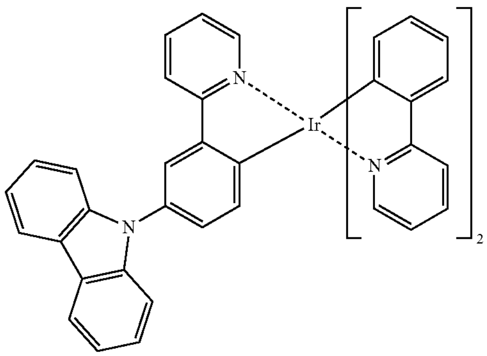
PD26
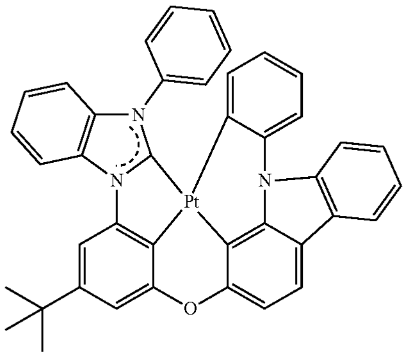
PD27
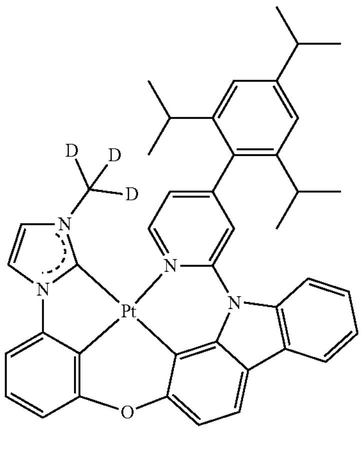
-continued
PD28
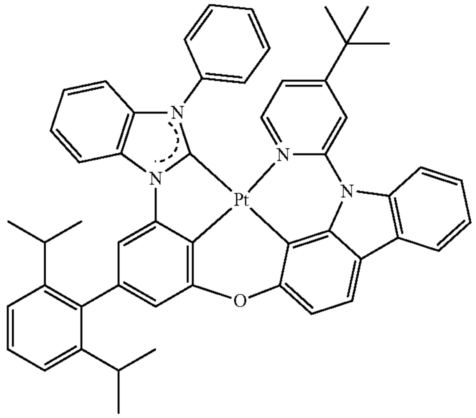
PD29
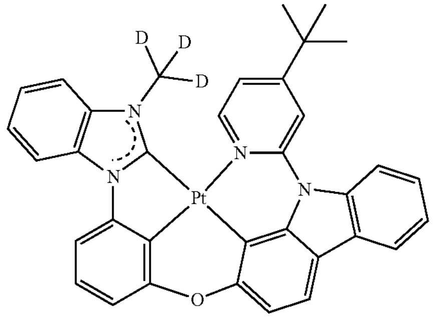
PD30
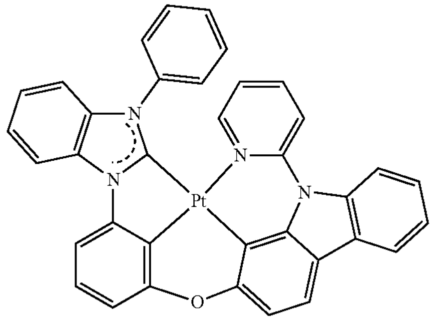
PD31
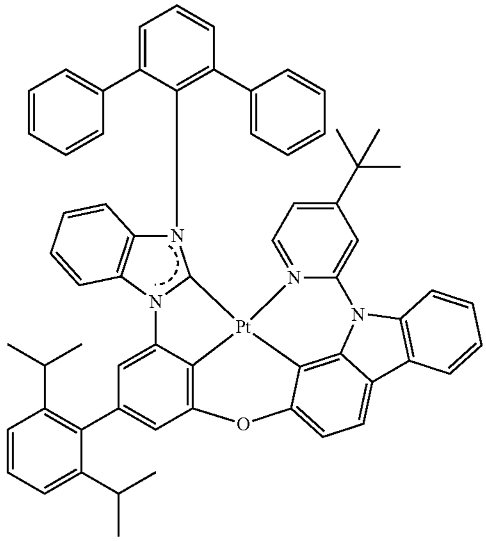

-continued
PD32
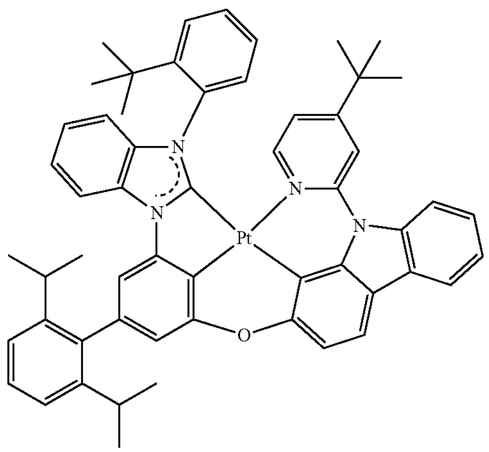
PD33
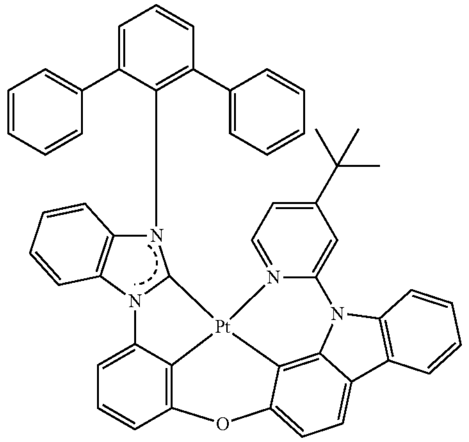
PD34
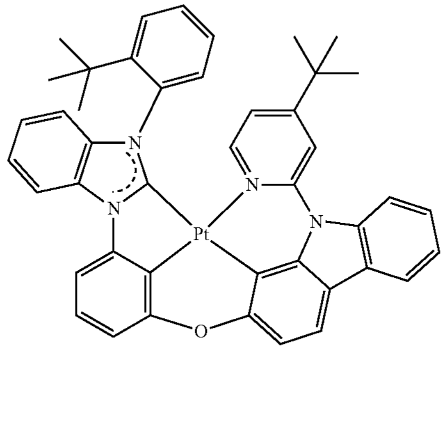
-continued
PD35
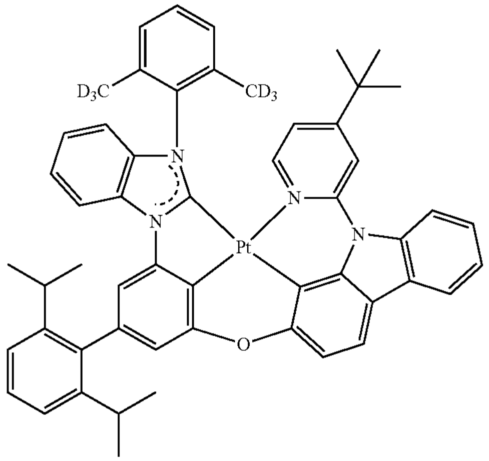
PD36
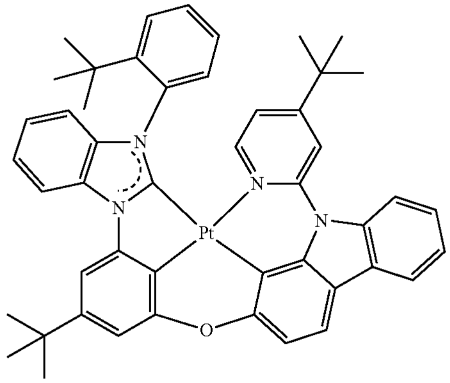
PD37
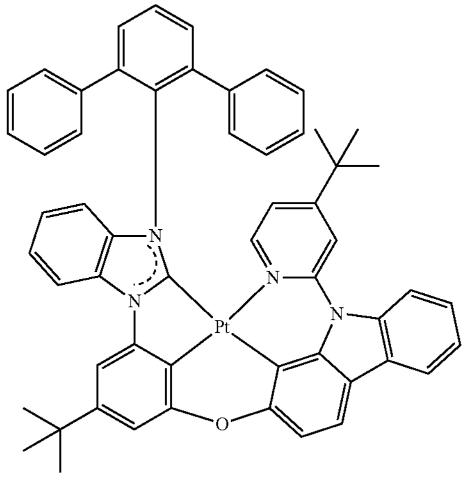

-continued

PD38

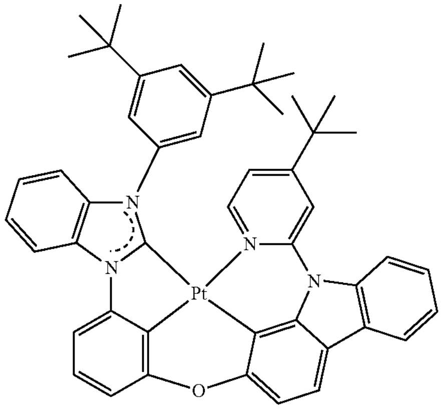

PD39

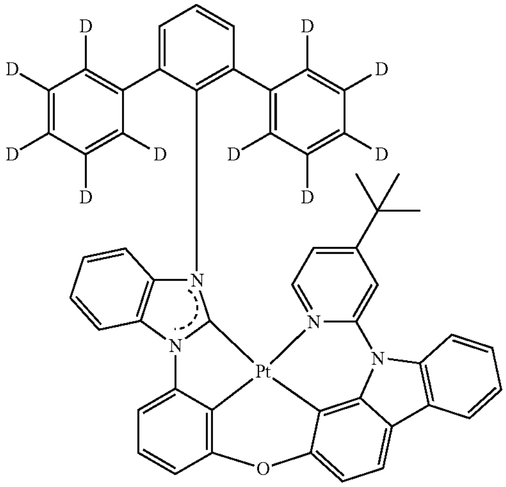

-continued

Dopant-2

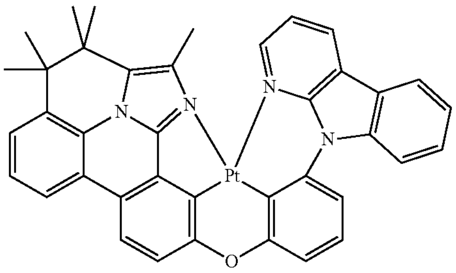

Fluorescent Dopant

The fluorescent dopant may include an amine group-containing compound, a styryl group-containing compound, or any combination thereof.

In some embodiments, the fluorescent dopant may include a compound represented by Formula 501:

Formula 501

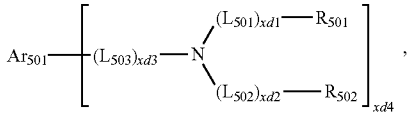

wherein, in Formula 501, $Ar_{501}$, $L_{501}$ to $L_{503}$, $R_{501}$, and $R_{502}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, xd1 to xd3 may each independently be 0, 1, 2, or 3, and xd4 may be 1, 2, 3, 4, 5, or 6.

In some embodiments, in Formula 501, $Ar_{501}$ may include a condensed ring group (e.g., an anthracene group, a chrysene group, or a pyrene group) in which at least three monocyclic groups are condensed.

In some embodiments, xd4 in Formula 501 may be 2.

In some embodiments, the fluorescent dopant may include one compound selected from Compounds FD1 to FD36, DPVBi, DPAVBi, or any combination thereof:

FD1

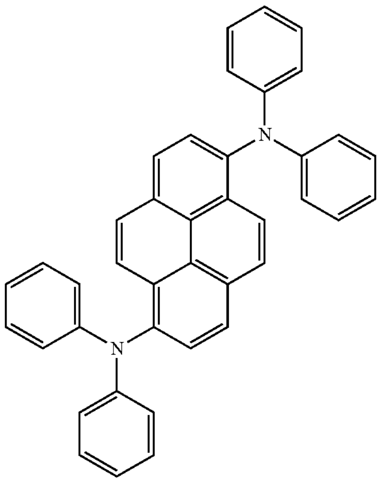

FD2

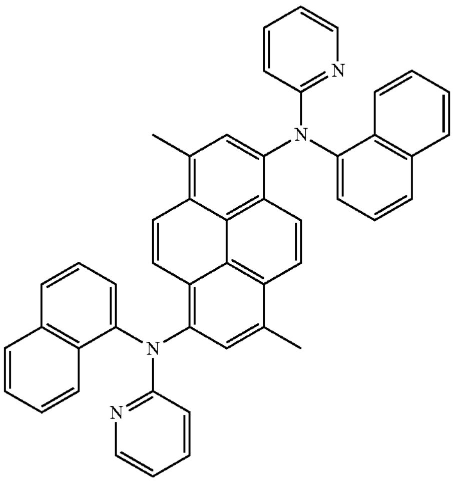

-continued
FD3
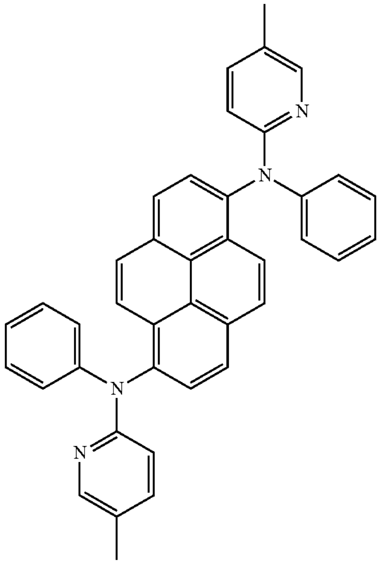
FD4
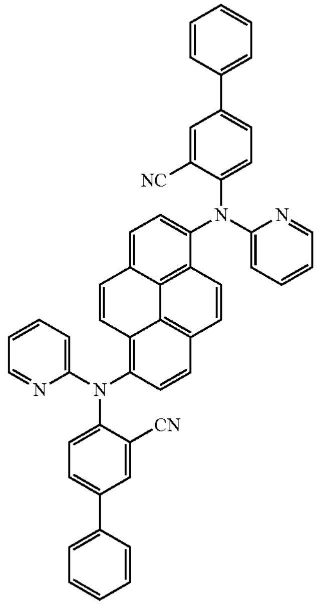
FD5
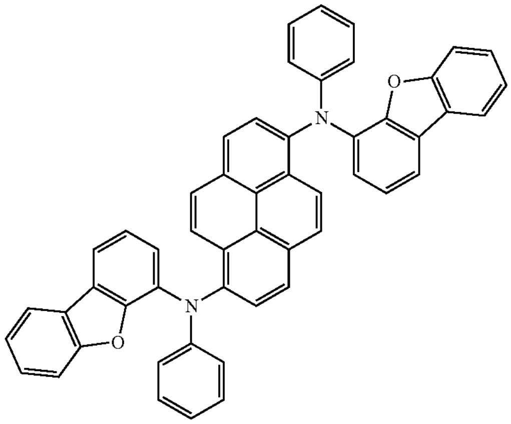
FD6
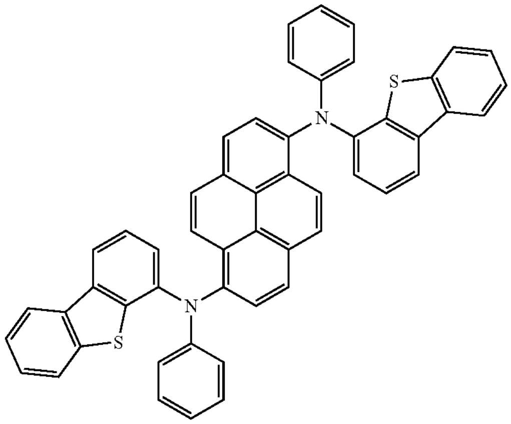
FD7
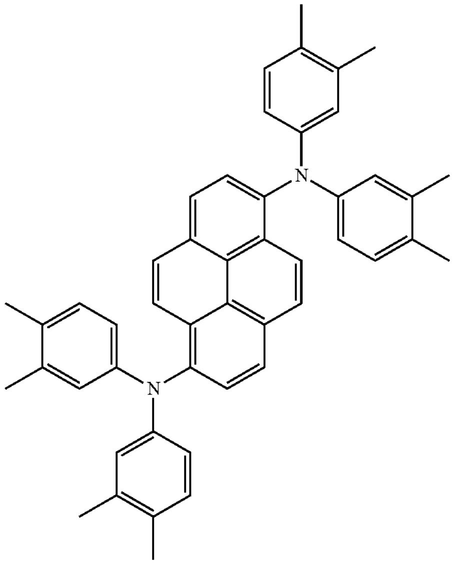
FD8
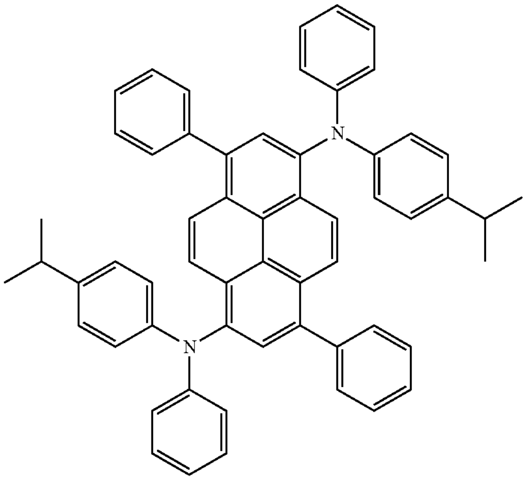

-continued
FD9
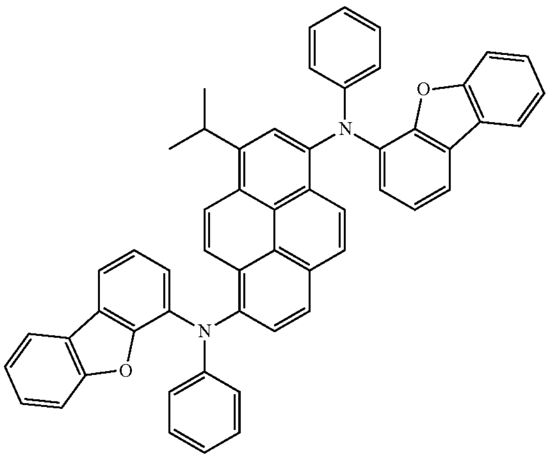
FD10
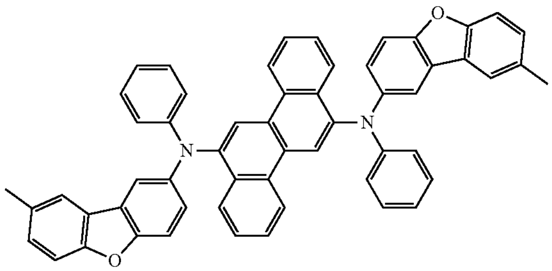
FD11
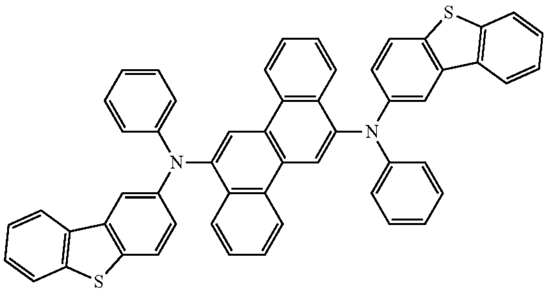
FD12
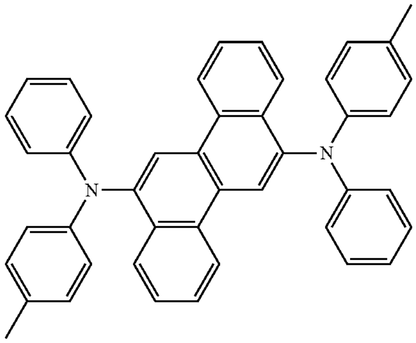
FD13
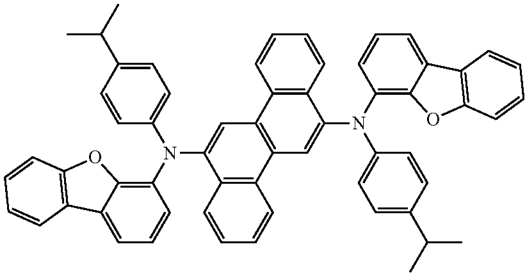
FD14
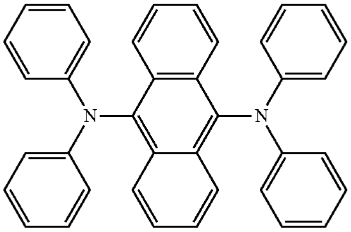
FD15
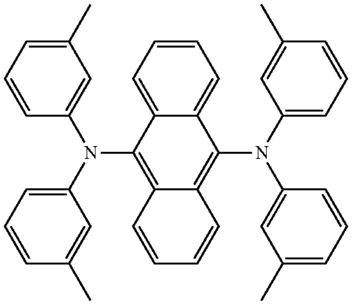
FD16
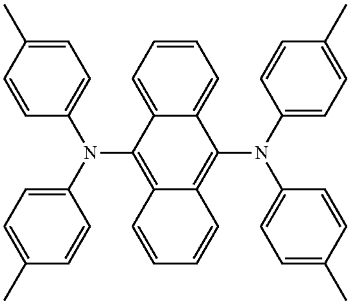

-continued
FD17
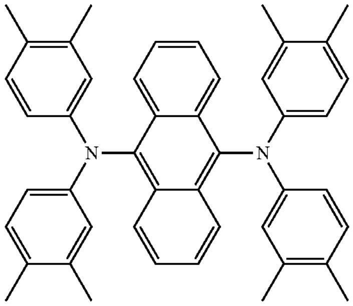
FD18
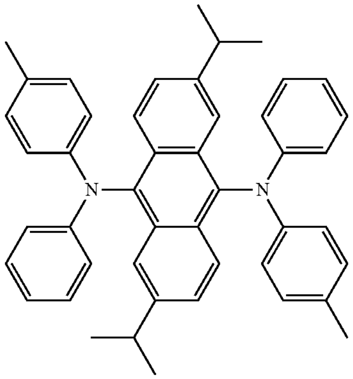
FD19
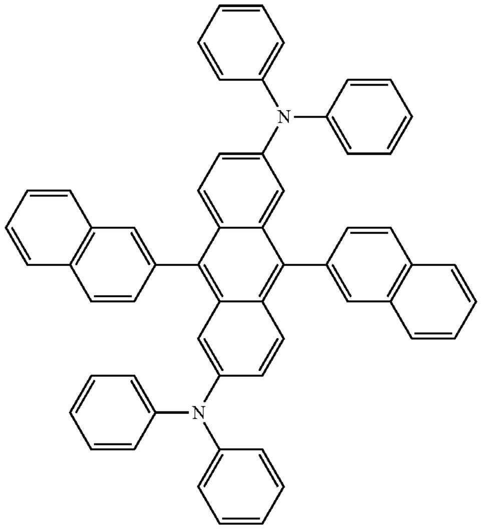
FD20
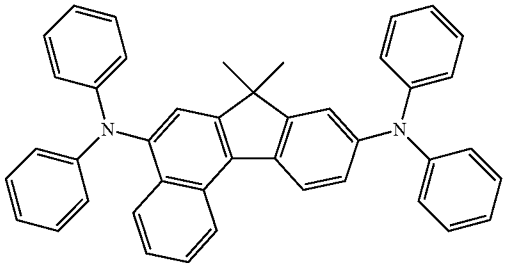
FD21
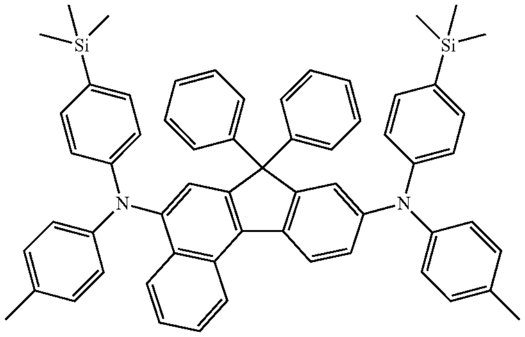
FD22
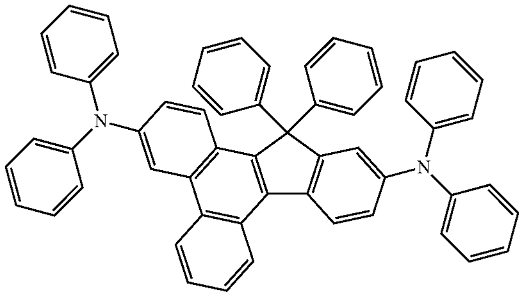
FD23
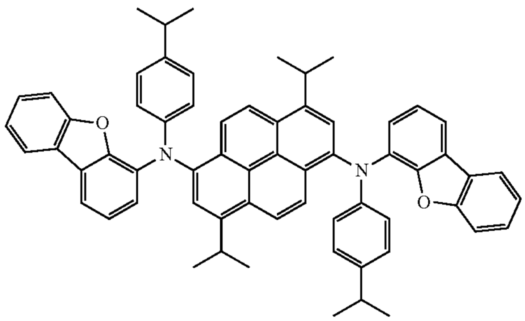
FD24
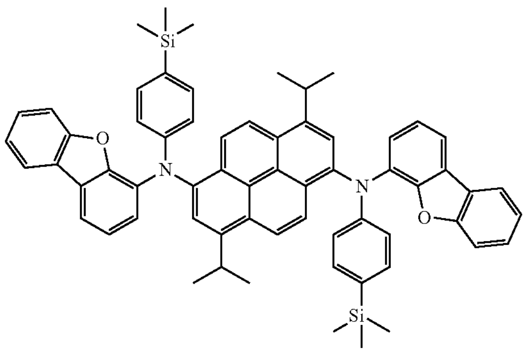

-continued
FD25
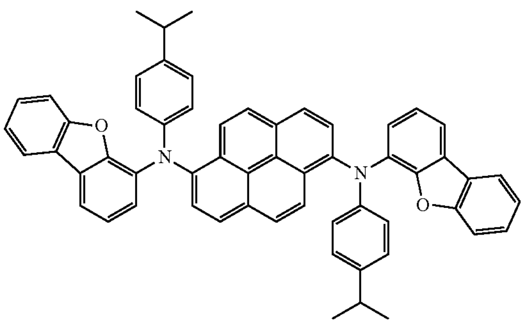
FD26
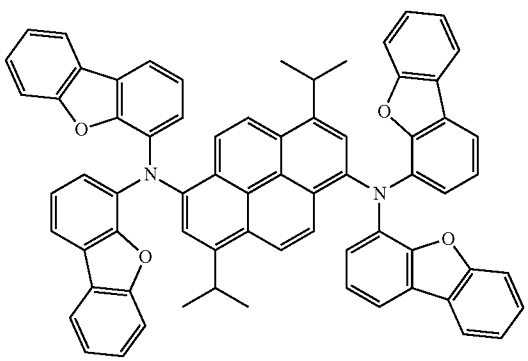
FD27
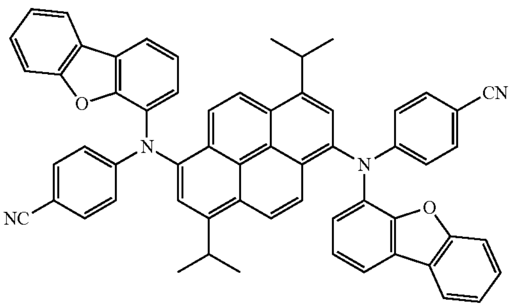
FD28
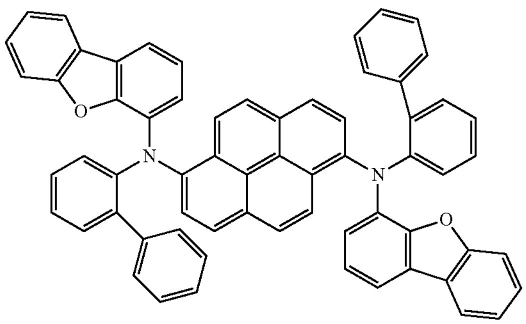
FD29
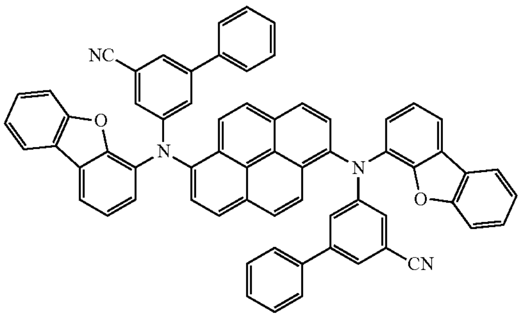
FD30
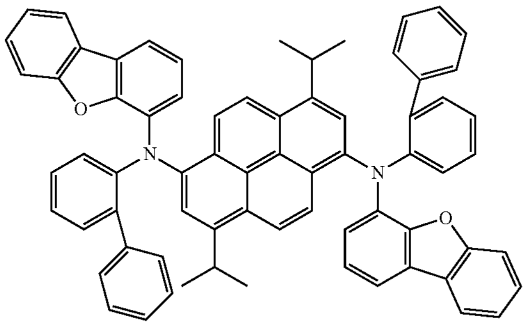
FD31
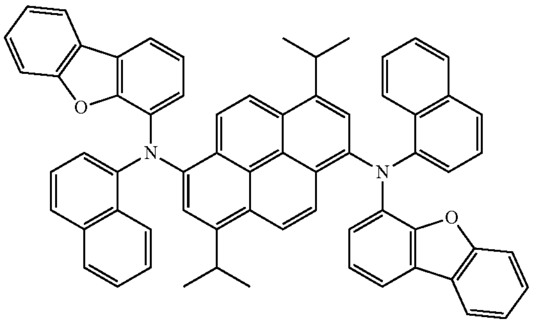
FD32
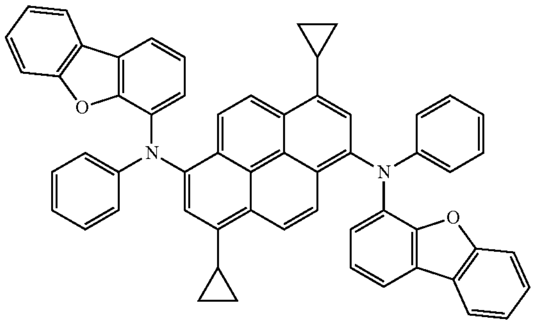

-continued

FD33

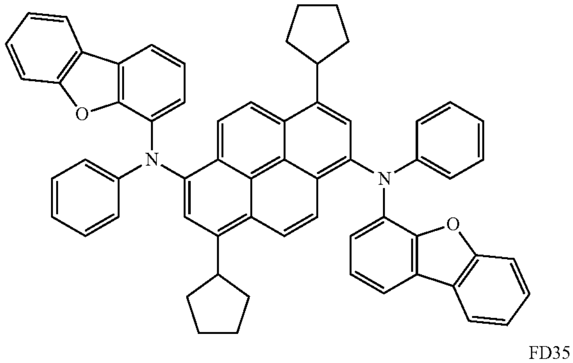

FD34

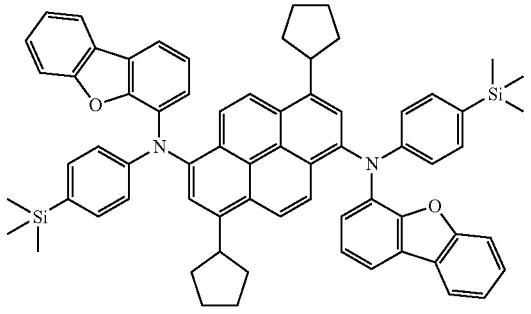

FD35

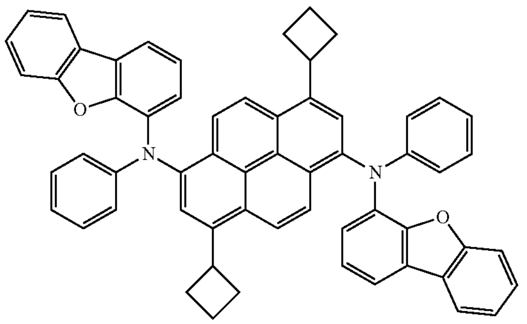

FD36

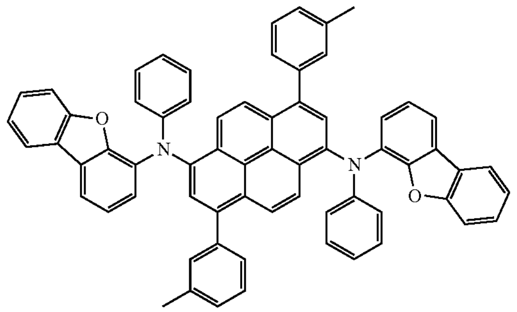

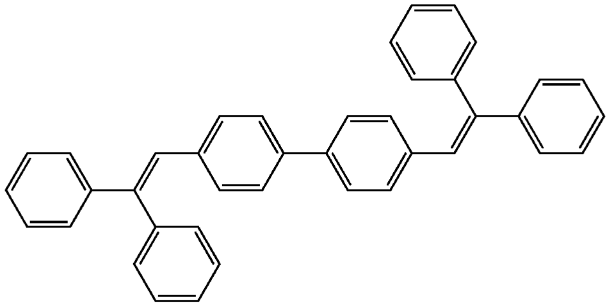

DPVBi

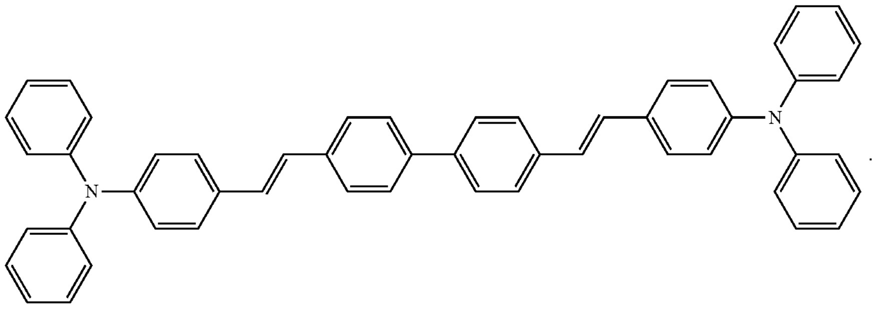

DPAVBi

Delayed Fluorescence Material

The emission layer may include a delayed fluorescence material.

The delayed fluorescence material described herein may be any suitable compound that may emit delayed fluorescence according to a delayed fluorescence emission mechanism.

The delayed fluorescence material included in the emission layer may serve as a host or a dopant, depending on types (or kinds) of other materials included in the emission layer.

In some embodiments, a difference between a triplet energy level (eV) of the delayed fluorescence material and a singlet energy level (eV) of the delayed fluorescence material may be about 0 eV or greater and about 0.5 eV or less. When the difference between a triplet energy level (eV) of the delayed fluorescence material and a singlet energy level (eV) of the delayed fluorescence material is within this range, up-conversion from a triplet state to a singlet state in the delayed fluorescence material may effectively (or suitably) occur, thus improving luminescence efficiency and/or the like of the light-emitting device 10.

In some embodiments, the delayed fluorescence material may include: i) a material including at least one electron donor (e.g., a π electron-rich $C_3$-$C_{60}$ cyclic group such as a carbazole group and/or the like) and at least one electron acceptor (e.g., a sulfoxide group, a cyano group, a π electron-deficient nitrogen-containing $C_1$-$C_{60}$ cyclic group, and/or the like); ii) a material including a $C_8$-$C_{60}$ polycyclic group including at least two cyclic groups condensed to each other and sharing boron (B); and/or the like.

Examples of the delayed fluorescence material may include Compounds DF1 to DF9 and Dopant-1:

DF1

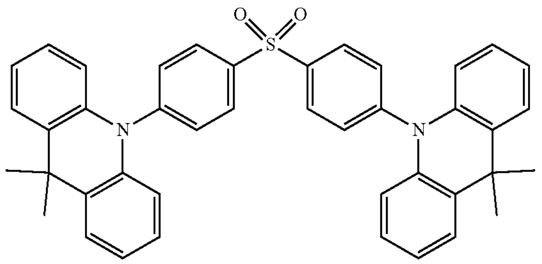

(DMAC-DPS)

DF2

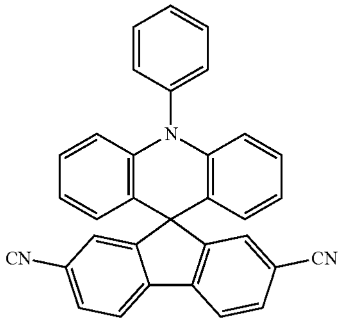

(ACRFLCN)

DF3

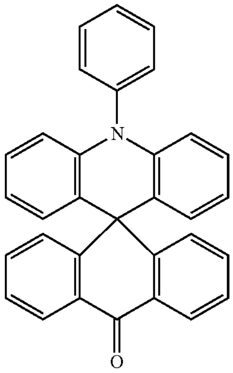

(ACRSA)

-continued

DF4

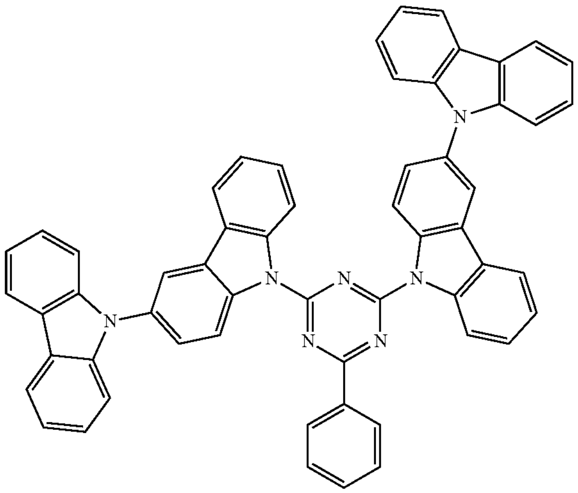

(CC2TA)

DF5

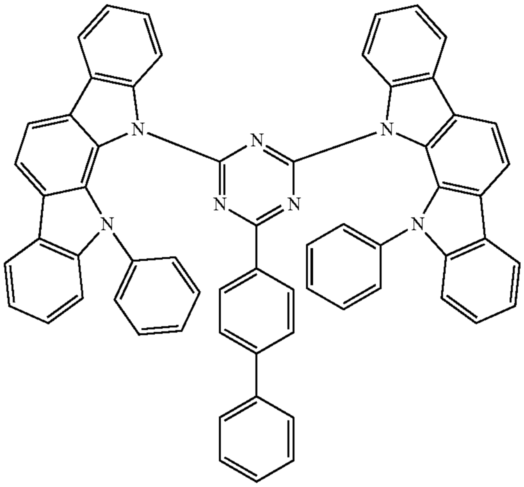

(PIC-TRZ)

DF6

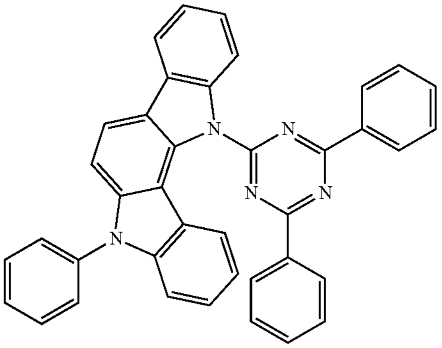

(PIC-TRZ2)

-continued

DF7

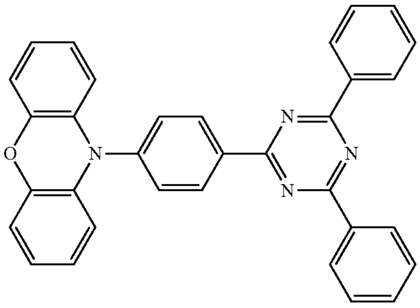

(PXZ-TRZ)

DF8

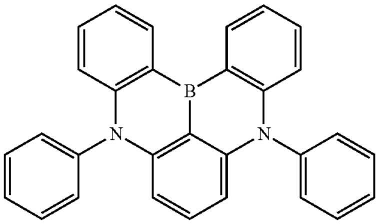

(DABNA-1)

DF9

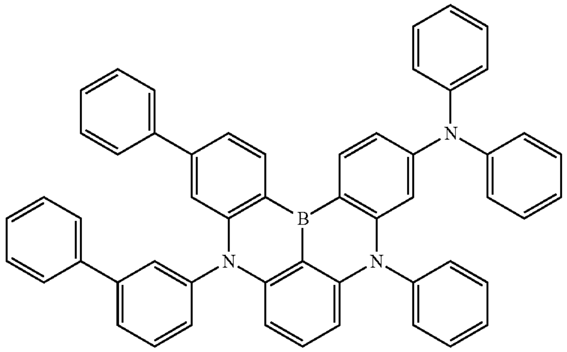

(DABNA-2)

Dopant-1

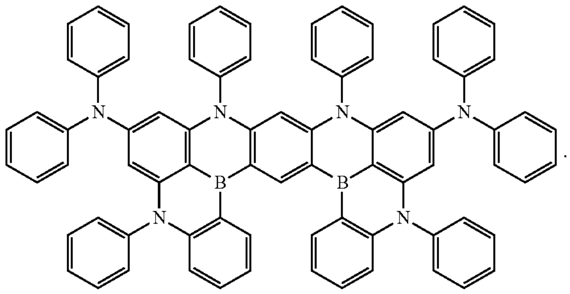

Quantum Dots

The emission layer may include quantum dots.

The term "quantum dot" as used herein refers to a crystal of a semiconductor compound and may include any suitable material capable of emitting emission wavelengths of various lengths according to the size of the crystal.

The diameter of the quantum dot may be, for example, in a range of about 1 nm to about 10 nm.

Quantum dots may be synthesized by a wet chemical process, an organic metal chemical vapor deposition process, a molecular beam epitaxy process, or any similar suitable process.

The wet chemical process is a method of growing a quantum dot particle crystal by mixing a precursor material with an organic solvent. When the crystal grows, the organic solvent may naturally serve as a dispersant coordinated on the surface of the quantum dot crystal and control the growth of the crystal. Thus, the wet chemical method may be easier to perform than the vapor deposition process such a metal organic chemical vapor deposition (MOCVD) or a molecular beam epitaxy (MBE) process. Further, the growth of quantum dot particles may be controlled with a lower manufacturing cost.

The quantum dot may include a group II-VI semiconductor compound; a group III-V semiconductor compound; a group III-VI semiconductor compound; a group I-III-VI semiconductor compound; a group IV-VI semiconductor compound; a group IV element or compound; or any combination thereof.

Examples of the group II-VI semiconductor compound may include a binary compound such as CdS, CdSe, CdTe, ZnS, ZnSe, ZnTe, ZnO, HgS, HgSe, HgTe, MgSe, and/or MgS; a ternary compound such as CdSeS, CdSeTe, CdSTe, ZnSeS, ZnSeTe, ZnSTe, HgSeS, HgSeTe, HgSTe, CdZnS, CdZnSe, CdZnTe, CdHgS, CdHgSe, CdHgTe, HgZnS, HgZnSe, HgZnTe, MgZnSe, and/or MgZnS; a quaternary compound such as CdZnSeS, CdZnSeTe, CdZnSTe, CdHgSeS, CdHgSeTe, CdHgSTe, HgZnSeS, HgZnSeTe, and/or HgZnSTe; and combinations thereof.

Examples of the group III-V semiconductor compound may include a binary compound such as GaN, GaP, GaAs, GaSb, AlN, AlP, AlAs, AlSb, InN, InP, InAs, and/or InSb; a ternary compound such as GaNP, GaNAs, GaNSb, GaPAs, GaPSb, AlNP, AlNAs, AlNSb, AlPAs, AlPSb, InGaP, InNP, InAlP, InNAs, InNSb, InPAs, and/or InPSb; a quaternary compound such as GaAlNP, GaAlNAs, GaAlNSb, GaAlPAs, GaAlPSb, GaInNP, GaInNAs, GaInNSb, GaInPAs, GaInPSb, InAlNP, InAlNAs, InAlNSb, InAlPAs, and/or InAlPSb; and combinations thereof. In some embodiments, the group III-V semiconductor compound may further include a group II element. Examples of the group III-V semiconductor compound further including the group II element may include InZnP, InGaZnP, InAlZnP, and the like.

Examples of the III-VI group semiconductor compound may include a binary compound such as GaS, GaSe, $Ga_2Se_3$, GaTe, InS, InSe, $In_2S_3$, $In_2Se_3$, InTe, and/or the like; a ternary compound such as $InGaS_3$, InGaSes, and/or the like; and combinations thereof.

Examples of the group I-III-VI semiconductor compound may include a ternary compound such as AgInS, $AgInS_2$, CuInS, $CuInS_2$, $CuGaO_2$, $AgGaO_2$, and/or $AgAlO_2$; and combinations thereof.

Examples of the group IV-VI semiconductor compound may include a binary compound such as SnS, SnSe, SnTe, PbS, PbSe, and/or PbTe; a ternary compound such as SnSeS, SnSeTe, SnSTe, PbSeS, PbSeTe, PbSTe, SnPbS, SnPbSe, and/or SnPbTe; a quaternary compound such as SnPbSSe, SnPbSeTe, and/or SnPbSTe; and combinations thereof.

The group IV element or compound may be a single element material such as Si and/or Ge; a binary compound such as SiC and/or SiGe; or any combination thereof.

Individual elements included in the multi-element compound, such as a binary compound, a ternary compound, and/or a quaternary compound, may be present in a particle thereof at a uniform or non-uniform concentration.

The quantum dot may have a single structure in which the concentration of each element included in the quantum dot is uniform, or a core-shell double structure. In some embodiments, materials included in the core may be different from materials included in the shell.

The shell of the quantum dot may serve as a protective layer for preventing or reducing chemical denaturation of the core to maintain semiconductor characteristics and/or as a charging layer for imparting electrophoretic characteristics to the quantum dot. The shell may be a monolayer or a multilayer. An interface between a core and a shell may have a concentration gradient where a concentration of elements present in the shell decreases toward the core.

Examples of the shell of the quantum dot may include metal oxide, metalloid oxide, nonmetal oxide, a semiconductor compound, and combinations thereof.

Examples of the metal oxide, the metalloid oxide, and the nonmetal oxide may include a binary compound such as $SiO_2$, $Al_2O_3$, $TiO_2$, ZnO, MnO, $Mn_2O_3$, $Mn_3O_4$, CuO, FeO, $Fe_2O_3$, $Fe_3O_4$, CoO, $Co_3O_4$, and/or NiO; a ternary compound such as $MgAl_2O_4$, $CoFe_2O_4$, $NiFe_2O_4$, and/or $CoMn_2O_4$; and combinations thereof. Examples of the semiconductor compound may include a group II-VI semiconductor compound; a group III-V semiconductor compound; a group III-VI semiconductor compound; a group I-III-VI semiconductor compound; a group IV-VI semiconductor compound; and combinations thereof. In some embodiments, the semiconductor compound may be CdS, CdSe, CdTe, ZnS, ZnSe, ZnTe, ZnSeS, ZnTeS, GaAs, GaP, GaSb, HgS, HgSe, HgTe, InAs, InP, InGaP, InSb, AlAs, AlP, AlSb, or any combination thereof.

The quantum dot may have a full width of half maximum (FWHM) of a spectrum of an emission wavelength of about 45 nm or less, about 40 nm or less, or about 30 nm or less. When the FWHM of the quantum dot is within any of these ranges, color purity and/or color reproducibility may be improved. In addition, because light emitted through the quantum dots is emitted in all directions, an optical viewing angle may be improved.

In one or more embodiments, the quantum dot may be specifically, a spherical, pyramidal, multi-arm, and/or cubic nanoparticle, nanotube, nanowire, nanofiber, and/or nanoplate particle.

By adjusting the size of the quantum dot, the energy band gap may also be adjusted, thereby obtaining light of various wavelengths in the quantum dot emission layer. By using quantum dots of various sizes, a light-emitting device that may emit light of various wavelengths may be realized. In some embodiments, the size of the quantum dot may be selected such that the quantum dot may emit red, green, and/or blue light. In addition, the size of the quantum dot may be selected such that the quantum dot may emit white light by combining various light colors.

Electron Transport Region in Interlayer 130

The electron transport region may have i) a single-layered structure including (e.g., consisting of) a single layer including (e.g., consisting of) a single material, ii) a single-layered structure including (e.g., consisting of) a single layer including a plurality of different materials, or iii) a multi-layered structure having a plurality of layers including a plurality of different materials.

The electron transport region may include a buffer layer, a hole blocking layer, an electron control layer, an electron transport layer, an electron injection layer, or any combination thereof.

In some embodiments, the electron transport region may have an electron transport layer/electron injection layer structure, a hole blocking layer/electron transport layer/electron injection layer structure, an electron control layer/electron transport layer/electron injection layer structure, or a buffer layer/electron transport layer/electron injection layer structure, wherein layers of each structure are sequentially stacked on the emission layer in each stated order.

The electron transport region (e.g., a buffer layer, a hole blocking layer, an electron control layer, and/or an electron transport layer in the electron transport region) may include a metal-free compound including at least one π electron-deficient nitrogen-containing $C_1$-$C_{60}$ cyclic group.

In some embodiments, the electron transport region may include a compound represented by Formula 601:

$$[Ar_{601}]_{xe11}\text{-}[(L_{601})_{xe1}\text{-}R_{601}]_{xe21}, \qquad \text{Formula 601}$$

wherein, in Formula 601, $Ar_{601}$ and $L_{601}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, xe11 may be 1, 2, or 3, xe1 may be 0, 1, 2, 3, 4, or 5, $R_{601}$ may be $C_3$-$C_{60}$ carbocyclic group unsubstituted or substituted with at least one $R_{10a}$, a $C_1$-$C_{60}$ heterocyclic group unsubstituted or substituted with at least one $R_{10a}$, —Si($Q_{601}$)($Q_{602}$)($Q_{603}$), —C(=O)($Q_{601}$), —S(=O)$_2$($Q_{601}$), or —P(=O)($Q_{601}$)($Q_{602}$), wherein $Q_{601}$ to $Q_{603}$ may each be understood by referring to the description of $Q_1$ provided herein, xe21 may be 1, 2, 3, 4, or 5, and at least one of $Ar_{601}$, $L_{601}$, and/or $R_{601}$ may each independently be a π electron-deficient nitrogen-containing $C_1$-$C_{60}$ cyclic group unsubstituted or substituted with at least one $R_{10a}$.

For example, in Formula 601, when xe11 is 2 or greater, at least two $Ar_{601}$(s) may be bound to each other via a single bond.

In some embodiments, in Formula 601, $Ar_{601}$ may be a substituted or unsubstituted anthracene group.

In some embodiments, the electron transport region may include a compound represented by Formula 601-1:

Formula 601-1

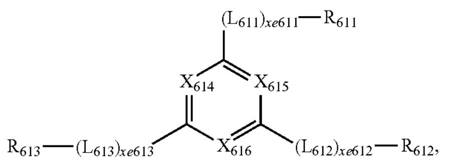

wherein, in Formula 601-1, $X_{614}$ may be N or C($R_{614}$), $X_{615}$ may be N or C($R_{615}$), $X_{616}$ may be N or C($R_{616}$), and at least one of $X_{614}$ to $X_{616}$ may be N, $L_{611}$ to $L_{613}$ may each be understood by referring to the description of $L_{601}$ provided herein, xe611 to xe613 may each be understood by referring to the description of xe1 provided herein, $R_{611}$ to $R_{613}$ may each be understood by referring to the description of $R_{601}$ provided herein, and $R_{614}$ to $R_{616}$ may each independently be hydrogen, deuterium, —F, —Cl, —Br, —I, a hydroxyl group, a cyano group, a nitro group, a $C_1$-$C_{20}$ alkyl group, a $C_1$-$C_{20}$ alkoxy group, a $C_3$-$C_{60}$ carbocyclic group unsubstituted or substituted with at least one $R_{10a}$, or a $C_1$-$C_{60}$ heterocyclic group unsubstituted or substituted with at least one $R_{10a}$.

For example, in Formulae 601 and 601-1, xe1 and xe611 to xe613 may each independently be 0, 1, or 2.
The electron transport region may include one compound selected from Compounds ET1 to ET45, 2,9-dimethyl-4,7-diphenyl-1,10-phenanthroline (BCP), 4,7-diphenyl-1,10-phenanthroline (Bphen), $Alq_3$, BAlq, TAZ, NTAZ, TSPO1, TPBI, or any combination thereof:
ET1
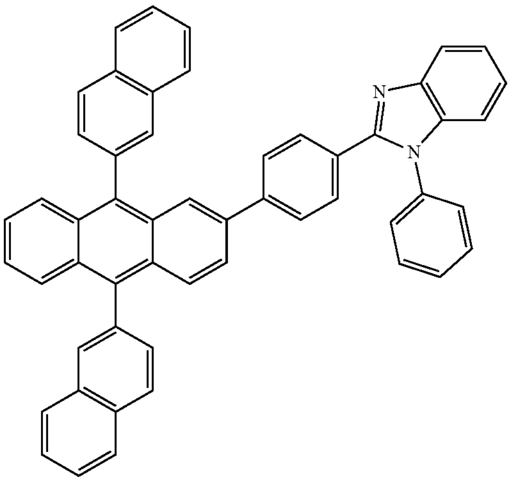
ET2
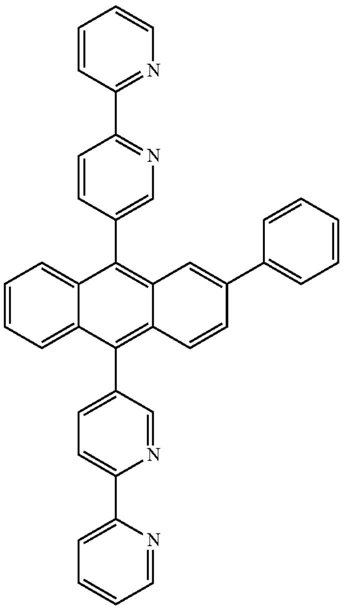
-continued
ET3
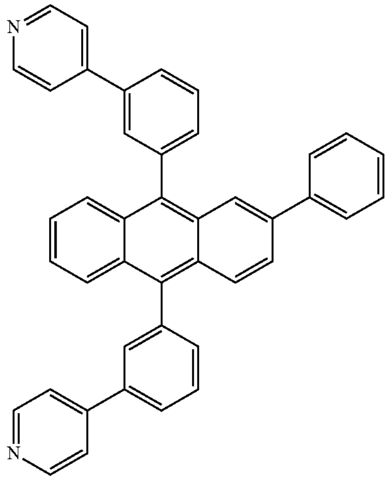
ET4
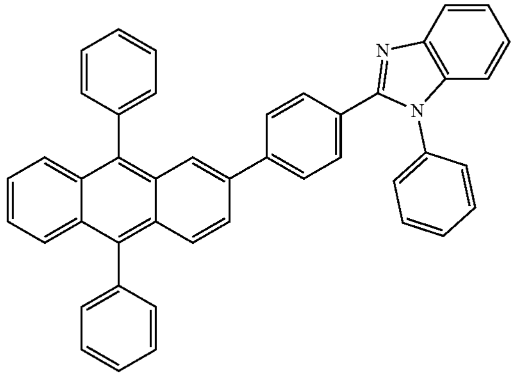
ET5
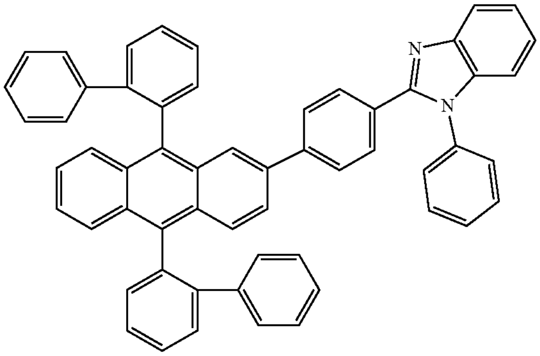
ET6
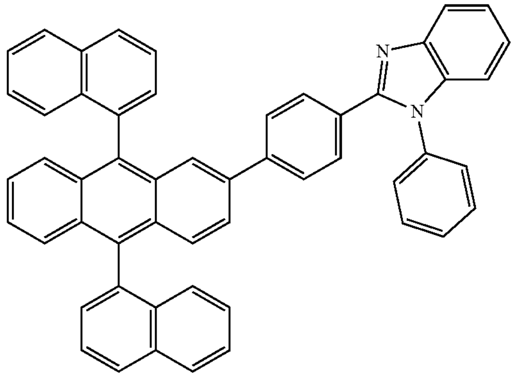

-continued
ET7
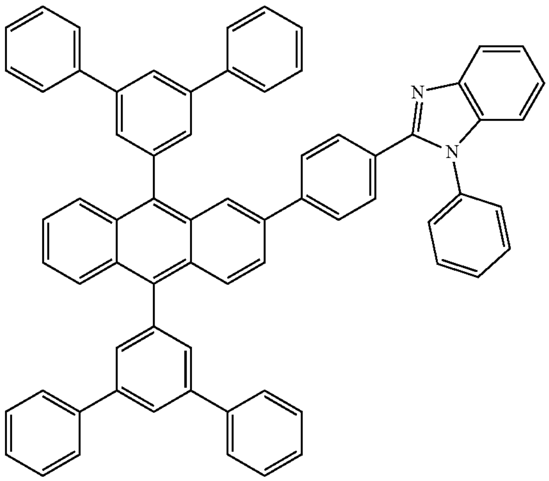
ET8
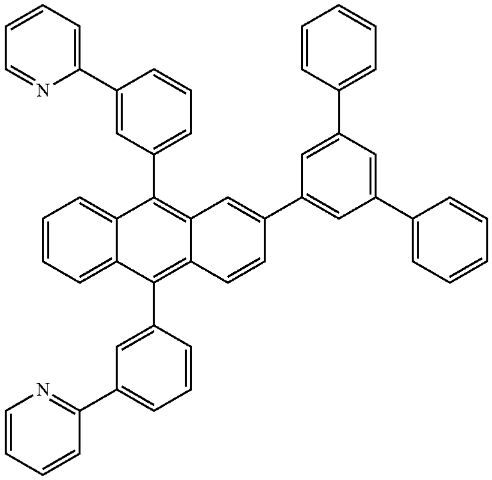
ET9
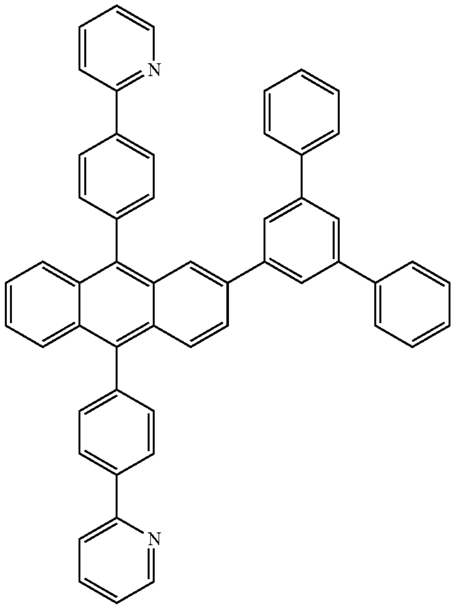
-continued
ET10
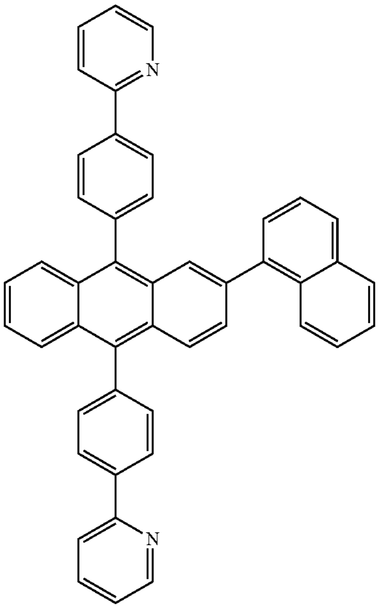
ET11
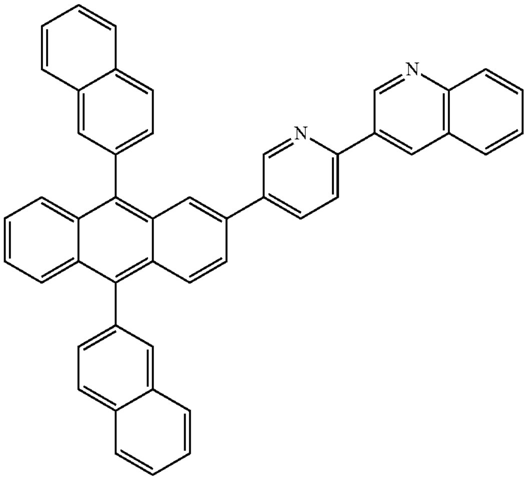
ET12
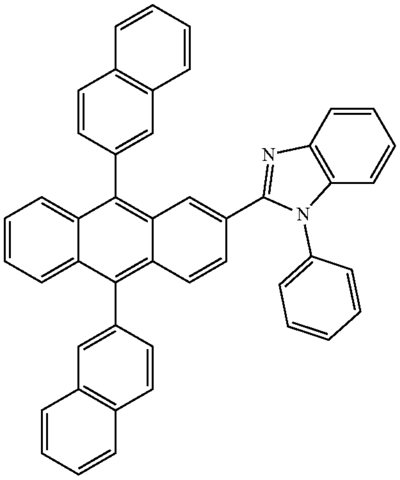

-continued
ET13
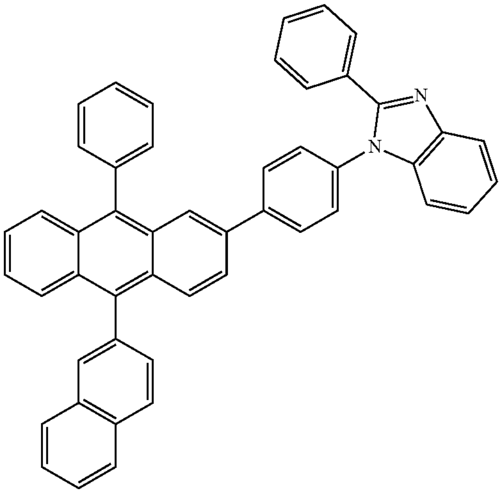
ET14
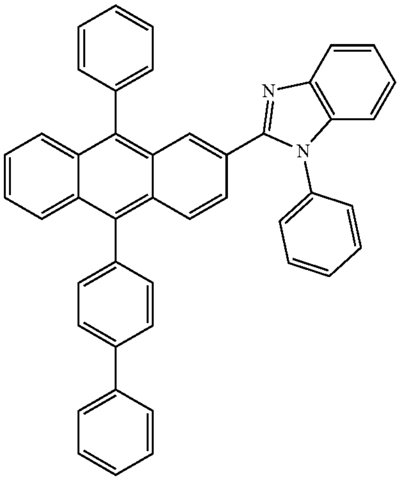
ET15
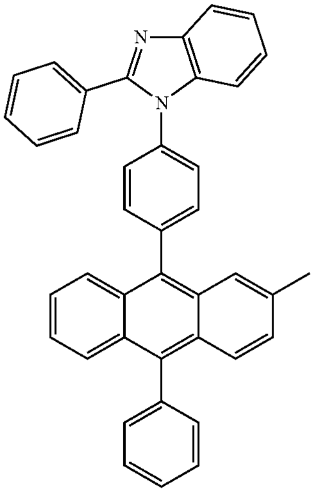
-continued
ET16
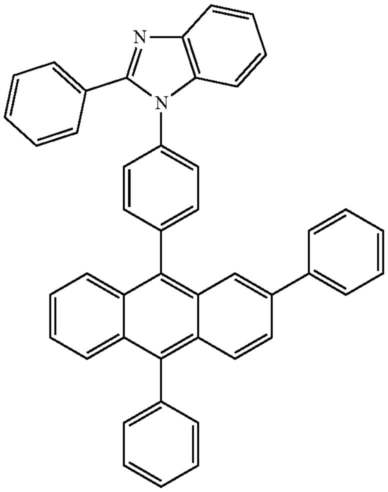
ET17
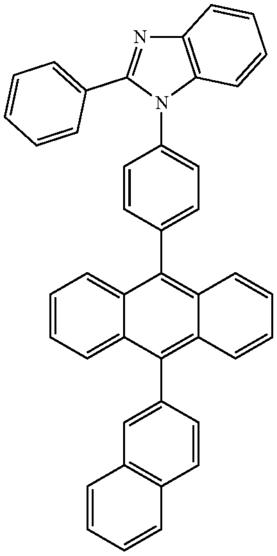
ET18
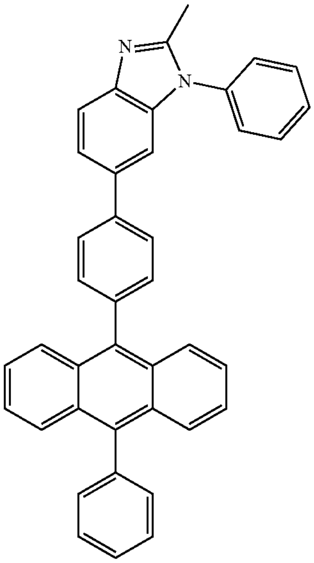

-continued
ET19
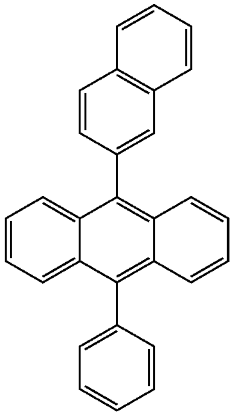
ET20
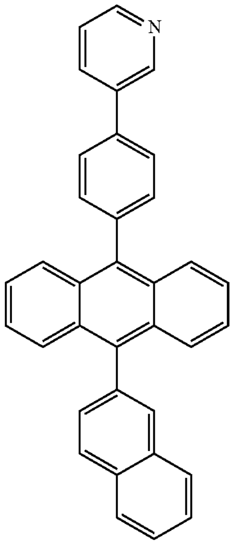
ET21
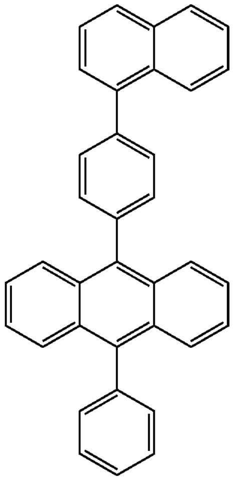
-continued
ET22
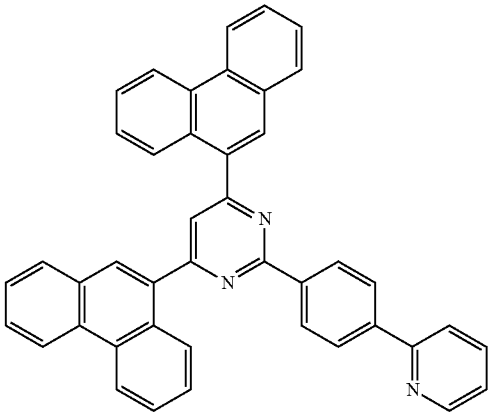
ET23
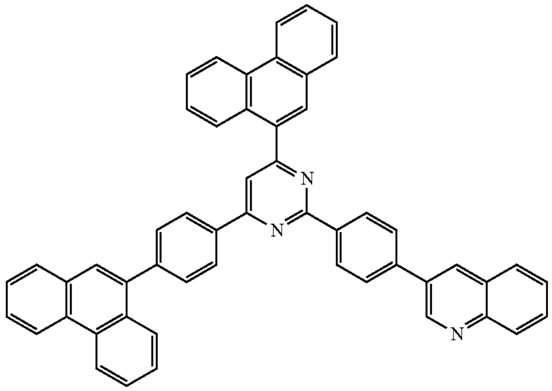
ET24
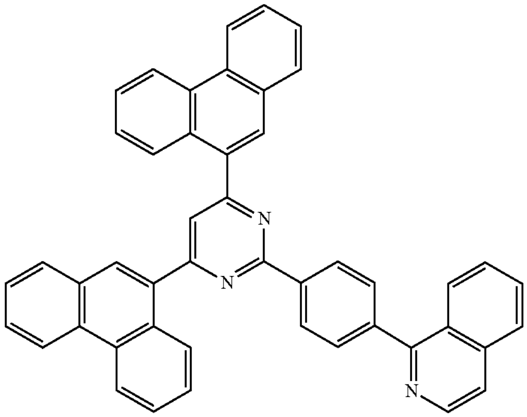

-continued
ET25
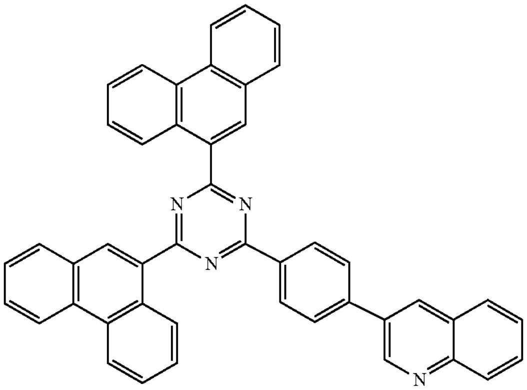
ET26
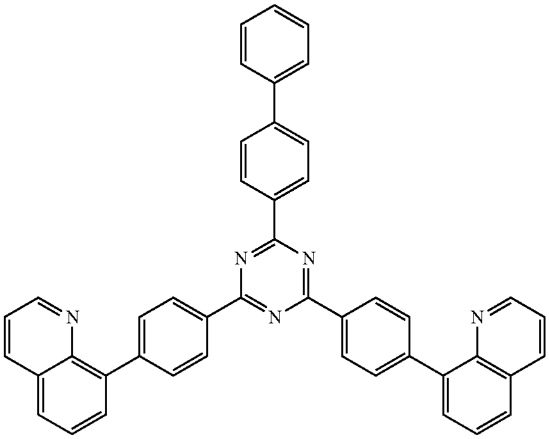
ET27
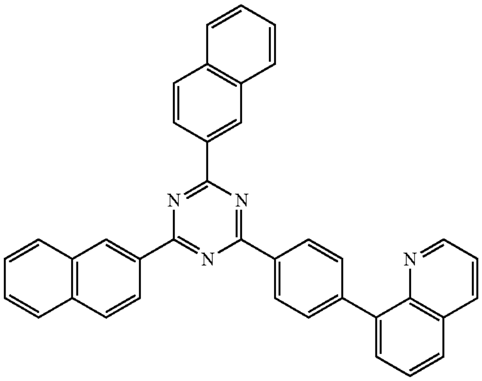
ET28
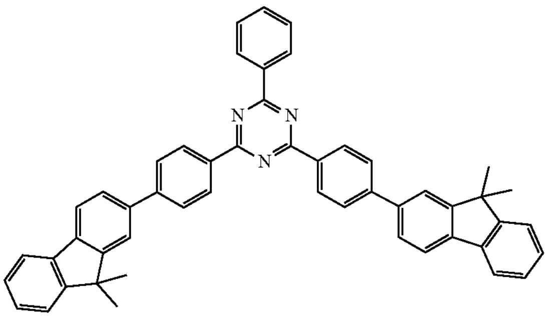
-continued
ET29
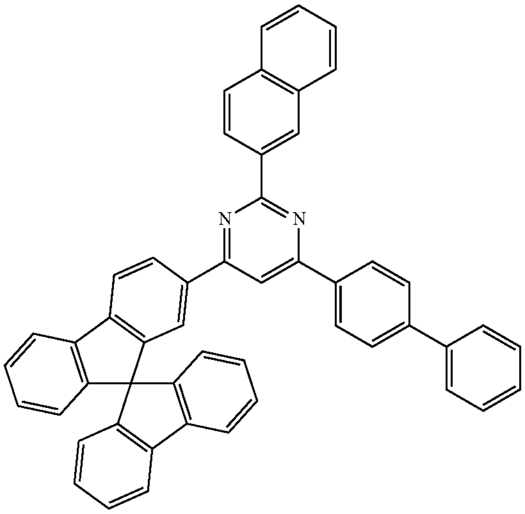
ET30
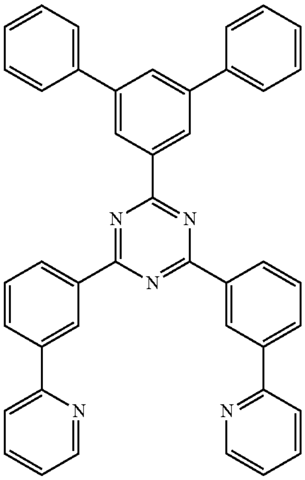
ET31
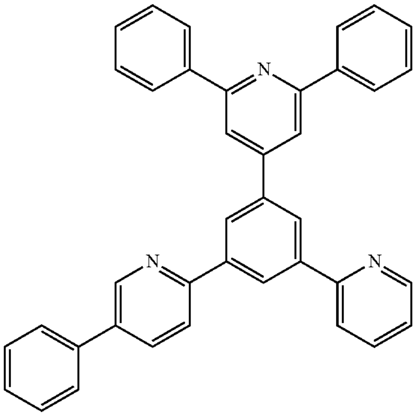

-continued
ET32
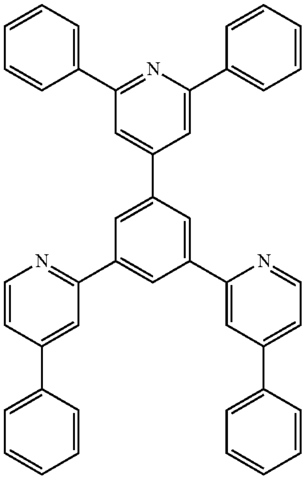
ET33
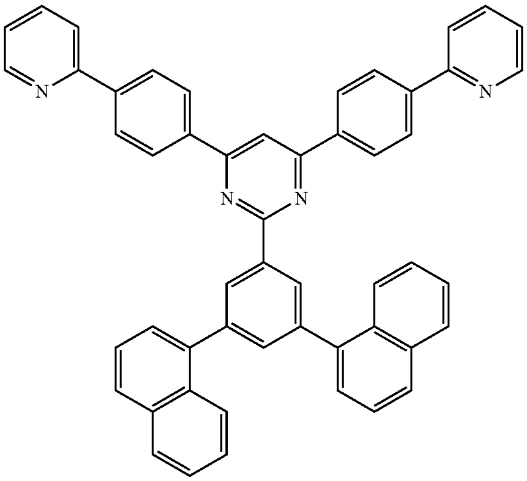
ET34
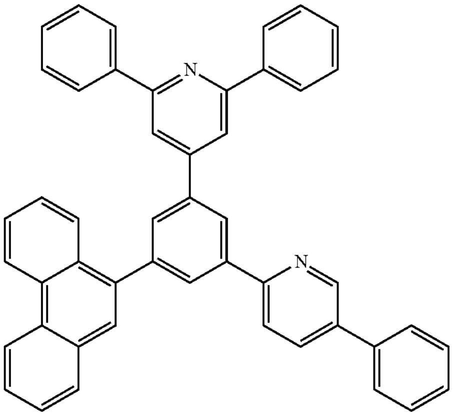
-continued
ET35
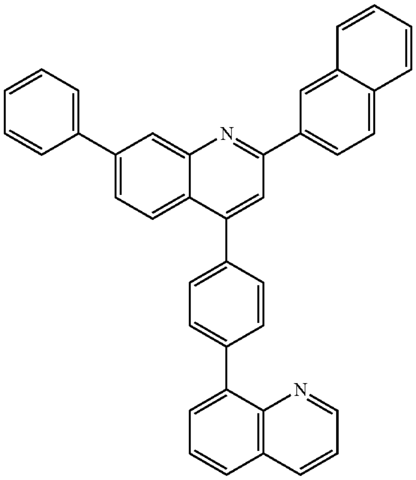
ET36
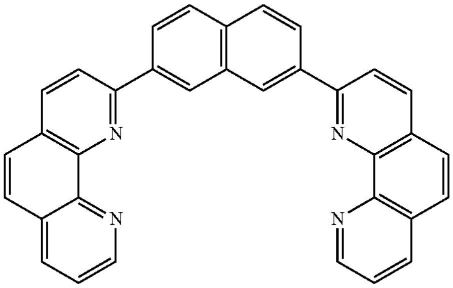
ET37
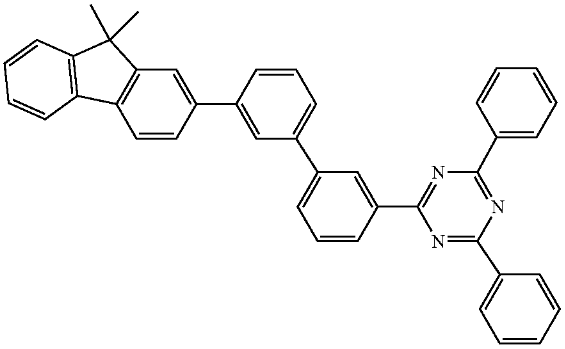
ET38
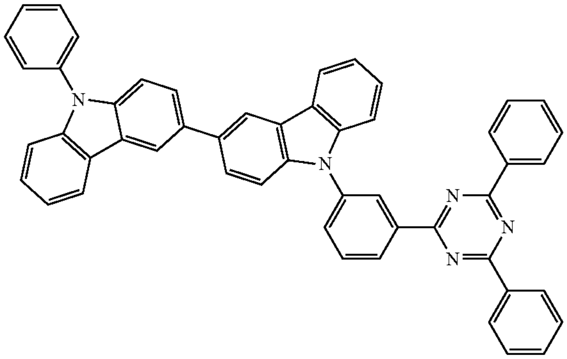

-continued
ET39
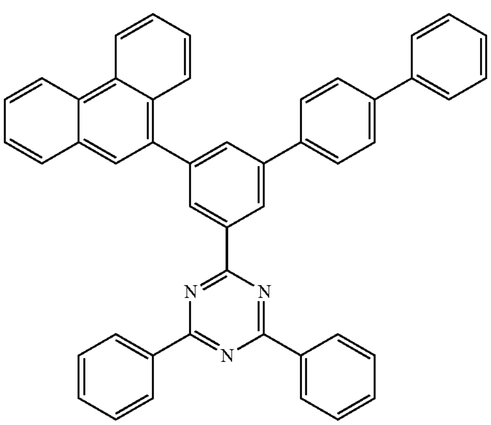
ET40
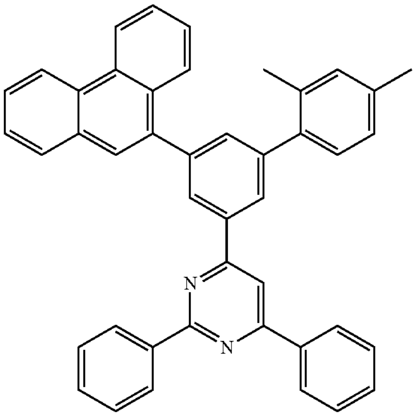
ET41
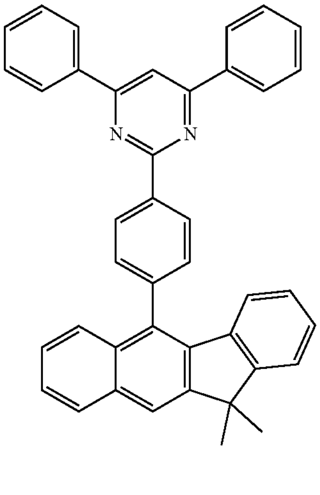
-continued
ET42
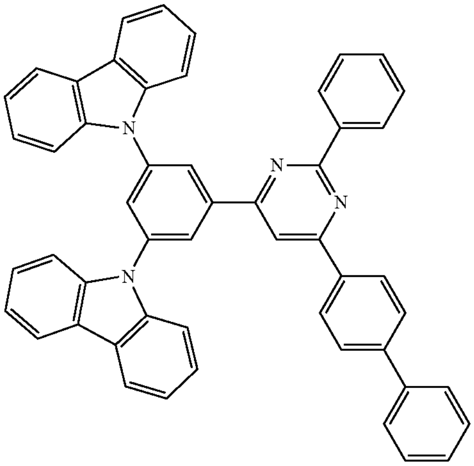
ET43
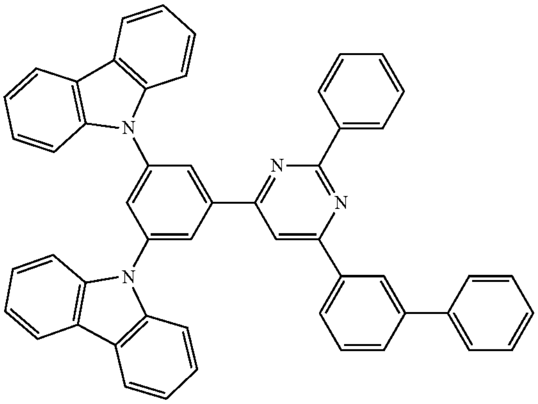
ET44
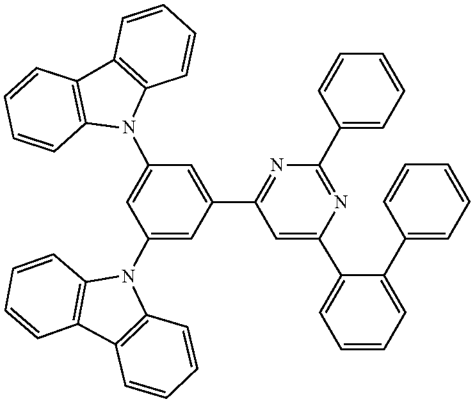
ET45
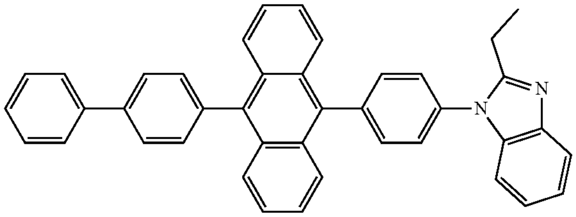

-continued

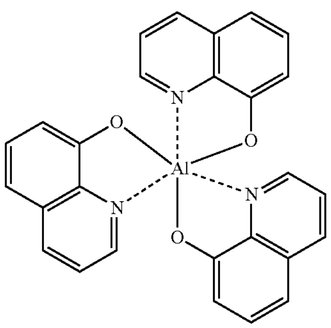

Alq3

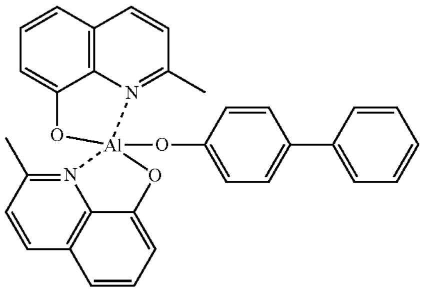

BAlq

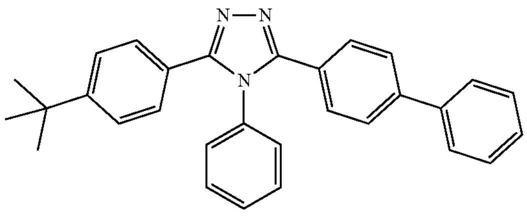

TAZ

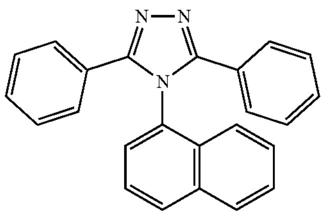

NTAZ

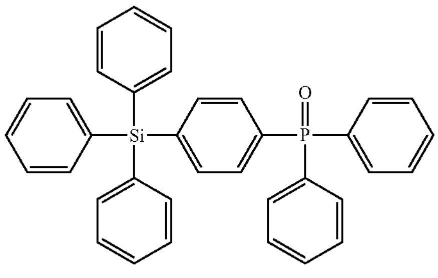

TSPO1

-continued

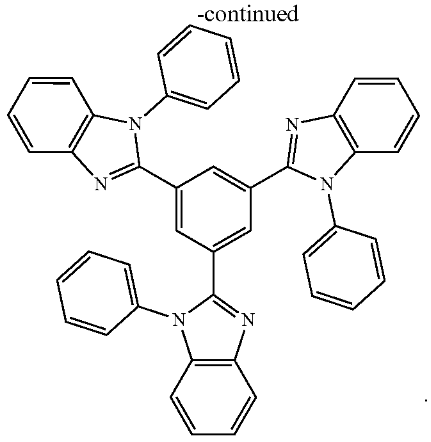

TPBI

The thickness of the electron transport region may be in a range of about 100 Å ngstroms (Å) to about 5,000 Å, for example, about 160 Å to about 4,000 Å. When the electron transport region includes a buffer layer, a hole blocking layer, an electron control layer, an electron transport layer, or any combination thereof, the thicknesses of the buffer layer, the hole blocking layer, or the electron control layer may each independently be in a range of about 20 Å to about 1,000 Å, for example, about 30 Å to about 300 Å, and the thickness of the electron transport layer may be in a range of about 100 Å to about 1,000 Å, for example, about 150 Å to about 500 Å. When the thicknesses of the buffer layer, the hole blocking layer, the electron control layer, the electron transport layer, and/or the electron transport region are each within their respective ranges, excellent (or improved) electron transport characteristics may be obtained without a substantial increase in driving voltage.

The electron transport region (for example, the electron transport layer in the electron transport region) may further include, in addition to the materials described above, a metal-containing material.

The metal-containing material may include an alkali metal complex, an alkaline earth metal complex, or any combination thereof. A metal ion of the alkali metal complex may be a lithium (Li) ion, a sodium (Na) ion, a potassium (K) ion, a rubidium (Rb) ion, and/or a cesium (Cs) ion. A metal ion of the alkaline earth metal complex may be a beryllium (Be) ion, a magnesium (Mg) ion, a calcium (Ca) ion, a strontium (Sr) ion, and/or a barium (Ba) ion. Each ligand coordinated with the metal ion of the alkali metal complex and the alkaline earth metal complex may independently be hydroxyquinoline, hydroxyisoquinoline, hydroxybenzoquinoline, hydroxyacridine, hydroxyphenanthridine, hydroxyphenyloxazole, hydroxyphenylthiazole, hydroxyphenyloxadiazole, hydroxyphenylthiadiazole, hydroxyphenylpyridine, hydroxyphenylbenzimidazole, hydroxyphenylbenzothiazole, bipyridine, phenanthroline, cyclopentadiene, or any combination thereof.

For example, the metal-containing material may include a Li complex. The Li complex may include, e.g., Compound ET-D1 (Liq) and/or Compound ET-D2:

ET-D1

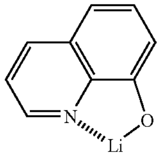

ET-D2

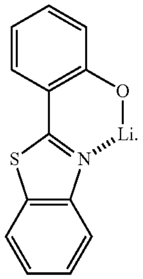

The electron transport region may include an electron injection layer that facilitates injection of electrons from the second electrode 150. The electron injection layer may be in direct contact with the second electrode 150.

The electron injection layer may have i) a single-layered structure including (e.g., consisting of) a single layer including (e.g., consisting of) a single material, ii) a single-layered structure including (e.g., consisting of) a single layer including a plurality of different materials, or iii) a multi-layered structure having a plurality of layers including a plurality of different materials.

The electron injection layer may include an alkali metal, an alkaline earth metal, a rare earth metal, an alkali metal-containing compound, an alkaline earth metal-containing compound, a rare earth metal-containing compound, an alkali metal complex, an alkaline earth metal complex, a rare earth metal complex, or any combination thereof.

The alkali metal may be Li, Na, K, Rb, Cs or any combination thereof. The alkaline earth metal may be Mg, Ca, Sr, Ba, or any combination thereof. The rare earth metal may be Sc, Y, Ce, Tb, Yb, Gd, or any combination thereof.

The alkali metal-containing compound, the alkaline earth metal-containing compound, and the rare earth metal-containing compound may respectively be selected from oxides, halides (e.g., fluorides, chlorides, bromides, and iodides), tellurides, and combinations thereof of the alkali metal, the alkaline earth metal, and the rare earth metal, respectively.

The alkali metal-containing compound may be selected from alkali metal oxides such as $Li_2O$, $Cs_2O$, and/or $K_2O$; alkali metal halides such as LiF, NaF, CsF, KF, LiI, NaI, CsI, and/or KI; and combinations thereof. The alkaline earth-metal-containing compound may include one or more selected from alkaline earth-metal oxides, such as BaO, SrO, CaO, $Ba_xSr_{1-x}O$ (wherein x is a real number satisfying $0<x<1$), and/or $Ba_xCa_{1-x}O$ (wherein x is a real number satisfying $0<x<1$). The rare earth metal-containing compound may include $YbF_3$, $ScF_3$, $Sc_2O_3$, $Y_2O_3$, $Ce_2O_3$, $GdF_3$, $TbF_3$, $YbI_3$, $ScI_3$, $TbI_3$, or any combination thereof. In some embodiments, the rare earth metal-containing compound may include a lanthanide metal telluride. Examples of the lanthanide metal telluride may include LaTe, CeTe, PrTe, NdTe, PmTe, SmTe, EuTe, GdTe, TbTe, DyTe, HoTe, ErTe, TmTe, YbTe, LuTe, $La_2Te_3$, $Ce_2Te_3$, $Pr_2Te_3$, $Nd_2Te_3$, $Pm_2Te_3$, $Sm_2Te_3$, $Eu_2Te_3$, $Gd_2Te_3$, $Tb_2Te_3$, $Dy_2Te_3$, $Ho_2Te_3$, $Er_2Te_3$, $Tm_2Te_3$, $Yb_2Te_3$, and $Lu_2Te_3$.

The alkali metal complex, the alkaline earth metal complex, and the rare earth metal complex may include: i) an ion of the alkali metal, alkaline earth metal, and rare earth metal described above, respectively, and ii) a ligand bonded to the metal ion, e.g., hydroxyquinoline, hydroxyisoquinoline, hydroxybenzoquinoline, hydroxyacridine, hydroxyphenanthridine, hydroxyphenyloxazole, hydroxyphenylthiazole, hydroxyphenyloxadiazole, hydroxyphenylthiadiazole, hydroxyphenylpyridine, hydroxyphenylbenzimidazole, hydroxyphenylbenzothiazole, bipyridine, phenanthroline, cyclopentadiene, or any combination thereof.

The electron injection layer may include (e.g., may consist of) an alkali metal, an alkaline earth metal, a rare earth metal, an alkali metal-containing compound, an alkaline earth metal-containing compound, a rare earth metal-containing compound, an alkali metal complex, an alkaline earth metal complex, a rare earth metal complex, or any combination thereof, as described above. In some embodiments, the electron injection layer may further include an organic material (e.g., a compound represented by Formula 601).

In some embodiments, the electron injection layer may include (e.g., may consist of) i) an alkali metal-containing compound (e.g., alkali metal halide), or ii) a) an alkali metal-containing compound (e.g., alkali metal halide); and b) an alkali metal, an alkaline earth metal, a rare earth metal, or any combination thereof. In some embodiments, the electron injection layer may be a KI:Yb co-deposition layer, a RbI:Yb co-deposition layer, and/or the like.

When the electron injection layer further includes an organic material, the alkali metal, the alkaline earth metal, the rare earth metal, the alkali metal-containing compound, the alkaline earth metal-containing compound, the rare earth metal-containing compound, the alkali metal complex, the alkaline earth metal complex, the rare earth metal complex, or any combination thereof may be homogeneously or non-homogeneously dispersed in a matrix including the organic material.

The thickness of the electron injection layer may be in a range of about 1 Å to about 100 Å, and in some embodiments, about 3 Å to about 90 Å. When the thickness of the electron injection layer is within any of these ranges, excellent (or improved) electron injection characteristics may be obtained without a substantial increase in driving voltage.

Second Electrode 150

The second electrode 150 may be on the interlayer 130. In one or more embodiments, the second electrode 150 may be a cathode that is an electron injection electrode. In this embodiment, a material for forming the second electrode 150 may be a material having a low work function, for example, a metal, an alloy, an electrically conductive compound, or any combination thereof.

The second electrode 150 may include lithium (Li), silver (Ag), magnesium (Mg), aluminum (Al), aluminum-lithium (Al—Li), calcium (Ca), magnesium-indium (Mg—In), magnesium-silver (Mg—Ag), ytterbium (Yb), silver-ytterbium (Ag—Yb), ITO, IZO, or any combination thereof. The second electrode 150 may be a transmissive electrode, a semi-transmissive electrode, or a reflective electrode.

The second electrode 150 may have a single-layered structure, or a multi-layered structure including two or more layers.

Capping Layer

A first capping layer may be located outside the first electrode 110, and/or a second capping layer may be located outside the second electrode 150. In some embodiments, the light-emitting device 10 may have a structure in which the first capping layer, the first electrode 110, the interlayer 130, and the second electrode 150 are sequentially stacked in this stated order, a structure in which the first electrode 110, the interlayer 130, the second electrode 150, and the second capping layer are sequentially stacked in this stated order, or a structure in which the first capping layer, the first electrode 110, the interlayer 130, the second electrode 150, and the second capping layer are sequentially stacked in this stated order.

In the light-emitting device 10, light emitted from the emission layer in the interlayer 130 may pass through the first electrode 110 (which may be a semi-transmissive electrode or a transmissive electrode) and through the first capping layer to the outside, and/or light emitted from the emission layer in the interlayer 130 may pass through the second electrode 150 (which may be a semi-transmissive electrode or a transmissive electrode) and through the second capping layer to the outside.

The first capping layer and the second capping layer may improve the external luminescence efficiency based on the principle of constructive interference. Accordingly, the optical extraction efficiency of the light-emitting device 10 may be increased, thus improving the luminescence efficiency of the light-emitting device 10.

The first capping layer and the second capping layer may each include a material having a refractive index of 1.6 or higher (at 589 nm).

The first capping layer and the second capping layer may each include the heterocyclic compound represented by Formula 1.

The first capping layer and the second capping layer may each independently be a capping layer including an organic material, an inorganic capping layer including an inorganic material, or an organic-inorganic composite capping layer including an organic material and an inorganic material.

At least one of the first capping layer and/or the second capping layer may each independently include one or more selected from carbocyclic compounds, heterocyclic compounds, amine group-containing compounds, porphine derivatives, phthalocyanine derivatives, naphthalocyanine derivatives, alkali metal complexes, alkaline earth metal complexes, and combinations thereof. The carbocyclic compound, the heterocyclic compound, and the amine group-containing compound may each independently be optionally substituted with a substituent of O, N, S, Se, Si, F, Cl, Br, I, or any combination thereof. In some embodiments, at least one of the first capping layer and/or the second capping layer may each independently include an amine group-containing compound.

In some embodiments, at least one of the first capping layer and/or the second capping layer may each independently include the compound represented by Formula 201, the compound represented by Formula 202, or any combination thereof.

In one or more embodiments, at least one of the first capping layer and/or the second capping layer may each independently include one compound selected from Compounds HT28 to HT33, one compound selected from Compounds CP1 to CP6, β-NPB, P4, or any combination thereof:

CP1

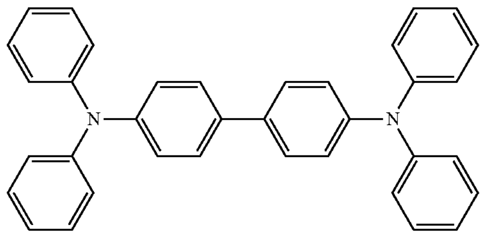

CP2

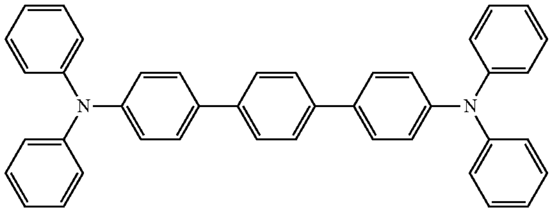

CP3

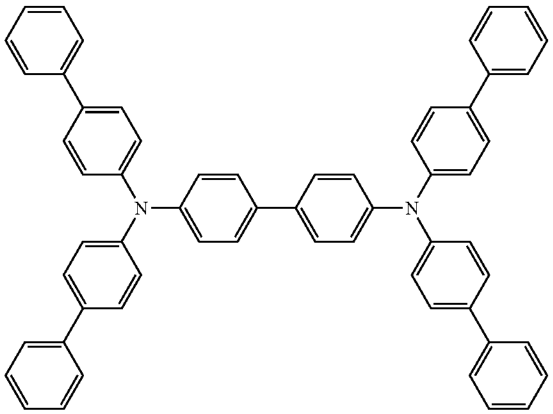

CP4

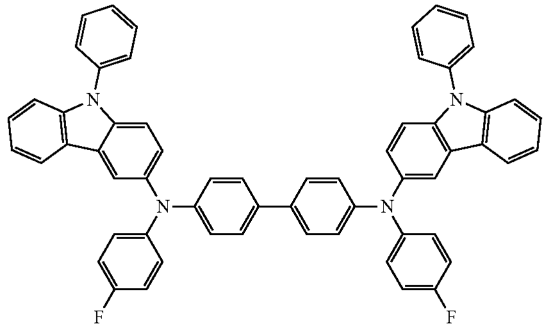

CP5

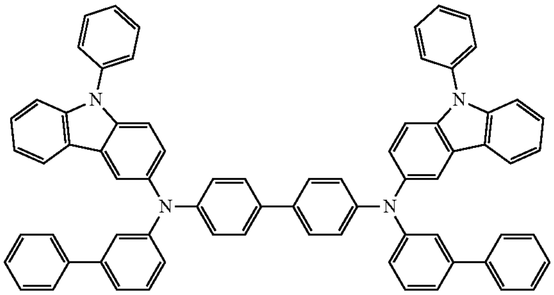

-continued

CP6

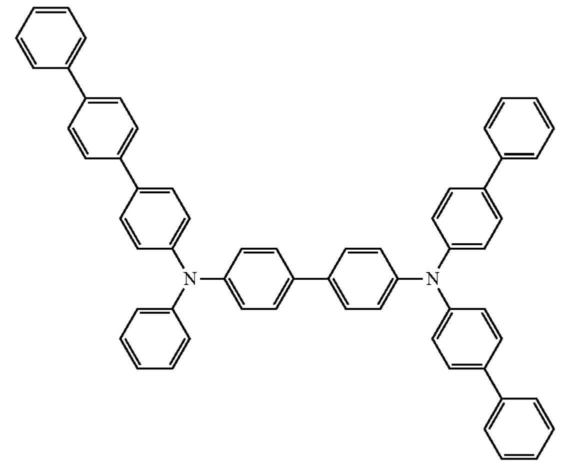

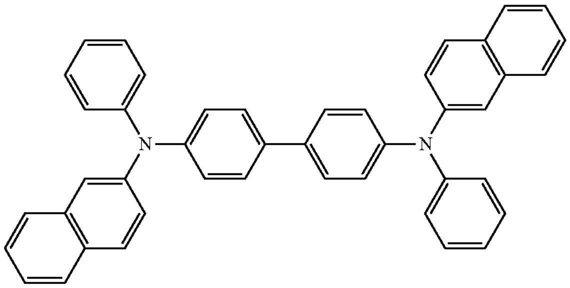

β-NPB

P4

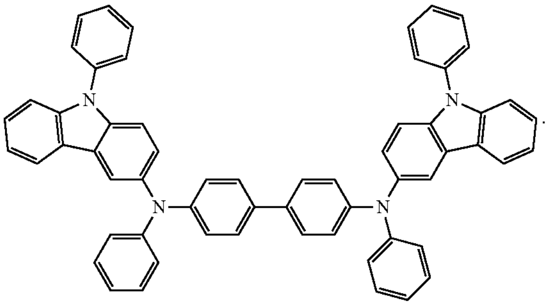

Electronic Apparatus

The light-emitting device may be included in various suitable electronic apparatuses. In some embodiments, an electronic apparatus including the light-emitting device may be a light-emitting apparatus or an authentication apparatus.

The electronic apparatus (e.g., a light-emitting apparatus) may further include, in addition to the light-emitting device, i) a color filter, ii) a color-conversion layer, or iii) a color filter and a color-conversion layer. The color filter and/or the color-conversion layer may be disposed on at least one traveling direction of light emitted from the light-emitting device. For example, light emitted from the light-emitting device may be blue light or white light. The light-emitting device may be understood by referring to the descriptions provided herein. In some embodiments, the color-conversion layer may include quantum dots. The quantum dot may be, for example, the quantum dot described herein.

The electronic apparatus may include a first substrate. The first substrate may include a plurality of sub-pixel areas, the color filter may include a plurality of color filter areas respectively corresponding to the plurality of sub-pixel areas, and the color-conversion layer may include a plurality of color-conversion areas respectively corresponding to the plurality of sub-pixel areas.

A pixel-defining film may be located between the plurality of sub-pixel areas to define each sub-pixel area.

The color filter may further include a plurality of color filter areas and light-blocking patterns between the plurality of color filter areas, and the color-conversion layer may further include a plurality of color-conversion areas and light-blocking patterns between the plurality of color-conversion areas.

The plurality of color filter areas (or a plurality of color-conversion areas) may include: a first area emitting (e.g., to emit) first color light; a second area emitting (e.g. to emit) second color light; and/or a third area emitting (e.g., to emit) third color light, and the first color light, the second color light, and/or the third color light may have different maximum emission wavelengths. In some embodiments, the first color light may be red light, the second color light may be green light, and the third color light may be blue light. In some embodiments, the plurality of color filter areas (or the plurality of color-conversion areas) may include (e.g., may each include) quantum dots. In some embodiments, the first area may include red quantum dots, the second area may include green quantum dots, and the third area may not include a quantum dot. The quantum dot may be understood by referring to the description of the quantum dot provided herein. The first area, the second area, and/or the third area may each further include an emitter.

In some embodiments, the light-emitting device may emit first light, the first area may absorb the first light to emit 1-1 color light, the second area may absorb the first light to emit 2-1 color light, and the third area may absorb the first light to emit 3-1 color light. In this embodiment, the 1-1 color light, the 2-1 color light, and the 3-1 color light may each have a different maximum emission wavelength. In some embodiments, the first light may be blue light, the 1-1 color light may be red light, the 2-1 color light may be green light, and the 3-1 color light may be blue light.

The electronic apparatus may further include a thin-film transistor, in addition to the light-emitting device. The thin-film transistor may include a source electrode, a drain electrode, and an active layer, wherein one of the source electrode or the drain electrode may be electrically connected (e.g., electrically coupled) to one of the first electrode or the second electrode of the light-emitting device.

The thin-film transistor may further include a gate electrode, a gate insulating film, and/or the like.

The active layer may include a crystalline silicon, an amorphous silicon, an organic semiconductor, and/or an oxide semiconductor.

The electronic apparatus may further include an encapsulation unit for sealing the light-emitting device. The encapsulation unit may be located between the color filter and/or the color-conversion layer and the light-emitting device. The encapsulation unit may allow light to pass to the outside from the light-emitting device and prevent or reduce the permeation of air and/or moisture to permeate to the light-emitting device at the same time. The encapsulation unit may be a sealing substrate including transparent glass and/or a plastic substrate. The encapsulation unit may be a thin-film encapsulating layer including at least one of an organic layer and/or an inorganic layer. When the encapsulation unit is a thin-film encapsulating layer, the electronic apparatus may be flexible.

In addition to the color filter and/or the color-conversion layer, various suitable functional layers may be disposed (e.g., provided) on the encapsulation unit, depending on the use of an electronic apparatus. Examples of the functional layer may include a touch screen layer, a polarizing layer, and the like. The touch screen layer may be a resistive touch screen layer, a capacitive touch screen layer, and/or an infrared beam touch screen layer. The authentication apparatus may be, for example, a biometric authentication apparatus that identifies an individual according to biometric information (e.g., a fingertip, a pupil, and/or the like).

The authentication apparatus may further include a biometric information collecting unit, in addition to the light-emitting device described above.

The electronic apparatus may be applicable to various suitable displays, an optical source, lighting, a personal computer (e.g., a mobile personal computer), a cellphone, a digital camera, an electronic note, an electronic dictionary, an electronic game console, a medical device (e.g., an electronic thermometer, a blood pressure meter, a glucometer, a pulse measuring device, a pulse wave measuring device, an electrocardiograph recorder, an ultrasonic diagnosis device, and/or an endoscope display device), a fish finder, various measurement devices, gauges (e.g., gauges of an automobile, an airplane, and/or a ship), and/or a projector.

Figure 2:
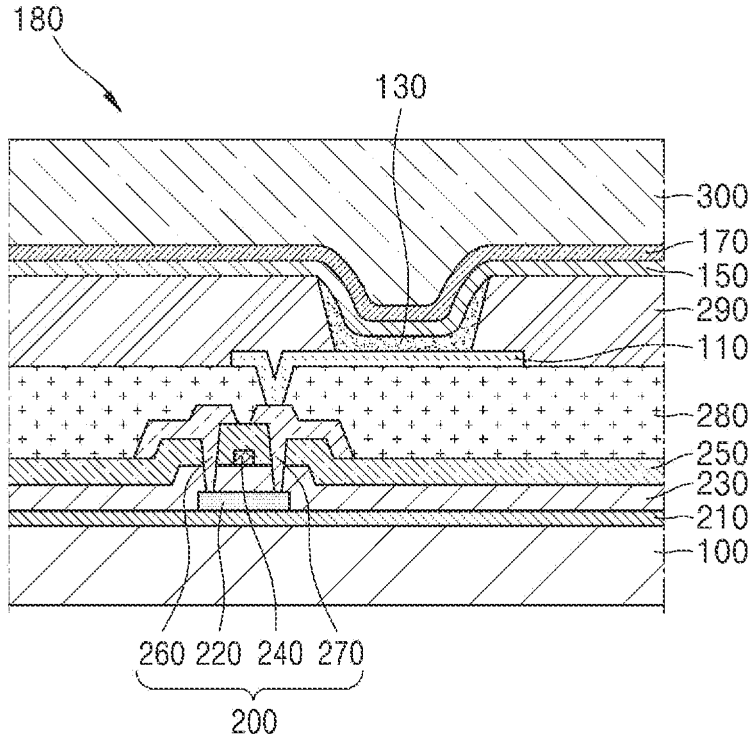
FIG. 2 is a schematic cross-sectional view of an electronic apparatus according to one or more embodiments.
Figure 3:
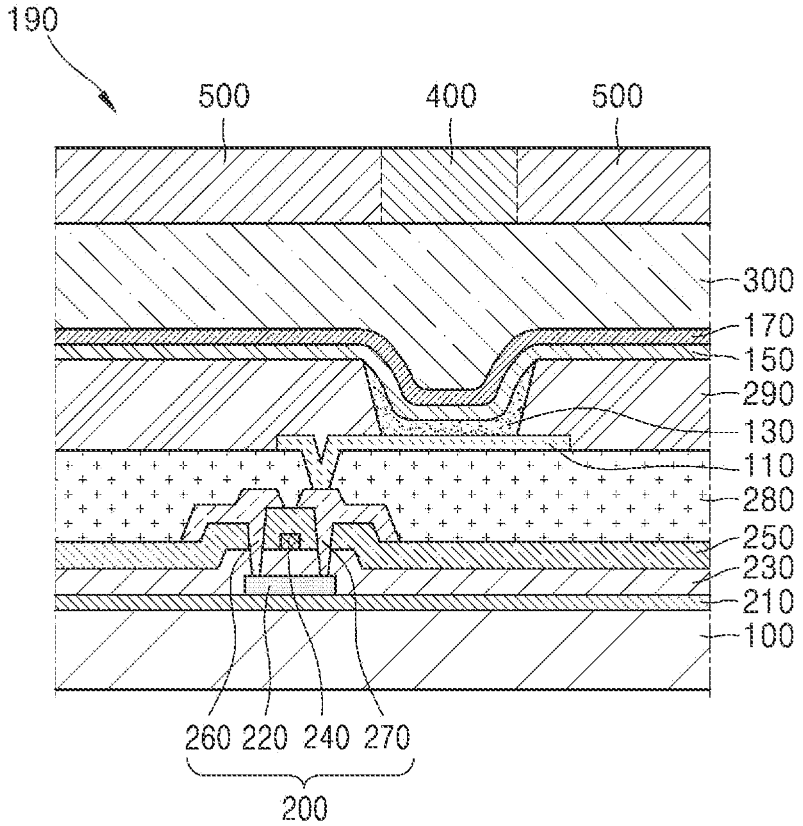
FIG. 3 is a schematic cross-sectional view of an electronic apparatus according to one or more other embodiments.

Descriptions of FIGS. 2 and 3

FIG. 2 is a schematic cross-sectional view of one or more embodiments of an electronic apparatus.

An electronic apparatus in FIG. 2 may include a substrate 100, a thin-film transistor, a light-emitting device, and an encapsulation unit 300 sealing the light-emitting device.

The substrate 100 may be a flexible substrate, a glass substrate, and/or a metal substrate. A buffer layer 210 may be on the substrate 100. The buffer layer 210 may prevent or reduce penetration of impurities through the substrate 100 and provide a flat (or substantially flat) surface on the substrate 100.

A thin-film transistor may be on the buffer layer 210. The thin-film transistor may include an active layer 220, a gate electrode 240, a source electrode 260, and a drain electrode 270.

The active layer 220 may include an inorganic semiconductor such as silicon and/or polysilicon, an organic semiconductor, and/or an oxide semiconductor, and may include a source area, a drain area, and a channel area.

A gate insulating film 230 for insulating the active layer 220 and the gate electrode 240 may be on the active layer 220, and the gate electrode 240 may be on the gate insulating film 230.

An interlayer insulating film 250 may be on the gate electrode 240. The interlayer insulating film 250 may be between the gate electrode 240 and the source electrode 260 and between the gate electrode 240 and the drain electrode 270 to provide insulation therebetween.

The source electrode 260 and the drain electrode 270 may be on the interlayer insulating film 250. The interlayer insulating film 250 and the gate insulating film 230 may be formed to expose the source area and the drain area of the active layer 220, and the source electrode 260 and the drain electrode 270 may be adjacent to the exposed source area and the exposed drain area of the active layer 220.

The thin-film transistor according to the present embodiments may be electrically connected (e.g., electrically coupled) to a light-emitting device to drive the light-emitting device, and may be protected by a passivation layer 280. The passivation layer 280 may include an inorganic insulating film, an organic insulating film, or a combination thereof. A light-emitting device may be on the passivation layer 280. The light-emitting device may include a first electrode 110, an interlayer 130, and a second electrode 150.

The first electrode 110 may be on the passivation layer 280. The passivation layer 280 may not fully cover the drain electrode 270 and may expose a set or specific area of the drain electrode 270, and the first electrode 110 may be connected to the exposed area of the drain electrode 270.

A pixel-defining film 290 may be on the first electrode 110. The pixel-defining film 290 may expose a set or specific area of the first electrode 110, and the interlayer 130 may be formed in the exposed area of the first electrode 110. The pixel-defining film 290 may be a polyimide or polyacryl organic film. In one or more embodiments, some higher (e.g., upper) layers of the interlayer 130 may extend to the upper portion of the pixel-defining film 290 and may be disposed in the form of (e.g., may form) a common layer.

The second electrode 150 may be on the interlayer 130, and a capping layer 170 may be additionally formed on the second electrode 150. The capping layer 170 may be formed to cover the second electrode 150.

The encapsulation unit 300 may be on the capping layer 170. The encapsulation unit 300 may be on the light-emitting device to protect a light-emitting device from moisture and/or oxygen. The encapsulation unit 300 may include: an inorganic film including silicon nitride ($SiN_x$), silicon oxide ($SiO_x$), indium tin oxide, indium zinc oxide, or any combination thereof; an organic film including PET, polyethylene naphthalate, polycarbonate, polyimide, polyethylene sulfonate, polyoxymethylene, polyarylate, hexamethyldisiloxane, an acrylic resin (e.g., polymethyl methacrylate, polyacrylic acid, and/or the like), an epoxy resin (e.g., aliphatic glycidyl ether (AGE) and/or the like), or any combination thereof; or a combination of the inorganic film and the organic film.

FIG. 3 is a schematic cross-sectional view of an electronic apparatus according to one or more other embodiments.

The electronic apparatus shown in FIG. 3 may be substantially identical to the electronic apparatus shown in FIG. 2, except that a light-shielding pattern 500 and a functional area 400 are additionally located on the encapsulation unit 300. The functional area 400 may be i) a color filter area, ii) a color-conversion area, or iii) a combination of a color filter area and a color-conversion area. In some embodiments, the light-emitting device shown in FIG. 3 included in electronic apparatus may be a tandem light-emitting device.

Manufacturing Method

The layers constituting the hole transport region, the emission layer, and the layers constituting the electron transport region may be formed in a set or specific region by using one or more suitable methods such as vacuum deposition, spin coating, casting, Langmuir-Blodgett (LB) deposition, ink-jet printing, laser printing, and/or laser-induced thermal imaging.

When layers constituting the hole transport region, the emission layer, and layers constituting the electron transport region are each independently formed by vacuum-deposition, the vacuum-deposition may be performed at a deposition temperature in a range of about 100° C. to about 500° C., at a vacuum degree in a range of about $10^{-8}$ torr to about $10^{-3}$ torr, and at a deposition rate in a range of about 0.01 Angstroms per second (Å/sec) to about 100 Å/sec, depending on the material to be included in each layer and the structure of each layer to be formed.

General Definitions of Terms

The term "$C_3$-$C_{60}$ carbocyclic group" as used herein refers to a cyclic group consisting of carbon atoms only and having 3 to 60 carbon atoms as ring-forming atoms. The term "$C_1$-$C_{60}$ heterocyclic group" as used herein refers to a cyclic group having 1 to 60 carbon atoms as ring-forming atoms, and at least one heteroatom as a ring-forming atom. The $C_3$-$C_{60}$ carbocyclic group and the $C_1$-$C_{60}$ heterocyclic group may each be a monocyclic group consisting of one ring or a polycyclic group in which at least two rings are condensed. For example, the total number of ring-forming atoms in the $C_1$-$C_{60}$ heterocyclic group may be in a range of 3 to 61.

The term "cyclic group" as used herein may include the $C_3$-$C_{60}$ carbocyclic group and the $C_1$-$C_{60}$ heterocyclic group.

The term "π electron-rich $C_3$-$C_{60}$ cyclic group" refers to a cyclic group having 3 to 60 carbon atoms and not including *—N═*' as a ring-forming moiety. The term "π electron-deficient nitrogen-containing $C_1$-$C_{60}$ cyclic group" as used herein refers to a heterocyclic group having 1 to 60 carbon atoms and *—N═*' as a ring-forming moiety.

In some embodiments, the $C_3$-$C_{60}$ carbocyclic group may be i) a T1 group or ii) a group in which at least two T1 groups are condensed (for example, the $C_3$-$C_{60}$ carbocyclic group may be a cyclopentadiene group, an adamantane group, a norbornane group, a benzene group, a pentalene group, a naphthalene group, an azulene group, an indacene group, an acenaphthylene group, a phenalene group, a phenanthrene group, an anthracene group, a fluoranthene group, a triphenylene group, a pyrene group, a chrysene group, a perylene group, a pentaphene group, a heptalene group, a naphthacene group, a picene group, a hexacene group, a pentacene group, a rubicene group, a coronene group, an ovalene group, an indene group, a fluorene group, a spiro-bifluorene group, a benzofluorene group, an indenophenanthrene group, and/or an indenoanthracene group), the $C_1$-$C_{60}$ heterocyclic group may be i) a T2 group, ii) a group in which at least two T2 groups are condensed, or iii) a group in which at least one T2 group is condensed with at least one T1 group (for example, the $C_1$-$C_{60}$ heterocyclic group may be a pyrrole group, a thiophene group, a furan group, an indole group, a benzoindole group, a naphthoindole group, an isoindole group, a benzoisoindole group, a naphthoisoindole group, a benzosilole group, a benzothiophene group, a benzofuran group, a carbazole group, a dibenzosilole group, a dibenzothiophene group, a dibenzofuran group, an indenocarbazole group, an indolocarbazole group, a benzofurocarbazole group, a benzothienocarbazole group, a benzosilolocarbazole group, a benzoindolocarbazole group, a benzocarbazole group, a benzonaphthofuran group, a benzonapthothiophene group, a benzonaphthosilole group, a benzofurodibenzofuran group, a benzofurodibenzothiophene group, a benzothienodibenzothiophene group, a pyrazole group, an imidazole group, a triazole group, an oxazole group, an isoxazole group, an oxadiazole group, a thiazole group, an isothiazole group, a thiadiazole group, a benzopyrazole group, a benzimidazole group, a benzoxazole group, a benzoisoxazole group, a benzothiazole group, a benzoisothiazole group, a pyridine group, a pyrimidine group, a pyrazine group, a pyridazine group, a triazine group, a quinoline group, an isoquinoline group, a benzoquinoline group, a benzoisoquinoline group, a quinoxaline group, a benzoquinoxaline group, a quinazoline group, a benzoquinazoline group, a phenanthroline group, a cinnoline group, a phthalazine group, a naphthyridine group, an imidazopyridine group, an imidazopyrimidine group, an imidazotriazine group, an imidazopyrazine group, an imidazopyridazine group, an azacarbazole group, an azafluorene group, an azadibenzosilole group, an azadibenzothiophene group, an azadibenzofuran group, and/or the like), the π electron-rich $C_3$-$C_{60}$ cyclic group may be i) a T1 group, ii) a condensed group in which at least two T1 groups are condensed, iii) a T3 group, iv) a condensed group in which at least two T3 groups are condensed, or v) a condensed group in which at least one T3 group is condensed with at least one T1 group (for example, the π electron-rich $C_3$-$C_{60}$ cyclic group may be a $C_3$-$C_{60}$ carbocyclic group, a 1H-pyrrole group, a silole group, a borole group, a 2H-pyrrole group, a 3H-pyrrole group, a thiophene group, a furan group, an indole group, a benzoindole group, a naphthoindole group, an isoindole group, a benzoisoindole group, a naphthoisoindole group, a benzosilole group, a benzothiophene group, a benzofuran group, a carbazole group, a dibenzosilole group, a dibenzothiophene group, a dibenzofuran group, an indenocarbazole group, an indolocarbazole group, a benzofurocarbazole group, a benzothienocarbazole group, a benzosilolocarbazole group, a benzoindolocarbazole group, a benzocarbazole group, a benzonaphthofuran group, a benzonapthothiophene group, a benzonaphthosilole group, a benzofurodibenzofuran group, a benzofurodibenzothiophene group, a benzothienodibenzothiophene group, and/or the like), and the π electron-deficient nitrogen-containing $C_1$-$C_{60}$ cyclic group may be i) a T4 group, ii) a group in which at least two T4 groups are condensed, iii) a group in which at least one T4 group is condensed with at least one T1 group, iv) a group in which at least one T4 group is condensed with at least one T3 group, or v) a group in which at least one T4 group, at least one T1 group, and at least one T3 group are condensed (for example, the π electron-deficient nitrogen-containing $C_1$-$C_{60}$ cyclic group may be a pyrazole group, an imidazole group, a triazole group, an oxazole group, an isoxazole group, an oxadiazole group, a thiazole group, an isothiazole group, a thiadiazole group, a benzopyrazole group, a benzimidazole group, a benzoxazole group, a benzoisoxazole group, a benzothiazole group, a benzoisothiazole group, a pyridine group, a pyrimidine group, a pyrazine group, a pyridazine group, a triazine group, a quinoline group, an isoquinoline group, a benzoquinoline group, a benzoisoquinoline group, a quinoxaline group, a benzoquinoxaline group, a quinazoline group, a benzoquinazoline group, a phenanthroline group, a cinnoline group, a phthalazine group, a naphthyridine group, an imidazopyridine group, an imidazopyrimidine group, an imidazotriazine group, an imidazopyrazine group, an imidazopyridazine group, an azacarbazole group, an azafluorene group, an azadibenzosilole group, an azadibenzothiophene group, an azadibenzofuran group, and/or the like), wherein the T1 group may be a cyclopropane group, a cyclobutane group, a cyclopentane group, a cyclohexane group, a cycloheptane group, a cyclooctane group, a cyclobutene group, a cyclopentene group, a cyclopentadiene group, a cyclohexene group, a cyclohexadiene group, a cycloheptene group, an adamantane group, a norbornane (or bicyclo[2.2.1]heptane) group, a norbornene group, a bicyclo[1.1.1]pentane group, a bicyclo[2.1.1]hexane group, a bicyclo[2.2.2]octane group, or a benzene group, the T2 group may be a furan group, a thiophene group, a 1H-pyrrole group, a silole group, a borole group, a 2H-pyrrole group, a 3H-pyrrole group, an imidazole group, a pyrazole group, a triazole group, a tetrazole group, an oxazole group, an isoxazole group, an oxadiazole group, a thiazole group, an isothiazole group, a thiadiazole group, an azasilole group, an azaborole group, a pyridine group, a pyrimidine group, a pyrazine group, a pyridazine group, a triazine group, a tetrazine group, a pyrrolidine group, an imidazolidine group, a dihydropyrrole group, a piperidine group, a tetrahydropyridine group, a dihydropyridine group, a hexahydropyrimidine group, a tetrahydropyrimidine group, a dihydropyrimidine group, a piperazine group, a tetrahydropyrazine group, a dihydropyrazine group, a tetrahydropyridazine group, or a dihydropyridazine group, the T3 group may be a furan group, a thiophene group, a 1H-pyrrole group, a silole group, or a borole group, and the T4 group may be a 2H-pyrrole group, a 3H-pyrrole group, an imidazole group, a pyrazole group, a triazole group, a tetrazole group, an oxazole group, an isoxazole group, an oxadiazole group, a thiazole group, an isothiazole group, a thiadiazole group, an azasilole group, an azaborole group, a pyridine group, a pyrimidine group, a pyrazine group, a pyridazine group, a triazine group, or a tetrazine group.

The term "cyclic group", "$C_3$-$C_{60}$ carbocyclic group", "$C_1$-$C_{60}$ heterocyclic group", "π electron-rich $C_3$-$C_{60}$ cyclic group", and/or "π electron-deficient nitrogen-containing $C_1$-$C_{60}$ cyclic group" as used herein may be a group condensed with any suitable cyclic group, a monovalent group, and/or a polyvalent group (e.g., a divalent group, a trivalent group, a quadrivalent group, and/or the like), depending on the structure of the formula to which the term is applied. For example, a "benzene group" may be a benzene ring, a phenyl group, a phenylene group, or the like, and this may be understood by one of ordinary skill in the art, depending on the structure of the formula including the "benzene group".

In some embodiments, examples of the monovalent $C_3$-$C_{60}$ carbocyclic group and the monovalent $C_1$-$C_{60}$ heterocyclic group may include a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group, and examples of the divalent $C_3$-$C_{60}$ carbocyclic group and the divalent $C_1$-$C_{60}$ heterocyclic group may include a $C_3$-$C_{10}$ cycloalkylene group, a $C_1$-$C_{10}$ heterocycloalkylene group, a $C_3$-$C_{10}$ cycloalkenylene group, a $C_1$-$C_{10}$ heterocycloalkenylene group, a $C_6$-$C_{60}$ arylene group, a $C_1$-$C_{60}$ heteroarylene group, a divalent non-aromatic condensed polycyclic group, and a divalent non-aromatic condensed heteropolycyclic group.

The term "$C_1$-$C_{60}$ alkyl group" as used herein refers to a linear or branched aliphatic hydrocarbon monovalent group having 1 to 60 carbon atoms, and examples thereof may include a methyl group, an ethyl group, an n-propyl group, an isopropyl group, an n-butyl group, a sec-butyl group, an isobutyl group, a tert-butyl group, an n-pentyl group, a tert-pentyl group, a neopentyl group, an isopentyl group, a sec-pentyl group, a 3-pentyl group, a sec-isopentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an iso-nonyl group, a sec-nonyl group, a tert-nonyl group, an n-decyl group, an isodecyl group, a sec-decyl group, and a tert-decyl group. The term "$C_1$-$C_{60}$ alkylene group" as used herein refers to a divalent group having substantially the same structure as the $C_1$-$C_{60}$ alkyl group.

The term "$C_2$-$C_{60}$ alkenyl group" as used herein refers to a hydrocarbon group having at least one carbon-carbon double bond in the middle and/or at the terminus of the $C_2$-$C_{60}$ alkyl group. Examples thereof may include an ethenyl group, a propenyl group, and a butenyl group. The term "$C_2$-$C_{60}$ alkenylene group" as used herein refers to a divalent group having substantially the same structure as the $C_2$-$C_{60}$ alkenyl group.

The term "$C_2$-$C_{60}$ alkynyl group" as used herein refers to a monovalent hydrocarbon group having at least one carbon-carbon triple bond in the middle and/or at the terminus of the $C_2$-$C_{60}$ alkyl group. Examples thereof may include an ethynyl group and a propynyl group. The term "$C_2$-$C_{60}$ alkynylene group" as used herein refers to a divalent group having substantially the same structure as the $C_2$-$C_{60}$ alkynyl group.

The term "$C_1$-$C_{60}$ alkoxy group" as used herein refers to a monovalent group represented by $-OA_{101}$ (wherein $A_{101}$ is a $C_1$-$C_{60}$ alkyl group). Examples thereof may include a methoxy group, an ethoxy group, and an isopropyloxy group.

The term "$C_3$-$C_{10}$ cycloalkyl group" as used herein refers to a monovalent saturated hydrocarbon monocyclic group including 3 to 10 carbon atoms. Examples of the $C_3$-$C_{10}$ cycloalkyl group as used herein may include a cyclopropyl group, a cyclobutyl group, a cyclopentyl group, a cyclohexyl group, a cycloheptyl group, a cyclooctyl group, an adamantanyl group, a norbornanyl (bicyclo[2.2.1]heptyl) group, a bicyclo[1.1.1]pentyl group, a bicyclo[2.1.1]hexyl group, and a bicyclo[2.2.2]octyl group. The term "$C_3$-$C_{10}$ cycloalkylene group" as used herein refers to a divalent group having substantially the same structure as the $C_3$-$C_{10}$ cycloalkyl group.

The term "$C_1$-$C_{10}$ heterocycloalkyl group" as used herein refers to a monovalent cyclic group including at least one heteroatom, other than carbon atoms, as a ring-forming atom, and having 1 to 10 carbon atoms. Examples thereof may include a 1,2,3,4-oxatriazolidinyl group, a tetrahydrofuranyl group, and a tetrahydrothiophenyl group. The term "$C_1$-$C_{10}$ heterocycloalkylene group" as used herein refers to a divalent group having substantially the same structure as the $C_1$-$C_{10}$ heterocycloalkyl group.

The term "$C_3$-$C_{10}$ cycloalkenyl group" as used herein refers to a monovalent cyclic group that has 3 to 10 carbon atoms and at least one carbon-carbon double bond in its ring, and is not aromatic. Examples thereof may include a cyclopentenyl group, a cyclohexenyl group, and a cycloheptenyl group. The term "$C_3$-$C_{10}$ cycloalkenylene group" as used herein refers to a divalent group having substantially the same structure as the $C_3$-$C_{10}$ cycloalkenyl group.

The term "$C_1$-$C_{10}$ heterocycloalkenyl group" as used herein refers to a monovalent cyclic group including at least one heteroatom other than carbon atoms as a ring-forming atom, 1 to 10 carbon atoms, and at least one double bond in its ring. Examples of the $C_1$-$C_{10}$ heterocycloalkenyl group may include a 4,5-dihydro-1,2,3,4-oxatriazolyl group, a 2,3-dihydrofuranyl group, and a 2,3-dihydrothiophenyl group. The term "$C_1$-$C_{10}$ heterocycloalkylene group" as used herein refers to a divalent group having substantially the same structure as the $C_1$-$C_{10}$ heterocycloalkenyl group.

The term "$C_6$-$C_{60}$ aryl group" as used herein refers to a monovalent group having a carbocyclic aromatic system having 6 to 60 carbon atoms. The term "$C_6$-$C_{60}$ arylene group" as used herein refers to a divalent group having substantially the same structure as the $C_6$-$C_{60}$ aryl group. Examples of the $C_6$-$C_{60}$ aryl group may include a phenyl group, a pentalenyl group, a naphthyl group, an azulenyl group, an indacenyl group, an acenaphthyl group, a phenalenyl group, a phenanthrenyl group, an anthracenyl group, a fluoranthenyl group, a triphenylenyl group, a pyrenyl group, a chrysenyl group, a perylenyl group, a pentaphenyl group, a heptalenyl group, a naphthacenyl group, a picenyl group, a hexacenyl group, a pentacenyl group, a rubicenyl group, a coronenyl group, and an ovalenyl group. When the $C_6$-$C_{60}$ aryl group and the $C_6$-$C_{60}$ arylene group each independently include two or more rings, the respective rings may be fused.

The term "$C_1$-$C_{60}$ heteroaryl group" as used herein refers to a monovalent group having a heterocyclic aromatic system further including at least one heteroatom, other than carbon atoms, as a ring-forming atom, and 1 to 60 carbon atoms. The term "$C_1$-$C_{60}$ heteroarylene group" as used herein refers to a divalent group having substantially the same structure as the $C_1$-$C_{60}$ heteroaryl group. Examples of the $C_1$-$C_{60}$ heteroaryl group may include a pyridinyl group, a pyrimidinyl group, a pyrazinyl group, a pyridazinyl group, a triazinyl group, a quinolinyl group, a benzoquinolinyl group, an isoquinolinyl group, a benzoisoquinolinyl group, a quinoxalinyl group, a benzoquinoxalinyl group, a quinazolinyl group, a benzoquinazolinyl group, a cinnolinyl group, a phenanthrolinyl group, a phthalazinyl group, and a naphthyridinyl group.

When the $C_1$-$C_{60}$ heteroaryl group and the $C_1$-$C_{60}$ heteroarylene group each independently include two or more rings, the respective rings may be fused.

The term "monovalent non-aromatic condensed polycyclic group" as used herein refers to a monovalent group that has two or more condensed rings and only carbon atoms (e.g., 8 to 60 carbon atoms) as ring forming atoms, wherein the molecular structure when considered as a whole is non-aromatic. Examples of the monovalent non-aromatic condensed polycyclic group may include an indenyl group, a fluorenyl group, a spiro-bifluorenyl group, a benzofluorenyl group, an indenophenanthrenyl group, and an indenoanthracenyl group. The term "divalent non-aromatic condensed polycyclic group" as used herein refers to a divalent group having substantially the same structure as the monovalent non-aromatic condensed polycyclic group.

The term "monovalent non-aromatic condensed heteropolycyclic group" as used herein refers to a monovalent group that has two or more condensed rings and at least one heteroatom, other than carbon atoms (e.g., 1 to 60 carbon atoms), as a ring-forming atom, wherein the molecular structure when considered as a whole is non-aromatic. Examples of the monovalent non-aromatic condensed heteropolycyclic group may include a pyrrolyl group, a thiophenyl group, a furanyl group, an indolyl group, a benzoindolyl group, a naphthoindolyl group, an isoindolyl group, a benzoisoindolyl group, a naphthoisoindolyl group, a benzosilolyl group, a benzothiophenyl group, a benzofuranyl group, a carbazolyl group, a dibenzosilolyl group, a dibenzothiophenyl group, a dibenzofuranyl group, an azacarbazolyl group, an azafluorenyl group, an azadibenzosilolyl group, an azadibenzothiophenyl group, an azadibenzofuranyl group, a pyrazolyl group, an imidazolyl group, a triazolyl group, a tetrazolyl group, an oxazolyl group, an isoxazolyl group, a thiazolyl group, an isothiazolyl group, an oxadiazolyl group, a thiadiazolyl group, a benzopyrazolyl group, a benzimidazolyl group, a benzoxazolyl group, a benzothiazolyl group, a benzooxadiazolyl group, a benzothiadiazolyl group, an imidazopyridinyl group, an imidazopyrimidinyl group, an imidazotriazinyl group, an imidazopyrazinyl group, an imidazopyridazinyl group, an indenocarbazolyl group, an indolocarbazolyl group, a benzofurocarbazolyl group, a benzothienocarbazolyl group, a benzosilolocarbazolyl group, a benzoindolocarbazolyl group, a benzocarbazolyl group, a benzonaphthofuranyl group, a benzonaphthothiophenyl group, a benzonaphthosilolyl group, a benzofurodibenzofuranyl group, a benzofurodibenzothiophenyl group, and a benzothienodibenzothiophenyl group. The term "divalent non-aromatic condensed heteropolycyclic group" as used herein refers to a divalent group having substantially the same structure as the monovalent non-aromatic condensed heteropolycyclic group.

The term "$C_6$-$C_{60}$ aryloxy group" as used herein refers to a monovalent group represented by —$OA_{102}$ (wherein $A_{102}$ is the $C_6$-$C_{60}$ aryl group). The term "$C_6$-$C_{60}$ arylthio group" as used herein refers to a monovalent group represented by —$SA_{103}$ (wherein $A_{103}$ is the $C_6$-$C_{60}$ aryl group).

The term "$C_7$-$C_{60}$ aryl alkyl group" as used herein refers to a monovalent group represented by -$A_{104}A_{105}$ (wherein $A_{104}$ is a $C_1$-$C_{54}$ alkylene group, and $A_{105}$ is a $C_6$-$C_{59}$ aryl group). The term "$C_2$-$C_{60}$ heteroaryl alkyl group" as used herein refers to a monovalent group represented by -$A_{106}A_{107}$ (wherein $A_{106}$ is a $C_1$-$C_{59}$ alkylene group, and $A_{107}$ is a $C_1$-$C_{59}$ heteroaryl group).

The term "$R_{10a}$" as used herein may be:

deuterium, —F, —Cl, —Br, —I, a hydroxyl group, a cyano group, or a nitro group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each unsubstituted or substituted with deuterium, —F, —Cl, —Br, —I, a hydroxyl group, a cyano group, a nitro group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, a $C_7$-$C_{60}$ aryl alkyl group, a $C_2$-$C_{60}$ heteroaryl alkyl group, —$Si(Q_{11})(Q_{12})(Q_{13})$, —$N(Q_{11})(Q_{12})$, —$B(Q_{11})(Q_{12})$, —$C(=O)(Q_{11})$, —$S(=O)_2(Q_{11})$, —$P(=O)(Q_{11})(Q_{12})$, or any combination thereof;

a $C_3$-$C_{60}$ carbocyclic group, a $C_1$-$C_{60}$ heterocyclic group, a $C_6$-$C_{60}$ aryloxy group, a $C_6$-$C_{60}$ arylthio group, a $C_7$-$C_{60}$ aryl alkyl group, or a $C_2$-$C_{60}$ heteroaryl alkyl group, each unsubstituted or substituted with deuterium, —F, —Cl, —Br, —I, a hydroxyl group, a cyano group, a nitro group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, a $C_7$-$C_{60}$ aryl alkyl group, a $C_2$-$C_{60}$ heteroaryl alkyl group, —$Si(Q_{21})(Q_{22})(Q_{23})$, —$N(Q_{21})(Q_{22})$, —$B(Q_{21})(Q_{22})$, —$C(=O)(Q_{21})$, —$S(=O)_2(Q_{21})$, —$P(=O)(Q_{21})(Q_{22})$, or any combination thereof; or —$Si(Q_{31})(Q_{32})(Q_{33})$, —$N(Q_{31})(Q_{32})$, —$B(Q_{31})(Q_{32})$, —$C(=O)(Q_{31})$, —$S(=O)_2(Q_{31})$, or —$P(=O)(Q_{31})(Q_{32})$.

$Q_1$ to $Q_3$, $Q_{11}$ to $Q_{13}$, $Q_{21}$ to $Q_{23}$, and $Q_{31}$ to $Q_{33}$ may each independently be: hydrogen; deuterium; —F; —Cl; —Br; —I; a hydroxyl group; a cyano group; a nitro group; a $C_1$-$C_{60}$ alkyl group; a $C_2$-$C_{60}$ alkenyl group; a $C_2$-$C_{60}$ alkynyl group; a $C_1$-$C_{60}$ alkoxy group; a $C_3$-$C_{60}$ carbocyclic group or a $C_1$-$C_{60}$ heterocyclic group, each unsubstituted or substituted with deuterium, —F, a cyano group, a $C_1$-$C_{60}$ alkyl group, a $C_1$-$C_{60}$ alkoxy group, a phenyl group, a biphenyl group, or any combination thereof; a $C_7$-$C_{60}$ aryl alkyl group; or a $C_2$-$C_{60}$ heteroaryl alkyl group.

The term "heteroatom" as used herein refers to any atom other than a carbon atom. Examples of the heteroatom may include O, S, N, P, Si, B, Ge, Se, and combinations thereof.

A third-row transition metal as used herein may include hafnium (Hf), tantalum (Ta), tungsten (W), rhenium (Re), osmium (Os), iridium (Ir), platinum (Pt), and/or gold (Au).

"Ph" used herein represents a phenyl group, "Me" used herein represents a methyl group, "Et" used herein represents an ethyl group, "ter-Bu" or "Bu$^t$" used herein represents a tert-butyl group, and "OMe" used herein represents a methoxy group.

The term "biphenyl group" as used herein refers to a phenyl group substituted with a phenyl group. The "biphenyl group" belongs to (or falls under) "a substituted phenyl group" having a "$C_6$-$C_{60}$ aryl group" as a substituent.

The term "terphenyl group" as used herein refers to a phenyl group substituted with a biphenyl group. The "terphenyl group" belongs to (or falls under) "a substituted phenyl group" having a "$C_6$-$C_{60}$ aryl group substituted with a $C_6$-$C_{60}$ aryl group" as a substituent.

The symbols * and *' as used herein, unless defined otherwise, refer to a binding site to an adjacent atom in a corresponding formula or moiety.

Hereinafter, compounds and a light-emitting device according to one or more embodiments will be described in more detail with reference to Synthesis Examples and Examples. The wording "B was used instead of A" used in describing Synthesis Examples means that an amount of B used was identical to an amount of A used in terms of molar equivalents.

SYNTHESIS EXAMPLES

Synthesis Example of Compound 2

Compound 2 was Synthesized According to Reaction Scheme 1.

Reaction Scheme 1

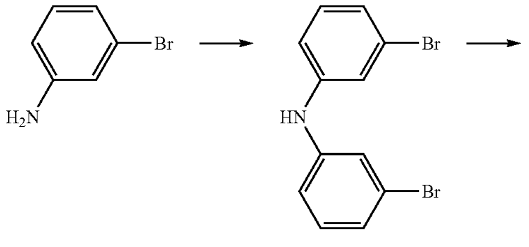

2a

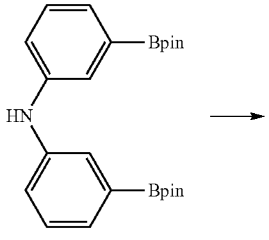

2b

-continued

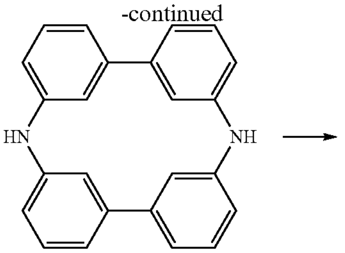

2c

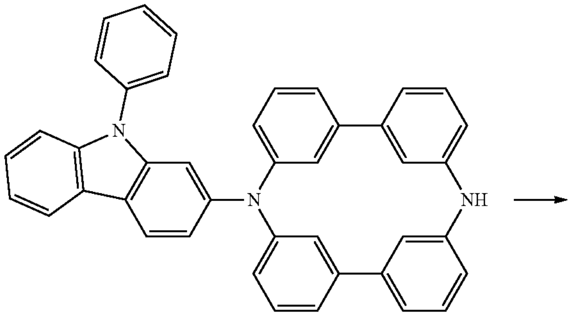

2d

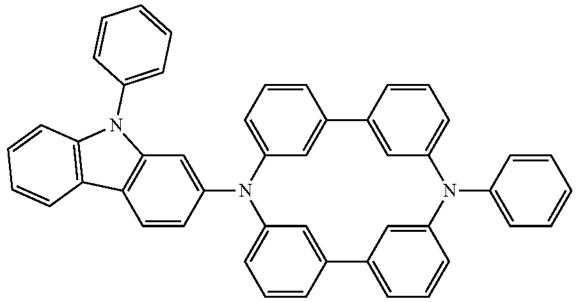

2

1-1. Synthesis of Intermediate 2a

3-Bromoaniline (1.0 eq.), 1-bromo-3-iodobenzene (2.2 eq.), tris(dibenzylideneacetone)dipalladium(0) (0.05 eq.), tri-tert-butylphosphine (0.10 eq.), and sodium tert-butoxide (2.0 eq.) were dissolved in toluene, followed by stirring under a nitrogen atmosphere at a temperature of 80° C. for 1 hour. Once the mixture was cooled and washed three times using ethyl acetate and water, the resulting organic layer was dried using $MgSO_4$ under reduced pressure. Intermediate 2a was obtained through column chromatography (yield: 60%).

1-2. Synthesis of Intermediate 2b

Intermediate 2a (1.0 eq.), bis(pinacolato)diboron (3.0 eq.), potassium acetate (4.0 eq.), and palladium acetate (0.05 eq.) were dissolved in 1,4-dioxane, followed by stirring under a nitrogen atmosphere at a temperature of 80° C. for 8 hours. Once the mixture was cooled and washed three times using ethyl acetate and water, the resulting organic layer was dried using $MgSO_4$ under reduced pressure. Intermediate 2b was obtained through column chromatography (yield: 75%).

1-3. Synthesis of Intermediate 2c

Intermediate 2a (1.0 eq.), Intermediate 2b (1.2 eq.), tetrakis(triphenylphosphine)palladium (0.05 eq.), and potassium carbonate (2.0 eq.) were dissolved in a solution of THF and $H_2O$ at a volume ratio of 4:1, followed by stirring under a nitrogen atmosphere at a temperature of 80° C. for 12 hours. Once the mixture was cooled and washed three times using ethyl acetate and water, the resulting organic layer was dried using $MgSO_4$ under reduced pressure. Intermediate 2c was obtained through column chromatography (yield: 35%).

1-4. Synthesis of Intermediate 2d

Intermediate 2c (1.0 eq.), 2-bromo-9-phenyl-9H-carbazole (1.1 eq.), tris(dibenzylideneacetone)dipalladium(0) (0.05 eq.), tri-tert-butylphosphine (0.10 eq.), and sodium tert-butoxide (2.0 eq.) were dissolved in toluene, followed by stirring under a nitrogen atmosphere at a temperature of 80° C. for 1 hour. Once the mixture was cooled and washed three times using ethyl acetate and water, the resulting organic layer was dried using $MgSO_4$ under reduced pressure. Intermediate 2d was obtained through column chromatography (yield: 90%). By fast-atom bombardment mass spectrometry (FAB-MS), mass number m/z=651.27 was observed as a molecular ion peak. Thus, Compound 2 was identified.

1-5. Synthesis of Compound 2

Intermediate 2d (1.0 eq.), bromobenzene (1.1 eq.), tris (dibenzylideneacetone)dipalladium(0) (0.05 eq.), tri-tert-butylphosphine (0.10 eq.), and sodium tert-butoxide (2.0 eq.) were dissolved in toluene, followed by stirring under a nitrogen atmosphere at a temperature of 80° C. for 1 hour. Once the mixture was cooled and washed three times using ethyl acetate and water, the resulting organic layer was dried using $MgSO_4$ under reduced pressure. Compound 2 was obtained through column chromatography (yield: 90%).

Synthesis Example of Compound 3

Compound 3 was Synthesized According to Reaction Scheme 2.

Reaction Scheme 2

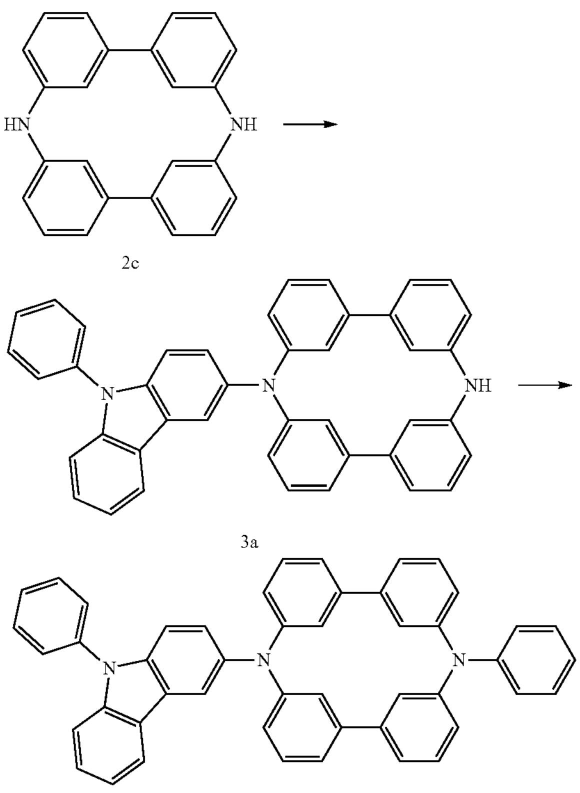

2c

3a

3

2-1. Synthesis of Intermediate 3a

Intermediate 2c (1.0 eq.), 3-iodo-9-phenyl-9H-carbazole (1.1 eq.), tris(dibenzylideneacetone)dipalladium(0) (0.05 eq.), tri-tert-butylphosphine (0.10 eq.), and sodium tert-butoxide (2.0 eq.) were dissolved in toluene, followed by stirring under a nitrogen atmosphere at a temperature of 80° C. for 1 hour. Once the mixture was cooled and washed three times using ethyl acetate and water, the resulting organic layer was dried using $MgSO_4$ under reduced pressure. Intermediate 3a was obtained through column chromatography (yield: 90%).

2-2. Synthesis of Compound 3

Intermediate 3a (1.0 eq.), bromobenzene (1.1 eq.), tris (dibenzylideneacetone)dipalladium(0) (0.05 eq.), tri-tert-butylphosphine (0.10 eq.), and sodium tert-butoxide (2.0 eq.) were dissolved in toluene, followed by stirring under a nitrogen atmosphere at a temperature of 80° C. for 1 hour. Once the mixture was cooled and washed three times using ethyl acetate and water, the resulting organic layer was dried using $MgSO_4$ under reduced pressure. Compound 3 was obtained through column chromatography (yield: 90%). By fast-atom bombardment mass spectrometry (FAB-MS), mass number m/z=651.27 was observed as a molecular ion peak. Thus, Compound 3 was identified.

Synthesis Example of Compound 11

Compound 11 was Synthesized According to Reaction Scheme 3.

Reaction Scheme 3

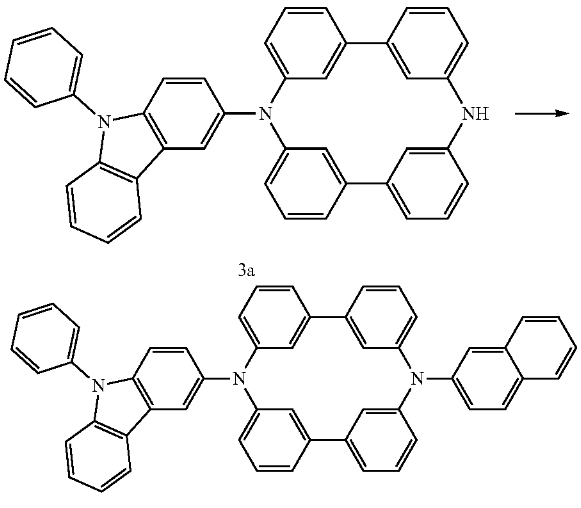

3a

11

3-1. Synthesis of Compound 11

Intermediate 3a (1.0 eq.), 2-bromonaphthalene (1.1 eq.), tris(dibenzylideneacetone)dipalladium(0) (0.05 eq.), tri-tert-butylphosphine (0.10 eq.), and sodium tert-butoxide (2.0 eq.) were dissolved in toluene, followed by stirring under a nitrogen atmosphere at a temperature of 80° C. for 1 hour. Once the mixture was cooled and washed three times using ethyl acetate and water, the resulting organic layer was dried using $MgSO_4$ under reduced pressure. Compound 11 was obtained through column chromatography (yield: 85%).

By FAB-MS, mass number m/z=701.28 was observed as a molecular ion peak. Thus, Compound 11 was identified.

Synthesis Example of Compound 15

Compound 15 was Synthesized According to Reaction Scheme 4.

Reaction Scheme 4

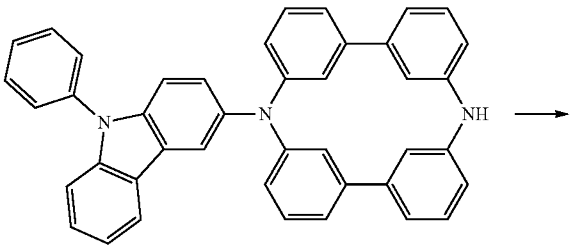

3a

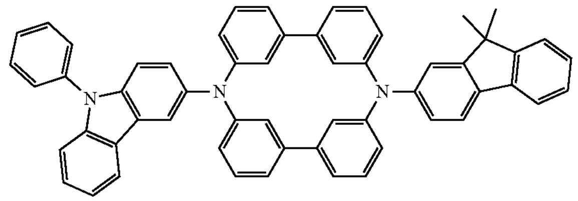

15

4-1. Synthesis of Compound 15

Intermediate 3a (1.0 eq.), 2-bromo-9,9-dimethyl-9H-fluorene (1.1 eq.), tris(dibenzylideneacetone)dipalladium(0) (0.05 eq.), tri-tert-butylphosphine (0.10 eq.), and sodium tert-butoxide (2.0 eq.) were dissolved in toluene, followed by stirring under a nitrogen atmosphere at a temperature of 80° C. for 1 hour. Once the mixture was cooled and washed three times using ethyl acetate and water, the resulting organic layer was dried using $MgSO_4$ under reduced pressure. Compound 15 was obtained through column chromatography (yield: 85%).

By FAB-MS, mass number m/z=767.33 was observed as a molecular ion peak. Thus, Compound 15 was identified.

Synthesis Example of Compound 30

Compound 30 was Synthesized According to Reaction Scheme 5.

Reaction Scheme 5

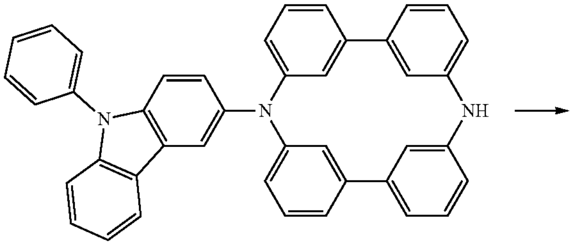

3a

-continued

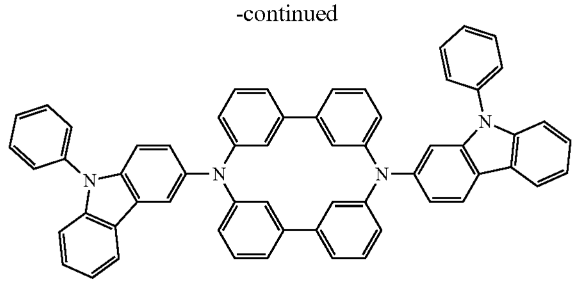

30

5-1. Synthesis of Compound 30

Intermediate 3a (1.0 eq.), 2-bromo-9-phenyl-9H-carbazole (1.1 eq.), tris(dibenzylideneacetone)dipalladium(0) (0.05 eq.), tri-tert-butylphosphine (0.10 eq.), and sodium tert-butoxide (2.0 eq.) were dissolved in toluene, followed by stirring under a nitrogen atmosphere at a temperature of 80° C. for 1 hour. Once the mixture was cooled and washed three times using ethyl acetate and water, the resulting organic layer was dried using $MgSO_4$ under reduced pressure. Compound 30 was obtained through column chromatography (yield: 87%).

By fast-atom bombardment mass spectrometry (FAB-MS), mass number m/z=816.32 was observed as a molecular ion peak. Thus, Compound 30 was identified.

Synthesis Example of Compound 159

Compound 159 was Synthesized According to Reaction Scheme 6.

Reaction Scheme 6

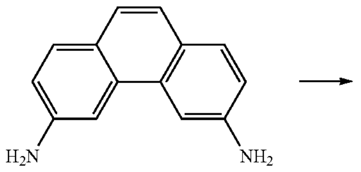

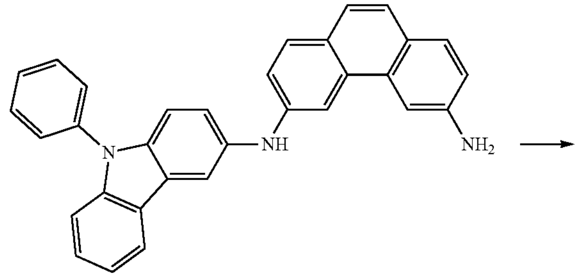

159a

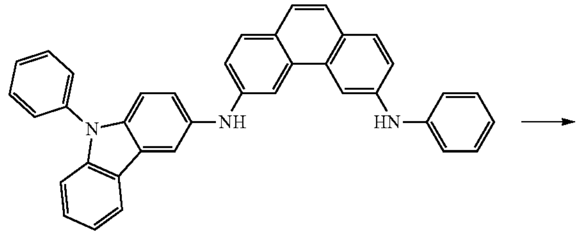

159b

-continued

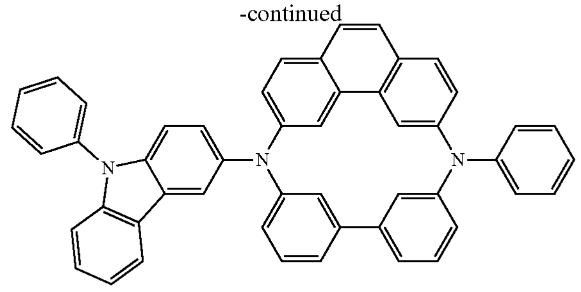

159

6-1. Synthesis of Intermediate 159a 3,6-di(azaneyl)phenanthrene (1.0 eq.), 3-bromo-9-phenyl-9H-carbazole (1.0 eq.), tris(dibenzylideneacetone)dipalladium(0) (0.05 eq.), tri-tert-butylphosphine (0.10 eq.), and sodium tert-butoxide (2.0 eq.) were dissolved in toluene, followed by stirring under a nitrogen atmosphere at a temperature of 80° C. for 1 hour. Once the mixture was cooled and washed three times using ethyl acetate and water, the resulting organic layer was dried using $MgSO_4$ under reduced pressure. Intermediate 159a was obtained through column chromatography (yield: 60%).

6-2. Synthesis of Intermediate 159b

Intermediate 159a (1.0 eq.), bromobenzene (1.0 eq.), tris(dibenzylideneacetone)dipalladium(0) (0.05 eq.), tri-tert-butylphosphine (0.10 eq.), and sodium tert-butoxide (2.0 eq.) were dissolved in toluene, followed by stirring under a nitrogen atmosphere at a temperature of 80° C. for 1 hour. Once the mixture was cooled and washed three times using ethyl acetate and water, the resulting organic layer was dried using $MgSO_4$ under reduced pressure. Intermediate 159b was obtained through column chromatography (yield: 60%).

6-3. Synthesis of Compound 159

Intermediate 159b (1.0 eq.), 3,3'-dibromo-1,1'-biphenyl (1.0 eq.), tris(dibenzylideneacetone)dipalladium(0) (0.05 eq.), tri-tert-butylphosphine (0.10 eq.), and sodium tert-butoxide (2.0 eq.) were dissolved in toluene, followed by stirring under a nitrogen atmosphere at a temperature of 80° C. for 1 hour. Once the mixture was cooled and washed three times using ethyl acetate and water, the resulting organic layer was dried using $MgSO_4$ under reduced pressure. Compound 159 was obtained through column chromatography (yield: 40%).

By FAB-MS, mass number m/z=791.33 was observed as a molecular ion peak. Thus, Compound 159 was identified.

Synthesis Example of Compound 195

Compound 195 was Synthesized According to Reaction Scheme 7.

Reaction Scheme 7

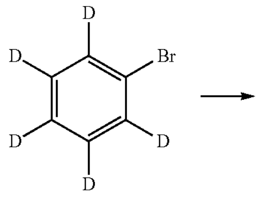

-continued

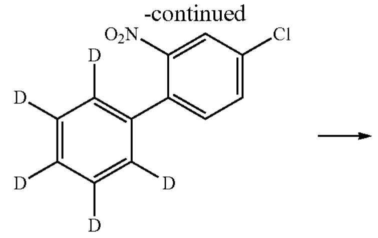

195a

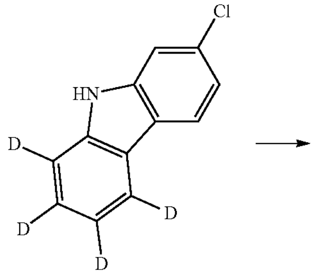

195b

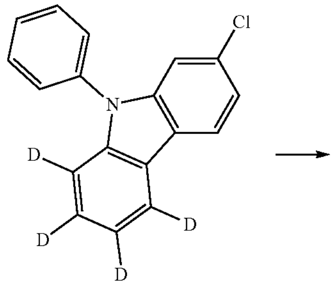

195c

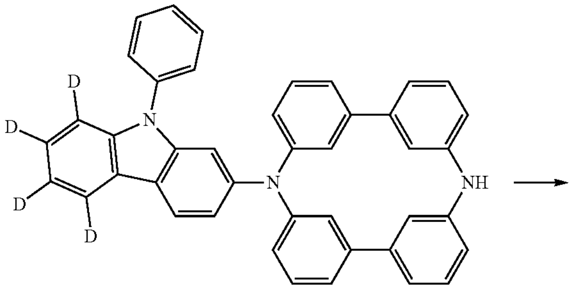

195d

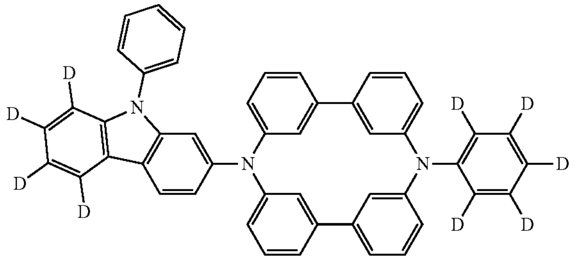

195

7-1. Synthesis of Intermediate 195a 1-bromobenzene-2,3,4,5,6-$d_5$ (1.0 eq.), (4-chloro-2-nitrophenyl)boronic acid (1.1 eq.), tetrakis(triphenylphosphine) palladium (0.05 eq.), potassium carbonate (2.0 eq.) were dissolved in a solution of THF and $H_2O$ at a volume ratio of 4:1, followed by stirring under a nitrogen atmosphere at a temperature of 80° C. for 12 hours. Once the mixture was cooled and washed three times using ethyl acetate and water, the resulting organic layer was dried using $MgSO_4$ under reduced pressure. Intermediate 195a was obtained through column chromatography (yield: 65%).

7-2. Synthesis of Intermediate 195b

Intermediate 195a (1.0 eq.) and triphenylphosphine (1.5 eq.) were added dropwise with dichloroethane, followed by stirring under a nitrogen atmosphere at a temperature of 220° C. for 12 hours. Once the mixture was cooled and washed three times using ethyl acetate and water, the resulting organic layer was dried using $MgSO_4$ under reduced pressure. Intermediate 195b was obtained through column chromatography (yield: 55%).

7-3. Synthesis of Intermediate 195c

Intermediate 195b (1.0 eq.), iodobenzene (10 eq.), CuI (0.2 eq.), 1,10-phenanthroline (0.40 eq.), and sodium tert-butoxide (3.0 eq.) were dissolved in dimethyl formamide (DMF), followed by stirring under a nitrogen atmosphere at a temperature of 160° C. for 24 hours. Once the mixture was cooled and washed five times using ethyl acetate and water, the resulting organic layer was dried using $MgSO_4$ under reduced pressure. Intermediate 195c was obtained through column chromatography (yield: 80%).

7-4. Synthesis of Intermediate 195d

Intermediate 2c (1.0 eq.), Intermediate 195c (1.05 eq.), tris(dibenzylideneacetone)dipalladium(0) (0.05 eq.), tri-tert-butylphosphine (0.10 eq.), and sodium tert-butoxide (2.0 eq.) were dissolved in toluene, followed by stirring under a nitrogen atmosphere at a temperature of 80° C. for 1 hour. Once the mixture was cooled and washed three times using ethyl acetate and water, the resulting organic layer was dried using $MgSO_4$ under reduced pressure. Intermediate 195d was obtained through column chromatography (yield: 87%).

7-5. Synthesis of Compound 195

Intermediate 195d (1.0 eq.), 1-bromobenzene-2,3,4,5,6-$d_5$ (1.0 eq.), tris(dibenzylideneacetone)dipalladium(0) (0.05 eq.), tri-tert-butylphosphine (0.10 eq.), and sodium tert-butoxide (2.0 eq.) were dissolved in toluene, followed by stirring under a nitrogen atmosphere at a temperature of 80° C. for 1 hour. Once the mixture was cooled and washed three times using ethyl acetate and water, the resulting organic layer was dried using $MgSO_4$ under reduced pressure. Compound 195 was obtained through column chromatography (yield: 87%).

By fast-atom bombardment mass spectrometry (FAB-MS), mass number m/z=660.32 was observed as a molecular ion peak. Thus, Compound 195 was identified.

Synthesis Example of Compound 198

Compound 198 was Synthesized According to Reaction Scheme 8.

Reaction Scheme 8

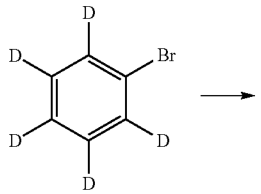

-continued

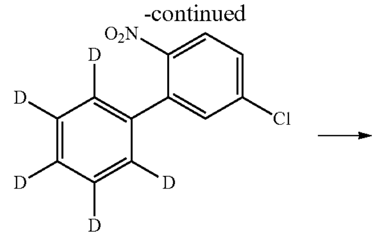

198a

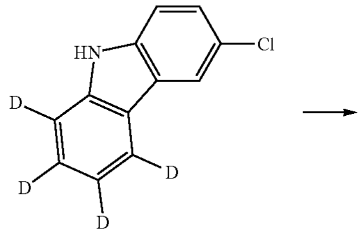

198b

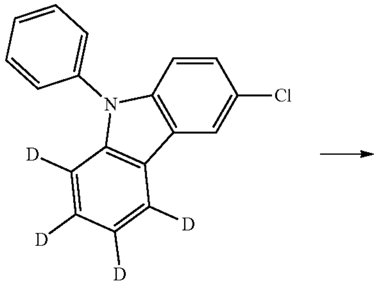

198c

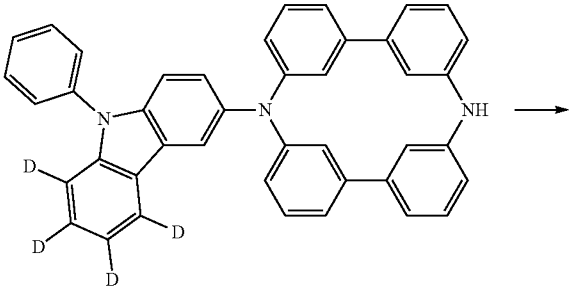

198d

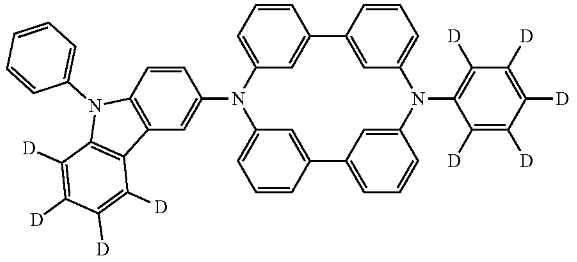

198

8-1. Synthesis of Intermediate 198a 1-bromobenzene-2,3,4,5,6-$d_5$ (1.0 eq.), (5-chloro-2-nitrophenyl)boronic acid (1.1 eq.), tetrakis(triphenylphosphine) palladium (0.05 eq.), and potassium carbonate (2.0 eq.) were dissolved in a solution of THF and $H_2O$ at a volume ratio of 4:1, followed by stirring under a nitrogen atmosphere at a temperature of 80° C. for 12 hours. Once the mixture was cooled and washed three times using ethyl acetate and water, the resulting organic layer was dried using $MgSO_4$ under reduced pressure. Intermediate 198a was obtained through column chromatography (yield: 60%).

8-2. Synthesis of Intermediate 198b

Intermediate 198a (1.0 eq.) and triphenylphosphine (1.5 eq.) were added dropwise with dichloroethane, followed by stirring under a nitrogen atmosphere at a temperature of 220° C. for 12 hours. Once the mixture was cooled and washed three times using ethyl acetate and water, the resulting organic layer was dried using $MgSO_4$ under reduced pressure. Intermediate 198b was obtained through column chromatography (yield: 60%).

8-3. Synthesis of Intermediate 198c

Intermediate 198b (1.0 eq.), iodobenzene (10 eq.), CuI (0.2 eq.), 1,10-phenanthroline (0.40 eq.), and sodium tert-butoxide (3.0 eq.) were dissolved in DMF, followed by stirring under a nitrogen atmosphere at a temperature of 160° C. for 24 hours. Once the mixture was cooled and washed five times using ethyl acetate and water, the resulting organic layer was dried using $MgSO_4$ under reduced pressure. Intermediate 198c was obtained through column chromatography (yield: 80%).

8-4. Synthesis of Intermediate 198d

Intermediate 3a (1.0 eq.), Intermediate 198c (1.05 eq.), tris(dibenzylideneacetone)dipalladium(0) (0.05 eq.), tri-tert-butylphosphine (0.10 eq.), and sodium tert-butoxide (2.0 eq.) were dissolved in toluene, followed by stirring under a nitrogen atmosphere at a temperature of 110° C. for 1 hour. Once the mixture was cooled and washed three times using ethyl acetate and water, the resulting organic layer was dried using $MgSO_4$ under reduced pressure. Intermediate 198d was obtained through column chromatography (yield: 80%).

8-5. Synthesis of Compound 198

Intermediate 198d (1.0 eq.), 1-bromobenzene-2,3,4,5,6-$d_5$ (1.0 eq.), tris(dibenzylideneacetone)dipalladium(0) (0.05 eq.), tri-tert-butylphosphine (0.10 eq.), and sodium tert-butoxide (2.0 eq.) were dissolved in toluene, followed by stirring under a nitrogen atmosphere at a temperature of 80° C. for 1 hour. Once the mixture was cooled and washed three times using ethyl acetate and water, the resulting organic layer was dried using $MgSO_4$ under reduced pressure. Compound 198 was obtained through column chromatography (yield: 88%).

By fast-atom bombardment mass spectrometry (FAB-MS), mass number m/z=660.32 was observed as a molecular ion peak. Thus, Compound 198 was identified.

Example 1

As an anode, a 15 Ohms per square centimeter ($\Omega/cm^2$) (1,200 Å) ITO glass substrate (available from Corning Co., Ltd) was cut to a size of 50 millimeters (mm)×50 mm×0.7 mm, sonicated in isopropyl alcohol and pure water for 5 minutes in each solvent, cleaned with ultraviolet rays for 30 minutes, and then ozone, and was mounted on a vacuum deposition apparatus.

2-TNATA was vacuum-deposited on the anode to form a hole injection layer having a thickness of 600 Å, Compound 2 was then deposited on the hole injection layer to form a hole transport layer having a thickness of 300 Å.

9,10-di(naphthalene-2-yl)anthracene (DNA) as a host and 4,4'-bis[2-(4-(N,N-diphenylamino)phenyl)vinyl]biphenyl (DPAVBi) as a dopant were co-deposited on the hole transport layer at a weight ratio of 98:2 to form an emission layer having a thickness of 300 Å.

Then, $Alq_3$ was deposited on the emission layer to form an electron transport layer having a thickness of 300 Å. Subsequently, LiF was deposited on the electron transport layer to a thickness of 10 Å. Next, Al was vacuum-deposited thereon to form a cathode having a thickness of 3,000 Å, thereby completing the manufacture of an organic light-emitting device having a structure of ITO (1,200 Å)/2-TNATA (600 Å)/Compound 2 (300 Å)/DNA (host)+DPAVBi (dopant) (98:2) (300 Å)/Alq3 (300 Å)/LiF (10 Å)/Al (3,000 Å).

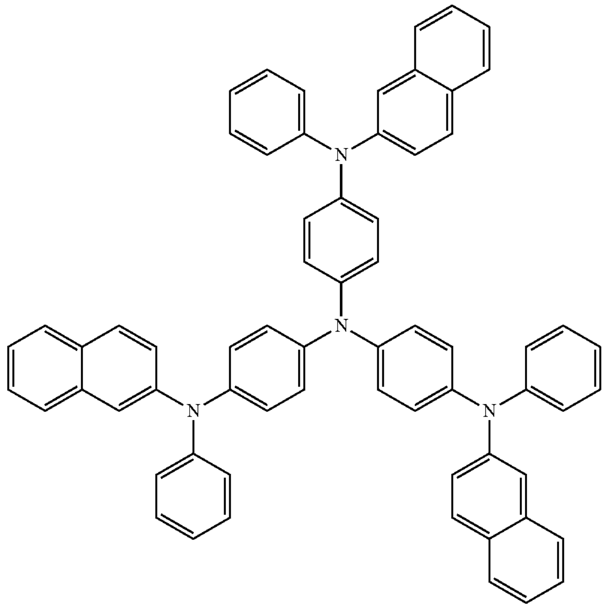

2-TNATA

-continued

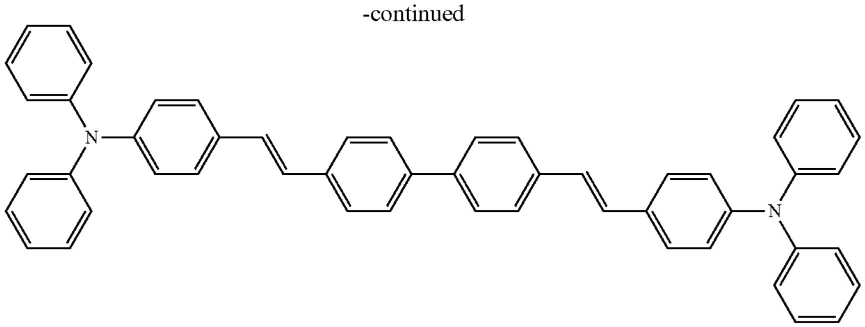

DPAVBi

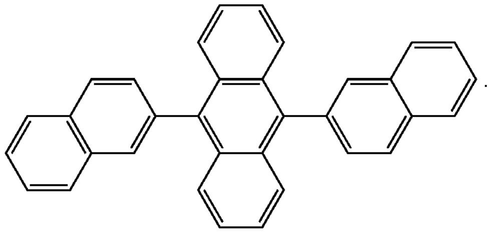

DNA

Examples 2 to 8 and Comparative Examples 1 to 6

Organic light-emitting devices were manufactured in substantially the same manner as in Example 1, except that the compounds shown in Table 1 were used instead of Compound 2 in forming each hole transport layer.

Evaluation Example 2

H The device performances (driving voltage, luminance, and luminescence efficiency (Cd/A)) of the organic light-emitting device manufactured in Examples 1 to 8 and Comparative Examples 1 to 7 at a current density of 50 mA/cm$^2$ were measured, and the half lifespans of the devices were measured at a current density of 100 mA/cm$^2$. The results thereof are shown in Table 1.

The luminance was measured using a luminance meter PR650 powered by a current voltmeter (Keithley SMU 236).

The efficiency was measured using a luminance meter PR650 powered by a current voltmeter (Keithley SMU 236).

The half lifespan indicates a time for the luminance of the organic light-emitting device to decline to 59% of its initial luminance (at 100 mA/cm$^2$).

TABLE 1

| No. | Hole transporting material | Driving voltage (V) | Current density (mA/cm$^2$) | Luminance (cd/m$^2$) | Efficiency (cd/A) | Emission color | Half lifespan (hr@100 mA/cm$^2$) |
|---|---|---|---|---|---|---|---|
| Example 1 | Compound 2 | 4.15 | 50 | 3300 | 7.45 | Blue | 495 |
| Example 2 | Compound 3 | 4.17 | 50 | 3250 | 7.25 | Blue | 505 |
| Example 3 | Compound 11 | 4.10 | 50 | 3230 | 7.4 | Blue | 490 |
| Example 4 | Compound 15 | 4.22 | 50 | 3270 | 7.5 | Blue | 410 |
| Example 5 | Compound 30 | 4.25 | 50 | 3280 | 7.35 | Blue | 385 |
| Example 6 | Compound 159 | 4.05 | 50 | 3150 | 7.3 | Blue | 390 |
| Example 7 | Compound 195 | 4.15 | 50 | 3350 | 7.15 | Blue | 500 |
| Example 8 | Compound 198 | 4.12 | 50 | 3350 | 7.25 | Blue | 510 |
| Comparative Example 1 | NPB | 7.01 | 50 | 2645 | 5.29 | Blue | 258 |
| Comparative Example 2 | Compound A | 5.35 | 50 | 3010 | 5.9 | Blue | 270 |
| Comparative Example 3 | Compound B | 4.75 | 50 | 3030 | 6.1 | Blue | 265 |
| Comparative Example 4 | Compound C | 5.54 | 50 | 3065 | 5.94 | Blue | 277 |
| Comparative Example 5 | Compound D | 4.82 | 50 | 3105 | 6.05 | Blue | 350 |
| Comparative Example 6 | Compound E | 5.94 | 50 | 2910 | 5.32 | Blue | 120 |
| Comparative Example 7 | Compound F | 5.21 | 50 | 3020 | 6.15 | Blue | 410 |

2
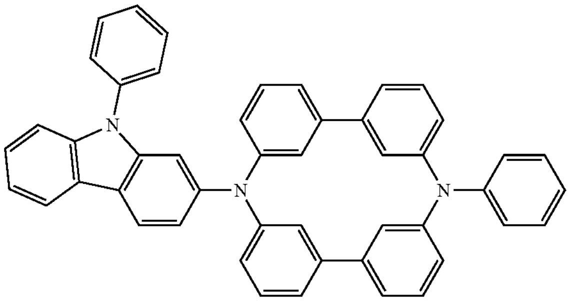
3
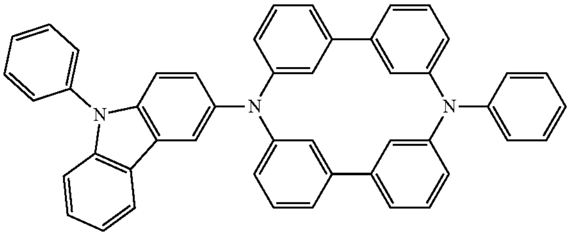
11
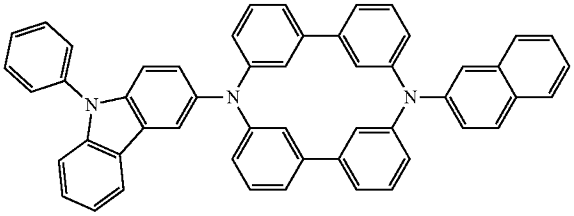
15
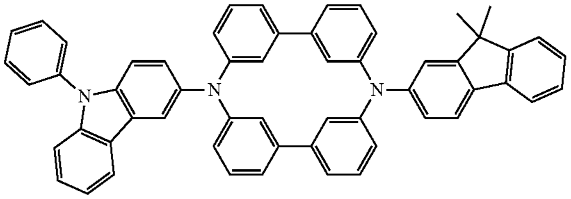
30
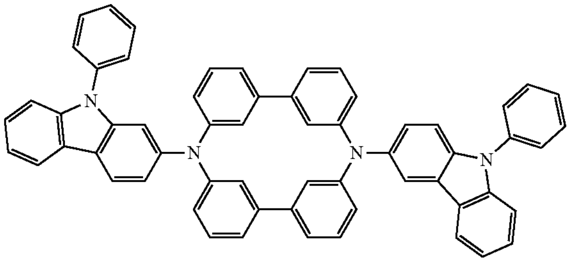
159
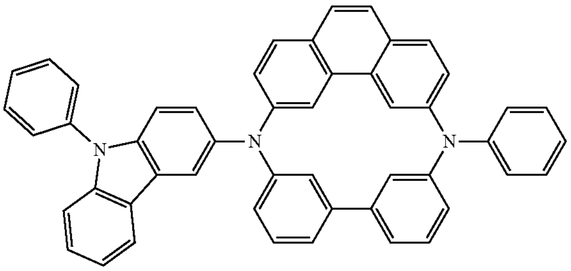
-continued
195
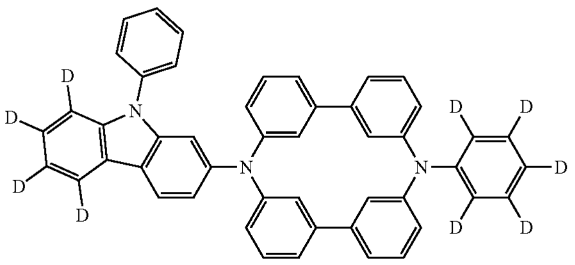
198
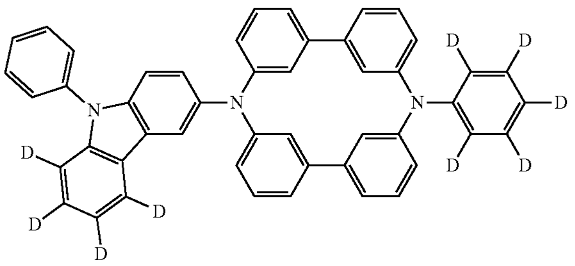
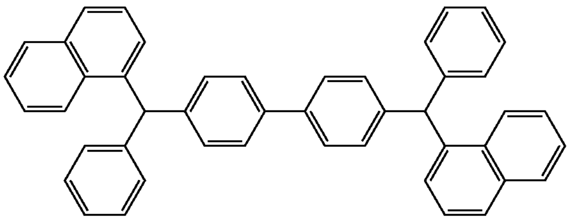
NPB
A
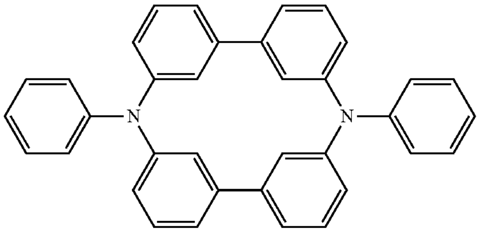
B
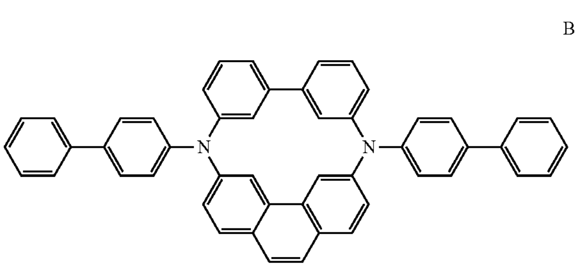

-continued

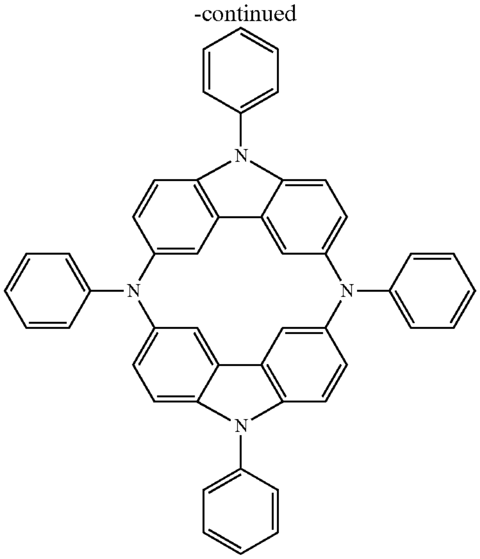

D

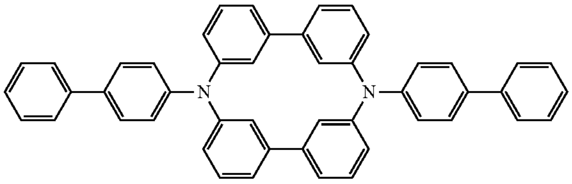

E

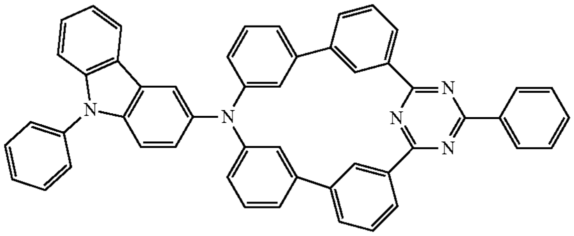

F

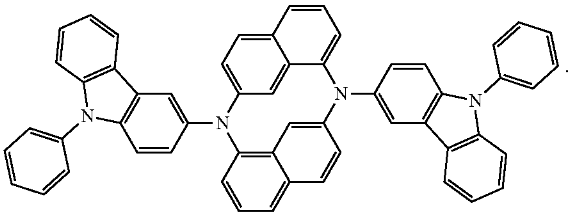

Referring to the results of Table 1, the organic light-emitting devices of Example 1 to 8 including the heterocyclic compound represented by Formula 1 in the hole transport layer were found to have improved driving voltage and I-V-L (e.g., current-voltage-luminance) characteristics with improved efficiency, as compared with the organic light-emitting devices of Comparative Examples 1 to 7. In addition, the organic light-emitting devices of Examples 1 to 8 were found to have improved lifespan, as compared with the organic light-emitting devices of Comparative Examples 1 to 7.

From the foregoing description, it is believed that the light-emitting device that includes the heterocyclic compound represented by Formula 1 may have excellent or suitable luminescence efficiency and excellent emission lifespan. Thus, a high-quality electronic apparatus may be manufactured by using the light-emitting device.

The apparatus, the device and/or any other relevant devices or components according to embodiments of the present invention described herein may be implemented utilizing any suitable hardware, firmware (e.g. an application-specific integrated circuit), software, or a combination of software, firmware, and hardware. For example, the various components of the device and/or apparatus may be formed on one integrated circuit (IC) chip or on separate IC chips. Further, the various components of the device and/or apparatus may be implemented on a flexible printed circuit film, a tape carrier package (TCP), a printed circuit board (PCB), or formed on one substrate. Further, the various components of the device and/or apparatus may be a process or thread, running on one or more processors, in one or more computing devices, executing computer program instructions and interacting with other system components for performing the various functionalities described herein. The computer program instructions are stored in a memory which may be implemented in a computing device using a standard memory device, such as, for example, a random access memory (RAM). The computer program instructions may also be stored in other non-transitory computer readable media such as, for example, a CD-ROM, flash drive, or the like. Also, a person of skill in the art should recognize that the functionality of various computing devices may be combined or integrated into a single computing device, or the functionality of a particular computing device may be distributed across one or more other computing devices without departing from the scope of the exemplary embodiments of the present invention.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope as defined by the following claims and equivalents thereof.

What is claimed is:

1. A light-emitting device comprising:

a first electrode;

a second electrode facing the first electrode;

an interlayer between the first electrode and the second electrode, the interlayer comprising an emission layer; and a heterocyclic compound represented by Formula 1:

Formula 1

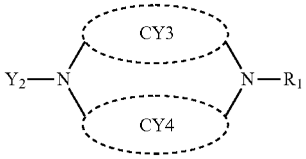

Formula 2

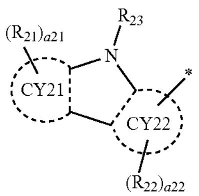

-continued

Formula 3

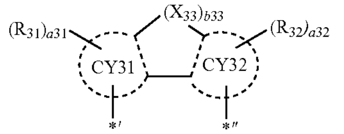

Formula 4

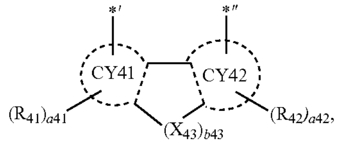

wherein, in Formulae 1 to 4, $Y_2$ is a group represented by Formula 2, ring CY3 is a group represented by Formula 3, ring CY4 is a group represented by Formula 4, ring CY21, ring CY22, ring CY31, ring CY32, ring CY41, and ring CY42 are each independently a $C_3$-$C_{60}$ carbocyclic group or a $C_1$-$C_{60}$ heterocyclic group, $X_{33}$ is a single bond, O, S, $B(R_{33})$, $N(R_{33})$, $C(R_{33})(R_{34})$, $Si(R_{33})(R_{34})$, or $C(R_{33})$=$C(R_{34})$, $b_{33}$ is an integer from 0 to 3, when $b_{33}$ is 0, $X_{33}$ is not present, $X_{43}$ is a single bond, O, S, $B(R_{43})$, $N(R_{43})$, $C(R_{43})(R_{44})$, $Si(R_{43})(R_{44})$, or $C(R_{43})$=$C(R_{44})$, $b_{43}$ is an integer from 0 to 3, when $b_{43}$ is 0, $X_{43}$ is not present, $R_1$, $R_{21}$ to $R_{23}$, $R_{31}$ to $R_{34}$, and $R_{41}$ to $R_{44}$ are each independently hydrogen, deuterium, —F, —Cl, —Br, —I, a hydroxyl group, a cyano group, a nitro group, a $C_1$-$C_{60}$ alkyl group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, a $C_6$-$C_{60}$ aryloxy group unsubstituted or substituted with at least one $R_{10a}$, a $C_6$-$C_{60}$ arylthio group unsubstituted or substituted with at least one $R_{10a}$, a $C_7$-$C_{60}$ aryl alkyl group unsubstituted or substituted with at least one $R_{10a}$, a $C_2$-$C_{60}$ heteroaryl alkyl group unsubstituted or substituted with at least one $R_{10a}$, —$Si(Q_1)(Q_2)(Q_3)$, —$N(Q_1)(Q_2)$, —$B(Q_1)(Q_2)$, —$C(=O)(Q_1)$, —$S(=O)_2(Q_1)$, or —$P(=O)(Q_1)(Q_2)$, a21, a22, a31, a32, a41, and a42 are each independently an integer from 0 to 10, wherein, in Formula 2,

* indicates a binding site to nitrogen (N) bound to $Y_2$ in Formula 1, wherein, in Formulae 3 and 4,

*' indicates a binding site to nitrogen (N) bound to $Y_2$ in Formula 1, and

*" indicates a binding site to nitrogen (N) bound to $R_1$ in Formula 1, wherein $R_{10a}$ is:

deuterium, —F, —Cl, —Br, —I, a hydroxyl group, a cyano group, or a nitro group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each unsubstituted or substituted with deuterium, —F, —Cl, —Br, —I, a hydroxyl group, a cyano group, a nitro group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, a $C_7$-$C_{60}$ aryl alkyl group, a $C_2$-$C_{60}$ heteroaryl alkyl group, —$Si(Q_{11})(Q_{12})(Q_{13})$, —$N(Q_{11})(Q_{12})$, —$B(Q_{11})(Q_{12})$, —$C(=O)(Q_{11})$, —$S(=O)_2(Q_{11})$, —$P(=O)(Q_{11})(Q_{12})$, or any combination thereof;

a $C_3$-$C_{60}$ carbocyclic group, a $C_1$-$C_{60}$ heterocyclic group, a $C_6$-$C_{60}$ aryloxy group, a $C_6$-$C_{60}$ arylthio group, a $C_7$-$C_{60}$ aryl alkyl group, or a $C_2$-$C_{60}$ heteroaryl alkyl group, each unsubstituted or substituted with deuterium, —F, —Cl, —Br, —I, a hydroxyl group, a cyano group, a nitro group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, a $C_7$-$C_{60}$ aryl alkyl group, a $C_2$-$C_{60}$ heteroaryl alkyl group, —$Si(Q_{21})(Q_{22})(Q_{23})$, —$N(Q_{21})(Q_{22})$, —$B(Q_{21})(Q_{22})$, —$C(=O)(Q_{21})$, —$S(=O)_2(Q_{21})$, —$P(=O)(Q_{21})(Q_{22})$, or any combination thereof; or —$Si(Q_{31})(Q_{32})(Q_{33})$, —$N(Q_{31})(Q_{32})$, —$B(Q_{31})(Q_{32})$, —$C(=O)(Q_{31})$, —$S(=O)_2(Q_{31})$, or —$P(=O)(Q_{31})(Q_{32})$, and wherein $Q_1$ to $Q_3$, $Q_{11}$ to $Q_{13}$, $Q_{21}$ to $Q_{23}$, and $Q_{31}$ to $Q_{33}$ are each independently: hydrogen; deuterium; —F; —Cl; —Br; —I; a hydroxyl group; a cyano group; a nitro group; a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ carbocyclic group or a $C_1$-$C_{60}$ heterocyclic group, each unsubstituted or substituted with deuterium, —F, a cyano group, a $C_1$-$C_{60}$ alkyl group, a $C_1$-$C_{60}$ alkoxy group, a phenyl group, a biphenyl group, a $C_1$-$C_{60}$ heterocyclic group, or any combination thereof; a $C_7$-$C_{60}$ aryl alkyl group; or a $C_2$-$C_{60}$ heteroaryl alkyl group.

2. The light-emitting device of claim 1, wherein the interlayer further comprises a hole transport region between the first electrode and the emission layer, and an electron transport region between the emission layer and the second electrode, the hole transport region comprises a hole injection layer, a hole transport layer, an emission auxiliary layer, an electron blocking layer, or any combination thereof, and the electron transport region comprises a buffer layer, a hole blocking layer, an electron control layer, an electron transport layer, an electron injection layer, or any combination thereof.

3. The light-emitting device of claim 2, wherein the hole transport region comprises the heterocyclic compound represented by Formula 1.

4. The light-emitting device of claim 2, wherein the hole injection layer comprises the heterocyclic compound represented by Formula 1.

5. The light-emitting device of claim 1, wherein the emission layer is configured to emit blue light.

6. The light-emitting device of claim 1, wherein, in Formulae 1 to 4, ring CY21, ring CY22, ring CY31, ring CY32, ring CY41, and ring CY42 are each independently a benzene group, a naphthalene group, an anthracene group, a dibenzofuran group, a dibenzothiophene group, a carbazole group, a fluorene group, or a dibenzosilole group.

7. The light-emitting device of claim 1, wherein, in Formula 2, at least one selected from the group consisting of ring CY21 and ring CY22 is a benzene group.

8. The light-emitting device of claim 1, wherein, in Formula 2, ring CY22 is represented by one of ring CY22-1 to ring CY22-4:

CY22-1

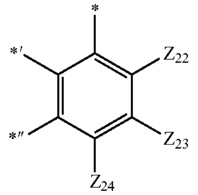

CY22-2

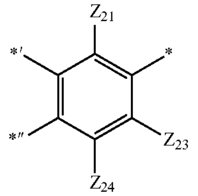

CY22-3

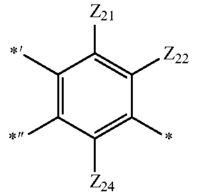

CY22-4

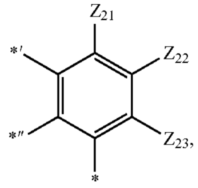

wherein, in ring CY22-1 to ring CY22-4, $Z_{21}$ to $Z_{24}$ are each independently the same as the description of $R_{22}$,

* indicates a binding site to nitrogen (N) bound to $Y_2$ in Formula 1,

*' indicates a binding site to nitrogen (N) bound to $R_{23}$ in Formula 2, and

*" indicates a binding site to ring CY21 in Formula 2.

9. The light-emitting device of claim 1, wherein, in Formulae 3 and 4, $X_{33}$ is O, S, $N(R_{33})$, $C(R_{33})(R_{34})$, or $C(R_{33})=C(R_{34})$, and $X_{43}$ is O, S, $N(R_{43})$, $C(R_{43})(R_{44})$, or $C(R_{43})=C(R_{44})$.

10. The light-emitting device of claim 1, wherein, in Formula 3, $b_{33}$ is 0 or 1.

11. The light-emitting device of claim 1, wherein, in Formula 3, at least one selected from the group consisting of ring CY31 and ring CY32 is a benzene group.

12. The light-emitting device of claim 1, wherein, the group represented by Formula 3 is represented by one of Formulae 3-1 to Formula 3-9:

3-1

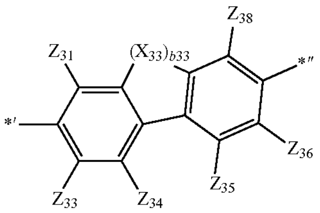

-continued 3-2

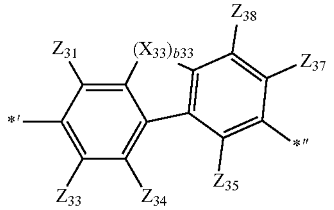

3-3

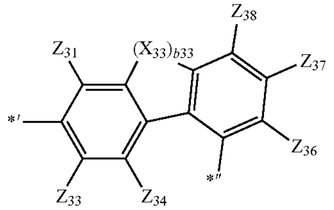

3-4

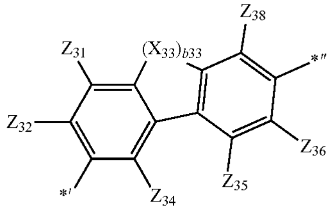

3-5

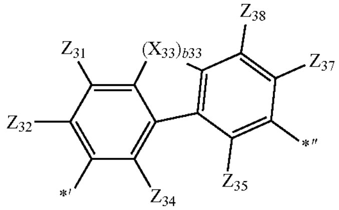

3-6

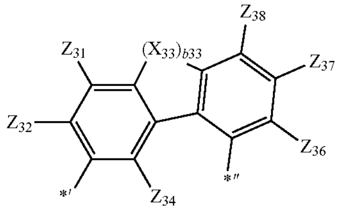

3-7

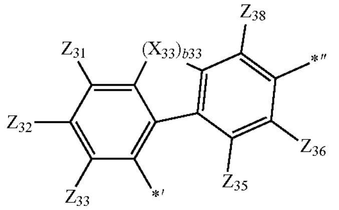

3-8

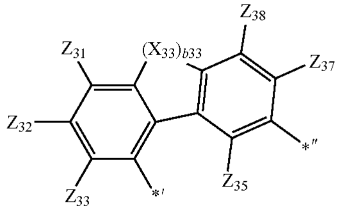

-continued 3-9

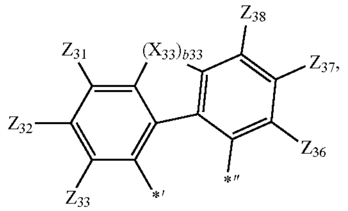

and wherein, in Formulae 3-1 to 3-9, $Z_{31}$ to $Z_{38}$ are each independently the same as the description of $R_{31}$, and $X_{33}$, b33, *', and *" are respectively the same as the descriptions of $X_{33}$, b33, *', and *".

13. The light-emitting device of claim 1, wherein, in Formula 4, $b_{43}$ is 0, and $X_{43}$ is not present.

14. The light-emitting device of claim 1, wherein, in Formula 4, at least one selected from the group consisting of ring CY41 and ring CY42 is a benzene group.

15. The light-emitting device of claim 1, wherein the group represented by Formula 4 is represented by one of Formulae 4-1 to 4-9:

4-1

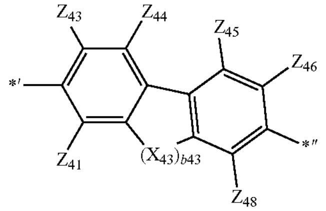

4-2

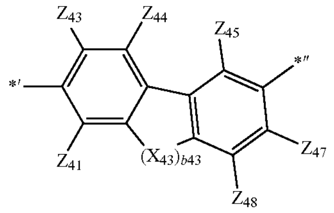

4-3

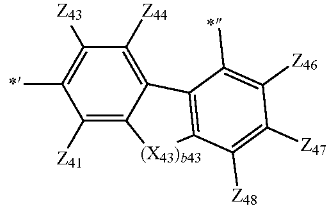

4-4

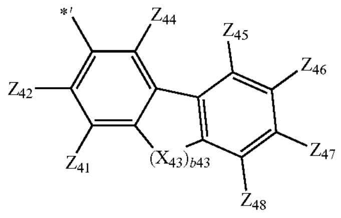

-continued 4-5

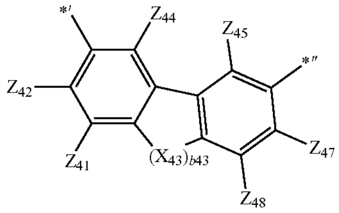

4-6

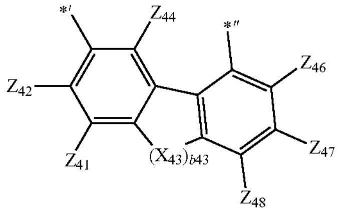

4-7

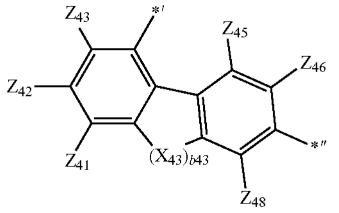

4-8

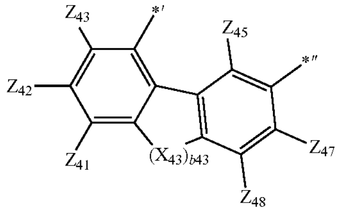

4-9

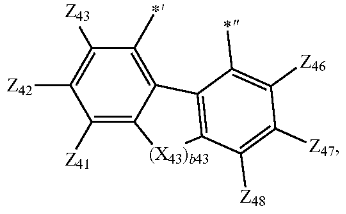

and wherein, in Formulae 4-1 to 4-9, $Z_{41}$ to $Z_{48}$ are each independently the same as the description of $R_{41}$, and $X_{43}$, b43, *', and *" are respectively the same as the descriptions of $X_{43}$, b43, *', and *".

16. The light-emitting device of claim 1, wherein, in Formulae 1 to 4, $R_1$, $R_{21}$ to $R_{23}$, $R_{31}$ to $R_{34}$, and $R_{41}$ to $R_{44}$ are each independently:

hydrogen, deuterium, —F, or a cyano group; or a phenyl group, a biphenyl group, a naphthyl group, a fluorenyl group, a carbazolyl group, a dibenzofuranyl group, or a dibenzothiophenyl group, each unsubstituted or substituted with deuterium, —F, a cyano group, a $C_1$-$C_{20}$ alkyl group, a phenyl group, a biphenyl group, a naphthyl group, a $C_1$-$C_{20}$ alkyl phenyl group, a fluorenyl group, a carbazolyl group, a dibenzofuranyl group, a dibenzothiophenyl group, or any combination thereof.

17. The light-emitting device of claim 1, wherein $R_1$ in Formula 1 is:
hydrogen, deuterium, or a cyano group; or
a group represented by one of Formulae 1-1 to 1-57:
1-1
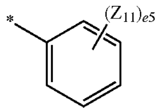
1-2
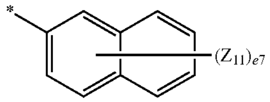
1-3
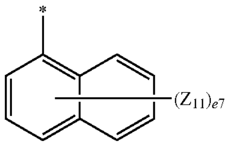
1-4
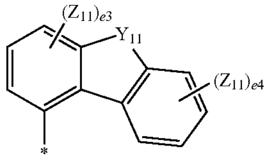
1-5
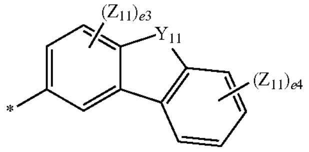
1-6
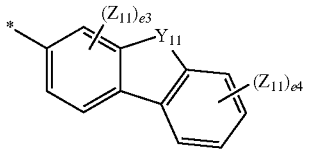
1-7
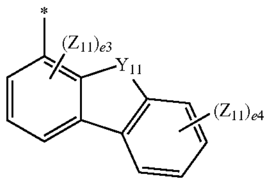
1-8
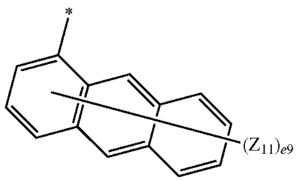
1-9
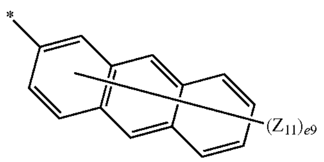
-continued
1-10
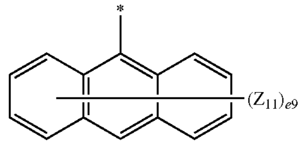
1-11
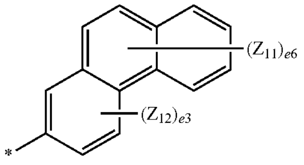
1-12
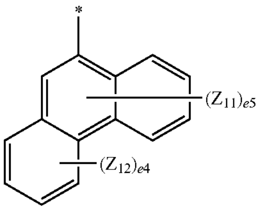
1-13
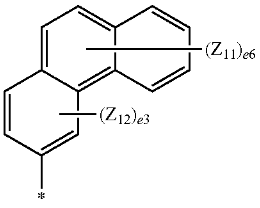
1-14
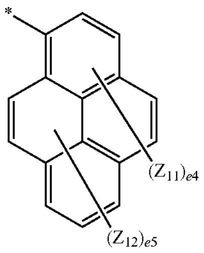
1-15
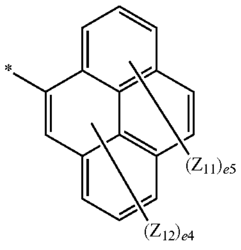
1-16
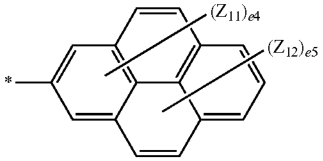

-continued
1-17
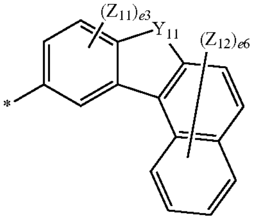
1-18
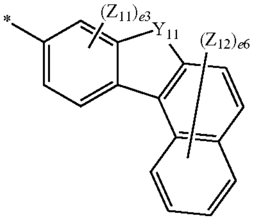
1-19
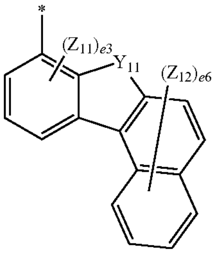
1-20
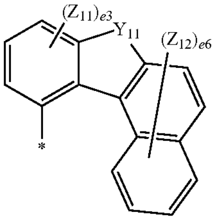
1-21
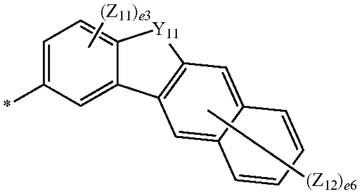
1-22
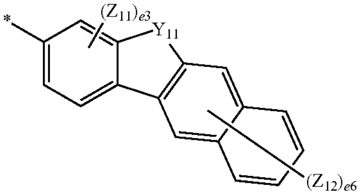
1-23
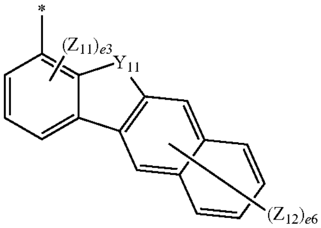
-continued
1-24
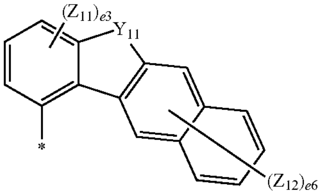
1-25
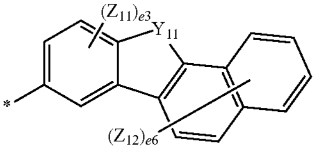
1-26
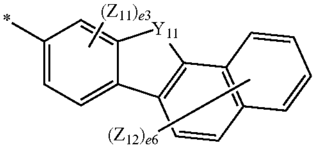
1-27
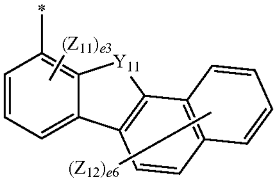
1-28
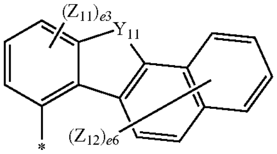
1-29
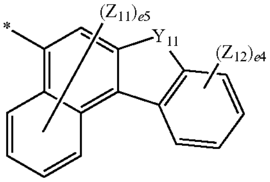
1-30
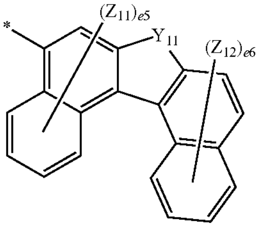
1-31
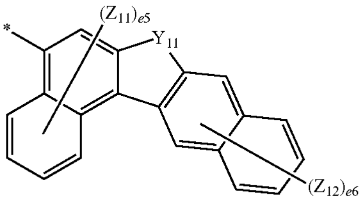

-continued
1-32
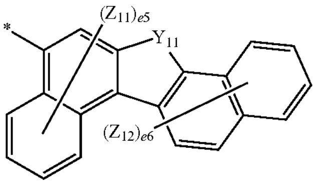
1-33
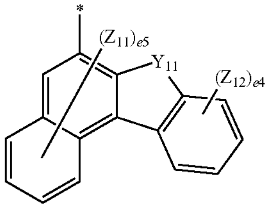
1-34
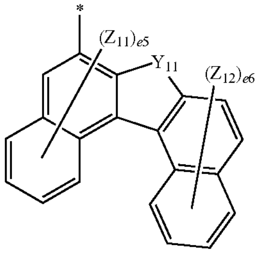
1-35
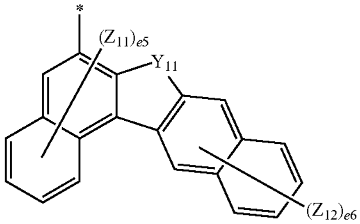
1-36
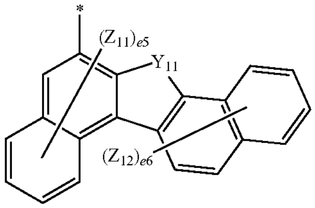
1-37
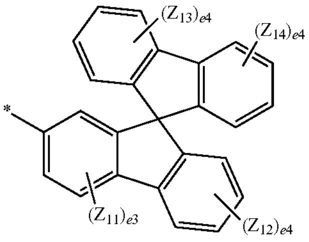
1-38
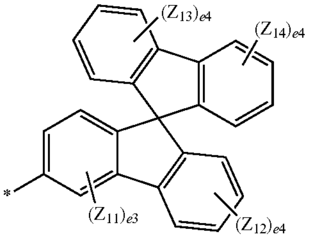
-continued
1-39
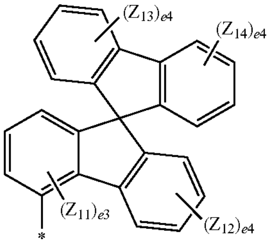
1-40
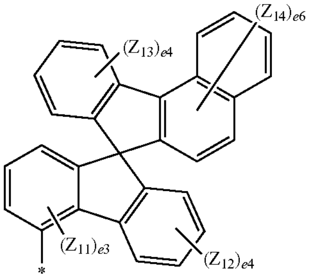
1-41
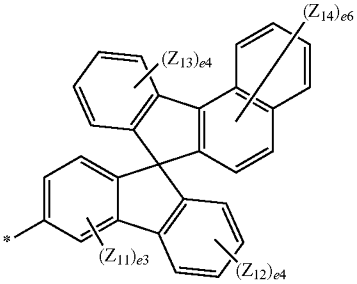
1-42
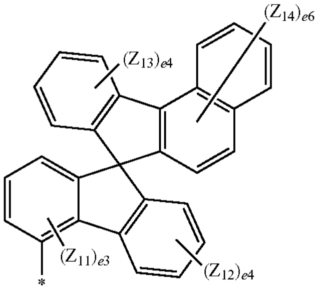
1-43
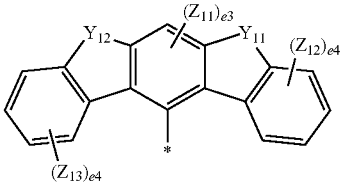
1-44
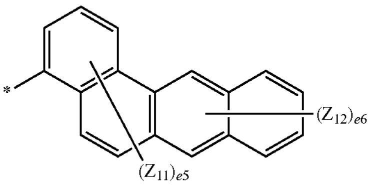

-continued
1-45
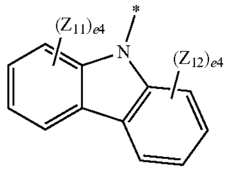
1-46
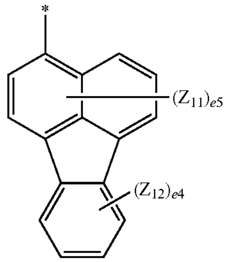
1-47
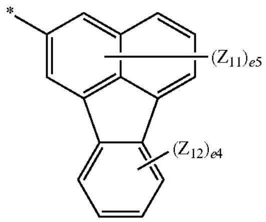
1-48
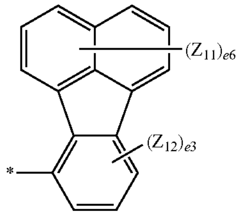
1-49
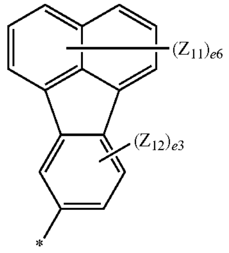
1-50
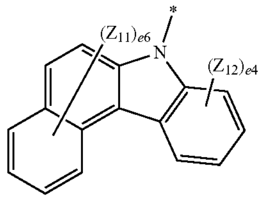
1-51
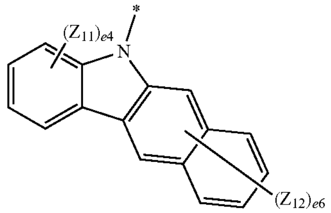
-continued
1-52
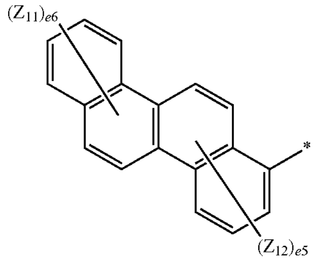
1-53
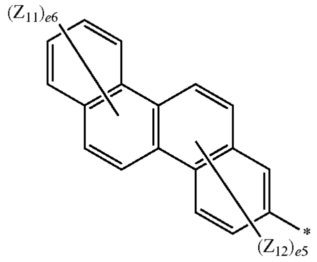
1-54
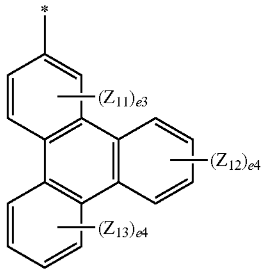
1-55
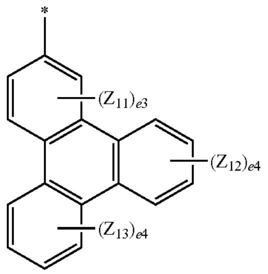
1-56
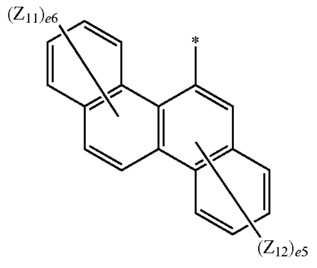
1-57
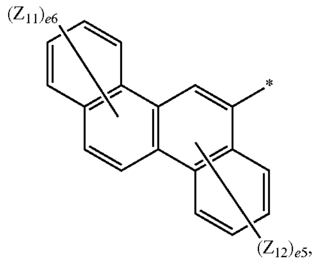

and wherein, in Formulae 1-1 to 1-57, $Y_{11}$ is O, S, $B(R_{11})$, $N(R_{11})$, $C(R_{11})(R_{12})$, or $Si(R_{11})(R_{12})$, $Y_{12}$ is O, S, $B(R_{21})$, $N(R_{21})$, $C(R_{21})(R_{22})$, or $Si(R_{21})(R_{22})$, $Z_{11}$, $Z_{12}$, $Z_{13}$, $Z_{14}$, $R_{11}$, $R_{12}$, $R_{21}$, and $R_{22}$ are each independently the same as the description of $R_{10a}$ in claim 1, e3 is an integer from 0 to 3, e4 is an integer from 0 to 4, e5 is an integer from 0 to 5, e6 is an integer from 0 to 6, e7 is an integer from 0 to 7, e9 is an integer from 0 to 9, and

* indicates a binding site to an adjacent atom.

18. An electronic apparatus comprising the light-emitting device of claim 1.

19. The electronic apparatus of claim 18, further comprising: a thin-film transistor, wherein the thin-film transistor comprises a source electrode and a drain electrode, and the first electrode of the light-emitting device is electrically connected to at least one selected from the group consisting of the source electrode and the drain electrode of the thin-film transistor.

20. The electronic apparatus of claim 18, further comprising: a color filter, a color-conversion layer, a touchscreen layer, a polarizing layer, or any combination thereof.

* * * * *